(12) United States Patent
Tsukuda et al.

(10) Patent No.: US 8,193,351 B2
(45) Date of Patent: Jun. 5, 2012

(54) HSP90 INHIBITOR

(75) Inventors: Takuo Tsukuda, Kanagawa (JP);
Ken-Ichi Kawasaki, Kanagawa (JP);
Susumu Komiyama, Kanagawa (JP);
Yoshiaki Isshiki, Shizuoka (JP);
Yasuhiko Shiratori, Kanagawa (JP);
Kiyoshi Hasegawa, Kanagawa (JP);
Takaaki Fukami, Kanagawa (JP);
Takaaki Miura, Shizuoka (JP); Naomi Ono, Kanagawa (JP); Toshikazu Yamazaki, Kanagawa (JP); Young-Jun Na, Gyeonggi-do (KR); Dong-Oh Yoon, Gyeonggi-do (KR); Sung-Jin Kim, Gyeonggi-do (KR)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 288 days.

(21) Appl. No.: 12/302,149

(22) PCT Filed: May 25, 2007

(86) PCT No.: PCT/JP2007/060666
§ 371 (c)(1),
(2), (4) Date: Apr. 2, 2009

(87) PCT Pub. No.: WO2007/138994
PCT Pub. Date: Dec. 6, 2007

(65) Prior Publication Data
US 2009/0247524 A1    Oct. 1, 2009

(30) Foreign Application Priority Data

May 26, 2006 (JP) ................................. 2006-146982
Mar. 30, 2007 (JP) ................................. 2007-094057

(51) Int. Cl.
C07D 239/47 (2006.01)
C07D 251/42 (2006.01)
A61K 31/506 (2006.01)
A61K 31/53 (2006.01)
A61P 35/00 (2006.01)

(52) U.S. Cl. ........ 544/194; 544/219; 544/321; 514/245; 514/272

(58) Field of Classification Search .................. 544/194, 544/219, 321; 514/245, 272
See application file for complete search history.

(56) References Cited

U.S. PATENT DOCUMENTS

| | | |
|---|---|---|
| 6,210,974 B1 | 4/2001 | Gold |
| 2004/0204386 A1 | 10/2004 | Bhatt et al. |
| 2008/0214586 A1 | 9/2008 | Eggenweiler et al. |
| 2010/0056510 A1 | 3/2010 | Shimma et al. |

FOREIGN PATENT DOCUMENTS

| | | |
|---|---|---|
| EP | 0165653 A1 | 12/1985 |
| EP | 1321169 A1 | 6/2003 |
| JP | 51-070780 | 6/1976 |
| JP | 60208968 A | 10/1985 |
| JP | 2001-505554 | 4/2001 |
| JP | 2005-225787 | 8/2005 |
| JP | 2005530689 A1 | 10/2005 |
| JP | 2009067729 A1 | 4/2009 |
| WO | WO9744326 A1 | 11/1997 |
| WO | WO98/19648 A2 | 5/1998 |
| WO | WO 99/51223 | 10/1999 |
| WO | WO01/27088 A1 | 4/2001 |
| WO | WO0162233 A1 | 8/2001 |
| WO | WO 02/02123 | 1/2002 |
| WO | WO 02/09696 | 2/2002 |
| WO | WO 02/36075 | 5/2002 |
| WO | WO 02/36171 | 5/2002 |
| WO | WO03/037346 | 5/2003 |
| WO | WO 03/037860 | 5/2003 |
| WO | WO 03/055860 | 7/2003 |
| WO | WO 2004/050087 | 6/2004 |
| WO | WO 2005/021552 | 3/2005 |
| WO | WO 2006/008503 | 1/2006 |
| WO | WO 2006/122631 | 11/2006 |
| WO | WO 2006/123165 | 11/2006 |
| WO | WO2007058627 A1 | 5/2007 |
| WO | WO2007138994 A1 | 6/2007 |
| WO | WO 2008/105526 | 9/2008 |
| WO | WO2009097578 A1 | 8/2009 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141 802-810, 1999.*
Golub et al., Science, 286, 531-537, 1999.*
Cecil Textbook of Medicine, edited by Bennet, J.C., and Plum F., 20th edition,vol. 1, 1004-1010, 1996.*

(Continued)

*Primary Examiner* — Venkataraman Balasubramanian
(74) *Attorney, Agent, or Firm* — Fish & Richardson P.C.

(57) ABSTRACT

Compounds represented by formula (1) shown below, pharmaceutically acceptable salts thereof, and pharmaceutical compositions comprising such compounds are provided.

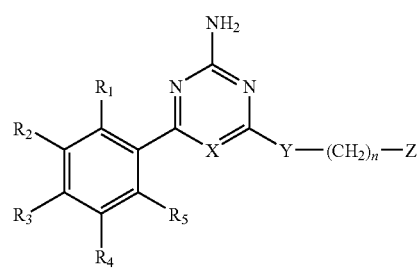

(1)

19 Claims, No Drawings

OTHER PUBLICATIONS

Database Caplus on STN, AN 1932:57919, DN 26:57919, Dziewonski et al, "Derivatives of naphthalic acid. Synthesis of 3,4-dihydroxynaphthalic acid," *Roczniki Chemii*, 11:870-883 (1931).

Augustin et al., "Reaktionen mit N-Acylimino-dithiokohlensäurediestern," *Journal für praktische Chemie (Leipzig)*, 322(1):55-68 (1980) (English abstract).

Banerji et al., "The Clinical Applications of Heat Shock Protein Inhibitors in Cancer—Present and Future," *Curr. Cancer Drug Targets*, 3:385-390 (2003).

Chiosis et al., "A small molecule designed to bind the adenine nucleotide pocket of Hsp90 causes Her2 degradation and the growth arrest and differentiation of breast cancer cells," *Chem. Biol.*, 8:289-299 (2001).

Dai and Whitesell, "HSP90: a rising star on the horizon of anticancer targets," *Future Oncol.*, 1(4):529-540 (2005).

Gong et al., "Synthesis, SAR, and antitumor properties of diamino-C,N-diarylpyrimidine positional isomers: inhibitors of lysophosphatidic acid acyltransferase-β," *Bioorg. Med. Chem. Letters*, 14:2303-2308 (2004).

Neckers and Neckers, "Heat-shock protein 90 inhibitors as novel cancer chemotherapeutics—an update," *Expert Opin. Emerg. Drugs*, 137-149 (2005).

Japanese Patent Office, International Search Report for App. Ser. No. PCT/JP2007/060666 mailed Jun. 19, 2007, 7 pages.

Paull et al., "Display and analysis of patterns of differential activity of drugs against human tumor cell lines: development of mean graph and COMPARE algorithm," J. Natl. Cancer Inst., 81:1088-92 (1989).

Yamazaki et al., "Nucleotide sequence of a full-length cDNA for 90 kDa heat-shock protein from human peripheral blood lymphocytes," Nucleic Acids Res., 17(17):7108 (1989).

Supplementary European Search Report for App. Ser. No. EP 07 74 4100, dated Nov. 5, 2010, 3 pages.

International Preliminary Report on Patentability for App. Ser. No. PCT/JP2008/053599, dated Sep. 1, 2009, 5 pages.

Japanese Patent Office, International Search Report for App. Ser. No. PCT/JP2008/053599, mailed May 13, 2008, 3 pages.

* cited by examiner

US 8,193,351 B2

HSP90 INHIBITOR

CROSS-REFERENCE TO RELATED APPLICATIONS

This application is the National Stage of International Application Serial No. PCT/JP2007/060666, filed on May 25, 2007, which claims the benefit of Japanese Application Serial Nos. 2006-146982, filed on May 26, 2006, and 2007-094057, filed on Mar. 30, 2007.

TECHNICAL FIELD

The present invention relates to 6-aryl-4-mercapto/oxy-(1,3,5)triazin/(1,3)pyrimidin-2-amine derivatives and pharmaceutically acceptable salts thereof, pharmaceuticals comprising such, synthetic intermediates of said derivatives and salts, and such.

BACKGROUND ART

Molecular chaperones are a group of proteins that are catalytically involved in the folding or association of other proteins. Heat-shock protein 90 (HSP90) is a constitutively expressed molecular chaperone that governs the maturation of many regulatory factors that are key to cell growth and survival, as well as the maintenance of their stability. HSP90 is a molecular chaperone with a molecular weight of approximately 90,000, and is abundant in cells (approximately 1% to 2% of total soluble proteins) and uniformly distributed in the cytoplasm. HSP90 is known to interact with many molecules involved in the intracellular signal transduction system.

More specifically, it is known to be involved in the functional expression of not only signal transduction system proteins (for example, RAF-1, AKT/PKB, c-SRC, and ERBB2) and cell-cycle regulatory proteins (for example, CDK-1, CDK-4, mouse double minute 2, and TP53), but also apoptosis pathway proteins (for example, survivin and apoptosis protease activating factor 1) and such, and is suggested to be deeply involved in cell cycle regulation, and malignant transformation, growth, and survival signals. It is considered that inhibiting the function of HSP90 can at the same time inhibit the function of the above-mentioned proteins; therefore, HSP90 recently receives attention as a target of anticancer agents. Furthermore, there are reports that a number of genetic defects accumulate in the process of malignant transformation, and that in tumor cells, such modified proteins require chaperone activity more so than normal proteins. It is also reported that the expression level of HSP90 is increased in various cancers (Non-Patent Documents 1 and 2).

Accordingly, research and development of HSP90 inhibitors as anticancer agents is progressing. For example, clinical trials of single agent 17-allyamino-17-demethoxygeldanamycin (17-AAG) are carried out on advanced epithelial ovarian carcinoma, primary peritoneal carcinoma, metastatic renal cell carcinoma, von Hippel-Lindau disease, renal tumors, chemotherapy refractory breast cancer, advanced medullary carcinoma, differentiated thyroid carcinoma, metastatic melanoma, relapsed/refractory pediatric malignancies, and relapsed/refractory pediatric patients with solid tumors or leukemia.

Clinical trials are also performed to evaluate the concomitant use of 17-AAG with various anticancer agents. The diseases targeted by this concomitant use are solid tumors (concomitant agent: bortezomib), advanced solid tumors (concomitant agent: gemcitabine and cisplatin, docetaxel, paclitaxel), relapsed, refractory, and high-risk acute leukemia (concomitant agent: cytarabine), chronic myelogenous leukemia (concomitant agent: cytarabine, imatinib), fludarabine-refractory B-cell chronic lymphocytic leukemia (concomitant agent: fludarabine and rituximab), and hematologic malignancies (concomitant agent: bortezomib). Single-agent clinical trials for 17-dimethylaminoethylamino-17-demethoxygeldanamycin (17-DMAG) are carried out on solid tumors and advanced solid tumors (Non-Patent Documents 1 and 2).

According to a press released by Infinity Pharmaceutical Inc., clinical trials on IPI-504, which is a 17-AAG analog, are performed on gastrointestinal tumor and multiple myeloma.

Additionally, research and development of Radicicol (KF-58333) (Non-Patent Document 3), purine derivatives such as PU24FCl (Patent Documents 1 and 2, and Non-Patent Document 4), pyrazole derivatives such as CCT-018159 (Patent Documents 3 to 5), pyrimidothiophene derivatives (Patent Document 6), 2-amino-4-phenylquinazoline derivatives (Patent Document 7), 2-amino-4-phenylpyrimidine derivatives (Patent Document 8), 2-amino-4-phenylthieno[2,3-d]pyrimidine derivatives (Patent Document 9) and such as low-molecular weight HSP90 inhibitors is under progress.

Cancer cells which are under stressful conditions such as abnormal protein expression, hypoxia, and nutritional starvation, are highly dependent on HSP90. Therefore, cancer cells are considered to show higher sensitivity towards HSP90 inhibitors. This is also supported by the pharmacokinetic analysis of 17-AAG in animal models, which is reported to show higher accumulation potential of 17-AAG in cancerous regions than in normal tissues. Accordingly, HSP90 inhibitors are expected to act specifically on cancer cells but not on normal cells, and may become a new type of anticancer agent not found in conventional anticancer agents. In addition, HSP90 inhibitors have been reported to enhance the efficacy of cytotoxic agents (Patent Document 10), which also makes them an interesting anticancer agent.

However, it has been pointed out that the use of geldanamycin derivatives and radicicol derivatives as pharmaceuticals is problematic in terms of their physical properties such as toxicity, stability, and water solubility. So far, there are no HSP90 inhibitors that have actually reached the market. Therefore, there has been a demand for a new compound class of HSP90 inhibitors that are different from these compounds.

In addition to anticancer and antitumor activity, HSP90 inhibitors have been reported to be useful as anti-inflammatory agents, anti-infectious-disease agents, agents for treating autoimmunity, agents for treating ischemia, and agents for enhancing nerve regeneration (Patent Documents 11-13). They are also reported to be useful as therapeutic agents for disorders, in which fibrogenesis can be induced, including pulmonary fibrosis, scleroderma, polymyositis, systemic lupus erythematosus, rheumatoid arthritis, hepatic cirrhosis, keloid formation, interstitial nephritis, and such (Patent Document 14). Single-agent clinical trials of the aforementioned 17-AAG are also conducted for systemic mastocytosis.

On the other hand, several simple-structure compounds are known for 6-aryl-4-mercapto/oxy-(1,3,5)triazin/(1,3)pyrimidin-2-amine derivatives (Patent Document 15 and Non-Patent Document 5); however, neither anticancer effects nor inhibitory effects on HSP90 have been reported. Furthermore, the present inventors could not confirm anticancer effects in such simple-structure 6-aryl-4-mercapto/oxy-(1,3,5)triazin/(1,3)pyrimidin-2-amine derivatives.

There are other reports that 6-phenyl-N-phenyl-(1,3,5)triazin/(1,3)pyrimidin-2,4-diamine derivatives which are structurally similar to 6-aryl-4-mercapto/oxy-(1,3,5)triazin/(1,3)

pyrimidin-2-amine derivatives have inhibitory effects on lysophosphatidic acid acyl transferase β (LPAAT-β) and are useful as anticancer agents (Patent Documents 16 and 17, and Non-Patent Document 6). However, the present inventors confirmed that such 6-phenyl-N-phenyl(1,3,5)triazin/(1,3) pyrimidin-2,4-diamine derivatives do not have inhibitory effects on HSP90. Currently, no LPAAT-β inhibitor is submitted to clinical trials as an anticancer agent, and anticancer effects of LPAAT-β inhibitors are limited to experimental results. Furthermore, LPAAT-β inhibitors cannot be expected to be useful as anticancer agents having the above-described HSP90-inhibiting effect, in particular, the unique effect of simultaneously acting on multiple promising targets.

[Patent Document 1] WO2002/036075
[Patent Document 2] WO2003/037860
[Patent Document 3] WO2003/055860
[Patent Document 4] WO2004/050087
[Patent Document 5] Japanese Patent Application Kokai Publication No. (JP-A) 2005-225787 (unexamined, published Japanese patent application)
[Patent Document 6] WO2005/021552
[Patent Document 7] WO2006/122631
[Patent Document 8] WO2006/123165
[Patent Document 9] WO2006/008503
[Patent Document 10] WO2002/036171
[Patent Document 11] WO2002/009696
[Patent Document 12] WO99/51223
[Patent Document 13] U.S. Pat. No. 6,210,974
[Patent Document 14] WO2002/002123
[Patent Document 15] JP-A S51-70780
[Patent Document 16] WO2003/037346
[Patent Document 17] US2004/0204386
[Non-patent Document 1] Future Oncol. (2005), 1(4), 529-540
[Non-patent Document 2] Expert Opin. on Emerging Drugs (2005), 10(1), 137-149
[Non-patent Document 3] Curr. Cancer Drug Targets. 2003 October, 3(5), 385-390
[Non-patent Document 4] Chem. Biol. 2001 March, 8(3), 289-299
[Non-patent Document 5] Journal fuer Praktische Chemie (Leipzig) (1980), 322(1), 55-68
[Non-patent Document 6] Bioorg. Med. Chem. Lett. (2004), 14, 2303-2308

DISCLOSURE OF THE INVENTION

Problems to be Solved by the Invention

The present invention was made based on the above circumstances. An objective of the present invention is to provide a new class of compounds having HSP90 inhibitory activity, which are useful as anticancer agents or such, and to provide compounds that are useful as synthetic intermediates thereof.

Means for Solving the Problems

In view of the above circumstances, the present inventors completed the present invention by searching for compounds having HSP90 inhibitory activity, and discovering that certain types of 6-aryl-4-mercapto/oxy-(1,3,5)triazin/(1,3)pyrimidin-2-amine derivatives surprisingly have HSP90 inhibitory activity. Furthermore, they discovered compounds that are useful as their synthetic intermediates, and thereby completed the present invention.

More specifically, the present invention provides the following compounds, pharmaceutical compositions comprising these compounds, and their synthetic intermediates:

[1] a compound represented by formula (1) or a pharmaceutically acceptable salt thereof:

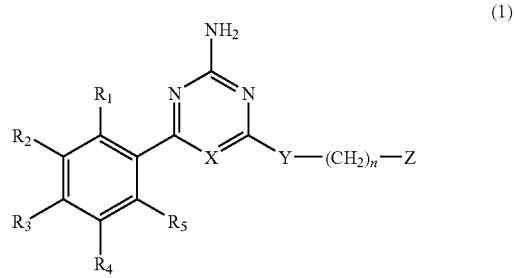

(1)

wherein,
X represents CH or N;
Y represents O or S;
Z represents an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{6-12}$ aryl group, an optionally substituted 5- to 12-membered heteroaryl group, or an optionally substituted 3- to 12-membered heterocycle;
n is an integer from 0 to 2;
$R_1$ represents a hydrogen atom, halogen atom, cyano group, $C_{1-6}$ alkyl group, $C_{1-4}$ haloalkyl group, $C_{2-6}$ alkenyl group, $C_{2-6}$ alkynyl group, $C_{1-6}$ alkoxy group, or $C_{1-6}$ alkylthio group;
$R_2$ represents a hydrogen atom, halogen atom, $C_{1-6}$ alkyl group, $C_{2-6}$ alkenyl group, or $C_{2-6}$ alkynyl group, or $R_2$ and $R_3$ together form a ring;
$R_3$ represents a hydrogen atom, halogen atom, hydroxyl group, $C_{1-6}$ alkyl group, $C_{2-6}$ alkenyl group, $C_{2-6}$ alkynyl group, carboxyl group, an optionally substituted $C_{1-6}$ alkoxy group, $C_{1-6}$ alkylthio group, $C_{1-6}$ alkoxycarbonyl group, $C_{6-12}$ aryl group, 5- to 12-membered heteroaryl group, or a group represented by formula (2):

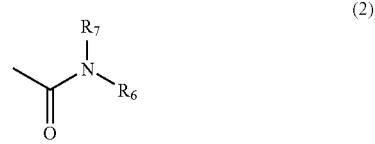

(2)

or $R_2$ and $R_3$, $R_3$ and $R_4$, or $R_3$, $R_4$, and $R_5$ together form a ring;
$R_4$ represents a hydrogen atom, halogen atom, hydroxyl group, $C_{1-6}$ alkyl group, $C_{2-6}$ alkenyl group, $C_{2-6}$ alkynyl group, carboxyl group, an optionally substituted $C_{1-6}$ alkoxy group, $C_{1-6}$ alkylthio group, $C_{1-6}$ alkoxycarbonyl group, $C_{6-12}$ aryl group, 5- to 12-membered heteroaryl group, or a group represented by formula (3):

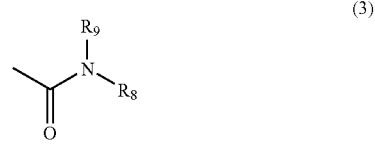

(3)

or $R_3$ and $R_4$, $R_4$ and $R_5$, or $R_3$, $R_4$, and $R_5$ together form a ring;

$R_5$ represents a hydrogen atom, halogen atom, $C_{1-6}$ alkyl group, $C_{2-6}$ alkenyl group, or $C_{2-6}$ alkynyl group; or $R_4$ and $R_5$, or $R_3$, $R_4$, and $R_5$ together form a ring;

at least two of $R_1$, $R_2$, $R_3$, $R_4$, and $R_5$ are not hydrogen atoms;

$R_6$ and $R_7$ may be the same or different and represent a hydrogen atom, an optionally substituted $C_{1-6}$ alkyl group, $C_{2-6}$ alkenyl group, or $C_{2-6}$ alkynyl group, $C_{6-12}$ aryl group, 5- to 12-membered heteroaryl group, or $R_6$ and $R_7$ together form an optionally substituted 3- to 12-membered heterocycle;

$R_8$ and $R_9$ may be the same or different and represent a hydrogen atom, an optionally substituted $C_{1-6}$ alkyl group, $C_{2-6}$ alkenyl group, $C_{2-6}$ alkynyl group, $C_{6-12}$ aryl group, an optionally substituted 3 to 12-membered heterocycle, or 5- to 12-membered heteroaryl group, or $R_8$ and $R_9$ together form an optionally substituted 3- to 12-membered heterocycle;

[2] the compound or a pharmaceutically acceptable salt thereof according to [1], wherein $R_1$ is a halogen atom, $C_{1-4}$ alkyl group or $C_{1-4}$ haloalkyl group;

[3] the compound or a pharmaceutically acceptable salt thereof according to [2], wherein $R_1$ is a chlorine atom;

[4] the compound or a pharmaceutically acceptable salt thereof according to [2], wherein $R_1$ is a methyl group;

[5] the compound or a pharmaceutically acceptable salt thereof according to any one of [1] to [4], wherein $R_2$ is a hydrogen atom;

[6] the compound or a pharmaceutically acceptable salt thereof according to any one of [1] to [5], wherein $R_5$ is a hydrogen atom;

[7] the compound or a pharmaceutically acceptable salt thereof according to any one of [1] to [6], wherein $R_3$ is a halogen atom or $C_{1-6}$ alkyl group; and $R_4$ represents a $C_{1-6}$ alkyl group, an optionally substituted $C_{1-6}$ alkoxy group, or a group represented by formula (3):

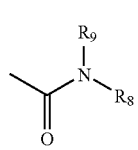

(3)

wherein $R_8$ and $R_9$ are as defined in [1];

[8] the compound or a pharmaceutically acceptable salt thereof according to any one of [1] to [7], wherein, $R_3$ is a halogen atom; and $R_4$ is a $C_{1-6}$ alkoxy group optionally substituted with a cyano group, or a group represented by formula (3):

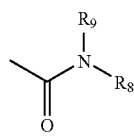

(3)

wherein $R_8$ and $R_9$ may be the same or different, and represent a hydrogen atom or a $C_{1-6}$ alkyl group;

[9] the compound or a pharmaceutically acceptable salt thereof according to any one of [1] to [8], wherein $R_3$ is a chlorine atom;

[10] the compound or a pharmaceutically acceptable salt thereof according to any one of [1] to [5], wherein $R_3$, $R_4$, and $R_5$ together form a ring;

[11] the compound or a pharmaceutically acceptable salt thereof according to [10], wherein the compound is represented by formula (4):

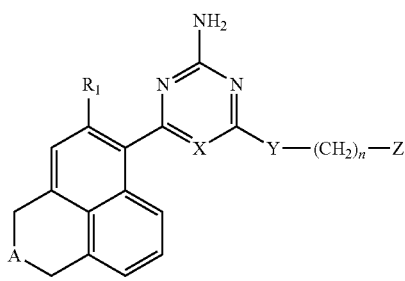

(4)

wherein A represents O or S; and X, Y, Z, n, and $R_1$ are as defined in [1];

[12] the compound or a pharmaceutically acceptable salt thereof according to any one of [1] to [11], wherein Z is a substituted $C_{1-10}$ alkyl group, a substituted $C_{3-10}$ cycloalkyl group, a substituted $C_{2-10}$ alkenyl group, a substituted $C_{2-10}$ alkynyl group, a substituted $C_{6-12}$ aryl group, a substituted 5- to 12-membered heteroaryl group, or a substituted 3- to 12-membered heterocycle;

[13] the compound or a pharmaceutically acceptable salt thereof according to any one of [1] to [12], wherein Z is a substituted $C_{1-10}$ alkyl group, a substituted $C_{6-12}$ aryl group, or a substituted 3- to 12-membered heterocycle;

[14] the compound or a pharmaceutically acceptable salt thereof according to [12] or [13], wherein the substituent in Z is a hydroxyl group, oxo group, a group represented by formula (5):

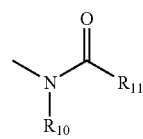

(5)

(wherein $R_{10}$ and $R_{11}$ may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or $R_{10}$ and $R_{11}$ together form an optionally substituted 3- to 12-membered heterocycle);

a group represented by formula (6):

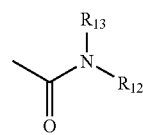

(6)

(wherein $R_{12}$ and $R_{13}$ may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or an optionally substituted 5- to 12-membered heteroaryl group, or $R_{12}$ and $R_{13}$ are taken together to form an optionally substituted 3- to 12-membered heterocycle);

a group represented by the formula (34):

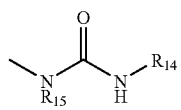

(wherein R₁₄ and R₁₅ may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or R₁₄ and R₁₅ are taken together to form an optionally substituted 3- to 12-membered heterocycle);
a group represented by formula (35):

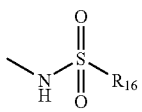

(wherein R₁₆ represents an optionally substituted $C_{1-6}$ alkyl group, an optionally substituted $C_{1-6}$ alkenyl group, or an optionally substituted $C_{1-6}$ alkynyl group); or
a group represented by formula (36):

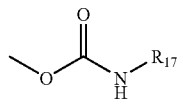

(wherein R₁₇ represents a hydrogen atom, an optionally substituted $C_{1-6}$ alkyl group, an optionally substituted $C_{1-6}$ alkenyl group, or an optionally substituted $C_{1-6}$ alkynyl group);
[15] the compound or a pharmaceutically acceptable salt thereof according to any one of [12] to [14], wherein the substituent in Z is a hydroxyl group, oxo group, a group represented by formula (5):

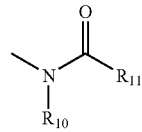

(wherein R₁₀ is a hydrogen atom; and R₁₁ is an optionally substituted $C_{1-6}$ alkyl group);
a group represented by formula (6):

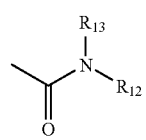

(wherein R₁₂ and R₁₃ may be the same or different, and represent a hydrogen atom, or an optionally substituted $C_{1-6}$ alkyl group);

a group represented by formula (34):

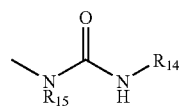

(wherein R₁₄ and R₁₅ are hydrogen atoms);
a group represented by formula (35):

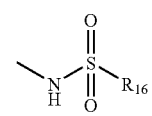

(wherein R₁₆ represents a $C_{1-6}$ alkyl group); or
a group represented by formula (36):

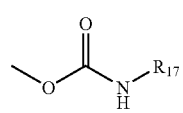

(wherein R₁₇ represents a hydrogen atom);
[16] the compound or a pharmaceutically acceptable salt thereof according to any one of [1] to [15], wherein X is CH;
[17] the compound or a pharmaceutically acceptable salt thereof according to any one of [1] to [16], wherein Y is S;
[18] a compound or a pharmaceutically acceptable salt thereof, wherein the compound is selected from the group consisting of:
(1): {5-[4-amino-6-(2-methoxyphenylsulfanyl)-[1,3,5]triazin-2-yl]-2,4-dicyclophenoxy}-acetonitrile;
(2): 5-(4-amino-6-benzylsulfanyl-[1,3,5]triazin-2-yl)-2,4-dichloro-N-(2-hydroxyethyl)-benzamide;
(3): 4-(2,4-dichlorophenyl)-6-(2,5-dimethoxyphenylsulfanyl)-[1,3,5]triazin-2-ylamine;
(4): 4-(5-benzyloxy-2,4-dichlorophenyl)-6-benzylsulfanyl[1,3,5]triazin-2-ylamine;
(5): 4-benzylsulfanyl-6-(2,4-dichlorophenyl)-[1,3,5]triazin-2-ylamine;
(6): 4-(2,4-dichlorophenyl)-6-(2-methoxyphenylsulfanyl)-[1,3,5]triazin-2-ylamine;
(7): 4-(2-aminophenylsulfanyl)-6-(2,4-dichlorophenyl)-[1,3,5]triazin-2-ylamine;
(8): {5-[4-amino-6-(2,5-dimethoxyphenylsulfanyl)-[1,3,5]triazin-2-yl]-2,4-dichlorophenoxy}-acetonitrile;
(9): [5-(4-amino-6-phenylsulfanyl-[1,3,5]triazin-2-yl)-2,4-dichlorophenoxy]-acetonitrile;
(10): {5-[4-amino-6-(pyrimidin-2-ylsulfanyl)-[1,3,5]triazin-2-yl]-2,4-dichlorophenoxy}-acetonitrile;
(11): {5-[4-amino-6-(5-methyl-[1,3,4]thiadiazol-2-ylsulfanyl)-[1,3,5]triazin-2-yl]-2,4-dichlorophenoxy}-acetonitrile;
(12): {5-[4-amino-6-(1H-benzimidazol-2-ylsulfanyl)-[1,3,5]triazin-2-yl]-2,4-dichlorophenoxy}-acetonitrile;
(13): {5-[4-amino-6-(benzothiazol-2-ylsulfanyl)-[1,3,5]trazin-2-yl]-2,4-dichlorophenoxy}-acetonitrile;
(14): [5-(4-amino-6-cyclopropylmethylsulfanyl-[1,3,5]triazin-2-yl)-2,4-dichlorophenoxy]-acetonitrile;

(15): (5-{4-amino-6-[2-methoxy-4-(4-methyl-piperazin-1-carbonyl)-phenylsulfanyl]-[1,3,5]triazin-2-yl}-2,4-dichlorophenoxy)-acetonitrile;

(16): 4-[4-amino-6-(2,4-dichloro-5-cyanomethoxyphenyl)-[1,3,5]triazin-2-ylsulfanyl]-N-(2,3-dihydroxypropyl)-3-methoxybenzamide;

(17): (5-{4-amino-6-[4-(4-methyl-piperazin-1-carbonyl)-phenylsulfanyl]-[1,3,5]triazin-2-yl}-2,4-dichlorophenoxy)-acetonitrile;

(18): (5-{4-amino-6-[4-(piperazin-1-carbonyl)-phenylsulfanyl]-[1,3,5]triazin-2-yl}-2,4-dichlorophenoxy)-acetonitrile;

(19): 4-[4-amino-6-(2,4-dichloro-5-cyanomethoxyphenyl)-[1,3,5]triazin-2-ylsulfanyl]-N-(2,3-dihydroxypropyl)-benzamide;

(20): 4-[4-amino-6-(2,4-dichloro-5-cyanomethoxyphenyl)-[1,3,5]triazin-2-ylsulfanyl]-N-(2-hydroxy-1-hydroxymethyl-ethyl)-benzamide;

(21): (5-{4-amino-6-[2-methoxy-4-(piperazine-1-carbonyl)-phenylsulfanyl]-[1,3,5]triazin-2-yl}-2,4-dichlorophenoxy)-acetonitrile;

(22): 4-[4-amino-6-(2,4-dichloro-5-cyanomethoxyphenyl)-[1,3,5]triazin-2-ylsulfanyl]-3-methoxy-N-(1-methyl-piperidin-4-yl)-benzamide;

(23): 4-[4-amino-6-(2,4-dichloro-5-cyanomethoxyphenyl)-[1,3,5]triazin-2-ylsulfanyl]-3-methoxy-N-piperidin-4-yl-benzamide;

(24): 4-(2,4-dichloro-5-pyrimidin-2-yl-phenyl)-6-methylsulfanyl-[1,3,5]triazin-2-ylamine;

(25): N-{2-[4-amino-6-(2,4-dichloro-5-pyrimidin-2-yl-phenyl)-[1,3,5]triazin-2-ylsulfanyl]-ethyl}-acetamide;

(26): 5-(4-amino-6-benzylsulfanyl-[1,3,5]triazin-2-yl)-2,4-dichlorobenzamide;

(27): 5-(4-amino-6-benzylsulfanyl-[1,3,5]triazin-2-yl)-2,4-dichloro-N-(2,3-dihydroxypropyl)-benzamide;

(28): 5-(4-amino-6-benzylsulfanyl-[1,3,5]triazin-2-yl)-2,4-dichloro-N-(2-hydroxy-1-hydroxymethyl-ethyl)-benzamide;

(29): 5-(4-amino-6-benzylsulfanyl-[1,3,5]triazin-2-yl)-2,4-dichloro-N-(1-methyl-piperidin-4-yl)-benzamide;

(30): [5-(4-amino-6-benzylsulfanyl-[1,3,5]triazin-2-yl)-2,4-dichlorophenyl]-(4-methyl-piperazin-1-yl)-methanone;

(31): [5-(4-amino-6-benzylsulfanyl-[1,3,5]triazin-2-yl)-2,4-dichlorophenyl]-morpholin-4-yl-methanone;

(32): 5-(4-amino-6-benzylsulfanyl-[1,3,5]triazin-2-yl)-2,4-dimethylbenzoic acid methyl ester;

(33): 5-[4-amino-6-(2-methoxyphenylsulfanyl)-[1,3,5]triazin-2-yl]-2,4-dimethylbenzoic acid methyl ester;

(34): 5-[4-amino-6-(2,5-dimethoxyphenylsulfanyl)-[1,3,5]triazin-2-yl]-2,4-dimethylbenzoic acid methyl ester;

(35): 5-[4-amino-6-(2-hydroxyethylsulfanyl)-[1,3,5]triazin-2-yl]-2,4-dimethylbenzoic acid methyl ester;

(36): 5-[4-amino-6-(3-hydroxypropylsulfanyl)-[1,3,5]triazin-2-yl]-2,4-dimethylbenzoic acid methyl ester;

(37): 5-[4-amino-6-(2,3-dihydroxypropylsulfanyl)-[1,3,5]triazin-2-yl]-2,4-dimethylbenzoic acid methyl ester;

(38): 5-[4-amino-6-(2-methoxyphenylsulfanyl)-[1,3,5]triazin-2-yl]-2,4-dichloro-N-(2-hydroxyethyl)-benzamide;

(39): 4-(2,4-dichlorophenyl)-6-(2,5-dimethoxyphenylsulfanyl)-pyrimidin-2-ylamine;

(40): 4-(2,5-dimethoxyphenylsulfanyl)-6-naphthalen-1-yl-pyrimidin-2-ylamine;

(41): 4-(2,5-dimethoxyphenylsulfanyl)-6-(2,5-dimethylphenyl)-pyrimidin-2-ylamine;

(42): 4-(2,5-dimethoxyphenylsulfanyl)-6-(2,4,5-trimethylphenyl)-pyrimidin-2-ylamine;

(43): 4-[2-amino-6-(2,5-dimethoxyphenylsulfanyl)-pyrimidin-4-yl]-3-methylphenol;

(44): 3-{4-[2-amino-6-(2,5-dimethoxyphenylsulfanyl)-pyrimidin-4-yl]-3-methylphenoxy}-propan-1-ol (45): {4-[2-amino-6-(2,5-dimethoxyphenylsulfanyl)-pyrimidin-4-yl]-3-methylphenoxy}-acetonitrile;

(46): 2-{4-[2-amino-6-(2,5-dimethoxyphenylsulfanyl)-pyrimidin-4-yl]-3-methylphenoxy}-acetamide;

(47): 2-{4-[2-amino-6-(2,5-dimethoxyphenylsulfanyl)-pyrimidin-4-yl]-3-methylphenoxy}-ethanol;

(48): 4-(5-benzyloxy-2,4-dichlorophenyl)-6-(2,5-dimethoxyphenylsulfanyl)-pyrimidin-2-ylamine;

(49): 4-(2,5-dimethoxyphenylsulfanyl)-6-(2,4,6-trimethylphenyl)-pyrimidin-2-ylamine;

(50): 5-[2-amino-6-(2,5-dimethoxyphenylsulfanyl)-pyrimidin-4-yl]-2,4-dichlorophenyl;

(51): 4-(2,5-dimethoxyphenylsulfanyl)-6-(2-methyl-4-prop-2-ynyloxy-phenyl)-pyrimidin-2-ylamine;

(52): {5-[2-amino-6-(2,5-dimethoxyphenylsulfanyl)-pyrimidin-4-yl]-2,4-dichlorophenyoxy}-acetonitrile;

(53): {5-[2-amino-6-(2-aminophenylsulfanyl)-pyrimidin-4-yl]-2,4-dichlorophenoxy}-acetonitrile;

(54): {5-[2-amino-6-(1H-benzimidazol-2-ylsulfanyl)-pyrimidin-4-yl]-2,4-dichlorophenoxy}-acetonitrile;

(55): 2-[2-amino-6-(2,4-dichloro-5-cyanomethoxyphenyl)-pyrimidin-4-ylsulfanyl]-3H-imidazol-4-carboxylic acid ethyl ester;

(56): {5-[2-amino-6-(1-methyl-1H-imidazo-2-ylsulfanyl)-pyrimidin-4-yl]-2,4-dichlorophenoxy}-acetonitrile;

(57): 3-[4-amino-6-(2,4-dichloro-5-cyanomethoxyphenyl)-[1,3,5]triazin-2-ylsulfanyl]-propionic acid methyl ester;

(58): {5-[4-amino-6-(3-hydroxypropylsulfanyl)-[1,3,5]triazin-2-yl]-2,4-dichlorophenoxy}-acetonitrile;

(59): N-{2-[4-amino-6-(2,4-dichloro-5-cyanomethoxyphenyl)-[1,3,5]triazin-2-ylsulfanyl]-ethyl}-acetamide;

(60): 3-[4-amino-6-(2,4-dichloro-5-cyanomethoxyphenyl)-[1,3,5]triazin-2-ylsulfanyl]-N-methyl-propionamide;

(61): 3-[4-amino-6-(2,4-dichloro-5-cyanomethoxyphenyl)-[1,3,5]triazin-2-ylsulfanyl]-N-(2-hydroxyethyl)-propionamide;

(62): 3-[4-amino-6-(2,4-dichloro-5-cyanomethoxyphenyl)-[1,3,5]triazin-2-ylsulfanyl]-propionamide;

(63): {5-[4-amino-6-(3-morpholin-4-yl-3-oxo-propylsulfanyl)-[1,3,5]triazin-2-yl]-2,4-dichlorophenoxy}-acetonitrile;

(64): 3-[4-amino-6-(2,4-dichloro-5-cyanomethoxyphenyl)-[1,3,5]triazin-2-ylsulfanyl]-N-(2-hydroxyethoxy)-propionamide;

(65): 3-[4-amino-6-(2,4-dichloro-5-cyanomethoxyphenyl)-[1,3,5]triazin-2-ylsulfanyl]-N-pyridin-4-yl methyl-propionamide;

(66): 3-[4-amino-6-(2,4-dichloro-5-cyanomethoxyphenyl)-[1,3,5]triazin-2-ylsulfanyl]-N-pyridin-4-yl-propionamide;

(67): 3-[4-amino-6-(2,4-dichloro-5-cyanomethoxyphenyl)-[1,3,5]triazin-2-ylsulfanyl]-N-(2-dimethylamino-ethyl)-propionamide;

(68): 3-[4-amino-6-(2,4-dichloro-5-cyanomethoxyphenyl)-[1,3,5]triazin-2-ylsulfanyl]-N-(2-morpholin-4-yl-ethyl)-propionamide;

(69): 3-[4-amino-6-(2,4-dichloro-5-cyanomethoxyphenyl)-[1,3,5]triazin-2-ylsulfanyl]-N-thiazol-2-yl-propionamide;

(70): 2-[4-amino-6-(2,4-dichloro-5-cyanomethoxyphenyl)-[1,3,5]triazin-2-ylsulfanyl]-N-methyl-acetamide;

(71): 4-(5-chloro-1H,3H-benzo[de]isochromen-6-yl)-6-(2-methoxyphenylsulfanyl)-[1,3,5]triazin-2-ylamine;

(72): 4-(5-chloro-1H,3H-benzo[de]isochromen-6-yl)-6-(2-chlorophenylsulfanyl)-[1,3,5]triazin-2-ylamine;
(73): 4-(5-chloro-1H,3H-benzo[de]isochromen-6-yl)-6-(3-chlorophenylsulfanyl)-[1,3,5]triazin-2-ylamine;
(74): 4-(5-chloro-1H,3H-benzo[de]isochromen-6-yl)-6-(4-chlorophenylsulfanyl)-[1,3,5]triazin-2-ylamine;
(75): 4-(5-chloro-1H,3H-benzo[de]isochromen-6-yl)-6-(4-methylsulfanyl-phenylsulfanyl)-[1,3,5]triazin-2-ylamine;
(76): 4-(5-chloro-1H,3H-benzo[de]isochromen-6-yl)-6-(3-methoxyphenylsulfanyl)-[1,3,5]triazin-2-ylamine;
(77): 4-(5-chloro-1H,3H-benzo[de]isochromen-6-yl)-6-(4-methoxyphenylsulfanyl)-[1,3,5]triazin-2-ylamine;
78): 4-(5-chloro-1H,3H-benzo[de]isochromen-6-yl)-6-(2,5-difluorophenylsulfanyl)-[1,3,5]triazin-2-ylamine;
(79): 4-(5-chloro-1H,3H-benzo[de]isochromen-6-yl)-6-(2-fluorophenylsulfanyl)-[1,3,5]triazin-2-ylamine;
(80): 4-(5-chloro-1H,3H-benzo[de]isochromen-6-yl)-6-(4-fluorophenylsulfanyl)-[1,3,5]triazin-2-ylamine;
(81): 4-(2-bromophenoxy)-6-(5-chloro-1H,3H-benzo[de]isochromen-6-yl)-[1,3,5]triazin-2-ylamine;
(82): 4-(5-chloro-1H,3H-benzo[de]isochromen-6-yl)-6-(3,4-dimethoxyphenoxy)-[1,3,5]triazin-2-ylamine;
(83): 4-(5-chloro-1H,3H-benzo[de]isochromen-6-yl)-6-(3,5-dimethoxyphenoxy)-[1,3,5]triazin-2-ylamine;
(84): 4-(5-chloro-1H,3H-benzo[de]isochromen-6-yl)-6-(1H-imidazol-2-ylsulfanyl)-[1,3,5]triazin-2-ylamine;
(85): 4-(5-chloro-1H,3H-benzo[de]isochromen-6-yl)-6-(naphthalen-1-ylsulfanyl)-[1,3,5]triazin-2-ylamine;
(86): 4-(5-chloro-1H,3H-benzo[de]isochromen-6-yl)-6-(naphthalen-2-ylsulfanyl)-[1,3,5]triazin-2-ylamine;
(87): 4-(5-chloro-1H,3H-benzo[de]isochromen-6-yl)-6-(3,4-dimethoxy-phenylsulfanyl)-[1,3,5]triazin-2-ylamine;
(88): 4-(5-chloro-1H,3H-benzo[de]isochromen-6-yl)-6-(3-trifluoromethoxyphenylsulfanyl)-[1,3,5]triazin-2-ylamine;
(89): 4-(5-chloro-1H,3H-benzo[de]isochromen-6-yl)-6-(4-trifluoromethoxyphenylsulfanyl)-[1,3,5]triazin-2-ylamine;
(90): 4-(5-chloro-1H,3H-benzo[de]isochromen-6-yl)-6-(2,5-dichlorophenylsulfanyl)-[1,3,5]triazin-2-ylamine;
(91): 4-(2-bromophenylsulfanyl)-6-(5-chloro-1H,3H-benzo[de]isochromen-6-yl)-[1,3,5]triazin-2-ylamine;
(92): 4-(5-chloro-1H,3H-benzo[de]isochromen-6-yl)-6-cyclohexylsulfanyl-[1,3,5]triazin-2-ylamine;
(93): 4-(5-chloro-1H,3H-benzo[de]isochromen-6-yl)-6-isobutylsulfanyl-[1,3,5]triazin-2-ylamine;
(94): 4-(5-chloro-1H,3H-benzo[de]isochromen-6-yl)-6-isopropylsulfanyl-[1,3,5]triazin-2-ylamine;
(95): N-{4-[4-amino-6-(5-chloro-1H,3H-benzo[de]isochromen-6-yl)-[1,3,5]triazin-2-ylsulfanyl]-phenyl}-acetamide;
(96): 4-(5-chloro-1H,3H-benzo[de]isochromen-6-yl)-6-(4-methoxybenzylsulfanyl)-[1,3,5]triazin-2-ylamine;
(97): 4-(5-chloro-1H,3H-benzo[de]isochromen-6-yl)-6-(3-chlorobenzyloxy)-[1,3,5]triazin-2-ylamine;
(98): 4-(5-chloro-1H,3H-benzo[de]isochromen-6-yl)-6-(3-methoxyphenoxy)-[1,3,5]triazin-2-ylamine;
(99): {4-[4-amino-6-(5-chloro-1H,3H-benzo[de]isochromen-6-yl)-[1,3,5]triazin-2-yloxy]-phenyl}-methanol;
(100): 4-(5-chloro-1H,3H-benzo[de]isochromen-6-yl)-6-(4-methoxyphenoxy)-[1,3,5]triazin-2-ylamine;
(101): 4-(5-chloro-1H,3H-benzo[de]isochromen-6-yl)-6-(2-methoxyphenoxy)-[1,3,5]triazin-2-ylamine;
(102): N-{3-[4-amino-6-(5-chloro-1H,3H-benzo[de]isochromen-6-yl)-[1,3,5]triazin-2-yloxy]-phenyl}-acetamide;
(103): 2-{3-[4-amino-6-(5-chloro-1H,3H-benzo[de]isochromen-6-yl)-[1,3,5]triazin-2-yloxy]-phenyl}-ethanol;
(104): {3-[4-amino-6-(5-chloro-1H,3H-benzo[de]isochromen-6-yl)-[1,3,5]triazin-2-yloxy]-phenyl}-urea;
(105): 4-[4-amino-6-(5-chloro-1H,3H-benzo[de]isochromen-6-yl)-[1,3,5]triazin-2-ylsulfanyl]-phenol;
(106): 4-(5-chloro-1H,3H-benzo[de]isochromen-6-yl)-6-(4-nitrophenylsulfanyl)-[1,3,5]triazin-2-ylamine;
(107): 4-(5-chloro-1H,3H-benzo[de]isochromen-6-yl)-6-(2-methyl-furan-3-ylsulfanyl)-[1,3,5]triazin-2-ylamine;
(108): 4-(5-chloro-1H,3H-benzo[de]isochromen-6-yl)-6-(2,5-dimethoxyphenoxy)-[1,3,5]triazin-2-ylamine;
(109): 4-(3-aminophenylsulfanyl)-6-(5-chloro-1H,3H-benzo[de]isochromen-6-yl)-[1,3,5]triazin-2-ylamine;
(110): 4-(5-chloro-1H,3H-benzo[de]isochromen-6-yl)-6-propylsulfanyl-[1,3,5]triazin-2-ylamine;
(111): [4-amino-6-(5-chloro-1H,3H-benzo[de]isochromen-6-yl)-[1,3,5]triazin-2-ylsulfanyl]-acetic acid methyl ester;
(112): [4-amino-6-(5-chloro-1H,3H-benzo[de]isochromen-6-yl)-[1,3,5]triazin-2-ylsulfanyl]-acetic acid;
(113): N-{2-[4-amino-6-(5-chloro-1H,3H-benzo[de]isochromen-6-yl)-[1,3,5]triazin-2-ylsulfanyl]-ethyl}-acetamide;
(114): 4-(5-chloro-1H,3H-benzo[de]isochromen-6-yl)-6-(2-dimethylaminoethylsulfanyl)-[1,3,5]triazin-2-ylamine;
(115): 3-[4-amino-6-(5-chloro-1H,3H-benzo[de]isochromen-6-yl)-[1,3,5]triazin-2-ylsulfanyl]-propan-1-ol;
(116): 1-(4-{3-[4-amino-6-(5-chloro-1H,3H-benzo[de]isochromen-6-yl)-[1,3,5]triazin-2-yloxy]-phenyl}-piperazin-1-yl)-ethanone;
(117): 2-[4-amino-6-(5-chloro-1H,3H-benzo[de]isochromen-6-yl)-[1,3,5]triazin-2-ylsulfanyl]-phenol:
(118): 4-(5-chloro-1H,3H-benzo[de]isochromen-6-yl)-6-o tolylsulfanyl-[1,3,5]triazin-2-ylamine;
(119): 2-[4-amino-6-(5-chloro-1H,3H-benzo[de]isochromen-6-yl)-[1,3,5]triazin-2-ylsulfanyl]-acetamide;
(120): 4-(5-chloro-1H,3H-benzo[de]isochromen-6-yl)-6-(2-methoxybenzyloxy)-[1,3,5]triazin-2-ylamine;
(121): 4-(5-chloro-1H,3H-benzo[de]isochromen-6-yl)-6-(3-methoxybenzyloxy)-[1,3,5]triazin-2-ylamine;
(122): 4-(5-chloro-1H,3H-benzo[de]isochromen-6-yl)-6-(4-methoxybenzyloxy)-[1,3,5]triazin-2-ylamine;
(123): 4-(5-chloro-1H,3H-benzo[de]isochromen-6-yl)-6-(4-dimethylaminophenylsulfanyl)-[1,3,5]triazin-2-ylamine;
(124): 3-[4-amino-6-(5-chloro-1H,3H-benzo[de]isochromen-6-yl)-[1,3,5]triazin-2-ylsulfanyl]-propionic acid methyl ester;
(125): 3-[4-amino-6-(5-chloro-1H,3H-benzo[de]isochromen-6-yl)-[1,3,5]triazin-2-ylsulfanyl]-propionamide;
(126): 3-[4-amino-6-(5-chloro-1H,3H-benzo[de]isochromen-6-yl)-[1,3,5]triazin-2-ylsulfanyl]-propionic acid;
(127): N-{2-[4-amino-6-(5-chloro-1H,3H-benzo[de]isochromen-6-yl)-[1,3,5]triazin-2-yloxymethyl]-phenyl}-acetamide;
(128): N-{4-[4-amino-6-(5-chloro-1H,3H-benzo[de]isochromen-6-yl)-[1,3,5]triazin-2-yloxymethyl]-phenyl}-acetamide;
(129): N-{3-[4-amino-6-(5-chloro-1H,3H-benzo[de]isochromen-6-yl)-[1,3,5]triazin-2-yloxymethyl]-phenyl}-acetamide;
(130): (R)-2-[4-amino-6-(5-chloro-1H,3H-benzo[de]isochromen-6-yl)-[1,3,5]triazin-2-ylsulfanylmethyl]-4-oxopentanoic acid;
(131): 3-[4-amino-6-(5-chloro-1H,3H-benzo[de]isochromen-6-yl)-[1,3,5]triazin-2-ylsulfanyl]-2-methyl-propionic acid;
(132): 2-[4-amino-6-(5-chloro-1H,3H-benzo[de]isochromen-6-yl)-[1,3,5]triazin-2-ylsulfanyl]-ethanol;

(133): {2-[4-amino-6-(5-chloro-1H,3H-benzo[de]isochromen-6-yl)-[1,3,5]triazin-2-ylsulfanyl]-ethyl}-carbamic acid tert-butyl ester;
(134): 4-(5-chloro-1H,3H-benzo[de]isochromen-6-yl)-6-(3-dimethylaminophenylsulfanyl)-[1,3,5]triazin-2-ylamine;
(135): 3-[4-amino-6-(5-chloro-1H,3H-benzo[de]isochromen-6-yl)-[1,3,5]triazin-2-ylsulfanyl]-2-methyl-propionic acid methyl ester;
(136): (R)-2-acetylamino-3-[4-amino-6-(5-chloro-1H,3H-benzo[de]isochromen-6-yl)-[1,3,5]triazin-2-yl sulfanyl]-propionic acid methyl ester;
(137): 4-(4-aminophenylsulfanyl)-6-(5-chloro-1H,3H-benzo[de]isochromen-6-yl)-[1,3,5]triazin-2-ylamine;
(138): 4-(5-chloro-1H,3H-benzo[de]isochromen-6-yl)-6-(3-chloropropylsulfanyl)-[1,3,5]triazin-2-ylamine;
(139): 4-[4-(N,N-dimethylaminosulfonyl)amino-phenylsulfanyl]-6-(5-chloro-1H,3H-benzo[de]isochromen-6-yl)-[1,3,5]triazin-2-ylamine;
(140): N-{4-[4-amino-6-(5-chloro-1H,3H-benzo[de]isochromen-6-yl)-[1,3,5]triazin-2-ylsulfanylmethyl]-phenyl}-acetamide;
(141): 4-(5-chloro-1H,3H-benzo[de]isochromen-6-yl)-6-(3-dimethylaminopropylsulfanyl)-[1,3,5]triazin-2-ylamine;
(142): 4-(4-aminosulfonyl)amino-phenylsulfanyl-6-(5-chloro-1H,3H-benzo[de]isochromen-6-yl)-[1,3,5]triazin-2-ylamine;
(143): N-{2-[4-amino-6-(5-chloro-1H,3H-benzo[de]isochromen-6-yl)-[1,3,5]triazin-2-ylsulfanylmethyl]-phenyl}-acetamide;
(144): N-{3-[4-amino-6-(5-chloro-1H,3H-benzo[de]isochromen-6-yl)-[1,3,5]triazin-2-ylsulfanylmethyl]-phenyl}-acetamide;
(145): 4-(5-chloro-1H,3H-benzo[de]isochromen-6-yl)-6-(2,5-dimethoxyphenylsulfanyl)-[1,3,5]triazin-2-ylamine;
(146): 4-(7-chloro-isochroman-6-yl)-6-methylsulfanyl-[1,3,5]triazin-2-ylamine;
(147): 4-(5-chloro-isochroman-6-yl)-6-(2,5-dimethoxyphenylsulfanyl)-pyrimidin-2-ylamine;
(148): 4-(7-chloro-isochroman-6-yl)-6-(2,5-dimethoxyphenylsulfanyl)-pyrimidin-2-ylamine;
(149): N-{3-[4-amino-6-(5-chloro-1H,3H-benzo[de]isochromen-6-yl)-[1,3,5]triazin-2-ylsulfanyl]-propyl}-acetamide;
(150): N-{4-[4-amino-6-(5-chloro-1H,3H-benzo[de]isochromen-6-yl)-[1,3,5]triazin-2-ylsulfanyl]-butyl}-acetamide;
(151): N-{2-[4-amino-6-(5-chloro-1H,3H-benzo[de]isochromen-6-yl)-[1,3,5]triazin-2-ylsulfanyl]-ethyl}-propionamide;
(152): N-{2-[4-amino-6-(5-chloro-1H,3H-benzo[de]isochromen-6-yl)-[1,3,5]triazin-2-ylsulfanyl]-ethyl}-butylamide;
(153): N-{2-[4-amino-6-(5-chloro-1H,3H-benzo[de]isochromen-6-yl)-[1,3,5]triazin-2-ylsulfanyl]-ethyl}-isobutylamide;
(154): cyclopropane carboxylic acid {2-[4-amino-6-(5-chloro-1H,3H-benzo[de]isochromen-6-yl)-[1,3,5]triazin-2-ylsulfanyl]-ethyl}-amide;
(155): cyclopentane carboxylic acid {2-[4-amino-6-(5-chloro-1H,3H-benzo[de]isochromen-6-yl)-[1,3,5]triazin-2-ylsulfanyl]-ethyl}-amide;
(156): tetrahydro-pyran-4-carboxylic acid {2-[4-amino-6-(5-chloro-1H,3H-benzo[de]isochromen-6-yl)-[1,3,5]triazin-2-ylsulfanyl]-ethyl}-amide;
(157): piperidine-4-carboxylic acid {2-[4-amino-6-(5-chloro-1H,3H-benzo[de]isochromen-6-yl)-[1,3,5]triazin-2-ylsulfanyl]-ethyl}-amide;
(158): 1-methyl-piperidine-4-carboxylic acid {2-[4-amino-6-(5-chloro-1H,3H-benzo[de]isochromen-6-yl)-[1,3,5]triazin-2-ylsulfanyl]-ethyl}-amide;
(159): N-{2-[4-amino-6-(5-chloro-1H,3H-benzo[de]isochromen-6-yl)-[1,3,5]triazin-2-ylsulfanyl]-ethyl}-3-hydroxypropionamide;
(160): N-{2-[4-amino-6-(5-chloro-1H,3H-benzo[de]isochromen-6-yl)-[1,3,5]triazin-2-ylsulfanyl]-ethyl}-3,4-dihydroxybutylamide;
(161): N-{2-[4-amino-6-(5-chloro-1H,3H-benzo[de]isochromen-6-yl)-[1,3,5]triazin-2-ylsulfanyl]-ethyl}-4-hydroxy-3-hydroxymethylbutylamide;
(162): N-{2-[4-amino-6-(5-chloro-1H,3H-benzo[de]isochromen-6-yl)-[1,3,5]triazin-2-ylsulfanyl]-ethyl}-N-methyl-acetamide;
(163): 1-{2-[4-amino-6-(5-chloro-1H,3H-benzo[de]isochromen-6-yl)-[1,3,5]triazin-2-ylsulfanyl]-ethyl}-pyrrolidin-2-one;
(164): N-{3-[4-amino-6-(5-chloro-1H,3H-benzo[de]isochromen-6-yl)-[1,3,5]triazin-2-ylsulfanyl]-propyl}-propionamide;
(165): N-{3-[4-amino-6-(5-chloro-1H,3H-benzo[de]isochromen-6-yl)-[1,3,5]triazin-2-ylsulfanyl]-propyl}-N-methyl-acetamide;
(166): N-{3-[4-amino-6-(5-chloro-1H,3H-benzo[de]isochromen-6-yl)-[1,3,5]triazin-2-ylsulfanyl]-propyl}-3-hydroxypropionamide;
(167): N-{3-[4-amino-6-(5-chloro-1H,3H-benzo[de]isochromen-6-yl)-[1,3,5]triazin-2-ylsulfanyl]-propyl}-3,4-dihydroxy-butylamide;
(168): N-{3-[4-amino-6-(5-chloro-1H,3H-benzo[de]isochromen-6-yl)-[1,3,5]triazin-2-ylsulfanyl]-propyl}-4-hydroxy-3-hydroxymethyl-butylamide;
(169): 1-{3-[4-amino-6-(5-chloro-1H,3H-benzo[de]isochromen-6-yl)-[1,3,5]triazin-2-ylsulfanyl]-propyl}-pyrrolidin-2-one;
(170): cyclopropane carboxylic acid {3-[4-amino-6-(5-chloro-1H,3H-benzo[de]isochromen-6-yl)-[1,3,5]triazin-2-ylsulfanyl]-propyl}-amide;
(171): cyclopentane carboxylic acid {3-[4-amino-6-(5-chloro-1H,3H-benzo[de]isochromen-6-yl)-[1,3,5]triazin-2-ylsulfanyl]-propyl}-amide;
(172): tetrahydro-pyran-4-carboxylic acid {3-[4-amino-6-(5-chloro-1H,3H-benzo[de]isochromen-6-yl)-[1,3,5]triazin-2-ylsulfanyl]-propyl}-amide;
(173): piperidin-4-carboxylic acid {3-[4-amino-6-(5-chloro-1H,3H-benzo[de]isochromen-6-yl)-[1,3,5]triazin-2-ylsulfanyl]-propyl}-amide;
(174): N-{2-[4-amino-6-(5-chloro-1H,3H-benzo[de]isochromen-6-yl)-[1,3,5]triazin-2-ylsulfanyl]-ethyl}-formamide;
(175): {2-[4-amino-6-(5-chloro-1H,3H-benzo[de]isochromen-6-yl)-[1,3,5]triazin-2-ylsulfanyl]-ethyl}-urea;
(176): 1-{2-[4-amino-6-(5-chloro-1H,3H-benzo[de]isochromen-6-yl)-[1,3,5]triazin-2-ylsulfanyl]-ethyl}-3-methylurea;
(177): {2-[4-amino-6-(5-chloro-1H,3H-benzo[de]isochromen-6-yl)-[1,3,5]triazin-2-ylsulfanyl]-ethyl}-carbamic acid methyl ester;
(178): N-{2-[4-amino-6-(5-chloro-1H,3H-benzo[de]isochromen-6-yl)-[1,3,5]triazin-2-ylsulfanyl]-ethyl}-methanesulfonamide;
(179): N-{3-[4-amino-6-(5-chloro-1H,3H-benzo[de]isochromen-6-yl)-[1,3,5]triazin-2-ylsulfanyl]-ethyl}-amino sulfonamide;

(180): N-{3-[4-amino-6-(5-chloro-1H,3H-benzo[de]isochromen-6-yl)-[1,3,5]triazin-2-ylsulfanyl]-propyl}-formamide;
(181): {3-[4-amino-6-(5-chloro-1H,3H-benzo[de]isochromen-6-yl)-[1,3,5]triazin-2-ylsulfanyl]-propyl}-urea;
(182): 1-{3-[4-amino-6-(5-chloro-1H,3H-benzo[de]isochromen-6-yl)-[1,3,5]triazin-2-ylsulfanyl]-propyl}-3-methylurea;
(183): {3-[4-amino-6-(5-chloro-1H,3H-benzo[de]isochromen-6-yl)-[1,3,5]triazin-2-ylsulfanyl]-propyl}-carbamic acid methyl ester;
(184): N-{3-[4-amino-6-(5-chloro-1H,3H-benzo[de]isochromen-6-yl)-[1,3,5]triazin-2-ylsulfanyl]-propyl}-methanesulfonamide;
(185): N-{3-[4-amino-6-(5-chloro-1H,3H-benzo[de]isochromen-6-yl)-[1,3,5]triazin-2-ylsulfanyl]-propyl}-aminosulfonamide;
(186): 4-(5-chloro-1H,3H-benzo[de]isochromen-6-yl)-6-(2-methyl-oxazol-4-ylmethylsulfanyl)-[1,3,5]triazin-2-ylamine;
(187): N-{2-[4-amino-6-(5-chloro-1H,3H-benzo[de]isochromen-6-yl)-[1,3,5]triazin-2-ylsulfanyl]-ethyl}-3-dimethylaminopriopionamide;
(188): N-{2-[4-amino-6-(5-chloro-1H,3H-benzo[de]isochromen-6-yl)-[1,3,5]triazin-2-ylsulfanyl]-ethyl}-isonicotinamide;
(189): 1H-imidazole-2-carboxylic acid {2-[4-amino-6-(5-chloro-1H,3H-benzo[de]isochromen-6-yl)-[1,3,5]triazin-2-ylsulfanyl]-ethyl}-amide;
(190): 4-(5-chloro-1H,3H-benzo[de]isochromen-6-yl)-6-(2-dimethylamino-ethylsulfanyl)-[1,3,5]triazin-2-ylamine;
(191): 4-(2-aminoethylsulfanyl)-6-(5-chloro-1H,3H-benzo[de]isochromen-6-yl)-[1,3,5]triazin-2-ylamine;
(192): 4-(3-aminopropylsulfanyl)-6-(5-chloro-1H,3H-benzo[de]isochromen-6-yl)-[1,3,5]triazin-2-ylamine;
(193): 4-(5-chloro-1H,3H-benzo[de]isochromen-6-yl)-6-(2-methylaminoethylsulfanyl)-[1,3,5]triazin-2-ylamine;
(194): 4-(5-chloro-1H,3H-benzo[de]isochromen-6-yl)-6-(3-methylaminopropylsulfanyl)-[1,3,5]triazin-2-ylamine;
(195): 4-(5-chloro-1H,3H-benzo[de]isochromen-6-yl)-6-(2-pyrrolidin-1-yl-ethylsulfanyl)-[1,3,5]triazin-2-ylamine;
(196): 4-(5-chloro-1H,3H-benzo[de]isochromen-6-yl)-6-(3-pyrrolidin-1-yl-propylsulfanyl)-[1,3,5]triazin-2-ylamine;
(197): 4-(5-chloro-1H,3H-benzo[de]isochromen-6-yl)-6-(2-morpholin-4-yl-ethylsulfanyl)-[1,3,5]triazin-2-ylamine;
(198): 4-(5-chloro-1H,3H-benzo[de]isochromen-6-yl)-6-(3-morpholin-4-yl-propylsulfanyl)-[1,3,5]triazin-2-ylamine;
(199): 4-(5-chloro-1H,3H-benzo[de]isochromen-6-yl)-6-(2-piperazin-1-yl-ethylsulfanyl)-[1,3,5]triazin-2-ylamine;
(200): 4-(5-chloro-1H,3H-benzo[de]isochromen-6-yl)-6-(3-piperazin-1-yl-propylsulfanyl)-[1,3,5]triazin-2-ylamine;
(201): 4-(5-chloro-1H,3H-benzo[de]isochromen-6-yl)-6-[2-(pyridin-2-ylamino)-ethylsulfanyl]-[1,3,5]triazin-2-ylamine;
(202): 4-(5-chloro-1H,3H-benzo[de]isochromen-6-yl)-6-[2-(oxazol-4-ylamino)-ethylsulfanyl]-[1,3,5]triazin-2-ylamine;
(203): 2-[4-amino-6-(5-chloro-1H,3H-benzo[de]isochromen-6-yl)-[1,3,5]triazin-2-ylsulfanyl]-2,2-difluoroacetamide;
(204): 2-[4-amino-6-(5-chloro-1H,3H-benzo[de]isochromen-6-yl)-[1,3,5]triazin-2-ylsulfanyl]-N-methyl-acetamide;
(205): 3-[4-amino-6-(5-chloro-1H,3H-benzo[de]isochromen-6-yl)-[1,3,5]triazin-2-ylsulfanyl]-N-methyl-propionamide;
(206): 2-[4-amino-6-(5-chloro-1H,3H-benzo[de]isochromen-6-yl)-[1,3,5]triazin-2-ylsulfanyl]-N-ethyl-acetamide;
(207): 3-[4-amino-6-(5-chloro-1H,3H-benzo[de]isochromen-6-yl)-[1,3,5]triazin-2-ylsulfanyl]-N-ethyl-propionamide;
(208): 2-[4-amino-6-(5-chloro-1H,3H-benzo[de]isochromen-6-yl)-[1,3,5]triazin-2-ylsulfanyl]-N,N-dim ethyl-acetamide;
(209): 3-[4-amino-6-(5-chloro-1H,3H-benzo[de]isochromen-6-yl)-[1,3,5]triazin-2-ylsulfanyl]-N,N-dim ethyl-propionamide;
(210): 2-[4-amino-6-(5-chloro-1H,3H-benzo[de]isochromen-6-yl)-[1,3,5]triazin-2-ylsulfanyl]-N-isopropyl-acetamide;
(211): 3-[4-amino-6-(5-chloro-1H,3H-benzo[de]isochromen-6-yl)-[1,3,5]triazin-2-ylsulfanyl]-N-isopropyl-propionamide;
(212): 2-[4-amino-6-(5-chloro-1H,3H-benzo[de]isochromen-6-yl)-[1,3,5]triazin-2-ylsulfanyl]-N-propyl-acetamide;
(213): 3-[4-amino-6-(5-chloro-1H,3H-benzo[de]isochromen-6-yl)-[1,3,5]triazin-2-ylsulfanyl]-N-propyl-propionamide;
(214): 2-[4-amino-6-(5-chloro-1H,3H-benzo[de]isochromen-6-yl)-[1,3,5]triazin-2-ylsulfanyl]-N-cyclopentyl-acetamide;
(215): 3-[4-amino-6-(5-chloro-1H,3H-benzo[de]isochromen-6-yl)-[1,3,5]triazin-2-ylsulfanyl]-N-cyclopentyl-propionamide;
(216): 2-[4-amino-6-(5-chloro-1H,3H-benzo[de]isochromen-6-yl)-[1,3,5]triazin-2-ylsulfanyl]-N-(tetrahydropyran-4-yl)-acetamide;
(217): 3-[4-amino-6-(5-chloro-1H,3H-benzo[de]isochromen-6-yl)-[1,3,5]triazin-2-ylsulfanyl]-N-(tetrahydropyran-4-yl)-propionamide;
(218): 2-[4-amino-6-(5-chloro-1H,3H-benzo[de]isochromen-6-yl)-[1,3,5]triazin-2-ylsulfanyl]-N-pyridin-4-yl-acetamide;
(219): 3-[4-amino-6-(5-chloro-1H,3H-benzo[de]isochromen-6-yl)-[1,3,5]triazin-2-ylsulfanyl]-N-pyridin-4-yl-propionamide;
(220): 2-[4-amino-6-(5-chloro-1H,3H-benzo[de]isochromen-6-yl)-[1,3,5]triazin-2-ylsulfanyl]-N-thiazol-2-yl-acetamide;
(221): 3-[4-amino-6-(5-chloro-1H,3H-benzo[de]isochromen-6-yl)-[1,3,5]triazin-2-ylsulfanyl]-N-thiazol-2-yl-propionamide;
(222): 2-[4-amino-6-(5-chloro-1H,3H-benzo[de]isochromen-6-yl)-[1,3,5]triazin-2-ylsulfanyl]-1-pyrrolidin-1-yl-ethanone;
(223): 3-[4-amino-6-(5-chloro-1H,3H-benzo[de]isochromen-6-yl)-[1,3,5]triazin-2-ylsulfanyl]-1-pyrrolidin-1-yl-propan-1-one;
(224): 2-[4-amino-6-(5-chloro-1H,3H-benzo[de]isochromen-6-yl)-[1,3,5]triazin-2-ylsulfanyl]-1-morpholin-4-yl-ethanone;
(225): 3-[4-amino-6-(5-chloro-1H,3H-benzo[de]isochromen-6-yl)-[1,3,5]triazin-2-ylsulfanyl]-1-morpholin-4-yl-propan-1-one;
(226): 2-[4-amino-6-(5-chloro-1H,3H-benzo[de]isochromen-6-yl)-[1,3,5]triazin-2-ylsulfanyl]-1-piperazin-1-yl-ethanone;
(227): 3-[4-amino-6-(5-chloro-1H,3H-benzo[de]isochromen-6-yl)-[1,3,5]triazin-2-ylsulfanyl]-1-(4-methyl-piperazin-1-yl)-propan-1-one;

(228): 3-[4-amino-6-(5-chloro-1H,3H-benzo[de]isochromen-6-yl)-[1,3,5]triazin-2-ylsulfanyl]-1-piperazin-1-yl-propan-1-one;
(229): 2-[4-amino-6-(5-chloro-1H,3H-benzo[de]isochromen-6-yl)-[1,3,5]triazin-2-ylsulfanyl]-N-thiazol-2-yl-acetamide;
(230): 3-[4-amino-6-(5-chloro-1H,3H-benzo[de]isochromen-6-yl)-[1,3,5]triazin-2-ylsulfanyl]-N-thiazol-2-yl-propionamide;
(231): 3-[4-amino-6-(5-chloro-1H,3H-benzo[de]isochromen-6-yl)-[1,3,5]triazin-2-ylsulfanyl]-N-isopropyl-propionamide;
(232): 2-[4-amino-6-(5-chloro-1H,3H-benzo[de]isochromen-6-yl)-[1,3,5]triazin-2-ylsulfanyl]-N-isopropyl-acetamide;
(233): 2-[4-amino-6-(5-chloro-1H,3H-benzo[de]isochromen-6-yl)-[1,3,5]triazin-2-ylsulfanyl]-N-(2-hydroxyethyl)-acetamide;
(234): 3-[4-amino-6-(5-chloro-1H,3H-benzo[de]isochromen-6-yl)-[1,3,5]triazin-2-ylsulfanyl]-N-(2-hydroxyethyl)-propionamide;
(235): 2-[4-amino-6-(5-chloro-1H,3H-benzo[de]isochromen-6-yl)-[1,3,5]triazin-2-ylsulfanyl]-N-(2,3-dihydroxypropyl)-acetamide;
(236): 3-[4-amino-6-(5-chloro-1H,3H-benzo[de]isochromen-6-yl)-[1,3,5]triazin-2-ylsulfanyl]-N-(2,3-dihydroxypropyl)-propionamide;
(237): 2-[4-amino-6-(5-chloro-1H,3H-benzo[de]isochromen-6-yl)-[1,3,5]triazin-2-ylsulfanyl]-N-(3-hydroxy-2-hydroxymethyl-propyl)-acetamide;
(238): 3-[4-amino-6-(5-chloro-1H,3H-benzo[de]isochromen-6-yl)-[1,3,5]triazin-2-ylsulfanyl]-N-(3-hydroxy-2-hydroxymethyl-propyl)-propionamide;
(239): 4-[4-amino-6-(5-chloro-1H,3H-benzo[de]isochromen-6-yl)-[1,3,5]triazin-2-ylsulfanyl]-butylamide;
(240): 4-[4-amino-6-(5-chloro-1H,3H-benzo[de]isochromen-6-yl)-[1,3,5]triazin-2-ylsulfanyl]-N-methyl-butylamide;
(241): 4-[4-amino-6-(5-chloro-1H,3H-benzo[de]isochromen-6-yl)-[1,3,5]triazin-2-ylsulfanyl]-N,N-dim ethyl-butylamide;
(242): 4-[4-amino-6-(5-chloro-1H,3H-benzo[de]isochromen-6-yl)-[1,3,5]triazin-2-ylsulfanyl]-N-ethyl-butylamide;
(243): 4-[4-amino-6-(5-chloro-1H,3H-benzo[de]isochromen-6-yl)-[1,3,5]triazin-2-ylsulfanyl]-1-pyrrolidin-1-yl-butan-1-one;
(244): 4-[4-amino-6-(5-chloro-1H,3H-benzo[de]isochromen-6-yl)-[1,3,5]triazin-2-ylsulfanyl]-1-morpholin-4-yl-butan-1-one;
(245): 4-[4-amino-6-(5-chloro-1H,3H-benzo[de]isochromen-6-yl)-[1,3,5]triazin-2-ylsulfanyl]-1-piperazin-1-yl-butan-1-one;
(246): 4-[4-amino-6-(5-chloro-1H,3H-benzo[de]isochromen-6-yl)-[1,3,5]triazin-2-ylsulfanyl]-N-(2-hydroxyethyl)-butylamide;
(247): 4-[4-amino-6-(5-chloro-1H,3H-benzo[de]isochromen-6-yl)-[1,3,5]triazin-2-ylsulfanyl]-N-(tetrahydropyran-4-yl)-butylamide;
(248): 4-[4-amino-6-(5-chloro-1H,3H-benzo[de]isochromen-6-yl)-[1,3,5]triazin-2-ylsulfanyl]-N-piperidin-4-yl-butylamide;
(249): 4-[4-amino-6-(5-chloro-1H,3H-benzo[de]isochromen-6-yl)-[1,3,5]triazin-2-ylsulfanyl]-N-pyridin-4-yl-butylamide;
(250): 4-[4-amino-6-(5-chloro-1H,3H-benzo[de]isochromen-6-yl)-[1,3,5]triazin-2-ylsulfanyl]-N-thiazol-2-yl-butylamide;
(251): 1-[4-amino-6-(5-chloro-1H,3H-benzo[de]isochromen-6-yl)-[1,3,5]triazin-2-ylsulfanyl]-propan-2-one;
(252): 4-[4-amino-6-(5-chloro-1H,3H-benzo[de]isochromen-6-yl)-[1,3,5]triazin-2-ylsulfanyl]-butan-2-one;
(253): N-{2-[4-amino-6-(5-chloro-1H,3H-benzo[de]isochromen-6-yl)-[1,3,5]triazin-2-ylsulfanyl]-acetyl}-acetamide;
(254): N-{3-[4-amino-6-(5-chloro-1H,3H-benzo[de]isochromen-6-yl)-[1,3,5]triazin-2-ylsulfanyl]-propionyl}-acetamide;
(255): N-{4-[4-amino-6-(5-chloro-1H,3H-benzo[de]isochromen-6-yl)-[1,3,5]triazin-2-ylsulfanyl]-butyryl}-acetamide;
(256): N-{2-[4-amino-6-(5-chloro-1H,3H-benzo[de]isochromen-6-yl)-[1,3,5]triazin-2-ylsulfanyl]-acetyl}-methanesulfonamide;
(257): N-{3-[4-amino-6-(5-chloro-1H,3H-benzo[de]isochromen-6-yl)-[1,3,5]triazin-2-ylsulfanyl]-propionyl}-methanesulfonamide;
(258): N-{4-[4-amino-6-(5-chloro-1H,3H-benzo[de]isochromen-6-yl)-[1,3,5]triazin-2-ylsulfanyl]-butyryl}-methanesulfonamide;
(259): 4-(5-chloro-1H,3H-benzo[de]isochromen-6-yl)-6-(oxazol-2-ylmethylsulfanyl)-[1,3,5]triazin-2-yl amine;
(260): 4-(5-chloro-1H,3H-benzo[de]isochromen-6-yl)-6-(2-oxazol-2-yl-ethylsulfanyl)-[1,3,5]triazin-2-ylamine;
(261): 1-[4-amino-6-(5-chloro-1H,3H-benzo[de]isochromen-6-yl)-[1,3,5]triazin-2-ylsulfanyl]-propan-2-one O-methyl-oxime;
(262): 4-[4-amino-6-(5-chloro-1H,3H-benzo[de]isochromen-6-yl)-[1,3,5]triazin-2-ylsulfanyl]-butan-2-one O-methyl-oxime;
(263): [4-amino-6-(5-chloro-1H,3H-benzo[de]isochromen-6-yl)-[1,3,5]triazin-2-ylsulfanyl]-acetonitrile;
(264): 3-[4-amino-6-(5-chloro-1H,3H-benzo[de]isochromen-6-yl)-[1,3,5]triazin-2-ylsulfanyl]-propionitrile;
(265): 4-[4-amino-6-(5-chloro-1H,3H-benzo[de]isochromen-6-yl)-[1,3,5]triazin-2-ylsulfanyl]-butyronitrile;
(266): 4-(5-chloro-1H,3H-benzo[de]isochromen-6-yl)-6-(2-methoxy-ethylsulfanyl)-[1,3,5]triazin-2-ylamine;
(267): 4-(5-chloro-1H,3H-benzo[de]isochromen-6-yl)-6-(3-methoxypropylsulfanyl)-[1,3,5]triazin-2-ylamine;
(268): 4-(5-chloro-1H,3H-benzo[de]isochromen-6-yl)-6-[2-(2-methoxyethoxy)-ethylsulfanyl]-[1,3,5]triazin-2-ylamine;
(269): 4-[4-amino-6-(5-chloro-1H,3H-benzo[de]isochromen-6-yl)-[1,3,5]triazin-2-ylsulfanyl]-butan-1-ol;
(270): carbamic acid 2-[4-amino-6-(5-chloro-1H,3H-benzo[de]isochromen-6-yl)-[1,3,5]triazin-2-ylsulfanyl]-ethyl ester;
(271): carbamic acid 3-[4-amino-6-(5-chloro-1H,3H-benzo[de]isochromen-6-yl)-[1,3,5]triazin-2-ylsulfanyl]-propyl ester;
(272): carbamic acid 4-[4-amino-6-(5-chloro-1H,3H-benzo[de]isochromen-6-yl)-[1,3,5]triazin-2-ylsulfanyl]-butyl ester;
(273): sulfamic acid 2-[4-amino-6-(5-chloro-1H,3H-benzo[de]isochromen-6-yl)-[1,3,5]triazin-2-ylsulfanyl]-ethyl ester;
(274): sulfamic acid 3-[4-amino-6-(5-chloro-1H,3H-benzo[de]isochromen-6-yl)-[1,3,5]triazin-2-ylsulfanyl]-propyl ester;

(275): sulfamic acid 4-[4-amino-6-(5-chloro-1H,3H-benzo[de]isochromen-6-yl)-[1,3,5]triazin-2-ylsulfanyl]-butyl ester;
(276): 3-[4-amino-6-(5-chloro-1H,3H-benzo[de]isochromen-6-yl)-[1,3,5]triazin-2-ylsulfanyl]-propane-1,2-diol;
(277): 2-[4-amino-6-(5-chloro-1H,3H-benzo[de]isochromen-6-yl)-[1,3,5]triazin-2-ylsulfanylmethyl]-propane-1,3-diol;
(278): thiocarbamic acid 2-[4-amino-6-(5-chloro-1H,3H-benzo[de]isochromen-6-yl)-[1,3,5]triazin-2-ylsulfanyl]-ethyl ester;
(279): thiocarbamic acid 3-[4-amino-6-(5-chloro-1H,3H-benzo[de]isochromen-6-yl)-[1,3,5]triazin-2-ylsulfanyl]-propyl ester;
(280): 4-(5-chloro-1H,3H-benzo[de]isochromen-6-yl)-6-(2-methanesulfonyl-ethylsulfanyl)-[1,3,5]triazin-2-ylamine;
(281): 4-(5-chloro-1H,3H-benzo[de]isochromen-6-yl)-6-(3-methanesulfonyl-propylsulfanyl)-[1,3,5]triazin-2-ylamine;
(282): 3-[4-amino-6-(5-chloro-1H,3H-benzo[de]isochromen-6-yl)-[1,3,5]triazin-2-ylsulfanyl]-propan-1-sulfonamide;
(283): 2-[4-amino-6-(5-chloro-1H,3H-benzo[de]isochromen-6-yl)-[1,3,5]triazin-2-ylsulfanyl]-ethanesulfonamide;
(284): 4-(5-chloro-1H,3H-benzo[de]isochromen-6-yl)-6-(3,3,3-trifluoro-propylsulfanyl)-[1,3,5]triazin-2-ylamine;
(285): 4-(5-chloro-1H,3H-benzo[de]isochromen-6-yl)-6-(4,4,4-trifluoro-butylsulfanyl)-[1,3,5]triazin-2-ylamine;
(286): 4-(5-chloro-1H,3H-benzo[de]isochromen-6-yl)-6-(3-fluoropropylsulfanyl)-[1,3,5]triazin-2-ylamine;
(287): 4-(5-chloro-1H,3H-benzo[de]isochromen-6-yl)-6-(4-fluorobutylsulfanyl)-[1,3,5]triazin-2-ylamine;
(288): 4-(5-chloro-1H,3H-benzo[de]isochromen-6-yl)-6-(oxazol-2-ylmethylsulfanyl)-[1,3,5]triazin-2-yl amine;
(289): 4-(5-chloro-1H,3H-benzo[de]isochromen-6-yl)-6-(thiazol-2-ylmethylsulfanyl)-[1,3,5]triazin-2-yl amine;
(290): 4-(5-chloro-1H,3H-benzo[de]isochromen-6-yl)-6-(2-thiazol-2-yl-ethylsulfanyl)-[1,3,5]triazin-2-ylamine;
(291): 4-(5-chloro-1H,3H-benzo[de]isochromen-6-yl)-6-(1H-imidazol-2-ylmethylsulfanyl)-[1,3,5]triazin-2-ylamine;
(292): 4-(5-chloro-1H,3H-benzo[de]isochromen-6-yl)-6-[2-(1H-imidazol-2-yl)-ethylsulfanyl]-[1,3,5]triazin-2-ylamine;
(293): 4-(5-chloro-1H,3H-benzo[de]isochromen-6-yl)-6-(2-oxazol-3-yl-ethylsulfanyl)-[1,3,5]triazin-2-ylamine;
(294): 4-(5-chloro-1H,3H-benzo[de]isochromen-6-yl)-6-(pyridin-4-ylmethylsulfanyl)-[1,3,5]triazin-2-ylamine;
(295): 4-(5-chloro-1H,3H-benzo[de]isochromen-6-yl)-6-(2-pyridin-4-yl-ethylsulfanyl)-[1,3,5]triazin-2-ylamine;
(296): 4-(5-chloro-1H,3H-benzo[de]isochromen-6-yl)-6-(pyridin-2-ylmethylsulfanyl)-[1,3,5]triazin-2-ylamine;
(297): 4-(5-chloro-1H,3H-benzo[de]isochromen-6-yl)-6-(2-pyridin-2-yl-ethylsulfanyl)-[1,3,5]triazin-2-ylamine;
(298): 2-acetylamino-3-[4-amino-6-(5-chloro-1H,3H-benzo[de]isochromen-6-yl)-[1,3,5]triazin-2-ylsulfanyl]-propionamide;
(299): 2-acetylamino-3-[4-amino-6-(5-chloro-1H,3H-benzo[de]isochromen-6-yl)-[1,3,5]triazin-2-ylsulfanyl]-N-methyl-propionamide;
(300): 2-acetylamino-3-[4-amino-6-(5-chloro-1H,3H-benzo[de]isochromen-6-yl)-[1,3,5]triazin-2-ylsulfanyl]-N-ethyl-propionamide;
(301): 2-acetylamino-3-[4-amino-6-(5-chloro-1H,3H-benzo[de]isochromen-6-yl)-[1,3,5]triazin-2-ylsulfanyl]-N,N-dimethyl-propionamide;
(302): 2-amino-3-[4-amino-6-(5-chloro-1H,3H-benzo[de]isochromen-6-yl)-[1,3,5]triazin-2-ylsulfanyl]-N-methyl-propionamide;
(303): 2-amino-3-[4-amino-6-(5-chloro-1H,3H-benzo[de]isochromen-6-yl)-[1,3,5]triazin-2-ylsulfanyl]-N,N-dimethyl-propionamide;
(304): 2-[4-amino-6-(5-chloro-1H,3H-benzo[de]isochromen-6-yl)-[1,3,5]triazin-2-ylsulfanyl]-N-(2-methoxy-ethyl)-acetamide;
(305): 2-[4-amino-6-(5-chloro-1H,3H-benzo[de]isochromen-6-yl)-[1,3,5]triazin-2-ylsulfanyl]-N-cyano methyl-acetamide;
(306): 2-[4-amino-6-(5-chloro-1H,3H-benzo[de]isochromen-6-yl)-[1,3,5]triazin-2-ylsulfanyl]-N-(2-hydroxy-1-hydroxymethyl-ethyl)-acetamide;
(307): 2-[4-amino-6-(5-chloro-1H,3H-benzo[de]isochromen-6-yl)-[1,3,5]triazin-2-ylsulfanyl]-N-(2-diethylamino-ethyl)-acetamide;
(308): 2-[4-amino-6-(5-chloro-1H,3H-benzo[de]isochromen-6-yl)-[1,3,5]triazin-2-ylsulfanyl]-N-(1-methyl-piperidin-4-yl)-acetamide;
(309): 3-[4-amino-6-(5-chloro-1H,3H-benzo[de]isochromen-6-yl)-[1,3,5]triazin-2-ylsulfanyl]-N-(2-methoxy-ethyl)-propionamide;
(310): 1-{2-[4-amino-6-(5-chloro-1H,3H-benzo[de]isochromen-6-yl)-[1,3,5]triazin-2-ylsulfanyl]-ethyl}-imidazolin-2-one;
(311): 3-{2-[4-amino-6-(5-chloro-1H,3H-benzo[de]isochromen-6-yl)-[1,3,5]triazin-2-ylsulfanyl]-ethyl}-oxazolidin-2-one;
(312): 2-[4-amino-6-(5-chloro-1H,3H-benzo[de]isochromen-6-yl)-[1,3,5]triazin-2-ylsulfanyl]-1-pyrazin-2-yl-ethanone;
(313): 3-{2-[4-amino-6-(5-chloro-1H,3H-benzo[de]isochromen-6-yl)-[1,3,5]triazin-2-ylsulfanyl]-acetyl}-oxazolidin-2-one;
(314): 2-[2-amino-6-(5-chloro-1H,3H-benzo[de]isochromen-6-yl)-pyrimidin-4-ylsulfanyl]-acetamide;
(315): 2-[2-amino-6-(5-chloro-1H,3H-benzo[de]isochromen-6-yl)-pyrimidin-4-ylsulfanyl]-N-cyanomethyl-acetamide;
(316): 3-[2-amino-6-(5-chloro-1H,3H-benzo[de]isochromen-6-yl)-pyrimidin-4-ylsulfanyl]-propionamide;
(317): 3-[2-amino-6-(5-chloro-1H,3H-benzo[de]isochromen-6-yl)-pyrimidin-4-ylsulfanyl]-N-(2-hydroxy-ethyl)-propionamide;
(318): 3-[2-amino-6-(5-chloro-1H,3H-benzo[de]isochromen-6-yl)-pyrimidin-4-ylsulfanyl]-N-methyl-propionamide;
(319): 3-[2-amino-6-(5-chloro-1H,3H-benzo[de]isochromen-6-yl)-pyrimidin-4-ylsulfanyl]-N-(2-methoxy-ethyl)-propionamide;
(320): 3-[2-amino-6-(5-chloro-1H,3H-benzo[de]isochromen-6-yl)-pyrimidin-4-ylsulfanyl]-N—((R)-2,3-dihydroxy-propyl)-propionamide;
(321): 3-[2-amino-6-(5-chloro-1H,3H-benzo[de]isochromen-6-yl)-pyrimidin-4-ylsulfanyl]-2-methyl-propionamide;
(322): 3-[2-amino-6-(5-chloro-1H,3H-benzo[de]isochromen-6-yl)-pyrimidin-4-ylsulfanyl]-2,N-dimethyl-propionamide;
(323): 3-[2-amino-6-(5-chloro-1H,3H-benzo[de]isochromen-6-yl)-pyrimidin-4-ylsulfanyl]-N-(2-hydroxy-ethyl)-2-methyl-propionamide;

(324): 4-[2-amino-6-(5-chloro-1H,3H-benzo[de]isochromen-6-yl)-pyrimidin-4-ylsulfanyl]-butylamide;
(325): carbamic acid 2-[2-amino-6-(5-chloro-1H,3H-benzo[de]isochromen-6-yl)-pyrimidin-4-ylsulfanyl]-ethyl ester;
(326): 3-[2-amino-6-(5-chloro-1H,3H-benzo[de]isochromen-6-yl)-pyrimidin-4-ylsulfanyl]-propan-1-ol;
(327): N-{2-[2-amino-6-(5-chloro-1H,3H-benzo[de]isochromen-6-yl)-pyrimidin-4-ylsulfanyl]-ethyl}-acetamide;
(328): N-{3-[2-amino-6-(5-chloro-1H,3H-benzo[de]isochromen-6-yl)-pyrimidin-4-ylsulfanyl]-propyl}-acetamide;
(329): N-{2-[2-amino-6-(5-chloro-1H,3H-benzo[de]isochromen-6-yl)-pyrimidin-4-ylsulfanyl]-ethyl}-m ethanesulfonamide;
(330): 5-[2-amino-6-(5-chloro-1H,3H-benzo[de]isochromen-6-yl)-pyrimidin-4-ylsulfanylmethyl]-oxazolidin-2-one;
(331): N-{2-[2-amino-6-(5-chloro-1H,3H-benzo[de]isochromen-6-yl)-pyrimidin-4-ylsulfanyl]-ethyl}-2-hydroxyacetamide;
(332): {2-[2-amino-6-(5-chloro-1H,3H-benzo[de]isochromen-6-yl)-pyrimidin-4-ylsulfanyl]-ethyl}-urea;
(333): 2-[4-amino-6-(5-chloro-1H,3H-benzo[de]isochromen-6-yl)-[1,3,5]triazin-2-ylsulfanyl]-N-cyano methylacetamide;
(334): 3-[4-amino-6-(5-chloro-1H,3H-benzo[de]isochromen-6-yl)-[1,3,5]triazin-2-ylsulfanyl]-N-(2-methoxyethyl)-propionamide;
(335): 3-[4-amino-6-(5-chloro-1H,3H-benzo[de]isochromen-6-yl)-[1,3,5]triazin-2-ylsulfanyl]-N—((R)-2,3-dihydroxy-propyl)-propionamide;
(336): 3-[4-amino-6-(5-chloro-1H,3H-benzo[de]isochromen-6-yl)-[1,3,5]triazin-2-ylsulfanyl]-2-methyl-propionamide;
(337): 3-[4-amino-6-(5-chloro-1H,3H-benzo[de]isochromen-6-yl)-[1,3,5]triazin-2-ylsulfanyl]-2,N-dimethyl-propionamide;
(338): 3-[4-amino-6-(5-chloro-1H,3H-benzo[de]isochromen-6-yl)-[1,3,5]triazin-2-ylsulfanyl]-N-(2-hydroxyethyl)-2-methyl-propionamide;
(339): 4-[4-amino-6-(5-chloro-1H,3H-benzo[de]isochromen-6-yl)-[1,3,5]triazin-2-ylsulfanyl]-butyramide;
(340): 3-[4-amino-6-(5-chloro-1H,3H-benzo[de]isochromen-6-yl)-[1,3,5]triazin-2-ylsulfanyl]-propan-1-ol;
(341): 5-[4-amino-6-(5-chloro-1H,3H-benzo[de]isochromen-6-yl)-[1,3,5]triazin-2-ylsulfanylmethyl]-oxazolidin-2-one;
(342): N-{2-[4-amino-6-(5-chloro-1H,3H-benzo[de]isochromen-6-yl)-[1,3,5]triazin-2-ylsulfanyl]-ethyl}-2-hydroxy-acetamide; and
(343): 4-[4-amino-6-(5-chloro-1H,3H-2-thia-phenalen-6-yl)-[1,3,5]triazin-2-ylsulfanyl]-butyramide;
[19] a compound or a pharmaceutically acceptable salt thereof, wherein the compound is selected from the group consisting of:
(4): 4-(5-benzyloxy-2,4-dichlorophenyl)-6-benzylsulfanyl[1,3,5]triazin-2-ylamine;
(15): (5-{4-amino-6-[2-methoxy-4-(4-methyl-piperazin-1-carbonyl)-phenylsulfanyl]-[1,3,5]triazin-2-yl}-2,4-dichlorophenoxy)-acetonitrile;
(24): 4-(2,4-dichloro-5-pyrimidin-2-yl-phenyl)-6-methylsulfanyl-[1,3,5]triazin-2-ylamine;
(25): N-{2-[4-amino-6-(2,4-dichloro-5-pyrimidin-2-yl-phenyl)-[1,3,5]triazin-2-ylsulfanyl]-ethyl}-acetamide;
(26): 5-(4-amino-6-benzylsulfanyl-[1,3,5]triazin-2-yl)-2,4-dichlorobenzamide;
(28): 5-(4-amino-6-benzylsulfanyl-[1,3,5]triazin-2-yl)-2,4-dichloro-N-(2-hydroxy-1-hydroxymethylethyl)-benzamide;
(37): 5-[4-amino-6-(2,3-dihydroxypropylsulfanyl)-[1,3,5]triazin-2-yl]-2,4-dimethylbenzoic acid methyl ester;
(39): 4-(2,4-dichlorophenyl)-6-(2,5-dimethoxyphenylsulfanyl)-pyrimidin-2-ylamine;
(44): 3-{4-[2-amino-6-(2,5-dimethoxyphenylsulfanyl)-pyrimidin-4-yl]-3-methylphenoxy}-propan-1-ol;
(45): {4-[2-amino-6-(2,5-dimethoxyphenylsulfanyl)-pyrimidin-4-yl]-3-methylphenoxy}-acetonitrile;
(46): 2-{4-[2-amino-6-(2,5-dimethoxyphenylsulfanyl)-pyrimidin-4-yl]-3-methylphenoxy}-acetamide;
(48): 4-(5-benzyloxy-2,4-dichlorophenyl)-6-(2,5-dimethoxyphenylsulfanyl)-pyrimidin-2-ylamine;
(52): {5-[2-amino-6-(2,5-dimethoxyphenylsulfanyl)-pyrimidin-4-yl]-2,4-dichlorophenyoxy}-acetonitrile;
(54): {5-[2-amino-6-(1H-benzimidazol-2-ylsulfanyl)-pyrimidin-4-yl]-2,4-dichlorophenoxy}-acetonitrile;
(55): 2-[2-amino-6-(2,4-dichloro-5-cyanomethoxyphenyl)-pyrimidin-4-ylsulfanyl]-3H-imidazol-4-carboxylic acid ethyl ester;
(59): N-{2-[4-amino-6-(2,4-dichloro-5-cyanomethoxy-phenyl)-[1,3,5]triazin-2-ylsulfanyl]-ethyl}-acetamide;
(63): {5-[4-amino-6-(3-morpholin-4-yl-3-oxo-propylsulfanyl)-[1,3,5]triazin-2-yl]-2,4-dichlorophenoxy}-acetonitrile;
(82): 4-(5-chloro-1H,3H-benzo[de]isochromen-6-yl)-6-(3,4-dimethoxyphenoxy)-[1,3,5]triazin-2-ylamine;
(92): 4-(5-chloro-1H,3H-benzo[de]isochromen-6-yl)-6-cyclohexylsulfanyl-[1,3,5]triazin-2-ylamine;
(111): [4-amino-6-(5-chloro-1H,3H-benzo[de]isochromen-6-yl)-[1,3,5]triazin-2-ylsulfanyl]-acetic acid methyl ester;
(113): N-{2-[4-amino-6-(5-chloro-1H,3H-benzo[de]isochromen-6-yl)-[1,3,5]triazin-2-ylsulfanyl]-ethyl}-acetamide;
(119): 2-[4-amino-6-(5-chloro-1H,3H-benzo[de]isochromen-6-yl)-[1,3,5]triazin-2-ylsulfanyl]-acetamide;
(125): 3-[4-amino-6-(5-chloro-1H,3H-benzo[de]isochromen-6-yl)-[1,3,5]triazin-2-ylsulfanyl]-propionamide;
(143): N-{2-[4-amino-6-(5-chloro-1H,3H-benzo[de]isochromen-6-yl)-[1,3,5]triazin-2-ylsulfanylmethyl]-phenyl}-acetamide;
(145): 4-(5-chloro-1H,3H-benzo[de]isochromen-6-yl)-6-(2,5-dimethoxyphenylsulfanyl)-[1,3,5]triazin-2-ylamine;
(149): N-{3-[4-amino-6-(5-chloro-1H,3H-benzo[de]isochromen-6-yl)-[1,3,5]triazin-2-ylsulfanyl]-propyl}-acetamide;
(175): {2-[4-amino-6-(5-chloro-1H,3H-benzo[de]isochromen-6-yl)-[1,3,5]triazin-2-ylsulfanyl]-ethyl}-urea;
(178): N-{2-[4-amino-6-(5-chloro-1H,3H-benzo[de]isochromen-6-yl)-[1,3,5]triazin-2-ylsulfanyl]-ethyl}-methanesulfonamide;
(205): 3-[4-amino-6-(5-chloro-1H,3H-benzo[de]isochromen-6-yl)-[1,3,5]triazin-2-ylsulfanyl]-N-methyl-propionamide;
(234): 3-[4-amino-6-(5-chloro-1H,3H-benzo[de]isochromen-6-yl)-[1,3,5]triazin-2-ylsulfanyl]-N-(2-hydroxyethyl)-propionamide;
(270): carbamic acid 2-[4-amino-6-(5-chloro-1H,3H-benzo[de]isochromen-6-yl)-[1,3,5]triazin-2-ylsulfanyl]-ethyl ester;
(314): 2-[2-amino-6-(5-chloro-1H,3H-benzo[de]isochromen-6-yl)-pyrimidin-4-ylsulfanyl]-acetamide;
(315): 2-[2-amino-6-(5-chloro-1H,3H-benzo[de]isochromen-6-yl)-pyrimidin-4-ylsulfanyl]-N-cyanomethyl-acetamide;

(316): 3-[2-amino-6-(5-chloro-1H,3H-benzo[de]isochromen-6-yl)-pyrimidin-4-ylsulfanyl]-propionamide;
(317): 3-[2-amino-6-(5-chloro-1H,3H-benzo[de]isochromen-6-yl)-pyrimidin-4-ylsulfanyl]-N-(2-hydroxyethyl)-propionamide;
(318): 3-[2-amino-6-(5-chloro-1H,3H-benzo[de]isochromen-6-yl)-pyrimidin-4-ylsulfanyl]-N-methyl-propionamide;
(319): 3-[2-amino-6-(5-chloro-1H,3H-benzo[de]isochromen-6-yl)-pyrimidin-4-ylsulfanyl]-N-(2-methoxyethyl)-propionamide;
(320): 3-[2-amino-6-(5-chloro-1H,3H-benzo[de]isochromen-6-yl)-pyrimidin-4-ylsulfanyl]-N—((R)-2,3-dihydroxy-propyl)-propionamide;
(321): 3-[2-amino-6-(5-chloro-1H,3H-benzo[de]isochromen-6-yl)-pyrimidin-4-ylsulfanyl]-2-methyl-propionamide;
(322): 3-[2-amino-6-(5-chloro-1H,3H-benzo[de]isochromen-6-yl)-pyrimidin-4-ylsulfanyl]-2,N-dimethyl-propionamide;
(323): 3-[2-amino-6-(5-chloro-1H,3H-benzo[de]isochromen-6-yl)-pyrimidin-4-ylsulfanyl]-N-(2-hydroxyethyl)-2-methyl-propionamide;
(324): 4-[2-amino-6-(5-chloro-1H,3H-benzo[de]isochromen-6-yl)-pyrimidin-4-ylsulfanyl]-butylamide;
(325): carbamic acid 2-[2-amino-6-(5-chloro-1H,3H-benzo[de]isochromen-6-yl)-pyrimidin-4-ylsulfanyl]-ethyl ester;
(326): 3-[2-amino-6-(5-chloro-1H,3H-benzo[de]isochromen-6-yl)-pyrimidin-4-ylsulfanyl]-propan-1-ol;
(327): N-{2-[2-amino-6-(5-chloro-1H,3H-benzo[de]isochromen-6-yl)-pyrimidin-4-ylsulfanyl]-ethyl}-acetamide;
(328): N-{3-[2-amino-6-(5-chloro-1H,3H-benzo[de]isochromen-6-yl)-pyrimidin-4-ylsulfanyl]-propyl}-acetamide;
(329): N-{2-[2-amino-6-(5-chloro-1H,3H-benzo[de]isochromen-6-yl)-pyrimidin-4-ylsulfanyl]-ethyl}-methanesulfonamide;
(330): 5-[2-amino-6-(5-chloro-1H,3H-benzo[de]isochromen-6-yl)-pyrimidin-4-ylsulfanylmethyl]-oxazolidin-2-one;
(331): N-{2-[2-amino-6-(5-chloro-1H,3H-benzo[de]isochromen-6-yl)-pyrimidin-4-ylsulfanyl]-ethyl}-2-hydroxyacetamide;
(332): {2-[2-amino-6-(5-chloro-1H,3H-benzo[de]isochromen-6-yl)-pyrimidin-4-ylsulfanyl]-ethyl}-urea;
(333): 2-[4-amino-6-(5-chloro-1H,3H-benzo[de]isochromen-6-yl)-[1,3,5]triazin-2-ylsulfanyl]-N-cyano methylacetamide;
(334): 3-[4-amino-6-(5-chloro-1H,3H-benzo[de]isochromen-6-yl)-[1,3,5]triazin-2-ylsulfanyl]-N-(2-methoxyethyl)-propionamide;
(335): 3-[4-amino-6-(5-chloro-1H,3H-benzo[de]isochromen-6-yl)-[1,3,5]triazin-2-ylsulfanyl]-N—((R)-2,3-dihydroxy-propyl)-propionamide;
(336): 3-[4-amino-6-(5-chloro-1H,3H-benzo[de]isochromen-6-yl)-[1,3,5]triazin-2-ylsulfanyl]-2-methyl-propionamide;
(337): 3-[4-amino-6-(5-chloro-1H,3H-benzo[de]isochromen-6-yl)-[1,3,5]triazin-2-ylsulfanyl]-2,N-dimethyl-propionamide;
(338): 3-[4-amino-6-(5-chloro-1H,3H-benzo[de]isochromen-6-yl)-[1,3,5]triazin-2-ylsulfanyl]-N-(2-hydroxyethyl)-2-methyl-propionamide;
(339): 4-[4-amino-6-(5-chloro-1H,3H-benzo[de]isochromen-6-yl)-[1,3,5]triazin-2-ylsulfanyl]-butyramide;
(340): 3-[4-amino-6-(5-chloro-1H,3H-benzo[de]isochromen-6-yl)-[1,3,5]triazin-2-ylsulfanyl]-propan-1-ol;
(341): 5-[4-amino-6-(5-chloro-1H,3H-benzo[de]isochromen-6-yl)-[1,3,5]triazin-2-ylsulfanylmethyl]-oxazolidin-2-one;
(342): N-{2-[4-amino-6-(5-chloro-1H,3H-benzo[de]isochromen-6-yl)-[1,3,5]triazin-2-ylsulfanyl]-ethyl}-2-hydroxy-acetamide; and
(343): 4-[4-amino-6-(5-chloro-1H,3H-2-thia-phenalen-6-yl)-[1,3,5]triazin-2-ylsulfanyl]-butyramide;

[20] a pharmaceutical comprising as an active ingredient the compound or a pharmaceutically acceptable salt thereof according to any one of [1] to [19];

[21] an anticancer agent comprising as an active ingredient the compound or a pharmaceutically acceptable salt thereof according to any one of [1] to [19];

[22] an HSP90 inhibitor comprising as an active ingredient the compound or a pharmaceutically acceptable salt thereof according to any one of [1] to [19];

[23] a pharmaceutical composition comprising the compound or a pharmaceutically acceptable salt thereof according to any one of [1] to [19], and a pharmaceutically acceptable carrier;

[24] a compound represented by formula (7) or a salt thereof:

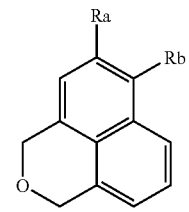

(7)

wherein,
Ra is a halogen atom, $C_{1-6}$ alkyl group, $C_{2-6}$ alkenyl group, $C_{2-6}$ alkynyl group, $C_{1-6}$ alkoxy group, $C_{1-6}$ alkylthio group, nitro group, or amino group; and
Rb is a halogen atom, cyano group, or amidino group;

[25] the compound of [24] or a salt thereof, wherein Rb is an amidino group;

[26] a compound represented by formula (8) or a salt thereof:

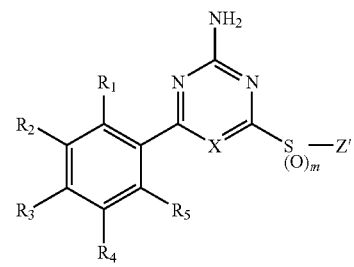

(8)

wherein,
X, $R_1$, $R_2$, $R_3$, $R_4$, and $R_5$ are as defined in [1];
Z' represents a hydrogen atom, an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{6-12}$ aryl group, an optionally substituted 5- to 12-membered heteroaryl group, or an optionally substituted 3- to 12-membered heterocycle;
m is an integer from 0 to 2; and Z' is a hydrogen atom when m is 0;

[27] the compound of [26] or a salt thereof, wherein Z' is a hydrogen atom, or an optionally substituted $C_{1-10}$ alkyl group;
[28] the compound of [27] or a salt thereof, wherein Z' is a hydrogen atom, $C_{1-6}$ alkyl group, or benzyl group;
[29] a method for treating cancer, which comprises the step of administering to a patient in need thereof an effective amount of the compound or a pharmaceutically acceptable salt thereof according to any one of [1] to [19]; and
[30] use of the compound or a pharmaceutically acceptable salt thereof according to any one of [1] to [19] for producing an anticancer agent.

Effects of the Invention

The compounds of the present invention represented by formula (1) have HSP90 inhibitory activity. Therefore, the compounds of the present invention when used alone or in combination with various anticancer agents are useful as antitumor agents or anticancer agents. Some of the compounds represented by formula (1) are also useful as synthetic intermediates of other compounds. The compounds represented by formulas (7) and (8) are useful as synthetic intermediates of the compounds represented by formula (1).

MODE FOR CARRYING OUT THE INVENTION

Hereinafter, the compounds of the present invention, methods for producing them, and pharmaceuticals comprising these compounds will be described.

DEFINITIONS

Herein, the term "$C_{1-10}$ alkyl group" refers to a straight or branched chain, saturated monovalent $C_{1-10}$ hydrocarbon group, and examples include a methyl group, ethyl group, propyl group, butyl group, pentyl group, hexyl group, heptyl group, octyl group, nonyl group, decyl group, isopropyl group, t-butyl group, sec-butyl group, 1-methylpropyl group, 1,1-dimethylpropyl group, 2,2-dimethylpropyl group, 1,2-dimethylpropyl group, 1,1,2-trimethylpropyl group, 1,2,2-trimethylpropyl group, 1,1,2,2-tetramethylpropyl group, 1-methylbutyl group, 2-methylbutyl group, 3-methylbutyl group, 1,1-dimethylbutyl group, 1,2-dimethylbutyl group, 1,1-dimethylbutyl group, 1,2-dimethyl butyl group, 1,3-dimethylbutyl group, 2,2-dimethylbutyl group, 2,3-dimethylbutyl group, 3,3-dimethylbutyl group, 1-ethylbutyl group, 2-ethylbutyl group, isopentyl group, and neopentyl group, and the like.

Herein, the term "$C_{1-6}$ alkyl group" refers to a straight or branched chain, saturated monovalent $C_{1-6}$ hydrocarbon group, and examples include a methyl group, ethyl group, propyl group, butyl group, pentyl group, hexyl group, isopropyl group, t-butyl group, sec-butyl group, 1-methylpropyl group, 1,1-dimethylpropyl group, 2,2-dimethylpropyl group, 1,2-dimethylpropyl group, 1,1,2-trimethylpropyl group, 1,2, 2-trimethylpropyl group, 1,1,2,2-tetramethylpropyl group, 1-methylbutyl group, 2-methylbutyl group, 3-methylbutyl group, 1,1-dimethylbutyl group, 1,2-dimethylbutyl group, 1,1-dimethylbutyl group, 1,2-dimethyl butyl group, 1,3-dimethylbutyl group, 2,2-dimethylbutyl group, 2,3-dimethylbutyl group, 3,3-dimethylbutyl group, 1-ethylbutyl group, 2-ethylbutyl group, isopentyl group, and neopentyl group, and the like.

The term "$C_{1-4}$ alkyl group" refers to a straight or branched chain, saturated monovalent $C_{1-4}$ hydrocarbon group, and examples include a methyl group, ethyl group, propyl group, butyl group, isopropyl group, sec-butyl group, and t-butyl group, and the like.

The term "$C_{1-4}$ haloalkyl group" refers to a "$C_{1-4}$ alkyl group" substituted with one or more halogen atoms. It is preferably a $C_{1-2}$ alkyl group substituted with one or more fluorine or chlorine, and examples include a trifluoromethyl group, difluoromethyl group, fluoromethyl group, pentafluoroethyl group, tetrafluoroethyl group, trifluoroethyl group, difluoroethyl group, fluoroethyl group, trichloromethyl group, dichloromethyl group, chloromethyl group, pentachloroethyl group, tetrachloroethyl group, trichloroethyl group, dichloroethyl group, and chloroethyl group, and the like.

The term "$C_{2-10}$ alkenyl group" refers to a $C_{2-10}$ hydrocarbon group having at least one double bond, and examples include an ethenyl(vinyl) group, 1-propenyl group, 2-propenyl (allyl) group, isopropenyl group, 1-butenyl group, 2-butenyl group, 3-butenyl(homoallyl) group, pentenyl group, hexenyl group, heptenyl group, and octenyl group, and the like.

The term "$C_{2-6}$ alkenyl group" refers to a $C_{2-6}$ hydrocarbon group having at least one double bond, and examples include an ethenyl(vinyl) group, 1-propenyl group, 2-propenyl (allyl) group, isopropenyl group, 1-butenyl group, 2-butenyl group, 3-butenyl(homoallyl) group, pentenyl group, and hexenyl group, and the like.

The term "$C_{2-4}$ alkenyl group" refers to a $C_{2-4}$ hydrocarbon group having at least one double bond, and examples include an ethenyl(vinyl) group, 1-propenyl group, 2-propenyl (allyl) group, isopropenyl group, 1-butenyl group, 2-butenyl group, and 3-butenyl(homoallyl) group, and the like.

The term "$C_{2-10}$ alkynyl group" refers to a $C_{2-10}$ hydrocarbon group having at least one triple bond, and examples include an ethynyl group, 1-propynyl group, 2-propynyl group, 1-butynyl group, 2-butynyl group, 3-butynyl group, pentynyl group, hexynyl group, heptynyl group, and octynyl group, and the like.

The term "$C_{2-6}$ alkynyl group" refers to a $C_{2-6}$ hydrocarbon group having at least one triple bond, and examples include an ethynyl group, 1-propynyl group, 2-propynyl group, 1-butynyl group, 2-butynyl group, 3-butynyl group, pentynyl group, and hexynyl group, and the like.

The term "$C_{2-4}$ alkynyl group" refers to a $C_{2-4}$ hydrocarbon group having at least one triple bond, and examples include a 1-propynyl group, 2-propynyl group, 1-butynyl group, 2-butynyl group, and 3-butynyl group, and the like.

The term "$C_{1-6}$ alkoxy group" refers to a —O—$C_{1-6}$ alkyl group, and examples include a methoxy group, ethoxy group, propoxy group, isopropoxy group, butoxy group, sec-butoxy group, isobutoxy group, t-butoxy group, pentoxy group, 3-methylbutoxy group, 2-methylbutoxy group, 1-methylbutoxy group, 1-ethylpropoxy group, hexyloxy group, 4-methylpentoxy group, 3-methylpentoxy group, 2-methylpentoxy group, 1-methylpentoxy group, 3-ethylbutoxy group, and 2-ethylbutoxy group, and the like.

The term "$C_{1-4}$ alkoxy group" refers to a —O—$C_{1-4}$ alkyl group, and examples include a methoxy group, ethoxy group, propoxy group, isopropoxy group, butoxy group, sec-butoxy group, isobutoxy group, t-butoxy group, and the like.

The term "$C_{1-4}$ alkoxy $C_{1-4}$ alkoxy group" refers to a —O—$C_{1-4}$ alkyl-O—$C_{1-4}$ alkyl group, and examples include a methoxymethoxy group, methoxyethoxy group, ethoxymethoxy group, ethoxyethoxy group, methoxypropoxy group, methoxybutoxy group, and the like.

The term "$C_{1-6}$ alkylthio group" refers to a —S—$C_{1-6}$ alkyl group, and examples include a methylthio group, ethylthio group, propylthio group, isopropylthio group, butylthio group, sec-butylthio group, isobutylthio group, t-butylthio group, pentylthio group, 3-methylbutylthio group, 2-methylbutylthio group, 1-methylbutylthio group, 1-ethylpropylthio group, hexylthio group, 4-methylpentylthio group, 3-methylpentylthio group, 2-methylpentylthio group, 1-methylpentylthio group, 3-ethylbutylthio group, 2-ethylbutylthio group, and the like.

The term "$C_{1-4}$ alkylthio group" refers to a —S—$C_{1-4}$ alkyl group, and examples include a methylthio group, ethylthio group, propylthio group, isopropylthio group, butylthio group, sec-butylthio group, isobutylthio group, t-butylthio group, and the like.

The term "halogen" refers to fluorine (F), chlorine (Cl), bromine (Br), or iodine (I), and is preferably fluorine or chlorine.

The term "$C_{3-10}$ cycloalkyl group" refers to a saturated $C_{3-10}$ carbocyclic group, and examples include a cyclopropyl group, cyclobutyl group, cyclopentyl group, cyclohexyl group, cycloheptyl group, cyclooctyl group, cyclononyl group, cyclodecyl group, and the like.

The term "$C_{6-12}$ aryl group" refers to a monocyclic or bicyclic aromatic carbon ring of six to twelve carbon ring atoms, and examples include a phenyl group, naphthyl group, indanyl group, indenyl group, isoindenyl group, and the like. A preferred example is a phenyl group.

The term "5 to 12-membered heteroaryl group" refers to a monocyclic or bicyclic aromatic heterocycle, wherein the number of atoms constituting the heterocyclic ring is five to twelve, and one or more (for example, one to four) of the heteroatoms that constitute the ring is selected from N, O, and S. Its binding position is not particularly limited, and it can be bound to any desired position. Specific examples include furan, thiophene, pyrrole, oxazole, isoxazole, thiazole, isothiazole, furazan, imidazole, pyran, thiopyran, pyridine, pyrazine, pyrimidine, pyridazine, benzofuran, isobenzofuran, benzothiophene, indole, isoindole, indolizine, chromene, benzopyran, quinoline, isoquinoline, quinolizine, naphthylizine, benzimidazole, indazole, quinoxaline, quinazoline, cinnoline, phthalazine, purine, pteridine, benzoxazole, benzothiazole, and thiadiazole, and the like.

"3 to 12-membered heterocycle" includes the above-described "5 to 12-membered heteroaryl group" and refers to an aromatic or non-aromatic heterocycle, wherein the number of atoms constituting the heterocyclic ring is three to twelve, and one or more (for example, one to four) of the heteroatoms that constitute the ring is selected from N, O and S. Its binding position is not particularly limited, and it can be bound to a desired position. Specific examples include pyrrolidine, oxazolidine, isoxazolidine, oxazoline, isoxazoline, thiazoline, isothiazolidine, thiazoline, isothiazoline, imidazolidine, imidazoline, furan, thiophene, pyrrole, oxazole, isoxazole, thiazole, isothiazole, furazan, imidazole, pyrazole, piperidine, piperazine, morpholine, thiomorpholine, tetrahydropyran, dioxane, tetrahydrothiopyran, pyran, thiopyran, pyridine, pyrazine, pyrimidine, pyridazine, benzofuran, isobenzofuran, benzothiophene, indole, isoindole, indolizine, chromene, benzopyran, quinoline, isoquinoline, quinolizine, naphthylizine, benzimidazole, indazole, quinoxaline, quinazoline, cinnoline, phthalazine, purine, pteridine, benzoxazole, benzothiazole, and thiadiazole and the like.

In the present specification, a "ring" may be simply stated to refer to a concept that encompasses all of the above-mentioned "$C_{3-10}$ cycloalkyl group", "$C_{6-12}$ aryl group", "5 to 12-membered heteroaryl group", and "3 to 12-membered heterocycle".

When Z is a substituted or optionally substituted group, the substituent is specifically selected from the following:

a halogen atom, hydroxyl group, oxo group, $C_{1-4}$ alkyl group, $C_{1-4}$ haloalkyl group, $C_{1-4}$ hydroxyalkyl group, $C_{1-4}$ alkenyl group, $C_{1-4}$ alkynyl group, $C_{1-4}$ alkoxy group optionally substituted with one or more halogen atoms, $C_{1-4}$ alkylthio group, cyano group, amidino group, carboxyl group, $C_{1-4}$ alkoxycarbonyl group, $C_{1-4}$ alkoxy $C_{1-4}$ alkoxy group, nitro group, $C_{3-10}$ cycloalkyl group, $C_{6-12}$ aryl group, 5- to 12-membered heteroaryl group, 3- to 12-membered heterocycle, or any one of the groups represented by formulas (9) to (33) below:

a group represented by formula (9) (note that the definitions are the same as in formula (5)):

wherein R and R' are the same or different, and represent a hydrogen atom, an optionally substituted $C_{1-6}$ alkyl group, an optionally substituted $C_{1-6}$ alkenyl group, an optionally substituted $C_{1-6}$ alkynyl group, an optionally substituted $C_{3-10}$ cycloalkyl group, an optionally substituted 5- to 12-membered heteroaryl group, or an optionally substituted 3- to 12-membered heterocycle, or R and R' together form an optionally substituted 3- to 12-membered heterocycle;

a group represented by formula (10):

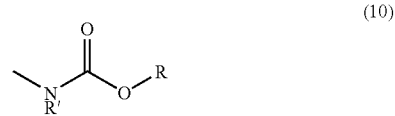

wherein R and R' are the same or different, and represent an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle;

a group represented by formula (11):

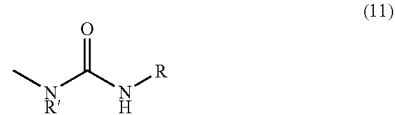

wherein R and R' are the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle;

a group represented by formula (12):

wherein R represents an optionally substituted $C_{1-6}$ alkyl group, an optionally substituted $C_{1-6}$ alkenyl group, or an optionally substituted $C_{1-6}$ alkynyl group;

a group represented by formula (13):

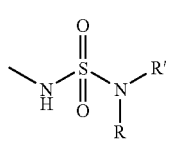
(13)

wherein R and R' are the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle;

a group represented by formula (14):

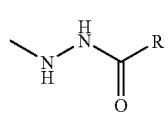
(14)

wherein R represents a hydrogen atom, an optionally substituted $C_{1-6}$ alkyl group, an optionally substituted $C_{1-6}$ alkenyl group, or an optionally substituted $C_{1-6}$ alkynyl group;

a group represented by formula (15):

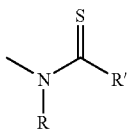
(15)

wherein R and R' are the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle);

a group represented by formula (16):

(16)

wherein R and R' are the same or different, and represent a hydrogen atom, an optionally substituted $C_{1-6}$ alkyl group, an optionally substituted $C_{1-6}$ alkenyl group, an optionally substituted $C_{1-6}$ alkynyl group, an optionally substituted 5- to 12-membered heteroaryl group, or an optionally substituted 3- to 12-membered heterocycle, or R and R' together form an optionally substituted 3- to 12-membered heterocycle;

a group represented by formula (17):

(17)

wherein R represents an optionally substituted $C_{1-6}$ alkyl group, an optionally substituted $C_{1-6}$ alkenyl group, or an optionally substituted $C_{1-6}$ alkynyl group;

a group represented by formula (18):

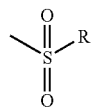
(18)

wherein R represents an optionally substituted $C_{1-6}$ alkyl group, an optionally substituted $C_{1-6}$ alkenyl group, or an optionally substituted $C_{1-6}$ alkynyl group;

a group represented by formula (19):

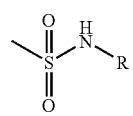
(19)

wherein R represents a hydrogen atom, an optionally substituted $C_{1-6}$ alkyl group, an optionally substituted $C_{1-6}$ alkenyl group, or an optionally substituted $C_{1-6}$ alkynyl group;

a group represented by formula (20):

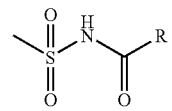
(20)

wherein R represents a hydrogen atom, an optionally substituted $C_{1-6}$ alkyl group, an optionally substituted $C_{1-6}$ alkenyl group, or an optionally substituted $C_{1-6}$ alkynyl group;

a group represented by formula (21):

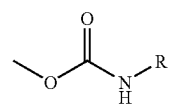
(21)

wherein R represents a hydrogen atom, an optionally substituted $C_{1-6}$ alkyl group, an optionally substituted $C_{1-6}$ alkenyl group, or an optionally substituted $C_{1-6}$ alkynyl group;

a group represented by formula (22):

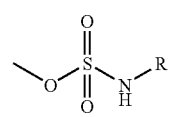
(22)

wherein R represents a hydrogen atom, an optionally substituted $C_{1-6}$ alkyl group, an optionally substituted $C_{1-6}$ alkenyl group, or an optionally substituted $C_{1-6}$ alkynyl group;

a group represented by formula (23):

(23)

wherein R represents an optionally substituted $C_{1-6}$ alkyl group, an optionally substituted $C_{1-6}$ alkenyl group, or an optionally substituted $C_{1-6}$ alkynyl group;
a group represented by formula (24) (note that the definitions are the same as in formula (6)):

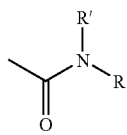
(24)

wherein R and R' may be the same or different, and represent a hydrogen atom, an optionally substituted $C_{1-6}$ alkyl group, an optionally substituted $C_{1-6}$ alkenyl group, an optionally substituted $C_{1-6}$ alkynyl group, an optionally substituted $C_{3-10}$ cycloalkyl group, an optionally substituted 5- to 12-membered heteroaryl group, or an optionally substituted 3- to 12-membered heterocycle, or R and R' together form an optionally substituted 3- to 12-membered heterocycle;
a group represented by formula (25):

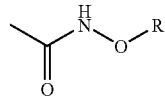
(25)

wherein R represents an optionally substituted $C_{1-6}$ alkyl group, an optionally substituted $C_{1-6}$ alkenyl group, or an optionally substituted $C_{1-6}$ alkynyl group;
a group represented by formula (26):

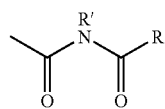
(26)

wherein R represents an optionally substituted $C_{1-6}$ alkyl group, an optionally substituted $C_{1-6}$ alkenyl group, or an optionally substituted $C_{1-6}$ alkynyl group;
a group represented by formula (27):

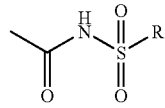
(27)

wherein R represents an optionally substituted $C_{1-6}$ alkyl group, an optionally substituted $C_{1-6}$ alkenyl group, or an optionally substituted $C_{1-6}$ alkynyl group;

a group represented by formula (28):

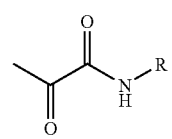
(28)

wherein R represents a hydrogen atom, an optionally substituted $C_{1-6}$ alkyl group, an optionally substituted $C_{1-6}$ alkenyl group, or an optionally substituted $C_{1-6}$ alkynyl group;
a group represented by formula (29):

(29)

wherein R and R' may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group;
a group represented by formula (30):

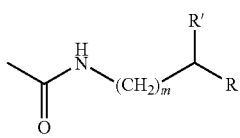
(30)

wherein m is an integer from 0 to 2; and R and R' may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle;
a group represented by formula (31):

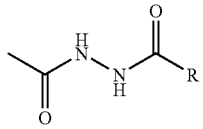
(31)

wherein R represents an optionally substituted $C_{1-6}$ alkyl group, an optionally substituted $C_{1-6}$ alkenyl group, or an optionally substituted $C_{1-6}$ alkynyl group;
a group represented by formula (32):

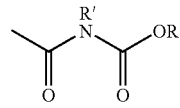
(32)

wherein R and R' may be the same or different, and represent an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle; or
a group represented by formula (33):

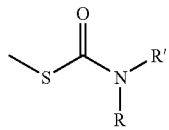
(33)

wherein R and R' may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or R and R' together form an optionally substituted 3- to 12-membered heterocycle.

More than one substituent may be present in Z mentioned above. When more than one substituent is present, they may be the same or different. The number of such substituents is preferably one or two.

In the above-mentioned formulas, when R and/or R' are "an optionally substituted $C_{1-6}$ alkyl group", "an optionally substituted $C_{1-6}$ alkenyl group", or "an optionally substituted $C_{1-6}$ alkynyl group", the substituent is specifically selected from a halogen atom, hydroxyl group, amino group, cyano group, $C_{1-4}$ alkoxy group, $C_{1-6}$ aryl group, 5- to 12-membered heteroaryl group, and 3- to 12-membered heterocycle. More than one of such substituents may be present, and when there is more than one, they may be the same or different. The number of such substituents is preferably one or two.

When R and/or R' are "an optionally substituted 5- to 12-membered heteroaryl group" or "an optionally substituted 3- to 12-membered heterocycle", the substituents are specifically selected from a halogen atom, hydroxyl group, amino group, $C_{1-4}$ alkylamino group, di $C_{1-4}$ alkylamino group, $C_{1-4}$ alkoxy group, cyano group, $C_{1-4}$ alkyl group, $C_{1-4}$ haloalkyl group, $C_{1-4}$ alkenyl group, and $C_{1-4}$ alkynyl group. More than one of such substituents may be present, and when there is more than one, each of them may be the same or different. The number of such substituents is preferably one or two. This heteroaryl ring is preferably imidazole, oxazole, thiazole, benzimidazole, pyrimidine, or pyrazine. This heterocycle is preferably imidazole, oxazole, thiazole, benzimidazole, pyrimidine, pyrazine, pyrrolidine, tetrahydropyran, pyrroline, oxazolidine, imidazolidine, piperidine, piperazine, or morpholine.

Furthermore, when R and R' together form "an optionally substituted 3- to 12-membered heterocycle", the substituent is specifically selected from a halogen atom, hydroxyl group, amino group, cyano group, $C_{1-4}$ alkyl group, $C_{1-4}$ haloalkyl group, $C_{1-4}$ alkenyl group, and $C_{1-4}$ alkynyl group. More than one of such substituents may be present, and when there is more than one, they may be the same or different. The number of such substituents is preferably one or two. This heterocycle is preferably pyrrolidine, oxazolidine, imidazolidine, piperidine, piperazine, or morpholine.

When $R_3$ is "an optionally substituted $C_{1-6}$ alkoxy group", the substituent is specifically selected from a halogen atom, hydroxyl group, amino group, cyano group, amide group ($H_2N(CO)$—), $C_{6-12}$ aryl group, 5- to 12-membered heteroaryl group, and 3- to 12-membered heterocycle. More than one of such substituents may be present, and when there is more than one, they may be the same or different. The number of such substituents is preferably one or two.

When $R_4$ is "an optionally substituted $C_{1-6}$ alkoxy group", the substituent is specifically selected from a halogen atom, hydroxyl group, amino group, cyano group, $C_{6-12}$ aryl group, 5- to 12-membered heteroaryl group, and 3- to 12-membered heterocycle. More than one of such substituents may be present, and when there is more than one, they may be the same or different. The number of such substituents is preferably one or two.

When $R_6$ and $R_7$ together form "an optionally substituted 3- to 12-membered heterocycle", the substituent is specifically a halogen atom, hydroxyl group, amino group, cyano group, $C_{1-4}$ alkyl group, $C_{1-4}$ haloalkyl group, $C_{1-4}$ alkenyl group, or $C_{1-4}$ alkynyl group. More than one of such substituents may be present, and when there is more than one, they may be the same or different. The number of such substituents is preferably one or two. Furthermore, when $R_6$ and/or $R_7$ are "an optionally substituted $C_{1-6}$ alkyl group", the substituent is specifically selected from a halogen atom, hydroxyl group, amino group, cyano group, $C_{6-12}$ aryl group, 5- to 12-membered heteroaryl group, and 3- to 12-membered heterocycle. More than one of such substituents may be present, and when there is more than one, they may be the same or different. The number of such substituents is preferably one or two.

When $R_8$ and $R_9$ are taken together to form an optionally substituted 3- to 12-membered heterocycle, the substituent is specifically a halogen atom, hydroxyl group, amino group, cyano group, $C_{1-4}$ alkyl group, $C_{1-4}$ haloalkyl group, $C_{1-4}$ alkenyl group, or $C_{1-4}$ alkynyl group. More than one of such substituents may be present, and when there is more than one, each of them may be the same or different. The number of such substituents is preferably one or two.

When $R_8$ and/or $R_9$ is "an optionally substituted $C_{1-6}$ alkyl group", the substituent is specifically selected from a halogen atom, hydroxyl group, amino group, cyano group, $C_{6-12}$ aryl group, 5- to 12-membered heteroaryl group, and 3- to 12-membered heterocycle. More than one of such substituents may be present, and when there is more than one, they may be the same or different. The number of such substituents is preferably one or two.

Furthermore, when $R_8$ and/or $R_9$ is "an optionally substituted 3- to 12-membered heterocycle", the substituent is specifically a halogen atom, hydroxyl group, amino group, cyano group, $C_{1-4}$ alkyl group, $C_{1-4}$ haloalkyl group, $C_{1-4}$ alkenyl group, or $C_{1-4}$ alkynyl group. More than one of such substituents may be present, and when there is more than one, they may be the same or different. The number of such substituents is preferably one or two.

(Salts)

The present invention includes pharmaceutically acceptable salts of the compounds represented by formula (1). These salts are produced by contacting the compounds with acids or bases that may be used in the production of pharmaceuticals. Examples of such salts include hydrochloride, hydrobromide, hydroiodide, sulfate, sulfonate, phosphate, phosphonate, carboxylate such as acetate, citrate, malate, and salicylate; alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts.

The present invention also includes chemically acceptable salts of the compounds represented by formula (7) and formula (8). These salts are produced by contacting the compounds with acids or bases. Examples of such salts include hydrochloride, hydrobromide, hydroiodide, sulfate, sulfonate, phosphate, phosphonate, carboxylate such as acetate, citrate, malate, and salicylate; alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts.

When the compounds of the present invention are obtained in their free form, they can be converted into salts that may be formed by the compounds, or into their hydrates or solvates, by standard methods.

(Isomers)

The compounds of the present invention include all stereoisomers (for example, enantiomers and diastereomers, including cis and trans geometric isomers), racemates of these isomers, and other mixtures.

The compounds of the present invention may exist in several tautomeric forms such as the enol and imine form, the keto and enamine form, or mixtures thereof. Tautomers exist as mixtures of a tautomeric set in solution. In solid form, usually one tautomer predominates. Even though one tautomer may be described, the present invention includes all tautomers of the compounds of the present invention.

(Diseases to be Treated)

The compounds of the present invention represented by formula (1) have HSP90 inhibitory effects. Therefore, the compounds of the present invention alone or in combination with various types of anticancer agents are useful as antitumor agents or anticancer agents. Specific diseases to be treated include advanced epithelial ovarian carcinoma, primary peritoneal carcinoma, metastatic renal cell carcinoma, von Hippel-Lindau disease, renal tumors, chemotherapy-refractory breast cancer, advanced medullary carcinoma, differentiated thyroid carcinoma, metastatic melanoma, relapsed/refractory pediatric malignancies, and relapsed/refractory pediatric solid tumors or leukemia, solid tumors, advanced solid tumors, relapsed, refractory, and high-risk acute leukemia, chronic myelogenous leukemia, fludarabine-refractory B-cell chronic lymphocytic leukemia, hematologic malignancies, gastrointestinal tumor, multiple myeloma, and such, for which clinical studies have already been carried out with HSP90 inhibitors.

In addition to the above, the compounds are useful as anti-inflammatory agents, anti-infectious disease agents, agents for treating autoimmune diseases, agents for treating ischemia, and pharmaceutical agents for promoting nerve regeneration. Besides cancers and tumors, specific examples of diseases to be treated include fibrogenic disorders such as scleroderma, polymyositis, systemic lupus erythematosus, rheumatoid arthritis, hepatic cirrhosis, keloid formation, interstitial nephritis, and pulmonary fibrosis; systemic mastocytosis; and Alzheimer's disease.

(Methods of Administration and Formulation)

When using the pharmaceutical compositions of the present invention, the methods for administering the compositions include, for example, oral, rectal, parenteral (intravenous, intramuscular, or subcutaneous), intracisternal, intravaginal, intraperitoneal, intravesical, and local (drip infusion, powder, ointment, gel, or cream) administration, and inhalation (intraoral or nasal spray). The forms of administration include, for example, tablets, capsules, granules, powders, pills, aqueous and non-aqueous oral solutions and suspensions, and parenteral solutions loaded into a container that is suitable for individual administration in small amounts. Furthermore, the form of administration can be adjusted according to various administration methods involving controlled-release formulations, such as subcutaneous transplantation.

The above-mentioned formulations are produced by known methods using additives such as excipients, lubricants (coating agents), binders, disintegrators, stabilizers, flavors, and diluents.

Examples of excipients include starches such as potato starch, corn starch, and starch; lactose; crystalline cellulose; and calcium hydrogen phosphate.

Examples of coating agents include ethyl cellulose, hydroxypropyl cellulose, hydroxypropyl methylcellulose, shellac, talc, carnauba wax, and paraffin.

Examples of binders include polyvinylpyrrolidone, macrogol, and the same compounds described as the excipients above.

Examples of disintegrators include the same compounds described as the excipients above, and chemically modified starches and celluloses such as croscarmellose sodium, sodium carboxymethylstarch, and crosslinked polyvinylpyrrolidone.

Examples of stabilizers include paraoxybenzoic acid esters such as methylparaben and propylparaben; alcohols such as chlorobutanol, benzylalcohol, and phenylethyl alcohol; benzalkonium chloride; phenols such as phenol and cresol; thimerosal; dehydroacetic acid; and sorbic acid.

Examples of flavors include commonly used sweeteners, acidifiers, and flavoring agents.

Furthermore, solvents used for producing liquid agents include ethanol, phenol, chlorocresol, purified water, distilled water, and such.

Examples of surfactants or emulsifiers include polysorbate 80, polyoxyl 40 stearate, and lauromacrogol.

When using the pharmaceutical compositions of the present invention, the doses of the compounds represented by formula (1) vary depending on the symptoms, age, weight, and relative health condition, presence of other medication, method of administration, and such. For example, when the compounds/pharmaceutical compositions of the present invention are used as anticancer agents, whether as oral agents or parenteral agents, the generally effective dose of an active ingredient (the compounds represented by formula (1)) for a patient (a warm-blooded animal, especially human) is preferably 1 mg/m$^2$-400 mg/m$^2$ per day, and more preferably 10 mg/m$^2$-200 mg/m$^2$ per day. The daily dose for an average adult patient is preferably in the range of 10 mg to 300 mg. This is desirably administered every day or once every two days, or administered in several portions depending on the symptoms.

A PREFERRED EMBODIMENT OF THE COMPOUNDS OF THE PRESENT INVENTION

X is preferably CH.

Y is preferably S.

Furthermore, Z is preferably an optionally substituted $C_{1-10}$ alkyl group, an optionally substituted $C_{3-10}$ cycloalkyl group, an optionally substituted $C_{1-10}$ alkenyl group, an optionally substituted $C_{1-10}$ alkynyl group, an optionally substituted $C_{6-12}$ aryl group, an optionally substituted 5- to 12-membered heteroaryl group, or an optionally substituted 3- to 12-membered heterocycle; more preferably an optionally substituted $C_{1-10}$ alkyl group, an optionally substituted $C_{6-12}$ aryl group, or an optionally substituted 3- to 12-membered heterocycle; and particularly preferably an optionally substituted $C_{1-10}$ alkyl group.

The substituents are preferably a hydroxyl group, oxo group, a group represented by formula (9) (note that the definitions are the same as in formula (5)):

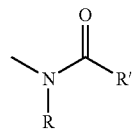

(9)

wherein R and R' may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group; or R and R' together form an optionally substituted 3- to 12-membered heterocycle;

a group represented by formula (24) (note that the definitions are the same as in formula (6)):

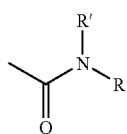

(24)

wherein R and R' may be the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or an optionally substituted 5- to 12-membered heteroaryl group; or R and R' together form an optionally substituted 3- to 12-membered heterocycle;

a group represented by formula (11) (note that the definitions are the same as in formula (34)):

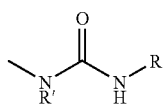

(11)

wherein R and R' may be the same or different, and represent a hydrogen atom (compound 332), an optionally substituted $C_{1-6}$ alkyl group, an optionally substituted $C_{1-6}$ alkenyl group, or an optionally substituted $C_{1-6}$ alkynyl group; or R and R' together form an optionally substituted 3- to 12-membered heterocycle;

a group represented by formula (12) (note that the definitions are the same as in formula (35)):

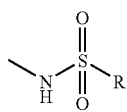

(12)

wherein R represents an optionally substituted $C_{1-6}$ alkyl group, an optionally substituted $C_{1-6}$ alkenyl group, or an optionally substituted $C_{1-6}$ alkynyl group; or a group represented by formula (21) (note that the definitions are the same as in formula (36)):

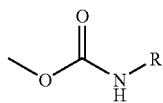

(21)

wherein R represents a hydrogen atom, an optionally substituted $C_{1-6}$ alkyl group, an optionally substituted $C_{1-6}$ alkenyl group, or an optionally substituted $C_{1-6}$ alkynyl group.

When Z is a substituted 3- to 12-membered heterocycle, a substituted oxazolidine is preferred, and the preferred substituent is an oxo group. The substituted 3- to 12-membered heterocycle is preferably an oxazolidin-2-one group.

In formula (9) mentioned above, the substituents in the optionally substituted $C_{1-6}$ alkyl group, optionally substituted $C_{1-6}$ alkenyl group, or optionally substituted $C_{1-6}$ alkynyl group are selected from a halogen atom, hydroxyl group, amino group, cyano group, $C_{6-12}$ aryl group, 5- to 12-membered heteroaryl group, and 3- to 12-membered heterocycle.

The substituents in the optionally substituted 3- to 12-membered heterocycle are specifically selected from a halogen atom, hydroxyl group, amino group, cyano group, $C_{1-4}$ alkyl group, $C_{1-4}$ haloalkyl group, $C_{1-4}$ alkenyl group, and $C_{1-4}$ alkynyl group.

In formula (24), the substituents in the optionally substituted $C_{1-6}$ alkyl group, optionally substituted $C_{1-6}$ alkenyl group, or optionally substituted $C_{1-6}$ alkynyl group are selected from a halogen atom, hydroxyl group, amino group, cyano group, $C_{1-4}$ alkoxy group, $C_{6-12}$ aryl group, 5- to 12-membered heteroaryl group, and 3- to 12-membered heterocycle.

The substituents in the optionally substituted 5- to 12-membered heteroaryl group are specifically selected from a halogen atom, hydroxyl group, amino group, cyano group, $C_{1-4}$ alkyl group, $C_{1-4}$ haloalkyl group, $C_{1-4}$ alkenyl group, and $C_{1-4}$ alkynyl group.

The substituents in the optionally substituted 3- to 12-membered heterocycle are specifically selected from a halogen atom, hydroxyl group, amino group, cyano group, $C_{1-4}$ alkyl group, $C_{1-4}$ haloalkyl group, $C_{1-4}$ alkenyl group, and $C_{1-4}$ alkynyl group.

In formula (11), the substituents in the optionally substituted $C_{1-6}$ alkyl group, optionally substituted $C_{1-6}$ alkenyl group, or optionally substituted $C_{1-6}$ alkynyl group are selected from a halogen atom, hydroxyl group, amino group, cyano group, $C_{6-12}$ aryl group, 5- to 12-membered heteroaryl group, and 3- to 12-membered heterocycle.

The substituents in the optionally substituted 3- to 12-membered heterocycle are specifically selected from a halogen atom, hydroxyl group, amino group, cyano group, $C_{1-4}$ alkyl group, $C_{1-4}$ haloalkyl group, $C_{1-4}$ alkenyl group, and $C_{1-4}$ alkynyl group.

In formula (12), the substituents in the optionally substituted $C_{1-6}$ alkyl group, optionally substituted $C_{1-6}$ alkenyl group, or optionally substituted $C_{1-6}$ alkynyl group are selected from a halogen atom, hydroxyl group, amino group, cyano group, $C_{6-12}$ aryl group, 5- to 12-membered heteroaryl group, and 3- to 12-membered heterocycle.

In formula (21), the substituents in the optionally substituted $C_{1-6}$ alkyl group, optionally substituted $C_{1-6}$ alkenyl group, or optionally substituted $C_{1-6}$ alkynyl group are selected from a halogen atom, hydroxyl group, amino group, cyano group, $C_{6-12}$ aryl group, 5- to 12-membered heteroaryl group, and 3- to 12-membered heterocycle.

The substituent in Z is more preferably a group represented by formula (9) (note that the definitions are the same as in formula (5)):

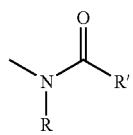

(9)

wherein R is a hydrogen atom, and R' is preferably an optionally substituted $C_{1-6}$ alkyl group, and more preferably a $C_{1-6}$ alkyl group optionally substituted with a hydroxyl group;

a group represented by formula (24) (note that the definitions are the same as in formula (6)):

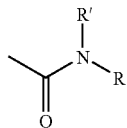
(24)

wherein R and R' may be the same or different, and are a hydrogen atom or an optionally substituted $C_{1-6}$ alkyl group, and the substituent is preferably a hydroxyl group, cyano group, or a $C_{1-4}$ alkoxy group;

a group represented by formula (11) (note that the definitions are the same as in formula (34)):

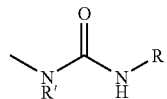
(11)

wherein R and R' are hydrogen atoms;

a group represented by formula (12) (note that the definitions are the same as in formula (35)):

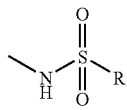
(12)

wherein R is a $C_{1-6}$ alkyl group; or a group represented by formula (21) (note that the definitions are the same as in formula (36)):

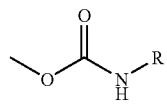
(21)

(wherein R is a hydrogen atom).

$R_1$ is preferably a halogen atom or a $C_{1-6}$ alkyl group, and is more preferably a chlorine atom or a methyl group.

$R_2$ is preferably a hydrogen atom.

In one embodiment, $R_3$, $R_4$, and $R_5$ preferably form a ring together. In this case, it is preferable that $R_3$, $R_4$, and $R_5$ form a ring together in the compounds represented by formula (4):

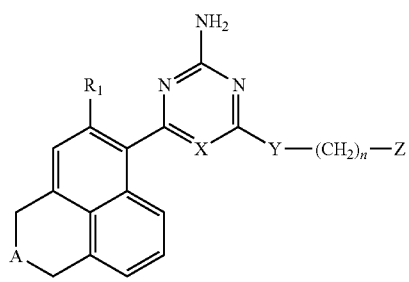
(4)

wherein A represents O or S; and X, Y, Z, n, and $R_1$ are defined as described above. More preferably, A is O.

In another preferred embodiment, $R_3$ is a halogen atom or a $C_{1-6}$ alkyl group; and $R_4$ is a $C_{1-6}$ alkyl group, an optionally substituted $C_{1-6}$ alkoxy group, or a group represented by formula (3):

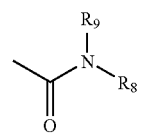
(3)

wherein $R_8$ and $R_9$ may be the same or different and represent a hydrogen atom, an optionally substituted $C_{1-6}$ alkyl group, $C_{2-6}$ alkenyl group, or $C_{2-6}$ alkynyl group, $C_{6-12}$ aryl group, or $C_{6-12}$ heteroaryl group; or $R_8$ and $R_9$ together form an optionally substituted 3- to 12-membered heterocycle.

In this case, more preferably, $R_3$ is a halogen atom; and $R_4$ is a $C_{1-6}$ alkoxy group optionally substituted with a cyano group, or a group represented by formula (3):

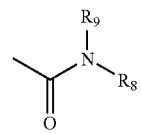
(3)

wherein $R_8$ and $R_9$ may be the same or different, and represent a hydrogen atom or $C_{1-6}$ alkyl group.

The compounds of the present invention specifically include:

(1): {5-[4-amino-6-(2-methoxyphenylsulfanyl)-[1,3,5]triazin-2-yl]-2,4-dicyclophenoxy}-acetonitrile;

(2): 5-(4-amino-6-benzylsulfanyl-[1,3,5]triazin-2-yl)-2,4-dichloro-N-(2-hydroxyethyl)-benzamide;

(3): 4-(2,4-dichlorophenyl)-6-(2,5-dimethoxyphenylsulfanyl)-[1,3,5]triazin-2-ylamine;

(4): 4-(5-benzyloxy-2,4-dichlorophenyl)-6-benzylsulfanyl [1,3,5]triazin-2-ylamine;

(5): 4-benzylsulfanyl-6-(2,4-dichlorophenyl)-[1,3,5]triazin-2-ylamine;

(6): 4-(2,4-dichlorophenyl)-6-(2-methoxyphenylsulfanyl)-[1,3,5]triazin-2-ylamine;

(7): 4-(2-aminophenylsulfanyl)-6-(2,4-dichlorophenyl)-[1,3,5]triazin-2-ylamine;

(8): {5-[4-amino-6-(2,5-dimethoxyphenylsulfanyl)-[1,3,5]triazin-2-yl]-2,4-dichlorophenoxy}-acetonitrile;

(9): [5-(4-amino-6-phenylsulfanyl-[1,3,5]triazin-2-yl)-2,4-dichlorophenoxy]-acetonitrile;

(10): {5-[4-amino-6-(pyrimidin-2-ylsulfanyl)-[1,3,5]triazin-2-yl]-2,4-dichlorophenoxy}-acetonitrile;

(11): {5-[4-amino-6-(5-methyl-[1,3,4]thiadiazol-2-ylsulfanyl)-[1,3,5]triazin-2-yl]-2,4-dichlorophenoxy}-acetonitrile;

(12): {5-[4-amino-6-(1H-benzimidazol-2-ylsulfanyl)-[1,3,5]triazin-2-yl]-2,4-dichlorophenoxy}-acetonitrile;

(13): {5-[4-amino-6-(benzothiazol-2-ylsulfanyl)-[1,3,5]trazin-2-yl]-2,4-dichlorophenoxy}-acetonitrile;

(14): [5-(4-amino-6-cyclopropylmethylsulfanyl-[1,3,5]triazin-2-yl)-2,4-dichlorophenoxy]-acetonitrile;

(15): (5-{4-amino-6-[2-methoxy-4-(4-methyl-piperazin-1-carbonyl)-phenylsulfanyl]-[1,3,5]triazin-2-yl}-2,4-dichlorophenoxy)-acetonitrile;

(16): 4-[4-amino-6-(2,4-dichloro-5-cyanomethoxyphenyl)-[1,3,5]triazin-2-ylsulfanyl]-N-(2,3-dihydroxypropyl)-3-methoxybenzamide;
(17): (5-{4-amino-6-[4-(4-methyl-piperazin-1-carbonyl)-phenylsulfanyl]-[1,3,5]triazin-2-yl}-2,4-dichlorophenoxy)-acetonitrile;
(18): (5-{4-amino-6-[4-(piperazin-1-carbonyl)-phenylsulfanyl]-[1,3,5]triazin-2-yl}-2,4-dichlorophenoxy)-acetonitrile;
(19): 4-[4-amino-6-(2,4-dichloro-5-cyanomethoxyphenyl)-[1,3,5]triazin-2-ylsulfanyl]-N-(2,3-dihydroxypropyl)-benzamide;
(20): 4-[4-amino-6-(2,4-dichloro-5-cyanomethoxyphenyl)-[1,3,5]triazin-2-ylsulfanyl]-N-(2-hydroxy-1-hydroxymethyl-ethyl)-benzamide;
(21): (5-{4-amino-6-[2-methoxy-4-(piperazine-1-carbonyl)-phenylsulfanyl]-[1,3,5]triazin-2-yl}-2,4-dichlorophenoxy)-acetonitrile;
(22): 4-[4-amino-6-(2,4-dichloro-5-cyanomethoxyphenyl)-[1,3,5]triazin-2-ylsulfanyl]-3-methoxy-N-(1-methyl-piperidin-4-yl)-benzamide;
(23): 4-[4-amino-6-(2,4-dichloro-5-cyanomethoxyphenyl)-[1,3,5]triazin-2-ylsulfanyl]-3-methoxy-N-piperidin-4-yl-benzamide;
(24): 4-(2,4-dichloro-5-pyrimidin-2-yl-phenyl)-6-methylsulfanyl-[1,3,5]triazin-2-ylamine;
(25): N-{2-[4-amino-6-(2,4-dichloro-5-pyrimidin-2-yl-phenyl)-[1,3,5]triazin-2-ylsulfanyl]-ethyl}-acetamide;
(26): 5-(4-amino-6-benzylsulfanyl-[1,3,5]triazin-2-yl)-2,4-dichlorobenzamide;
(27): 5-(4-amino-6-benzylsulfanyl-[1,3,5]triazin-2-yl)-2,4-dichloro-N-(2,3-dihydroxypropyl)-benzamide;
(28): 5-(4-amino-6-benzylsulfanyl-[1,3,5]triazin-2-yl)-2,4-dichloro-N-(2-hydroxy-1-hydroxymethyl-ethyl)-benzamide;
(29): 5-(4-amino-6-benzylsulfanyl-[1,3,5]triazin-2-yl)-2,4-dichloro-N-(1-methyl-piperidin-4-yl)-benzamide;
(30): [5-(4-amino-6-benzylsulfanyl-[1,3,5]triazin-2-yl)-2,4-dichlorophenyl]-(4-methyl-piperazin-1-yl)-methanone;
(31): [5-(4-amino-6-benzylsulfanyl-[1,3,5]triazin-2-yl)-2,4-dichlorophenyl]-morpholin-4-yl-methanone;
(32): 5-(4-amino-6-benzylsulfanyl-[1,3,5]triazin-2-yl)-2,4-dimethylbenzoic acid methyl ester;
(33): 5-[4-amino-6-(2-methoxyphenylsulfanyl)-[1,3,5]triazin-2-yl]-2,4-dimethylbenzoic acid methyl ester;
(34): 5-[4-amino-6-(2,5-dimethoxyphenylsulfanyl)-[1,3,5]triazin-2-yl]-2,4-dimethylbenzoic acid methyl ester;
(35): 5-[4-amino-6-(2-hydroxyethylsulfanyl)-[1,3,5]triazin-2-yl]-2,4-dimethylbenzoic acid methyl ester;
(36): 5-[4-amino-6-(3-hydroxypropylsulfanyl)-[1,3,5]triazin-2-yl]-2,4-dimethylbenzoic acid methyl ester;
(37): 5-[4-amino-6-(2,3-dihydroxypropylsulfanyl)-[1,3,5]triazin-2-yl]-2,4-dimethylbenzoic acid methyl ester;
(38): 5-[4-amino-6-(2-methoxyphenylsulfanyl)-[1,3,5]triazin-2-yl]-2,4-dichloro-N-(2-hydroxyethyl)-benzamide;
(39): 4-(2,4-dichlorophenyl)-6-(2,5-dimethoxyphenylsulfanyl)-pyrimidin-2-ylamine;
(40): 4-(2,5-dimethoxyphenylsulfanyl)-6-naphthalen-1-yl-pyrimidin-2-ylamine;
(41): 4-(2,5-dimethoxyphenylsulfanyl)-6-(2,5-dimethylphenyl)-pyrimidin-2-ylamine;
(42): 4-(2,5-dimethoxyphenylsulfanyl)-6-(2,4,5-trimethylphenyl)-pyrimidin-2-ylamine;
(43): 4-[2-amino-6-(2,5-dimethoxyphenylsulfanyl)-pyrimidin-4-yl]-3-methylphenol;
(44): 3-{4-[2-amino-6-(2,5-dimethoxyphenylsulfanyl)-pyrimidin-4-yl]-3-methylphenoxy}-propan-1-ol;
(45): {4-[2-amino-6-(2,5-dimethoxyphenylsulfanyl)-pyrimidin-4-yl]-3-methylphenoxy}-acetonitrile;
(46): 2-{4-[2-amino-6-(2,5-dimethoxyphenylsulfanyl)-pyrimidin-4-yl]-3-methylphenoxy}-acetamide;
(47): 2-{4-[2-amino-6-(2,5-dimethoxyphenylsulfanyl)-pyrimidin-4-yl]-3-methylphenoxy}-ethanol;
(48): 4-(5-benzyloxy-2,4-dichlorophenyl)-6-(2,5-dimethoxyphenylsulfanyl)-pyrimidin-2-ylamine;
(49): 4-(2,5-dimethoxyphenylsulfanyl)-6-(2,4,6-trimethylphenyl)-pyrimidin-2-ylamine;
(50): 5-[2-amino-6-(2,5-dimethoxyphenylsulfanyl)-pyrimidin-4-yl]-2,4-dichlorophenyl;
(51): 4-(2,5-dimethoxyphenylsulfanyl)-6-(2-methyl-4-prop-2-ynyloxy-phenyl)-pyrimidin-2-ylamine;
(52): {5-[2-amino-6-(2,5-dimethoxyphenylsulfanyl)-pyrimidin-4-yl]-2,4-dichlorophenyoxy}-acetonitrile;
(53): {5-[2-amino-6-(2-aminophenylsulfanyl)-pyrimidin-4-yl]-2,4-dichlorophenoxy}-acetonitrile;
(54): {5-[2-amino-6-(1H-benzimidazol-2-ylsulfanyl)-pyrimidin-4-yl]-2,4-dichlorophenoxy}-acetonitrile;
(55): 2-[2-amino-6-(2,4-dichloro-5-cyanomethoxyphenyl)-pyrimidin-4-ylsulfanyl]-3H-imidazol-4-carboxylic acid ethyl ester;
(56): {5-[2-amino-6-(1-methyl-1H-imidazol-2-ylsulfanyl)-pyrimidin-4-yl]-2,4-dichlorophenoxy}-acetonitrile;
(57): 3-[4-amino-6-(2,4-dichloro-5-cyanomethoxyphenyl)-[1,3,5]triazin-2-ylsulfanyl]-propionic acid methyl ester;
(58): {5-[4-amino-6-(3-hydroxypropylsulfanyl)-[1,3,5]triazin-2-yl]-2,4-dichlorophenoxy}-acetonitrile;
(59): N-{2-[4-amino-6-(2,4-dichloro-5-cyanomethoxyphenyl)-[1,3,5]triazin-2-ylsulfanyl]-ethyl}-acetamide;
(60): 3-[4-amino-6-(2,4-dichloro-5-cyanomethoxyphenyl)-[1,3,5]triazin-2-ylsulfanyl]-N-methyl-propionamide;
(61): 3-[4-amino-6-(2,4-dichloro-5-cyanomethoxyphenyl)-[1,3,5]triazin-2-ylsulfanyl]-N-(2-hydroxyethyl)-propionamide;
(62): 3-[4-amino-6-(2,4-dichloro-5-cyanomethoxyphenyl)-[1,3,5]triazin-2-ylsulfanyl]-propionamide;
(63): {5-[4-amino-6-(3-morpholin-4-yl-3-oxo-propylsulfanyl)-[1,3,5]triazin-2-yl]-2,4-dichlorophenoxy}-acetonitrile;
(64): 3-[4-amino-6-(2,4-dichloro-5-cyanomethoxyphenyl)-[1,3,5]triazin-2-ylsulfanyl]-N-(2-hydroxyethoxy)-propionamide;
(65): 3-[4-amino-6-(2,4-dichloro-5-cyanomethoxyphenyl)-[1,3,5]triazin-2-ylsulfanyl]-N-pyridin-4-yl methyl-propionamide;
(66): 3-[4-amino-6-(2,4-dichloro-5-cyanomethoxyphenyl)-[1,3,5]triazin-2-ylsulfanyl]-N-pyridin-4-yl-propionamide;
(67): 3-[4-amino-6-(2,4-dichloro-5-cyanomethoxyphenyl)-[1,3,5]triazin-2-ylsulfanyl]-N-(2-dimethylamino-ethyl)-propionamide;
(68): 3-[4-amino-6-(2,4-dichloro-5-cyanomethoxyphenyl)-[1,3,5]triazin-2-ylsulfanyl]-N-(2-morpholin-4-yl-ethyl)-propionamide;
(69): 3-[4-amino-6-(2,4-dichloro-5-cyanomethoxyphenyl)-[1,3,5]triazin-2-ylsulfanyl]-N-thiazol-2-yl-propionamide;
(70): 2-[4-amino-6-(2,4-dichloro-5-cyanomethoxyphenyl)-[1,3,5]triazin-2-ylsulfanyl]-N-methyl-acetamide;
(71): 4-(5-chloro-1H,3H-benzo[de]isochromen-6-yl)-6-(2-methoxyphenylsulfanyl)-[1,3,5]triazin-2-ylamine;
(72): 4-(5-chloro-1H,3H-benzo[de]isochromen-6-yl)-6-(2-chlorophenylsulfanyl)-[1,3,5]triazin-2-ylamine;
(73): 4-(5-chloro-1H,3H-benzo[de]isochromen-6-yl)-6-(3-chlorophenylsulfanyl)-[1,3,5]triazin-2-ylamine;

(74): 4-(5-chloro-1H,3H-benzo[de]isochromen-6-yl)-6-(4-chlorophenylsulfanyl)-[1,3,5]triazin-2-ylamine;

(75): 4-(5-chloro-1H,3H-benzo[de]isochromen-6-yl)-6-(4-methylsulfanyl-phenylsulfanyl)-[1,3,5]triazin-2-ylamine;

(76): 4-(5-chloro-1H,3H-benzo[de]isochromen-6-yl)-6-(3-methoxyphenylsulfanyl)-[1,3,5]triazin-2-ylamine;

(77): 4-(5-chloro-1H,3H-benzo[de]isochromen-6-yl)-6-(4-methoxyphenylsulfanyl)-[1,3,5]triazin-2-ylamine;

78): 4-(5-chloro-1H,3H-benzo[de]isochromen-6-yl)-6-(2,5-difluorophenylsulfanyl)-[1,3,5]triazin-2-yl amine;

(79): 4-(5-chloro-1H,3H-benzo[de]isochromen-6-yl)-6-(2-fluorophenylsulfanyl)-[1,3,5]triazin-2-ylamine;

(80): 4-(5-chloro-1H,3H-benzo[de]isochromen-6-yl)-6-(4-fluorophenylsulfanyl)-[1,3,5]triazin-2-ylamine;

(81): 4-(2-bromophenoxy)-6-(5-chloro-1H,3H-benzo[de]isochromen-6-yl)-[1,3,5]triazin-2-ylamine;

(82): 4-(5-chloro-1H,3H-benzo[de]isochromen-6-yl)-6-(3,4-dimethoxyphenoxy)-[1,3,5]triazin-2-ylamine;

(83): 4-(5-chloro-1H,3H-benzo[de]isochromen-6-yl)-6-(3,5-dimethoxyphenoxy)-[1,3,5]triazin-2-ylamine;

(84): 4-(5-chloro-1H,3H-benzo[de]isochromen-6-yl)-6-(1H-imidazol-2-ylsulfanyl)-[1,3,5]triazin-2-ylamine;

(85): 4-(5-chloro-1H,3H-benzo[de]isochromen-6-yl)-6-(naphthalen-1-ylsulfanyl)-[1,3,5]triazin-2-ylamine;

(86): 4-(5-chloro-1H,3H-benzo[de]isochromen-6-yl)-6-(naphthalen-2-ylsulfanyl)-[1,3,5]triazin-2-ylamine;

(87): 4-(5-chloro-1H,3H-benzo[de]isochromen-6-yl)-6-(3,4-dimethoxy-phenylsulfanyl)-[1,3,5]triazin-2-ylamine;

(88): 4-(5-chloro-1H,3H-benzo[de]isochromen-6-yl)-6-(3-trifluoromethoxyphenylsulfanyl)-[1,3,5]triazin-2-ylamine;

(89): 4-(5-chloro-1H,3H-benzo[de]isochromen-6-yl)-6-(4-trifluoromethoxyphenylsulfanyl)-[1,3,5]triazin-2-ylamine;

(90): 4-(5-chloro-1H,3H-benzo[de]isochromen-6-yl)-6-(2,5-dichlorophenylsulfanyl)-[1,3,5]triazin-2-ylamine;

(91): 4-(2-bromophenylsulfanyl)-6-(5-chloro-1H,3H-benzo[de]isochromen-6-yl)-[1,3,5]triazin-2-ylamine;

(92): 4-(5-chloro-1H,3H-benzo[de]isochromen-6-yl)-6-cyclohexylsulfanyl-[1,3,5]triazin-2-ylamine;

(93): 4-(5-chloro-1H,3H-benzo[de]isochromen-6-yl)-6-isobutylsulfanyl-[1,3,5]triazin-2-ylamine;

(94): 4-(5-chloro-1H,3H-benzo[de]isochromen-6-yl)-6-isopropylsulfanyl-[1,3,5]triazin-2-ylamine;

(95): N-{4-[4-amino-6-(5-chloro-1H,3H-benzo[de]isochromen-6-yl)-[1,3,5]triazin-2-ylsulfanyl]-phenyl}-acetamide;

(96): 4-(5-chloro-1H,3H-benzo[de]isochromen-6-yl)-6-(4-methoxybenzylsulfanyl)-[1,3,5]triazin-2-ylamine;

(97): 4-(5-chloro-1H,3H-benzo[de]isochromen-6-yl)-6-(3-chlorobenzyloxy)-[1,3,5]triazin-2-ylamine;

(98): 4-(5-chloro-1H,3H-benzo[de]isochromen-6-yl)-6-(3-methoxyphenoxy)-[1,3,5]triazin-2-ylamine;

(99): {4-[4-amino-6-(5-chloro-1H,3H-benzo[de]isochromen-6-yl)-[1,3,5]triazin-2-yloxy]-phenyl}-methanol;

(100): 4-(5-chloro-1H,3H-benzo[de]isochromen-6-yl)-6-(4-methoxyphenoxy)-[1,3,5]triazin-2-ylamine;

(101): 4-(5-chloro-1H,3H-benzo[de]isochromen-6-yl)-6-(2-methoxyphenoxy)-[1,3,5]triazin-2-ylamine;

(102): N-{3-[4-amino-6-(5-chloro-1H,3H-benzo[de]isochromen-6-yl)-[1,3,5]triazin-2-yloxy]-phenyl}-acetamide;

(103): 2-{3-[4-amino-6-(5-chloro-1H,3H-benzo[de]isochromen-6-yl)-[1,3,5]triazin-2-yloxy]-phenyl}-ethanol;

(104): {3-[4-amino-6-(5-chloro-1H,3H-benzo[de]isochromen-6-yl)-[1,3,5]triazin-2-yloxy]-phenyl}-urea;

(105): 4-[4-amino-6-(5-chloro-1H,3H-benzo[de]isochromen-6-yl)-[1,3,5]triazin-2-ylsulfanyl]-phenol;

(106): 4-(5-chloro-1H,3H-benzo[de]isochromen-6-yl)-6-(4-nitrophenylsulfanyl)-[1,3,5]triazin-2-ylamine;

(107): 4-(5-chloro-1H,3H-benzo[de]isochromen-6-yl)-6-(2-methyl-furan-3-ylsulfanyl)-[1,3,5]triazin-2-ylamine;

(108): 4-(5-chloro-1H,3H-benzo[de]isochromen-6-yl)-6-(2,5-dimethoxyphenoxy)-[1,3,5]triazin-2-ylamine;

(109): 4-(3-aminophenylsulfanyl)-6-(5-chloro-1H,3H-benzo[de]isochromen-6-yl)-[1,3,5]triazin-2-ylamine;

(110): 4-(5-chloro-1H,3H-benzo[de]isochromen-6-yl)-6-propylsulfanyl-[1,3,5]triazin-2-ylamine;

(111): [4-amino-6-(5-chloro-1H,3H-benzo[de]isochromen-6-yl)-[1,3,5]triazin-2-ylsulfanyl]-acetic acid methyl ester;

(112): [4-amino-6-(5-chloro-1H,3H-benzo[de]isochromen-6-yl)-[1,3,5]triazin-2-ylsulfanyl]-acetic acid;

(113): N-{2-[4-amino-6-(5-chloro-1H,3H-benzo[de]isochromen-6-yl)-[1,3,5]triazin-2-ylsulfanyl]-ethyl}-acetamide;

(114): 4-(5-chloro-1H,3H-benzo[de]isochromen-6-yl)-6-(2-dimethylaminoethylsulfanyl)-[1,3,5]triazin-2-ylamine;

(115): 3-[4-amino-6-(5-chloro-1H,3H-benzo[de]isochromen-6-yl)-[1,3,5]triazin-2-ylsulfanyl]-propan-1-ol;

(116): 1-(4-{3-[4-amino-6-(5-chloro-1H,3H-benzo[de]isochromen-6-yl)-[1,3,5]triazin-2-yloxy]-phenyl}-piperazin-1-yl)-ethanone;

(117): 2-[4-amino-6-(5-chloro-1H,3H-benzo[de]isochromen-6-yl)-[1,3,5]triazin-2-ylsulfanyl]-phenol:

(118): 4-(5-chloro-1H,3H-benzo[de]isochromen-6-yl)-6-o tolylsulfanyl-[1,3,5]triazin-2-ylamine;

(119): 2-[4-amino-6-(5-chloro-1H,3H-benzo[de]isochromen-6-yl)-[1,3,5]triazin-2-ylsulfanyl]-acetamide;

(120): 4-(5-chloro-1H,3H-benzo[de]isochromen-6-yl)-6-(2-methoxybenzyloxy)-[1,3,5]triazin-2-ylamine;

(121): 4-(5-chloro-1H,3H-benzo[de]isochromen-6-yl)-6-(3-methoxybenzyloxy)-[1,3,5]triazin-2-ylamine;

(122): 4-(5-chloro-1H,3H-benzo[de]isochromen-6-yl)-6-(4-methoxybenzyloxy)-[1,3,5]triazin-2-ylamine;

(123): 4-(5-chloro-1H,3H-benzo[de]isochromen-6-yl)-6-(4-dimethylaminophenylsulfanyl)-[1,3,5]triazin-2-ylamine;

(124): 3-[4-amino-6-(5-chloro-1H,3H-benzo[de]isochromen-6-yl)-[1,3,5]triazin-2-ylsulfanyl]-propionic acid methyl ester;

(125): 3-[4-amino-6-(5-chloro-1H,3H-benzo[de]isochromen-6-yl)-[1,3,5]triazin-2-ylsulfanyl]-propionamide;

(126): 3-[4-amino-6-(5-chloro-1H,3H-benzo[de]isochromen-6-yl)-[1,3,5]triazin-2-ylsulfanyl]-propionic acid;

(127): N-{2-[4-amino-6-(5-chloro-1H,3H-benzo[de]isochromen-6-yl)-[1,3,5]triazin-2-yloxymethyl]-phenyl}-acetamide;

(128): N-{4-[4-amino-6-(5-chloro-1H,3H-benzo[de]isochromen-6-yl)-[1,3,5]triazin-2-yloxymethyl]-phenyl}-acetamide;

(129): N-{3-[4-amino-6-(5-chloro-1H,3H-benzo[de]isochromen-6-yl)-[1,3,5]triazin-2-yloxymethyl]-phenyl}-acetamide;

(130): (R)-2-[4-amino-6-(5-chloro-1H,3H-benzo[de]isochromen-6-yl)-[1,3,5]triazin-2-ylsulfanylmethyl]-4-oxopentanoic acid;

(131): 3-[4-amino-6-(5-chloro-1H,3H-benzo[de]isochromen-6-yl)-[1,3,5]triazin-2-ylsulfanyl]-2-methyl-propionic acid;

(132): 2-[4-amino-6-(5-chloro-1H,3H-benzo[de]isochromen-6-yl)-[1,3,5]triazin-2-ylsulfanyl]-ethanol;

(133): {2-[4-amino-6-(5-chloro-1H,3H-benzo[de]isochromen-6-yl)-[1,3,5]triazin-2-ylsulfanyl]-ethyl}-carbamic acid tert-butyl ester;

(134): 4-(5-chloro-1H,3H-benzo[de]isochromen-6-yl)-6-(3-dimethylaminophenylsulfanyl)-[1,3,5]triazin-2-ylamine;

(135): 3-[4-amino-6-(5-chloro-1H,3H-benzo[de]isochromen-6-yl)-[1,3,5]triazin-2-ylsulfanyl]-2-methyl-propionic acid methyl ester;

(136): (R)-2-acetylamino-3-[4-amino-6-(5-chloro-1H,3H-benzo[de]isochromen-6-yl)-[1,3,5]triazin-2-yl sulfanyl]-propionic acid methyl ester;

(137): 4-(4-aminophenylsulfanyl)-6-(5-chloro-1H,3H-benzo[de]isochromen-6-yl)-[1,3,5]triazin-2-ylamine;

(138): 4-(5-chloro-1H,3H-benzo[de]isochromen-6-yl)-6-(3-chloropropylsulfanyl)-[1,3,5]triazin-2-ylamine;

(139): 4-[4-(N,N-dimethylaminosulfonyl)amino-phenylsulfanyl]-6-(5-chloro-1H,3H-benzo[de]isochromen-6-yl)-[1,3,5]triazin-2-ylamine;

(140): N-{4-[4-amino-6-(5-chloro-1H,3H-benzo[de]isochromen-6-yl)-[1,3,5]triazin-2-ylsulfanylmethyl]-phenyl}-acetamide;

(141): 4-(5-chloro-1H,3H-benzo[de]isochromen-6-yl)-6-(3-dimethylaminopropylsulfanyl)-[1,3,5]triazin-2-ylamine;

(142): 4-(4-aminosulfonyl)amino-phenylsulfanyl-6-(5-chloro-1H,3H-benzo[de]isochromen-6-yl)-[1,3,5]triazin-2-ylamine;

(143): N-{2-[4-amino-6-(5-chloro-1H,3H-benzo[de]isochromen-6-yl)-[1,3,5]triazin-2-ylsulfanylmethyl]-phenyl}-acetamide;

(144): N-{3-[4-amino-6-(5-chloro-1H,3H-benzo[de]isochromen-6-yl)-[1,3,5]triazin-2-ylsulfanylmethyl]-phenyl}-acetamide;

(145): 4-(5-chloro-1H,3H-benzo[de]isochromen-6-yl)-6-(2,5-dimethoxyphenylsulfanyl)-[1,3,5]triazin-2-ylamine;

(146): 4-(7-chloro-isochroman-6-yl)-6-methylsulfanyl-[1,3,5]triazin-2-ylamine;

(147): 4-(5-chloro-isochroman-6-yl)-6-(2,5-dimethoxyphenylsulfanyl)-pyrimidin-2-ylamine;

(148): 4-(7-chloro-isochroman-6-yl)-6-(2,5-dimethoxyphenylsulfanyl)-pyrimidin-2-ylamine;

(149): N-{3-[4-amino-6-(5-chloro-1H,3H-benzo[de]isochromen-6-yl)-[1,3,5]triazin-2-ylsulfanyl]-propyl}-acetamide;

(150): N-{4-[4-amino-6-(5-chloro-1H,3H-benzo[de]isochromen-6-yl)-[1,3,5]triazin-2-ylsulfanyl]-butyl}-acetamide;

(151): N-{2-[4-amino-6-(5-chloro-1H,3H-benzo[de]isochromen-6-yl)-[1,3,5]triazin-2-ylsulfanyl]-ethyl}-propionamide;

(152): N-{2-[4-amino-6-(5-chloro-1H,3H-benzo[de]isochromen-6-yl)-[1,3,5]triazin-2-ylsulfanyl]-ethyl}-butylamide;

(153): N-{2-[4-amino-6-(5-chloro-1H,3H-benzo[de]isochromen-6-yl)-[1,3,5]triazin-2-ylsulfanyl]-ethyl}-isobutylamide;

(154): cyclopropane carboxylic acid {2-[4-amino-6-(5-chloro-1H,3H-benzo[de]isochromen-6-yl)-[1,3,5]triazin-2-ylsulfanyl]-ethyl}-amide;

(155): cyclopentane carboxylic acid {2-[4-amino-6-(5-chloro-1H,3H-benzo[de]isochromen-6-yl)-[1,3,5]triazin-2-ylsulfanyl]-ethyl}-amide;

(156): tetrahydro-pyran-4-carboxylic acid {2-[4-amino-6-(5-chloro-1H,3H-benzo[de]isochromen-6-yl)-[1,3,5]triazin-2-ylsulfanyl]-ethyl}-amide;

(157): piperidine-4-carboxylic acid {2-[4-amino-6-(5-chloro-1H,3H-benzo[de]isochromen-6-yl)-[1,3,5]triazin-2-ylsulfanyl]-ethyl}-amide;

(158): 1-methyl-piperidine-4-carboxylic acid {2-[4-amino-6-(5-chloro-1H,3H-benzo[de]isochromen-6-yl)-[1,3,5]triazin-2-ylsulfanyl]-ethyl}-amide;

(159): N-{2-[4-amino-6-(5-chloro-1H,3H-benzo[de]isochromen-6-yl)-[1,3,5]triazin-2-ylsulfanyl]-ethyl}-3-hydroxypropionamide;

(160): N-{2-[4-amino-6-(5-chloro-1H,3H-benzo[de]isochromen-6-yl)-[1,3,5]triazin-2-ylsulfanyl]-ethyl}-3,4-dihydroxybutylamide;

(161): N-{2-[4-amino-6-(5-chloro-1H,3H-benzo[de]isochromen-6-yl)-[1,3,5]triazin-2-ylsulfanyl]-ethyl}-4-hydroxy-3-hydroxymethylbutylamide;

(162): N-{2-[4-amino-6-(5-chloro-1H,3H-benzo[de]isochromen-6-yl)-[1,3,5]triazin-2-ylsulfanyl]-ethyl}-N-methyl-acetamide;

(163): 1-{2-[4-amino-6-(5-chloro-1H,3H-benzo[de]isochromen-6-yl)-[1,3,5]triazin-2-ylsulfanyl]-ethyl}-pyrrolidin-2-one;

(164): N-{3-[4-amino-6-(5-chloro-1H,3H-benzo[de]isochromen-6-yl)-[1,3,5]triazin-2-ylsulfanyl]-propyl}-propionamide;

(165): N-{3-[4-amino-6-(5-chloro-1H,3H-benzo[de]isochromen-6-yl)-[1,3,5]triazin-2-ylsulfanyl]-propyl}-N-methyl-acetamide;

(166): N-{3-[4-amino-6-(5-chloro-1H,3H-benzo[de]isochromen-6-yl)-[1,3,5]triazin-2-ylsulfanyl]-propyl}-3-hydroxypropionamide;

(167): N-{3-[4-amino-6-(5-chloro-1H,3H-benzo[de]isochromen-6-yl)-[1,3,5]triazin-2-ylsulfanyl]-propyl}-3,4-dihydroxy-butylamide;

(168): N-{3-[4-amino-6-(5-chloro-1H,3H-benzo[de]isochromen-6-yl)-[1,3,5]triazin-2-ylsulfanyl]-propyl}-4-hydroxy-3-hydroxymethyl-butylamide;

(169): 1-{3-[4-amino-6-(5-chloro-1H,3H-benzo[de]isochromen-6-yl)-[1,3,5]triazin-2-ylsulfanyl]-propyl}-pyrrolidin-2-one;

(170): cyclopropane carboxylic acid {3-[4-amino-6-(5-chloro-1H,3H-benzo[de]isochromen-6-yl)-[1,3,5]triazin-2-ylsulfanyl]-propyl}-amide;

(171): cyclopentane carboxylic acid {3-[4-amino-6-(5-chloro-1H,3H-benzo[de]isochromen-6-yl)-[1,3,5]triazin-2-ylsulfanyl]-propyl}-amide;

(172): tetrahydro-pyran-4-carboxylic acid {3-[4-amino-6-(5-chloro-1H,3H-benzo[de]isochromen-6-yl)-[1,3,5]triazin-2-ylsulfanyl]-propyl}-amide;

(173): piperidin-4-carboxylic acid {3-[4-amino-6-(5-chloro-1H,3H-benzo[de]isochromen-6-yl)-[1,3,5]triazin-2-ylsulfanyl]-propyl}-amide;

(174): N-{2-[4-amino-6-(5-chloro-1H,3H-benzo[de]isochromen-6-yl)-[1,3,5]triazin-2-ylsulfanyl]-ethyl}-formamide;

(175): {2-[4-amino-6-(5-chloro-1H,3H-benzo[de]isochromen-6-yl)-[1,3,5]triazin-2-ylsulfanyl]-ethyl}-urea;

(176): 1-{2-[4-amino-6-(5-chloro-1H,3H-benzo[de]isochromen-6-yl)-[1,3,5]triazin-2-ylsulfanyl]-ethyl}-3-methylurea;

(177): {2-[4-amino-6-(5-chloro-1H,3H-benzo[de]isochromen-6-yl)-[1,3,5]triazin-2-ylsulfanyl]-ethyl}-carbamic acid methyl ester;

(178): N-{2-[4-amino-6-(5-chloro-1H,3H-benzo[de]isochromen-6-yl)-[1,3,5]triazin-2-ylsulfanyl]-ethyl}-methanesulfonamide;

(179): N-{3-[4-amino-6-(5-chloro-1H,3H-benzo[de]isochromen-6-yl)-[1,3,5]triazin-2-ylsulfanyl]-ethyl}-amino sulfonamide;

(180): N-{3-[4-amino-6-(5-chloro-1H,3H-benzo[de]isochromen-6-yl)-[1,3,5]triazin-2-ylsulfanyl]-propyl}-formamide;

(181): {3-[4-amino-6-(5-chloro-1H,3H-benzo[de]isochromen-6-yl)-[1,3,5]triazin-2-ylsulfanyl]-propyl}-urea;

(182): 1-{3-[4-amino-6-(5-chloro-1H,3H-benzo[de]isochromen-6-yl)-[1,3,5]triazin-2-ylsulfanyl]-propyl}-3-methylurea;
(183): {3-[4-amino-6-(5-chloro-1H,3H-benzo[de]isochromen-6-yl)-[1,3,5]triazin-2-ylsulfanyl]-propyl}-carbamic acid methyl ester;
(184): N-{3-[4-amino-6-(5-chloro-1H,3H-benzo[de]isochromen-6-yl)-[1,3,5]triazin-2-ylsulfanyl]-propyl}-methanesulfonamide;
(185): N-{3-[4-amino-6-(5-chloro-1H,3H-benzo[de]isochromen-6-yl)-[1,3,5]triazin-2-ylsulfanyl]-propyl}-aminosulfonamide;
(186): 4-(5-chloro-1H,3H-benzo[de]isochromen-6-yl)-6-(2-methyl-oxazol-4-ylmethylsulfanyl)-[1,3,5]triazin-2-ylamine;
(187): N-{2-[4-amino-6-(5-chloro-1H,3H-benzo[de]isochromen-6-yl)-[1,3,5]triazin-2-ylsulfanyl]-ethyl}-3-dimethylaminopriopionamide;
(188): N-{2-[4-amino-6-(5-chloro-1H,3H-benzo[de]isochromen-6-yl)-[1,3,5]triazin-2-ylsulfanyl]-ethyl}-isonicotinamide;
(189): 1H-imidazole-2-carboxylic acid {2-[4-amino-6-(5-chloro-1H,3H-benzo[de]isochromen-6-yl)-[1,3,5]triazin-2-ylsulfanyl]-ethyl}-amide;
(190): 4-(5-chloro-1H,3H-benzo[de]isochromen-6-yl)-6-(2-dimethylamino-ethylsulfanyl)-[1,3,5]triazin-2-ylamine;
(191): 4-(2-aminoethylsulfanyl)-6-(5-chloro-1H,3H-benzo[de]isochromen-6-yl)-[1,3,5]triazin-2-ylamine;
(192): 4-(3-aminopropylsulfanyl)-6-(5-chloro-1H,3H-benzo[de]isochromen-6-yl)-[1,3,5]triazin-2-ylamine;
(193): 4-(5-chloro-1H,3H-benzo[de]isochromen-6-yl)-6-(2-methylaminoethylsulfanyl)-[1,3,5]triazin-2-ylamine;
(194): 4-(5-chloro-1H,3H-benzo[de]isochromen-6-yl)-6-(3-methylaminopropylsulfanyl)-[1,3,5]triazin-2-ylamine;
(195): 4-(5-chloro-1H,3H-benzo[de]isochromen-6-yl)-6-(2-pyrrolidin-1-yl-ethylsulfanyl)-[1,3,5]triazin-2-ylamine;
(196): 4-(5-chloro-1H,3H-benzo[de]isochromen-6-yl)-6-(3-pyrrolidin-1-yl-propylsulfanyl)-[1,3,5]triazin-2-ylamine;
(197): 4-(5-chloro-1H,3H-benzo[de]isochromen-6-yl)-6-(2-morpholin-4-yl-ethylsulfanyl)-[1,3,5]triazin-2-ylamine;
(198): 4-(5-chloro-1H,3H-benzo[de]isochromen-6-yl)-6-(3-morpholin-4-yl-propylsulfanyl)-[1,3,5]triazin-2-ylamine;
(199): 4-(5-chloro-1H,3H-benzo[de]isochromen-6-yl)-6-(2-piperazin-1-yl-ethylsulfanyl)-[1,3,5]triazin-2-ylamine;
(200): 4-(5-chloro-1H,3H-benzo[de]isochromen-6-yl)-6-(3-piperazin-1-yl-propylsulfanyl)-[1,3,5]triazin-2-ylamine;
(201): 4-(5-chloro-1H,3H-benzo[de]isochromen-6-yl)-6-[2-(pyridin-2-ylamino)-ethylsulfanyl]-[1,3,5]triazin-2-ylamine;
(202): 4-(5-chloro-1H,3H-benzo[de]isochromen-6-yl)-6-[2-(oxazol-4-ylamino)-ethylsulfanyl]-[1,3,5]triazin-2-ylamine;
(203): 2-[4-amino-6-(5-chloro-1H,3H-benzo[de]isochromen-6-yl)-[1,3,5]triazin-2-ylsulfanyl]-2,2-difluoroacetamide;
(204): 2-[4-amino-6-(5-chloro-1H,3H-benzo[de]isochromen-6-yl)-[1,3,5]triazin-2-ylsulfanyl]-N-methyl-acetamide;
(205): 3-[4-amino-6-(5-chloro-1H,3H-benzo[de]isochromen-6-yl)-[1,3,5]triazin-2-ylsulfanyl]-N-methyl-propionamide;
(206): 2-[4-amino-6-(5-chloro-1H,3H-benzo[de]isochromen-6-yl)-[1,3,5]triazin-2-ylsulfanyl]-N-ethyl-acetamide;
(207): 3-[4-amino-6-(5-chloro-1H,3H-benzo[de]isochromen-6-yl)-[1,3,5]triazin-2-ylsulfanyl]-N-ethyl-propionamide;
(208): 2-[4-amino-6-(5-chloro-1H,3H-benzo[de]isochromen-6-yl)-[1,3,5]triazin-2-ylsulfanyl]-N,N-dim ethyl-acetamide;
(209): 3-[4-amino-6-(5-chloro-1H,3H-benzo[de]isochromen-6-yl)-[1,3,5]triazin-2-ylsulfanyl]-N,N-dim ethyl-propionamide;
(210): 2-[4-amino-6-(5-chloro-1H,3H-benzo[de]isochromen-6-yl)-[1,3,5]triazin-2-ylsulfanyl]-N-isopropyl-acetamide;
(211): 3-[4-amino-6-(5-chloro-1H,3H-benzo[de]isochromen-6-yl)-[1,3,5]triazin-2-ylsulfanyl]-N-isopropyl-propionamide;
(212): 2-[4-amino-6-(5-chloro-1H,3H-benzo[de]isochromen-6-yl)-[1,3,5]triazin-2-ylsulfanyl]-N-propyl-acetamide;
(213): 3-[4-amino-6-(5-chloro-1H,3H-benzo[de]isochromen-6-yl)-[1,3,5]triazin-2-ylsulfanyl]-N-propyl-propionamide;
(214): 2-[4-amino-6-(5-chloro-1H,3H-benzo[de]isochromen-6-yl)-[1,3,5]triazin-2-ylsulfanyl]-N-cyclopentyl-acetamide;
(215): 3-[4-amino-6-(5-chloro-1H,3H-benzo[de]isochromen-6-yl)-[1,3,5]triazin-2-ylsulfanyl]-N-cyclopentyl-propionamide;
(216): 2-[4-amino-6-(5-chloro-1H,3H-benzo[de]isochromen-6-yl)-[1,3,5]triazin-2-ylsulfanyl]-N-(tetrahydro-pyran-4-yl)-acetamide;
(217): 3-[4-amino-6-(5-chloro-1H,3H-benzo[de]isochromen-6-yl)-[1,3,5]triazin-2-ylsulfanyl]-N-(tetrahydro-pyran-4-yl)-propionamide;
(218): 2-[4-amino-6-(5-chloro-1H,3H-benzo[de]isochromen-6-yl)-[1,3,5]triazin-2-ylsulfanyl]-N-pyridin-4-yl-acetamide;
(219): 3-[4-amino-6-(5-chloro-1H,3H-benzo[de]isochromen-6-yl)-[1,3,5]triazin-2-ylsulfanyl]-N-pyridin-4-yl-propionamide;
(220): 2-[4-amino-6-(5-chloro-1H,3H-benzo[de]isochromen-6-yl)-[1,3,5]triazin-2-ylsulfanyl]-N-thiazol-2-yl-acetamide;
(221): 3-[4-amino-6-(5-chloro-1H,3H-benzo[de]isochromen-6-yl)-[1,3,5]triazin-2-ylsulfanyl]-N-thiazol-2-yl-propionamide;
(222): 2-[4-amino-6-(5-chloro-1H,3H-benzo[de]isochromen-6-yl)-[1,3,5]triazin-2-ylsulfanyl]-1-pyrrolidin-1-yl-ethanone;
(223): 3-[4-amino-6-(5-chloro-1H,3H-benzo[de]isochromen-6-yl)-[1,3,5]triazin-2-ylsulfanyl]-1-pyrrolidin-1-yl-propan-1-one;
(224): 2-[4-amino-6-(5-chloro-1H,3H-benzo[de]isochromen-6-yl)-[1,3,5]triazin-2-ylsulfanyl]-1-morpholin-4-yl-ethanone;
(225): 3-[4-amino-6-(5-chloro-1H,3H-benzo[de]isochromen-6-yl)-[1,3,5]triazin-2-ylsulfanyl]-1-morpholin-4-yl-propan-1-one;
(226): 2-[4-amino-6-(5-chloro-1H,3H-benzo[de]isochromen-6-yl)-[1,3,5]triazin-2-ylsulfanyl]-1-piperazin-1-yl-ethanone;
(227): 3-[4-amino-6-(5-chloro-1H,3H-benzo[de]isochromen-6-yl)-[1,3,5]triazin-2-ylsulfanyl]-1-(4-methyl-piperazin-1-yl)-propan-1-one;
(228): 3-[4-amino-6-(5-chloro-1H,3H-benzo[de]isochromen-6-yl)-[1,3,5]triazin-2-ylsulfanyl]-1-piperazin-1-yl-propan-1-one;
(229): 2-[4-amino-6-(5-chloro-1H,3H-benzo[de]isochromen-6-yl)-[1,3,5]triazin-2-ylsulfanyl]-N-thiazol-2-yl-acetamide;

(230): 3-[4-amino-6-(5-chloro-1H,3H-benzo[de]isochromen-6-yl)-[1,3,5]triazin-2-ylsulfanyl]-N-thiazol-2-yl-propionamide;
(231): 3-[4-amino-6-(5-chloro-1H,3H-benzo[de]isochromen-6-yl)-[1,3,5]triazin-2-ylsulfanyl]-N-isopropyl-propionamide;
(232): 2-[4-amino-6-(5-chloro-1H,3H-benzo[de]isochromen-6-yl)-[1,3,5]triazin-2-ylsulfanyl]-N-isopropyl-acetamide;
(233): 2-[4-amino-6-(5-chloro-1H,3H-benzo[de]isochromen-6-yl)-[1,3,5]triazin-2-ylsulfanyl]-N-(2-hydroxy-ethyl)-acetamide;
(234): 3-[4-amino-6-(5-chloro-1H,3H-benzo[de]isochromen-6-yl)-[1,3,5]triazin-2-ylsulfanyl]-N-(2-hydroxy-ethyl)-propionamide;
(235): 2-[4-amino-6-(5-chloro-1H,3H-benzo[de]isochromen-6-yl)-[1,3,5]triazin-2-ylsulfanyl]-N-(2,3-dihydroxypropyl)-acetamide;
(236): 3-[4-amino-6-(5-chloro-1H,3H-benzo[de]isochromen-6-yl)-[1,3,5]triazin-2-ylsulfanyl]-N-(2,3-dihydroxypropyl)-propionamide;
(237): 2-[4-amino-6-(5-chloro-1H,3H-benzo[de]isochromen-6-yl)-[1,3,5]triazin-2-ylsulfanyl]-N-(3-hydroxy-2-hydroxymethyl-propyl)-acetamide;
(238): 3-[4-amino-6-(5-chloro-1H,3H-benzo[de]isochromen-6-yl)-[1,3,5]triazin-2-ylsulfanyl]-N-(3-hydroxy-2-hydroxymethyl-propyl)-propionamide;
(239): 4-[4-amino-6-(5-chloro-1H,3H-benzo[de]isochromen-6-yl)-[1,3,5]triazin-2-ylsulfanyl]-butylamide;
(240): 4-[4-amino-6-(5-chloro-1H,3H-benzo[de]isochromen-6-yl)-[1,3,5]triazin-2-ylsulfanyl]-N-methyl-butylamide;
(241): 4-[4-amino-6-(5-chloro-1H,3H-benzo[de]isochromen-6-yl)-[1,3,5]triazin-2-ylsulfanyl]-N,N-dimethyl-butylamide;
(242): 4-[4-amino-6-(5-chloro-1H,3H-benzo[de]isochromen-6-yl)-[1,3,5]triazin-2-ylsulfanyl]-N-ethyl-butylamide;
(243): 4-[4-amino-6-(5-chloro-1H,3H-benzo[de]isochromen-6-yl)-[1,3,5]triazin-2-ylsulfanyl]-1-pyrrolidin-1-yl-butan-1-one;
(244): 4-[4-amino-6-(5-chloro-1H,3H-benzo[de]isochromen-6-yl)-[1,3,5]triazin-2-ylsulfanyl]-1-morpholin-4-yl-butan-1-one;
(245): 4-[4-amino-6-(5-chloro-1H,3H-benzo[de]isochromen-6-yl)-[1,3,5]triazin-2-ylsulfanyl]-1-piperazin-1-yl-butan-1-one;
(246): 4-[4-amino-6-(5-chloro-1H,3H-benzo[de]isochromen-6-yl)-[1,3,5]triazin-2-ylsulfanyl]-N-(2-hydroxy-ethyl)-butylamide;
(247): 4-[4-amino-6-(5-chloro-1H,3H-benzo[de]isochromen-6-yl)-[1,3,5]triazin-2-ylsulfanyl]-N-(tetrahydro-pyran-4-yl)-butylamide;
(248): 4-[4-amino-6-(5-chloro-1H,3H-benzo[de]isochromen-6-yl)-[1,3,5]triazin-2-ylsulfanyl]-N-piperidin-4-yl-butylamide;
(249): 4-[4-amino-6-(5-chloro-1H,3H-benzo[de]isochromen-6-yl)-[1,3,5]triazin-2-ylsulfanyl]-N-pyridin-4-yl-butylamide;
(250): 4-[4-amino-6-(5-chloro-1H,3H-benzo[de]isochromen-6-yl)-[1,3,5]triazin-2-ylsulfanyl]-N-thiazol-2-yl-butylamide;
(251): 1-[4-amino-6-(5-chloro-1H,3H-benzo[de]isochromen-6-yl)-[1,3,5]triazin-2-ylsulfanyl]-propan-2-one;
(252): 4-[4-amino-6-(5-chloro-1H,3H-benzo[de]isochromen-6-yl)-[1,3,5]triazin-2-ylsulfanyl]-butan-2-one;
(253): N-{2-[4-amino-6-(5-chloro-1H,3H-benzo[de]isochromen-6-yl)-[1,3,5]triazin-2-ylsulfanyl]-acetyl}-acetamide;
(254): N-{3-[4-amino-6-(5-chloro-1H,3H-benzo[de]isochromen-6-yl)-[1,3,5]triazin-2-ylsulfanyl]-propionyl}-acetamide;
(255): N-{4-[4-amino-6-(5-chloro-1H,3H-benzo[de]isochromen-6-yl)-[1,3,5]triazin-2-ylsulfanyl]-butyryl}-acetamide;
(256): N-{2-[4-amino-6-(5-chloro-1H,3H-benzo[de]isochromen-6-yl)-[1,3,5]triazin-2-ylsulfanyl]-acetyl}-methanesulfonamide;
(257): N-{3-[4-amino-6-(5-chloro-1H,3H-benzo[de]isochromen-6-yl)-[1,3,5]triazin-2-ylsulfanyl]-propionyl}-methanesulfonamide;
(258): N-{4-[4-amino-6-(5-chloro-1H,3H-benzo[de]isochromen-6-yl)-[1,3,5]triazin-2-ylsulfanyl]-butyryl}-methanesulfonamide;
(259): 4-(5-chloro-1H,3H-benzo[de]isochromen-6-yl)-6-(oxazol-2-ylmethylsulfanyl)-[1,3,5]triazin-2-yl amine;
(260): 4-(5-chloro-1H,3H-benzo[de]isochromen-6-yl)-6-(2-oxazol-2-yl-ethylsulfanyl)-[1,3,5]triazin-2-ylamine;
(261): 1-[4-amino-6-(5-chloro-1H,3H-benzo[de]isochromen-6-yl)-[1,3,5]triazin-2-ylsulfanyl]-propan-2-one O-methyl-oxime;
(262): 4-[4-amino-6-(5-chloro-1H,3H-benzo[de]isochromen-6-yl)-[1,3,5]triazin-2-ylsulfanyl]-butan-2-one O-methyl-oxime;
(263): [4-amino-6-(5-chloro-1H,3H-benzo[de]isochromen-6-yl)-[1,3,5]triazin-2-ylsulfanyl]-acetonitrile;
(264): 3-[4-amino-6-(5-chloro-1H,3H-benzo[de]isochromen-6-yl)-[1,3,5]triazin-2-ylsulfanyl]-propionitrile;
(265): 4-[4-amino-6-(5-chloro-1H,3H-benzo[de]isochromen-6-yl)-[1,3,5]triazin-2-ylsulfanyl]-butyronitrile;
(266): 4-(5-chloro-1H,3H-benzo[de]isochromen-6-yl)-6-(2-methoxy-ethylsulfanyl)-[1,3,5]triazin-2-ylamine;
(267): 4-(5-chloro-1H,3H-benzo[de]isochromen-6-yl)-6-(3-methoxypropylsulfanyl)-[1,3,5]triazin-2-ylamine;
(268): 4-(5-chloro-1H,3H-benzo[de]isochromen-6-yl)-6-[2-(2-methoxyethoxy)-ethylsulfanyl]-[1,3,5]triazin-2-ylamine;
(269): 4-[4-amino-6-(5-chloro-1H,3H-benzo[de]isochromen-6-yl)-[1,3,5]triazin-2-ylsulfanyl]-butan-1-ol;
(270): carbamic acid 2-[4-amino-6-(5-chloro-1H,3H-benzo[de]isochromen-6-yl)-[1,3,5]triazin-2-ylsulfanyl]-ethyl ester;
(271): carbamic acid 3-[4-amino-6-(5-chloro-1H,3H-benzo[de]isochromen-6-yl)-[1,3,5]triazin-2-ylsulfanyl]-propyl ester;
(272): carbamic acid 4-[4-amino-6-(5-chloro-1H,3H-benzo[de]isochromen-6-yl)-[1,3,5]triazin-2-ylsulfanyl]-butyl ester;
(273): sulfamic acid 2-[4-amino-6-(5-chloro-1H,3H-benzo[de]isochromen-6-yl)-[1,3,5]triazin-2-ylsulfanyl]-ethyl ester;
(274): sulfamic acid 3-[4-amino-6-(5-chloro-1H,3H-benzo[de]isochromen-6-yl)-[1,3,5]triazin-2-ylsulfanyl]-propyl ester;
(275): sulfamic acid 4-[4-amino-6-(5-chloro-1H,3H-benzo[de]isochromen-6-yl)-[1,3,5]triazin-2-ylsulfanyl]-butyl ester;
(276): 3-[4-amino-6-(5-chloro-1H,3H-benzo[de]isochromen-6-yl)-[1,3,5]triazin-2-ylsulfanyl]-propane-1,2-diol;
(277): 2-[4-amino-6-(5-chloro-1H,3H-benzo[de]isochromen-6-yl)-[1,3,5]triazin-2-ylsulfanylmethyl]-propane-1,3-diol;

(278): thiocarbamic acid 2-[4-amino-6-(5-chloro-1H,3H-benzo[de]isochromen-6-yl)-[1,3,5]triazin-2-ylsulfanyl]-ethyl ester;
(279): thiocarbamic acid 3-[4-amino-6-(5-chloro-1H,3H-benzo[de]isochromen-6-yl)-[1,3,5]triazin-2-ylsulfanyl]-propyl ester;
(280): 4-(5-chloro-1H,3H-benzo[de]isochromen-6-yl)-6-(2-methanesulfonyl-ethylsulfanyl)-[1,3,5]triazin-2-ylamine;
(281): 4-(5-chloro-1H,3H-benzo[de]isochromen-6-yl)-6-(3-methanesulfonyl-propylsulfanyl)-[1,3,5]triazin-2-ylamine;
(282): 3-[4-amino-6-(5-chloro-1H,3H-benzo[de]isochromen-6-yl)-[1,3,5]triazin-2-ylsulfanyl]-propan-1-sulfonamide;
(283): 2-[4-amino-6-(5-chloro-1H,3H-benzo[de]isochromen-6-yl)-[1,3,5]triazin-2-ylsulfanyl]-ethanesulfonamide;
(284): 4-(5-chloro-1H,3H-benzo[de]isochromen-6-yl)-6-(3,3,3-trifluoro-propylsulfanyl)-[1,3,5]triazin-2-ylamine;
(285): 4-(5-chloro-1H,3H-benzo[de]isochromen-6-yl)-6-(4,4,4-trifluoro-butylsulfanyl)-[1,3,5]triazin-2-ylamine;
(286): 4-(5-chloro-1H,3H-benzo[de]isochromen-6-yl)-6-(3-fluoropropylsulfanyl)-[1,3,5]triazin-2-ylamine;
(287): 4-(5-chloro-1H,3H-benzo[de]isochromen-6-yl)-6-(4-fluorobutylsulfanyl)-[1,3,5]triazin-2-ylamine;
(288): 4-(5-chloro-1H,3H-benzo[de]isochromen-6-yl)-6-(oxazol-2-ylmethylsulfanyl)-[1,3,5]triazin-2-yl amine;
(289): 4-(5-chloro-1H,3H-benzo[de]isochromen-6-yl)-6-(thiazol-2-ylmethylsulfanyl)-[1,3,5]triazin-2-yl amine;
(290): 4-(5-chloro-1H,3H-benzo[de]isochromen-6-yl)-6-(2-thiazol-2-yl-ethylsulfanyl)-[1,3,5]triazin-2-ylamine;
(291): 4-(5-chloro-1H,3H-benzo[de]isochromen-6-yl)-6-(1H-imidazol-2-ylmethylsulfanyl)-[1,3,5]triazin-2-ylamine;
(292): 4-(5-chloro-1H,3H-benzo[de]isochromen-6-yl)-6-[2-(1H-imidazol-2-yl)-ethylsulfanyl]-[1,3,5]triazin-2-ylamine;
(293): 4-(5-chloro-1H,3H-benzo[de]isochromen-6-yl)-6-(2-oxazol-3-yl-ethylsulfanyl)-[1,3,5]triazin-2-ylamine;
(294): 4-(5-chloro-1H,3H-benzo[de]isochromen-6-yl)-6-(pyridin-4-ylmethylsulfanyl)-[1,3,5]triazin-2-ylamine;
(295): 4-(5-chloro-1H,3H-benzo[de]isochromen-6-yl)-6-(2-pyridin-4-yl-ethylsulfanyl)-[1,3,5]triazin-2-ylamine;
(296): 4-(5-chloro-1H,3H-benzo[de]isochromen-6-yl)-6-(pyridin-2-ylmethylsulfanyl)-[1,3,5]triazin-2-ylamine;
(297): 4-(5-chloro-1H,3H-benzo[de]isochromen-6-yl)-6-(2-pyridin-2-yl-ethylsulfanyl)-[1,3,5]triazin-2-ylamine;
(298): 2-acetylamino-3-[4-amino-6-(5-chloro-1H,3H-benzo[de]isochromen-6-yl)-[1,3,5]triazin-2-ylsulfanyl]-propionamide;
(299): 2-acetylamino-3-[4-amino-6-(5-chloro-1H,3H-benzo[de]isochromen-6-yl)-[1,3,5]triazin-2-ylsulfanyl]-N-methyl-propionamide;
(300): 2-acetylamino-3-[4-amino-6-(5-chloro-1H,3H-benzo[de]isochromen-6-yl)-[1,3,5]triazin-2-ylsulfanyl]-N-ethyl-propionamide;
(301): 2-acetylamino-3-[4-amino-6-(5-chloro-1H,3H-benzo[de]isochromen-6-yl)-[1,3,5]triazin-2-ylsulfanyl]-N,N-dimethyl-propionamide;
(302): 2-amino-3-[4-amino-6-(5-chloro-1H,3H-benzo[de]isochromen-6-yl)-[1,3,5]triazin-2-ylsulfanyl]-N-methyl-propionamide;
(303): 2-amino-3-[4-amino-6-(5-chloro-1H,3H-benzo[de]isochromen-6-yl)-[1,3,5]triazin-2-ylsulfanyl]-N,N-dimethyl-propionamide;
(304): 2-[4-amino-6-(5-chloro-1H,3H-benzo[de]isochromen-6-yl)-[1,3,5]triazin-2-ylsulfanyl]-N-(2-methoxy-ethyl)-acetamide;
(305): 2-[4-amino-6-(5-chloro-1H,3H-benzo[de]isochromen-6-yl)-[1,3,5]triazin-2-ylsulfanyl]-N-cyano methyl-acetamide;
(306): 2-[4-amino-6-(5-chloro-1H,3H-benzo[de]isochromen-6-yl)-[1,3,5]triazin-2-ylsulfanyl]-N-(2-hydroxy-1-hydroxymethyl-ethyl)-acetamide;
(307): 2-[4-amino-6-(5-chloro-1H,3H-benzo[de]isochromen-6-yl)-[1,3,5]triazin-2-ylsulfanyl]-N-(2-diethylamino-ethyl)-acetamide;
(308): 2-[4-amino-6-(5-chloro-1H,3H-benzo[de]isochromen-6-yl)-[1,3,5]triazin-2-ylsulfanyl]-N-(1-methyl-piperidin-4-yl)-acetamide;
(309): 3-[4-amino-6-(5-chloro-1H,3H-benzo[de]isochromen-6-yl)-[1,3,5]triazin-2-ylsulfanyl]-N-(2-methoxy-ethyl)-propionamide;
(310): 1-{2-[4-amino-6-(5-chloro-1H,3H-benzo[de]isochromen-6-yl)-[1,3,5]triazin-2-ylsulfanyl]-ethyl}-imidazolin-2-one;
(311): 3-{2-[4-amino-6-(5-chloro-1H,3H-benzo[de]isochromen-6-yl)-[1,3,5]triazin-2-ylsulfanyl]-ethyl}-oxazolidin-2-one;
(312): 2-[4-amino-6-(5-chloro-1H,3H-benzo[de]isochromen-6-yl)-[1,3,5]triazin-2-ylsulfanyl]-1-pyrazin-2-yl-ethanone;
(313): 3-{2-[4-amino-6-(5-chloro-1H,3H-benzo[de]isochromen-6-yl)-[1,3,5]triazin-2-ylsulfanyl]-acetyl}-oxazolidin-2-one;
(314): 2-[2-amino-6-(5-chloro-1H,3H-benzo[de]isochromen-6-yl)-pyrimidin-4-ylsulfanyl]-acetamide;
(315): 2-[2-amino-6-(5-chloro-1H,3H-benzo[de]isochromen-6-yl)-pyrimidin-4-ylsulfanyl]-N-cyanomethyl-acetamide;
(316): 3-[2-amino-6-(5-chloro-1H,3H-benzo[de]isochromen-6-yl)-pyrimidin-4-ylsulfanyl]-propionamide;
(317): 3-[2-amino-6-(5-chloro-1H,3H-benzo[de]isochromen-6-yl)-pyrimidin-4-ylsulfanyl]-N-(2-hydroxyethyl)-propionamide;
(318): 3-[2-amino-6-(5-chloro-1H,3H-benzo[de]isochromen-6-yl)-pyrimidin-4-ylsulfanyl]-N-methyl-propionamide;
(319): 3-[2-amino-6-(5-chloro-1H,3H-benzo[de]isochromen-6-yl)-pyrimidin-4-ylsulfanyl]-N-(2-methoxy-ethyl)-propionamide;
(320): 3-[2-amino-6-(5-chloro-1H,3H-benzo[de]isochromen-6-yl)-pyrimidin-4-ylsulfanyl]-N—((R)-2,3-dihydroxy-propyl)-propionamide;
(321): 3-[2-amino-6-(5-chloro-1H,3H-benzo[de]isochromen-6-yl)-pyrimidin-4-ylsulfanyl]-2-methyl-propionamide;
(322): 3-[2-amino-6-(5-chloro-1H,3H-benzo[de]isochromen-6-yl)-pyrimidin-4-ylsulfanyl]-2,N-dimethyl-propionamide;
(323): 3-[2-amino-6-(5-chloro-1H,3H-benzo[de]isochromen-6-yl)-pyrimidin-4-ylsulfanyl]-N-(2-hydroxyethyl)-2-methyl-propionamide;
(324): 4-[2-amino-6-(5-chloro-1H,3H-benzo[de]isochromen-6-yl)-pyrimidin-4-ylsulfanyl]-butylamide;
(325): carbamic acid 2-[2-amino-6-(5-chloro-1H,3H-benzo[de]isochromen-6-yl)-pyrimidin-4-ylsulfanyl]-ethyl ester;
(326): 3-[2-amino-6-(5-chloro-1H,3H-benzo[de]isochromen-6-yl)-pyrimidin-4-ylsulfanyl]-propan-1-ol;
(327): N-{2-[2-amino-6-(5-chloro-1H,3H-benzo[de]isochromen-6-yl)-pyrimidin-4-ylsulfanyl]-ethyl}-acetamide;
(328): N-{3-[2-amino-6-(5-chloro-1H,3H-benzo[de]isochromen-6-yl)-pyrimidin-4-ylsulfanyl]-propyl}-acetamide;
(329): N-{2-[2-amino-6-(5-chloro-1H,3H-benzo[de]isochromen-6-yl)-pyrimidin-4-ylsulfanyl]-ethyl}-methanesulfonamide;

(330): 5-[2-amino-6-(5-chloro-1H,3H-benzo[de]isochromen-6-yl)-pyrimidin-4-ylsulfanylmethyl]-oxazolidin-2-one;
(331): N-{2-[2-amino-6-(5-chloro-1H,3H-benzo[de]isochromen-6-yl)-pyrimidin-4-ylsulfanyl]-ethyl}-2-hydroxy-acetamide;
(332): {2-[2-amino-6-(5-chloro-1H,3H-benzo[de]isochromen-6-yl)-pyrimidin-4-ylsulfanyl]-ethyl}-urea;
(333): 2-[4-amino-6-(5-chloro-1H,3H-benzo[de]isochromen-6-yl)-[1,3,5]triazin-2-ylsulfanyl]-N-cyano methyl-acetamide;
(334): 3-[4-amino-6-(5-chloro-1H,3H-benzo[de]isochromen-6-yl)-[1,3,5]triazin-2-ylsulfanyl]-N-(2-methoxy-ethyl)-propionamide;
(335): 3-[4-amino-6-(5-chloro-1H,3H-benzo[de]isochromen-6-yl)-[1,3,5]triazin-2-ylsulfanyl]-N—((R)-2,3-dihydroxy-propyl)-propionamide;
(336): 3-[4-amino-6-(5-chloro-1H,3H-benzo[de]isochromen-6-yl)-[1,3,5]triazin-2-ylsulfanyl]-2-methyl-propionamide;
(337): 3-[4-amino-6-(5-chloro-1H,3H-benzo[de]isochromen-6-yl)-[1,3,5]triazin-2-ylsulfanyl]-2,N-dimethyl-propionamide;
(338): 3-[4-amino-6-(5-chloro-1H,3H-benzo[de]isochromen-6-yl)-[1,3,5]triazin-2-ylsulfanyl]-N-(2-hydroxy-ethyl)-2-methyl-propionamide;
(339): 4-[4-amino-6-(5-chloro-1H,3H-benzo[de]isochromen-6-yl)-[1,3,5]triazin-2-ylsulfanyl]-butyramide;
(340): 3-[4-amino-6-(5-chloro-1H,3H-benzo[de]isochromen-6-yl)-[1,3,5]triazin-2-ylsulfanyl]-propan-1-ol;
(341): 5-[4-amino-6-(5-chloro-1H,3H-benzo[de]isochromen-6-yl)-[1,3,5]triazin-2-ylsulfanylmethyl]-oxazolidin-2-one;
(342): N-{2-[4-amino-6-(5-chloro-1H,3H-benzo[de]isochromen-6-yl)-[1,3,5]triazin-2-ylsulfanyl]-ethyl}-2-hydroxy-acetamide; and
(343): 4-[4-amino-6-(5-chloro-1H,3H-2-thia-phenalen-6-yl]-[1,3,5]triazin-2-ylsulfanyl]-butyramide.

Among them, preferred compounds of the present invention include:
(4): 4-(5-benzyloxy-2,4-dichlorophenyl)-6-benzylsulfanyl [1,3,5]triazin-2-ylamine;
(15): (5-{4-amino-6-[2-methoxy-4-(4-methyl-piperazin-1-carbonyl)-phenylsulfanyl]-[1,3,5]triazin-2-yl}-2,4-dichlorophenoxy)-acetonitrile;
(24): 4-(2,4-dichloro-5-pyrimidin-2-yl-phenyl)-6-methylsulfanyl-[1,3,5]triazin-2-ylamine;
(25): N-{2-[4-amino-6-(2,4-dichloro-5-pyrimidin-2-yl-phenyl)-[1,3,5]triazin-2-ylsulfanyl]-ethyl}-acetamide;
(26): 5-(4-amino-6-benzylsulfanyl-[1,3,5]triazin-2-yl)-2,4-dichlorobenzamide;
(28): 5-(4-amino-6-benzylsulfanyl-[1,3,5]triazin-2-yl)-2,4-dichloro-N-(2-hydroxy-1-hydroxymethylethyl)-benzamide;
(37): 5-[4-amino-6-(2,3-dihydroxypropylsulfanyl)-[1,3,5]triazin-2-yl]-2,4-dimethylbenzoic acid methyl ester;
(39): 4-(2,4-dichlorophenyl)-6-(2,5-dimethoxyphenylsulfanyl)-pyrimidin-2-ylamine;
(44): 3-{4-[2-amino-6-(2,5-dimethoxyphenylsulfanyl)-pyrimidin-4-yl]-3-methylphenoxy}-propan-1-ol;
(45): {4-[2-amino-6-(2,5-dimethoxyphenylsulfanyl)-pyrimidin-4-yl]-3-methylphenoxy}-acetonitrile;
(46): 2-{4-[2-amino-6-(2,5-dimethoxyphenylsulfanyl)-pyrimidin-4-yl]-3-methylphenoxy}-acetamide;
(48): 4-(5-benzyloxy-2,4-dichlorophenyl)-6-(2,5-dimethoxyphenylsulfanyl)-pyrimidin-2-ylamine;
(52): {5-[2-amino-6-(2,5-dimethoxyphenylsulfanyl)-pyrimidin-4-yl]-2,4-dichlorophenyoxy}-acetonitrile;
(54): {5-[2-amino-6-(1H-benzimidazol-2-ylsulfanyl)-pyrimidin-4-yl]-2,4-dichlorophenoxy}-acetonitrile;
(55): 2-[2-amino-6-(2,4-dichloro-5-cyanomethoxyphenyl)-pyrimidin-4-ylsulfanyl]-3H-imidazol-4-carboxylic acid ethyl ester;
(59): N-{2-[4-amino-6-(2,4-dichloro-5-cyanomethoxy-phenyl)-[1,3,5]triazin-2-ylsulfanyl]-ethyl}-acetamide;
(63): {5-[4-amino-6-(3-morpholin-4-yl-3-oxo-propylsulfanyl)-[1,3,5]triazin-2-yl]-2,4-dichlorophenoxy}-acetonitrile;
(82): 4-(5-chloro-1H,3H-benzo[de]isochromen-6-yl)-6-(3,4-dimethoxyphenoxy)-[1,3,5]triazin-2-ylamine;
(92): 4-(5-chloro-1H,3H-benzo[de]isochromen-6-yl)-6-cyclohexylsulfanyl-[1,3,5]triazin-2-ylamine;
(111): [4-amino-6-(5-chloro-1H,3H-benzo[de]isochromen-6-yl)-[1,3,5]triazin-2-ylsulfanyl]-acetic acid methyl ester;
(113): N-{2-[4-amino-6-(5-chloro-1H,3H-benzo[de]isochromen-6-yl)-[1,3,5]triazin-2-ylsulfanyl]-ethyl}-acetamide;
(119): 2-[4-amino-6-(5-chloro-1H,3H-benzo[de]isochromen-6-yl)-[1,3,5]triazin-2-ylsulfanyl]-acetamide;
(125): 3-[4-amino-6-(5-chloro-1H,3H-benzo[de]isochromen-6-yl)-[1,3,5]triazin-2-ylsulfanyl]-propionamide;
(143): N-{2-[4-amino-6-(5-chloro-1H,3H-benzo[de]isochromen-6-yl)-[1,3,5]triazin-2-ylsulfanylmethyl]-phenyl}-acetamide;
(145): 4-(5-chloro-1H,3H-benzo[de]isochromen-6-yl)-6-(2,5-dimethoxyphenylsulfanyl)-[1,3,5]triazin-2-ylamine;
(149): N-{3-[4-amino-6-(5-chloro-1H,3H-benzo[de]isochromen-6-yl)-[1,3,5]triazin-2-ylsulfanyl]-propyl}-acetamide;
(175): {2-[4-amino-6-(5-chloro-1H,3H-benzo[de]isochromen-6-yl)-[1,3,5]triazin-2-ylsulfanyl]-ethyl}-urea;
(178): N-{2-[4-amino-6-(5-chloro-1H,3H-benzo[de]isochromen-6-yl)-[1,3,5]triazin-2-ylsulfanyl]-ethyl}-methanesulfonamide;
(205): 3-[4-amino-6-(5-chloro-1H,3H-benzo[de]isochromen-6-yl)-[1,3,5]triazin-2-ylsulfanyl]-N-methyl-propionamide;
(234): 3-[4-amino-6-(5-chloro-1H,3H-benzo[de]isochromen-6-yl)-[1,3,5]triazin-2-ylsulfanyl]-N-(2-hydroxy-ethyl)-propionamide;
(270): carbamic acid 2-[4-amino-6-(5-chloro-1H,3H-benzo[de]isochromen-6-yl)-[1,3,5]triazin-2-ylsulfanyl]-ethyl ester;
(314): 2-[2-amino-6-(5-chloro-1H,3H-benzo[de]isochromen-6-yl)-pyrimidin-4-ylsulfanyl]-acetamide;
(315): 2-[2-amino-6-(5-chloro-1H,3H-benzo[de]isochromen-6-yl)-pyrimidin-4-ylsulfanyl]-N-cyanomethyl-acetamide;
(316): 3-[2-amino-6-(5-chloro-1H,3H-benzo[de]isochromen-6-yl)-pyrimidin-4-ylsulfanyl]-propionamide;
(317): 3-[2-amino-6-(5-chloro-1H,3H-benzo[de]isochromen-6-yl)-pyrimidin-4-ylsulfanyl]-N-(2-hydroxy-ethyl)-propionamide;
(318): 3-[2-amino-6-(5-chloro-1H,3H-benzo[de]isochromen-6-yl)-pyrimidin-4-ylsulfanyl]-N-methyl-propionamide;
(319): 3-[2-amino-6-(5-chloro-1H,3H-benzo[de]isochromen-6-yl)-pyrimidin-4-ylsulfanyl]-N-(2-methoxy-ethyl)-propionamide;
(320): 3-[2-amino-6-(5-chloro-1H,3H-benzo[de]isochromen-6-yl)-pyrimidin-4-ylsulfanyl]-N—((R)-2,3-dihydroxy-propyl)-propionamide;
(321): 3-[2-amino-6-(5-chloro-1H,3H-benzo[de]isochromen-6-yl)-pyrimidin-4-ylsulfanyl]-2-methyl-propionamide;
(322): 3-[2-amino-6-(5-chloro-1H,3H-benzo[de]isochromen-6-yl)-pyrimidin-4-ylsulfanyl]-2,N-dimethyl-propionamide;

(323): 3-[2-amino-6-(5-chloro-1H,3H-benzo[de]isochromen-6-yl)-pyrimidin-4-ylsulfanyl]-N-(2-hydroxyethyl)-2-methyl-propionamide;
(324): 4-[2-amino-6-(5-chloro-1H,3H-benzo[de]isochromen-6-yl)-pyrimidin-4-ylsulfanyl]-butylamide;
(325): carbamic acid 2-[2-amino-6-(5-chloro-1H,3H-benzo[de]isochromen-6-yl)-pyrimidin-4-ylsulfanyl]-ethyl ester;
(326): 3-[2-amino-6-(5-chloro-1H,3H-benzo[de]isochromen-6-yl)-pyrimidin-4-ylsulfanyl]-propan-1-ol;
(327): N-{2-[2-amino-6-(5-chloro-1H,3H-benzo[de]isochromen-6-yl)-pyrimidin-4-ylsulfanyl]-ethyl}-acetamide;
(328): N-{3-[2-amino-6-(5-chloro-1H,3H-benzo[de]isochromen-6-yl)-pyrimidin-4-ylsulfanyl]-propyl}-acetamide;
(329): N-{2-[2-amino-6-(5-chloro-1H,3H-benzo[de]isochromen-6-yl)-pyrimidin-4-ylsulfanyl]-ethyl}-methanesulfonamide;
(330): 5-[2-amino-6-(5-chloro-1H,3H-benzo[de]isochromen-6-yl)-pyrimidin-4-ylsulfanylmethyl]-oxazolidin-2-one;
(331): N-{2-[2-amino-6-(5-chloro-1H,3H-benzo[de]isochromen-6-yl)-pyrimidin-4-ylsulfanyl]-ethyl}-2-hydroxy-acetamide;
(332): {2-[2-amino-6-(5-chloro-1H,3H-benzo[de]isochromen-6-yl)-pyrimidin-4-ylsulfanyl]-ethyl}-urea;
(333): 2-[4-amino-6-(5-chloro-1H,3H-benzo[de]isochromen-6-yl)-[1,3,5]triazin-2-ylsulfanyl]-N-cyano methyl-acetamide;
(334): 3-[4-amino-6-(5-chloro-1H,3H-benzo[de]isochromen-6-yl)-[1,3,5]triazin-2-ylsulfanyl]-N-(2-methoxyethyl)-propionamide;
(335): 3-[4-amino-6-(5-chloro-1H,3H-benzo[de]isochromen-6-yl)-[1,3,5]triazin-2-ylsulfanyl]-N—((R)-2,3-dihydroxy-propyl)-propionamide;
(336): 3-[4-amino-6-(5-chloro-1H,3H-benzo[de]isochromen-6-yl)-[1,3,5]triazin-2-ylsulfanyl]-2-methyl-propionamide;
(337): 3-[4-amino-6-(5-chloro-1H,3H-benzo[de]isochromen-6-yl)-[1,3,5]triazin-2-ylsulfanyl]-2,N-dimethyl-propionamide;
(338): 3-[4-amino-6-(5-chloro-1H,3H-benzo[de]isochromen-6-yl)-[1,3,5]triazin-2-ylsulfanyl]-N-(2-hydroxyethyl)-2-methyl-propionamide;
(339): 4-[4-amino-6-(5-chloro-1H,3H-benzo[de]isochromen-6-yl)-[1,3,5]triazin-2-ylsulfanyl]-butyramide;
(340): 3-[4-amino-6-(5-chloro-1H,3H-benzo[de]isochromen-6-yl)-[1,3,5]triazin-2-ylsulfanyl]-propan-1-ol;
(341): 5-[4-amino-6-(5-chloro-1H,3H-benzo[de]isochromen-6-yl)-[1,3,5]triazin-2-ylsulfanylmethyl]-oxazolidin-2-one;
(342): N-{2-[4-amino-6-(5-chloro-1H,3H-benzo[de]isochromen-6-yl)-[1,3,5]triazin-2-ylsulfanyl]-ethyl}-2-hydroxy-acetamide; and
(343): 4-[4-amino-6-(5-chloro-1H,3H-2-thia-phenalen-6-yl)-[1,3,5]triazin-2-ylsulfanyl]-butyramide.

(Procedures)

Examples of methods for synthesizing the compounds of the present invention represented by formula (1) are described by the following reaction schemes.

1) General Procedure-1

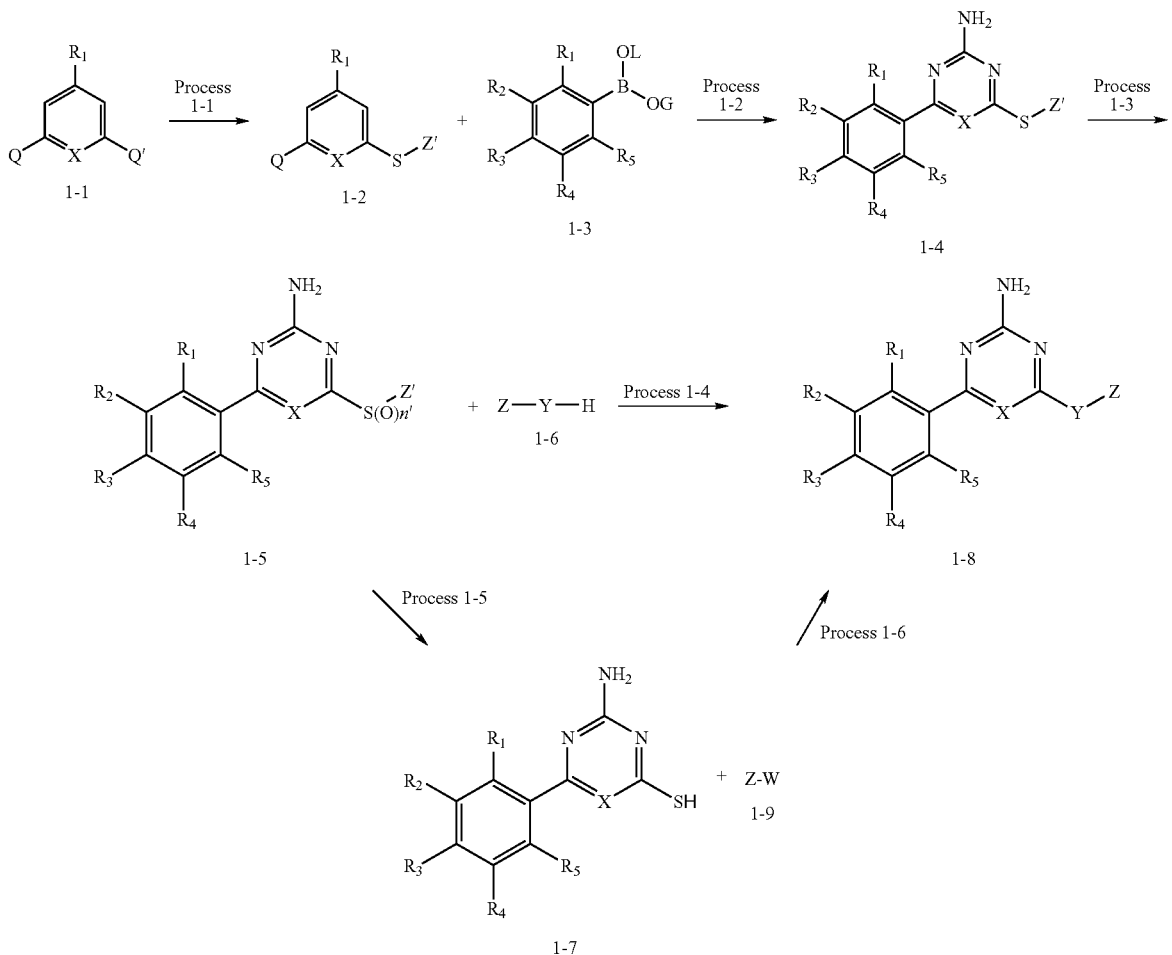

(In the formulas indicated above, X, Y, Z, $R_1$, $R_2$, $R_3$, $R_4$, and $R_5$ are the same as those defined in formula (1). Q and Q' represent a halogen atom, L and G represent a hydrogen atom, $C_{1-6}$ alkyl group, $C_{2-6}$ alkenyl group, or $C_{2-6}$ alkynyl group; or L and G may together form a 3- to 8-membered heterocycle optionally substituted with a $C_{1-4}$ alkyl group. n' is an integer from 1 to 2, and W represents a leaving group. Z' is a hydrogen atom or Z, and this Z is the same as that defined in formula (1).)

For the "leaving group" W indicated above, groups known to those skilled in the art can be suitably used. Specific examples of the "leaving group" include halogens such as chlorine (Cl), bromine (Br), and iodine, and sulfonic acid ester derivatives such as tosyloxy groups, mesyloxy groups and the like.

Compounds of the present invention represented by formula (1) can be obtained by the processes of 1-1 to 1-2. For compounds in which Z' is a substituted group, it is also possible to initially synthesize a simple compound (for example, compounds in which Z' may be an optionally substituted $C_{1-10}$ alkyl group, in particular, compounds in which Z' is a methyl group, benzyl group, or such), and then obtain compounds of the present invention represented by formula (1) through the steps shown in the processes of 1-3 to 1-6.

(Process 1-1)

Compound 1-2 can be obtained by reacting the commercially available compound 1-1 (for example, Q=Q'=Cl, X=N) with a thiol Z-SH (one equivalent to a large excess, or preferably three to five equivalents), in the presence or absence of a base in a solvent that is inert to the reaction.

The solvent to be used for the reaction is not particularly limited and may be any solvent so long as it is inert to the reaction, and N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, methanol, ethanol, water, toluene, hexane, and such may be used individually or in combination. Of them, N,N-dimethylformamide or tetrahydrofuran is preferred.

The reaction is carried out at a temperature between 0 and 120° C., or preferably between 0 and 30° C., and is usually completed in one to eight hours. Examples of a base that may be used include alkyl amines such as triethylamine or N,N-diisopropylethyl amine; pyridines such as pyridine, lutidine, collidine, or 4-dimethylaminopyridine; and metal carbonates such as potassium carbonate, sodium hydrogen carbonate, or cesium carbonate. Of them, triethylamine or N,N-diisopropylethylamine is preferred.

(Process 1-2)

Compound 1-4 can be obtained by reacting compound 1-2 obtained in Process 1-1 with compound 1-3 (one equivalent to a large excess, or preferably one to two equivalents), in the presence of a catalyst (catalytic amount to one equivalent, or preferably 0.01 to 0.1 equivalent) and a base (one equivalent or more), in a solvent that is inert to the reaction.

The solvent used for the reaction is not particularly limited and may be any solvent so long as it is inert to the reaction, and 1,2-dimethoxyethane, tetrahydrofuran, 1,4-dioxane, methanol, ethanol, isopropanol, toluene, N,N-dimethylformamide, water, or such may be used individually or in combination. Of them, a mixture of 1,2-dimethoxyethane and water is preferred.

The reaction is carried out at a temperature between room temperature and 100° C., or preferably between 70 and 100° C., and is usually completed in one to eight hours. Examples of a catalyst that may be used include phosphine palladium complexes such as tetrakis(triphenylphosphine)palladium(0) or dichloro[bis(triphenylphosphine)]palladium(II). Alternatively, a mixture of triphenylphosphine and a palladium source such as palladium (II) acetate or tris(dibenzylideneacetone) dipalladium may be used. Of them, palladium (II) acetate with triphenylphosphine is preferred. Examples of a base that may be used include potassium carbonate, sodium carbonate, sodium hydrogen carbonate, cesium carbonate, tripotassium phosphate, cesium fluoride, and potassium fluoride. Of them, sodium hydrogen carbonate is preferred.

(Process 1-3)

Compound 1-5 can be obtained by reacting compound 1-4 obtained from Process 1-2 with an oxidizing agent (one equivalent to a large excess or preferably one to two equivalents), in a solvent that is inert to the reaction.

The solvent used for the reaction is not particularly limited and may be any solvent so long as it is inert to the reaction, and dichloromethane, 1,2-dichloroethane, chloroform, tetrachloromethane, methanol, ethanol, isopropanol, toluene, hexane, ethyl acetate, acetic acid, trifluoroacetic acid, trifluoroethanol, water, or such may be used individually or in combination. Of them, dichloromethane is preferred.

The reaction is carried out at a temperature between 0 and 100° C., or preferably between 0 and 30° C., and is usually completed in one to eight hours. Examples of an oxidizing agent that may be used include m-chloroperbenzoic acid, peracetic acid, magnesium monoperoxyphthalate, sodium meta-periodate, tert-butylhydroperoxide, cumene hydroperoxide, a combination of hydrogen peroxide and vanadium oxide acetylacetonate, and a combination of oxone, sodium hypochlorite, and 2,2,6,6-tetramethylpiperidin-1-oxyl. Of them, m-chloroperbenzoic acid is preferred.

(Process 1-4)

Compound 1-8 can be obtained by reacting compound 1-5 obtained in Process 1-3 with compound 1-6 (one equivalent to a large excess, or preferably three to five equivalents), in the presence or absence of a base in a solvent that is inert to the reaction.

The solvent used for the reaction is not particularly limited and may be any solvent so long as it is inert to the reaction, and N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, methanol, ethanol, water, toluene, hexane, and such may be used individually or in combination. Of them, N,N-dimethylformamide or tetrahydrofuran is preferred.

The reaction is carried out at a temperature between 0 and 120° C., or preferably between 0 and 30° C., and is usually completed in one to eight hours. Examples of a base that may be used include alkyl amines such as triethylamine or N,N-diisopropylethyl amine; pyridines such as pyridine, lutidine, collidine, or 4-dimethylaminopyridine; and metal carbonates such as potassium carbonate, sodium hydrogen carbonate, or cesium carbonate. Of them, triethylamine or N,N-diisopropylethylamine is preferred.

(Process 1-5)

Compound 1-7 can be obtained by reacting compound 1-5 obtained in Process 1-3 with a thiol source (one equivalent to a large excess, or preferably 3-5 equivalents), in a solvent that is inert to the reaction. Examples of a thiol source that may be used include potassium thioacetate, thiourea, thioacetamide, hydrogen sulfide, and sodium sulfide. Of them, potassium thioacetate is preferred.

The solvent used for the reaction is not particularly limited and may be any solvent so long as it is inert to the reaction, and N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, methanol, ethanol, water, toluene, hexane, or such may be used individually or in combination. Of them, N,N-dimethylformamide is preferred. The reaction is carried out at a temperature between 0 and 100° C., or preferably between 0 and 30° C., and is usually completed in one to five hours.

(Process 1-6)

Compound 1-8 can be obtained by reacting compound 1-7 obtained in Process 1-5 with compound 1-9 (one equivalent to a large excess, or preferably one to three equivalents), in the presence of a base in a solvent that is inert to the reaction. Examples of a base that may be used for the reaction include alkyl amines such as triethyl amine or N,N-diisopropylethyl amine; pyridines such as pyridine, lutidine, collidine, or 4-dimethylaminopyridine; and metal carbonates such as potassium carbonate, sodium hydrogen carbonate, or cesium carbonate. Of them, triethylamine or N,N-diisopropylethylamine is preferred.

The solvent to be used for the reaction is not particularly limited and may be any solvent so long as it is inert to the reaction, and N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, toluene, hexane, or such may be used individually or in combination. Of them, N,N-dimethylformamide is preferred. The reaction is carried out at a temperature between 0 and 80° C., or preferably between 0 and 50° C., and is usually completed in one to eight hours.

2) General Procedure-2

Compound 1-4 described in General Procedure-1 (compound 2-3: when X=N, Z=methyl) can also be obtained by the procedure described below.

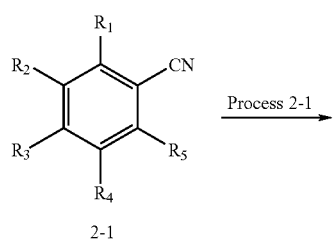

2-1

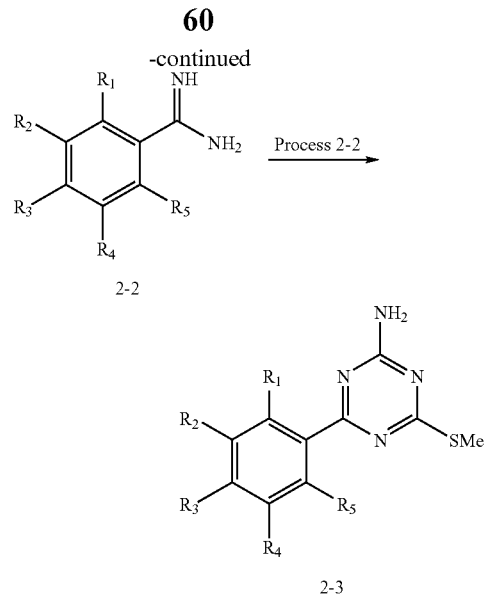

(In the formulas indicated above, $R_1$, $R_2$, $R_3$, $R_4$, and $R_5$ are the same as those defined in formula (1))

Process 2-1

Compound 2-2 can be obtained by reacting the commercially available compound 2-1 with alkylchloroaluminum amide (one equivalent to a large excess, or preferably one to five equivalents), in a solvent that is inert to the reaction. Alkylchloroaluminum amides can be obtained simply by reacting ammonium chloride with a trialkylaluminum, and a preferred trialkylaluminum is trimethylaluminum.

The solvent to be used for the reaction is not particularly limited and may be any solvent so long as it is inert to the reaction. For example, toluene, xylene, benzene, hexane, and 1,2-dichloroethane may be used individually or in combination, and of them, toluene is preferred. The reaction is carried out at a temperature between 0 and 150° C., or preferably between 80 and 110° C., and is usually completed in 24 to 48 hours. Furthermore, compound 2-2 can be obtained by reducing the amide oxime derivative obtained by reacting compound 2-1 with hydroxylamine, or it can be obtained by converting compound 2-1 into an imidate by the action of an alcohol under acidic hydrochloric acid conditions, and reacting this imidate with ammonia.

Process 2-2

Compound 2-3 can be obtained by reacting compound 2-2 obtained in Process 2-1 with dimethylcyanodithioiminocarbonate (one equivalent to a large excess, or preferably one to three equivalents), in the presence of a base (one equivalent to a large excess, or preferably one to three equivalents), in a solvent that is inert to the reaction. Examples of a base that may be used include alkyl amines such as triethylamine or N,N-diisopropylethyl amine; and pyridines such as pyridine, lutidine, collidine, or 4-dimethylaminopyridine. Of them, N,N-diisopropylethylamine is preferred.

The solvent to be used for the reaction is not particularly limited and may be any solvent so long as it is inert to the reaction. For example, methanol, ethanol, isopropanol, dichloromethane, 1,2-dichloroethane, 1,2-dimethoxyethane, tetrahydrofuran, dioxane, benzene, toluene, and cyclohexane may be used individually or in combination, and of them, ethanol is preferred. The reaction is carried out at a temperature between 0 and 100° C., or preferably between 70 and 90° C., and is usually completed in one to five hours.

3) General Procedure-3
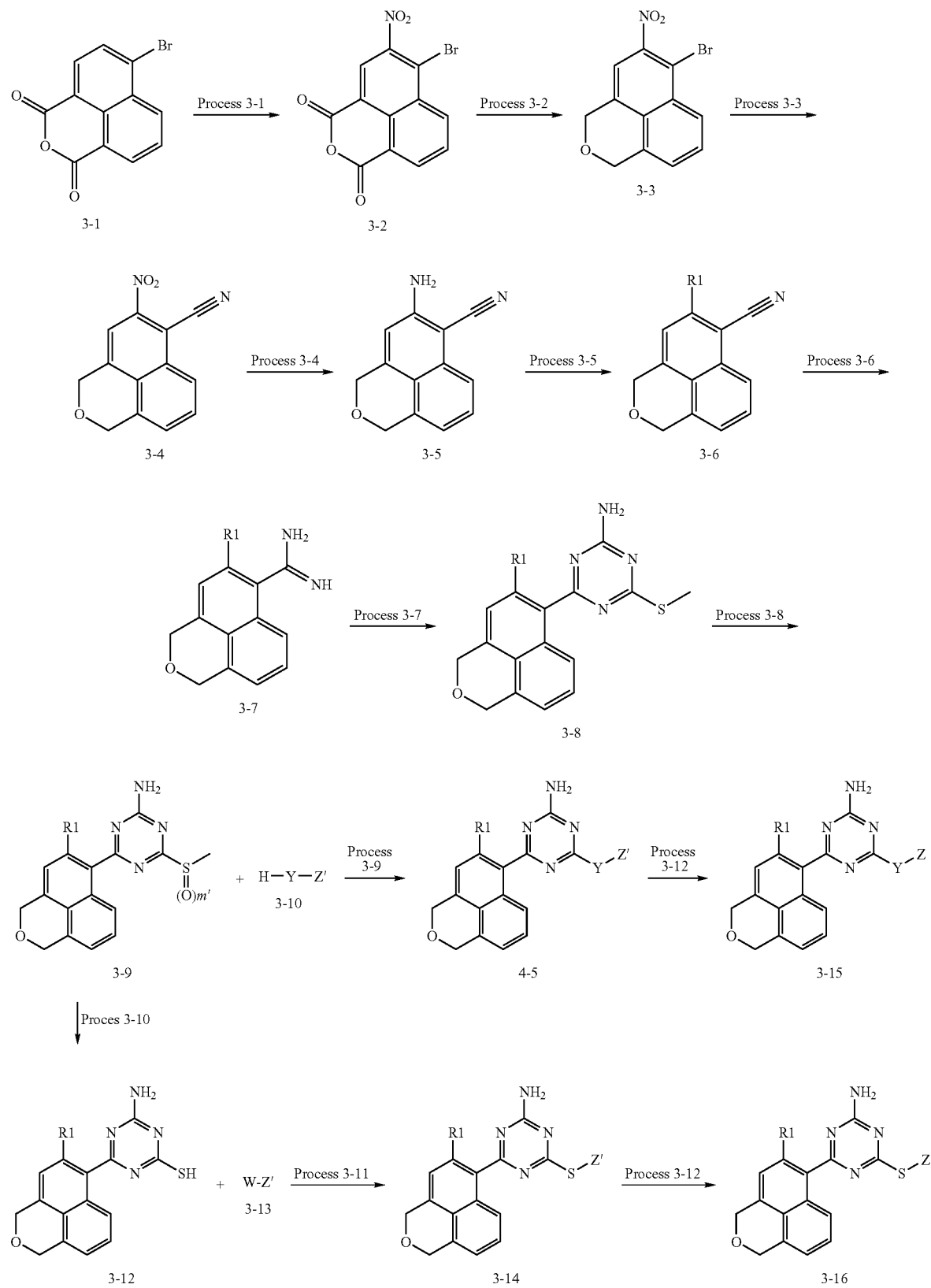

(In the formulas, Y, Z, and $R_1$ are the same as those defined in formula (1), and Z' is the same as that defined previously. m' is an integer from 1 to 2, and W represents a leaving group.)

The "leaving group" is the same as that indicated in Process 1.

(Process 3-1)

Compound 3-2 can be obtained by reacting the commercially available compound 3-1 with one equivalent to a large excess, or preferably one to ten equivalents of nitric acid, a metal nitrate such as sodium nitrate or urea-nitrate complex, in the presence of sulfuric acid in a solvent that is inert to the reaction. The solvent to be used for the reaction is not particularly limited and may be any solvent so long as it is inert to the reaction. For example, carboxylic acids such as acetic acid or propionic acid; or halogenated solvents such as 1,2-dichloroethane, methylene chloride, or chloroform may be used individually or in combination, and of them, sulfuric acid is preferred. The reaction is carried out at a temperature between 0 and 50° C., or preferably between 0 and 25° C., and is usually completed in one to three hours.

(Process 3-2)

Compound 3-3 can be obtained by reacting compound 3-2 obtained in Process 3-1 with a reducing agent (one equivalent to a large excess, or preferably one to three equivalents), in a solvent that is inert to the reaction. Examples of a reducing agent that may be used include sodium borohydride or a combination of sodium borohydride and trifluoroborane-diethyl ether complex, lithium borohydride or a combination of lithium borohydride and trifluoroborane-diethyl ether complex, borane reducing agents such as borane-tetrahydrofuran adduct, lithium aluminum hydride, and lithium triethylborohydride. Of them, a combination of lithium borohydride and trifluoroborane-diethyl ether complex is preferred.

The solvent to be used for the reaction is not particularly limited and may be any solvent so long as it is inert to the reaction, and ethers such as tert-butylmethylether, diethyl ether, 1,2-dimethoxyethane, tetrahydrofuran, and 1,4-dioxane; benzene, toluene, cyclohexane, dichloromethane, 1,2-dichloroethane, or such may be used individually or in combination. The reaction is carried out at a temperature between 0 and 100° C., or preferably between 0 and 50° C., and is usually completed in one to three hours.

(Process 3-3)

Compound 3-4 can be obtained by reacting compound 3-3 obtained in Process 3-2 with a cyanating agent (one equivalent to a large excess, or preferably one to three equivalents), in a solvent that is inert to the reaction. Examples of a cyanating agent that can be used include cuprous cyanide, or nickel (II) cyanide, and of them, cuprous cyanide is preferred. The solvent used for the reaction is not particularly limited and may be any solvent so long as it is inert to the reaction. N,N-dimethylformamide, N,N-dimethylacetamide, N-methyl-2-pyrrolidinone, dimethylsulfoxide, pyridine, quinoline, or such may be used individually or in combination. The reaction is carried out at a temperature between 30 and 200° C., or preferably between 100 and 130° C., and is usually completed in one to three hours.

(Process 3-4)

Compound 3-5 can be obtained by reacting compound 3-4 obtained in Process 3-3 with a reducing agent (one equivalent to a large excess, or preferably one to three equivalents), in a solvent that is inert to the reaction. The solvent used for the reaction is not particularly limited and may be any solvent so long as it is inert to the reaction. For example, various ethers such as 1,2-dimethoxyethane, diethyl ether, tetrahydrofuran, or dioxane, benzene, n-toluene, cyclohexane, ethyl acetate, methanol, ethanol, isopropanol, water, or such may be used individually or in combination, and of them, 1,2-dimethoxyethane is preferred. Methods for reduction include, for example, the method of using tin or tin (II) chloride, iron (0), zinc (0), or such under acidic hydrochloric acid conditions, the method of using palladium or platinum as a catalyst under a flow of hydrogen gas, or the method of using a combination of palladium and ammonium formate or such, and raney nickel. Of them, the method of using tin (II) chloride under acidic hydrochloric acid conditions is preferred. The reaction is carried out at a temperature between 0 and 100° C., or preferably between 0 and 30° C., and is usually completed in one to five hours.

(Process 3-5)

Compound 3-6 can be obtained by reacting compound 3-5 obtained in Process 3-4 under the so-called Sandmeyer reaction conditions in a solvent that is inert to the reaction. Examples of reagents that may be used in this reaction are one equivalent to a large excess, or preferably one to three equivalents of a combination of copper (II) chloride or copper (II) bromide and an alkyl nitrite such as tert-butyl nitrite or isoamyl nitrite, a combination of sodium nitrite and cuprous chloride or copper (II) bromide, a combination of sodium nitrite and copper (II) chloride or copper (II) bromide, or such. Of them, a combination of tert-butyl nitrite and copper (II) chloride or copper (II) bromide is preferred. The solvent used for the reaction is not particularly limited and may be any solvent so long as it is inert to the reaction. For example, acetonitrile, acetone, ethyl acetate, acetic acid, water, or such can be used individually or in combination, and of them, acetonitrile is preferred. The reaction is carried out at a temperature between 0 and 100° C., or preferably between 25 and 70° C., and is usually completed in one to three hours.

(Process 3-6) Amidination

Compound 3-7 can be obtained by reacting compound 3-6 obtained in Process 3-5 with an alkylchloroaluminum (one equivalent to a large excess, or preferably one to five equivalents amide), in a solvent that is inert to the reaction. Alkylchloroaluminum amides can be simply obtained by reacting ammonium chloride with a trialkylaluminum, and a preferred trialkylaluminum is trimethylaluminum.

The solvent to be used for the reaction is not particularly limited and may be any solvent so long as it is inert to the reaction. For example, toluene, xylene, benzene, hexane, and 1,2-dichloroethane may be used individually or in combination, and of them, toluene is preferred. The reaction is carried out at a temperature between 0 and 150° C., or preferably between 80 and 110° C., and is usually completed in 24 to 48 hours. Furthermore, compound 3-7 can be obtained by reducing the amide oxime derivative obtained by reacting compound 3-6 with hydroxylamine, or it can be obtained by converting compound 3-6 into an imidate by the action of an alcohol under acidic hydrochloric acid conditions, and reacting this imidate with ammonia.

(Process 3-7)

Compound 3-8 can be obtained by reacting compound 3-7 obtained in Process 3-6 with dimethylcyanodithioiminocarbonate (one equivalent to a large excess, or preferably one to three equivalents), in the presence of a base (one equivalent to a large excess, or preferably one to three equivalents), in a solvent that is inert to the reaction. Examples of a base that may be used include alkyl amines such as triethylamine or N,N-diisopropylethyl amine; and pyridines such as pyridine, lutidine, collidine, or 4-dimethylaminopyridine, and of them, N,N-diisopropylethylamine is preferred.

The solvent to be used for the reaction is not particularly limited and may be any solvent so long as it is inert to the reaction. For example, methanol, ethanol, isopropanol, dichloromethane, 1,2-dichloroethane, 1,2-dimethoxyethane, tetrahydrofuran, dioxane, benzene, toluene, or cyclohexane may be used individually or in combination, and of them, ethanol is preferred. The reaction is carried out at a temperature between 0 and 100° C., or preferably between 70 and 90° C., and is usually completed in one to five hours.
(Process 3-8)

Compound 3-9 can be obtained by reacting compound 3-8 obtained in Process 3-7 with an oxidizing agent (one equivalent to a large excess, or preferably one to two equivalents), in a solvent that is inert to the reaction. The solvent used for the reaction is not particularly limited and may be any solvent so long as it is inert to the reaction. Dichloromethane, 1,2-dichloroethane, chloroform, carbon tetrachloride, methanol, ethanol, isopropanol, toluene, hexane, ethyl acetate, acetic acid, trifluoroacetic acid, trifluoroethanol, water, or such may be used individually or in combination, and of them, dichloromethane is preferred. The reaction is carried out at a temperature between 0 and 100° C., or preferably between 0 and 30° C., and is usually completed in one to 24 hours. Examples of an oxidizing agent that may be used include m-chloroperbenzoic acid, peracetic acid, magnesium monoperoxyphthalate, sodium meta-periodate, tert-butylhydroperoxide, cumene hydroperoxide, a combination of hydrogen peroxide and vanadium oxide acetylacetonate, and a combination of oxone, sodium hypochlorite, and 2,2,6,6-tetramethylpiperidin-1-oxyl, and of them, m-chloroperbenzoic acid is preferred.
(Process 3-9)

Compound 3-11 can be obtained by reacting compound 3-9 obtained in Process 3-8 with compound 3-10 (one equivalent to a large excess, or preferably three to five equivalents), in the presence or absence of a base in a solvent that is inert to the reaction. The solvent used for the reaction is not particularly limited and may be any solvent so long as it is inert to the reaction. N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, methanol, ethanol, water, toluene, hexane, or such may be used individually or in combination, and of them, N,N-dimethylformamide or tetrahydrofuran is preferred.

The reaction is carried out at a temperature between 0 and 120° C., or preferably between 0 and 30° C., and is usually completed in one to eight hours. Examples of a base that may be used include alkyl amines such as triethylamine or N,N-diisopropylethyl amine; pyridines such as pyridine, lutidine, collidine, or 4-dimethylaminopyridine; metal carbonates such as potassium carbonate, sodium hydrogen carbonate, or cesium carbonate; and metal hydrides such as sodium hydride, and of them, triethylamine or sodium hydride is preferred.
(Process 3-10)

Compound 3-12 can be obtained by reacting compound 3-9 obtained in Process 3-8 with a thiol source (one equivalent to a large excess, or preferably 3-5 equivalents), in a solvent that is inert to the reaction. Examples of a thiol source that may be used include potassium thioacetate, thiourea, thioacetamide, hydrogen sulfide, and sodium hydrosulfide, and of them, potassium thioacetate is preferred.

The solvent used for the reaction is not particularly limited and may be any solvent so long as it is inert to the reaction. N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, methanol, ethanol, water, toluene, hexane, or such may be used individually or in combination, and of them, N,N-dimethylformamide is preferred. The reaction is carried out at a temperature between 0 and 100° C., or preferably between 0 and 30° C., and is usually completed in one to five hours.
(Process 3-11)

Compound 3-14 can be obtained by reacting compound 3-12 obtained in Process 3-10 with one equivalent to a large excess or preferably one to three equivalents of compound 3-13 in the presence of a base in a solvent that is inert to the reaction. Examples of a base that may be used for the reaction include alkyl amines such as triethyl amine or N,N-diisopropylethyl amine; pyridines such as pyridine, lutidine, collidine, or 4-dimethylaminopyridine; and metal carbonates such as potassium carbonate, sodium hydrogen carbonate, or cesium carbonate, and of them, triethylamine or N,N-diisopropylethylamine is preferred.

The solvent to be used for the reaction is not particularly limited and may be any solvent so long as it is inert to the reaction. N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, toluene, hexane, or such may be used individually or in combination, and of them, N,N-dimethylformamide is preferred. The reaction is carried out at a temperature between 0 and 80 degrees, or preferably between 0 and 50 degrees, and is usually completed in one to eight hours.
(Process 3-12)

Compounds 3-15 and 3-16 can be obtained by performing a simple chemical modification to compounds 3-11 and 3-14 obtained in Processes 3-9 and 3-11, when Z' has a substituent such as a hydroxyl group, amino group, or carboxyl group.

When Z' has a substituent such as a hydroxyl group or amino group, examples of the chemical modification include acylation, alkyloxycarbonylation, and alkylaminocarbonylation. Examples of acylation include condensation using acid halides or acid anhydrides, and condensation using a dehydrocondensation agent. Reacting a substituent such as a hydroxyl group or amino group with carboxylic acids yields the corresponding ester (acylated hydroxyl compounds), or amide (acylated amino compounds). For construction of ester bonds and amide bonds, common chemical agents that suitably activate carboxylic acids can be used, and known peptide synthesis techniques can also be suitably used. Reaction with halogenated formic acid esters or dicarboxylic acid diesters gives the corresponding carboxylic acid diester compounds (alkyloxycarbonylated hydroxyl compounds), or urethane compounds (alkyloxycarbonylated amino compounds), and reaction with isocyanic acid esters gives the corresponding urethane compounds (alkylaminocarbonylated hydroxyl compounds), or urea compounds (alkylaminocarbonylated amino compounds).

In the case of acylation, for example, compounds 3-15 and 3-16 can be produced by condensing compounds 3-11 and 3-14 with a suitable carboxylic acid (one equivalent to a large excess, or preferably one equivalent to three equivalents), in a suitable solvent, at a suitable temperature in the presence of one equivalent to a large excess, or preferably one to five equivalents of a suitable base and condensation agent, and in some cases, in the coexistence of one equivalent to a large excess, or preferably one to five equivalents of a suitable additive.

The solvent to be used for the reaction is not particularly limited and may be any solvent so long as it is inert to the reaction. Examples include carboxylic acid amides such as N,N-dimethylformamide, or N,N-dimethylacetamide; halogenated hydrocarbons such as dichloromethane, chloroform, carbon tetrachloride, or chlorobenzene; aromatic hydrocarbons such as benzene, toluene, or xylene; ketones such as acetone; ethers such as diethyl ether, tetrahydrofuran, or 1,4-dioxane; esters such as ethyl acetate; and nitriles such as acetonitrile. These solvents may be used individually or by mixing two or more of them.

The reaction temperature differs depending on the solvent, the type of base, and such. Production can be carried out by performing the reaction, for example, between 0° C. and the boiling point of the solvent, or preferably between 0° C. and room temperature. The reaction time differs depending on the reaction temperature, and is usually about 10 minutes to 100 hours, and preferably about 30 minutes to 24 hours.

Examples of condensation agents include N,N'-dicyclohexylcarbodiimide (DCC), N,N'-diisopropylcarbodiimide (DIPC), 1-ethyl-3-(3'-dimethylaminopropyl)carbodiimide (EDC), 1,1'-carbonylbis-1H-imidazole (CDI), 2-ethoxy-1-ethoxycarbonyl-1,2-dihydroquinoline (EEDQ), bromo-tris-pyrrolidino-phosphonium hexafluoro-phosphate (PyBrOP), benzotriazole-1-yloxytrispyrrolidino-phosphonium hexafluoro-phosphate (PyBOP), benzotriazol-1-yloxytris(dimethylamino)phosphonium hexafluoro-phosphate (BOP), O-benzotriazol-1-yl-N,N,N',N'-tetramethyl-uronium-hexafluoro-borate (HBTU), diphenyl phosphorazidate (DPPA), diethyl phosphorocyanidate (DEPC), diphenylphosphinyl chloride, bis(2-oxo-3-oxazolidinyl)phosphonic chloride (BOP-Cl), di(N-succinimidyl)carbonate, 2-chloro-1-methylpyridinium iodide, and 2-methyl-6-nitrobenzoic anhydride (MNBA).

Examples of an additive include N-hydroxysuccinimide (HOSu), 1-hydroxybenzotriazole (HOBt), and pentafluorophenol.

For example, as a coexisting base, tertiary amines represented by triethylamine, N,N-diisopropylethyl amine, N-methylmorpholine, or such; organic bases such as pyridine, N,N-dimethylaminopyridine, 1,8-diazabicyclo[5.4.0]-7-undecene (DBU), or such; and inorganic bases represented by sodium carbonate, potassium carbonate, cesium carbonate, or such may be used.

When Z' has a substituent such as a carboxyl group, for example, examples of chemical modification include esterification and amidation.

A substituent such as a carboxyl group reacts with alcohols or amines to give the corresponding ester compounds or amide compounds. For construction of ester bonds and amide bonds, the use of a common chemical agent for suitably activating carboxylic acids can be used, and known peptide synthesis techniques can be suitably used.

Compounds 3-15 and 3-16 can be produced by condensing compounds 3-11 and 3-14 with an alcohol derivative or amine derivative (one equivalent to a large excess, or preferably one equivalent to three equivalents), in a suitable solvent, at a suitable temperature, in the presence of one equivalent to a large excess, or preferably one to five equivalents of a suitable base and condensation agent or acid halide reagent, and in some cases, in the coexistence of one equivalent to a large excess, or preferably one to five equivalents of a suitable additive.

Examples of an acid halide agent include oxalyl chloride, and thionyl chloride. Examples of condensation agents include N,N'-dicyclohexylcarbodiimide (DCC), N,N'-diisopropylcarbodiimide (DIPC), 1-ethyl-3-(3'-dimethylaminopropyl)carbodiimide (EDC), 1,1'-carbonylbis-1H-imidazole (CDI), 2-ethoxy-1-ethoxycarbonyl-1,2-dihydroquinoline (EEDQ), bromo-tris-pyrrolidino-phosphonium hexafluoro-phosphate (PyBrOP), benzotriazole-1-yloxytrispyrrolidino-phosphonium hexafluoro-phosphate (PyBOP), benzotriazol-1-yloxytris(dimethylamino)phosphonium hexafluoro-phosphate (BOP), O-benzotriazol-1-yl-N,N,N',N'-tetramethyl-uronium-hexafluoro-borate (HBTU), diphenyl phosphorazidate (DPPA), diethyl phosphorocyanidate (DEPC), diphenylphosphinyl chloride, bis(2-oxo-3-oxazolidinyl)phosphonic chloride (BOP-Cl), di(N-succinimidyl)carbonate, 2-chloro-1-methylpyridinium iodide, and 2-methyl-6-nitrobenzoic anhydride (MNBA).

Examples of an additive include N-hydroxysuccinimide (HOSu), 1-hydroxybenzotriazole (HOBt), and pentafluorophenol.

For example, as a coexisting base, tertiary amines represented by triethylamine, N,N-diisopropylethyl amine, N-methylmorpholine, or such; organic bases such as pyridine, N,N-dimethylaminopyridine, 1,8-diazabicyclo[5.4.0]-7-undecene (DBU), or such; and inorganic bases represented by sodium carbonate, potassium carbonate, cesium carbonate, or such may be used.

The solvent to be used for the reaction is not particularly limited and may be any solvent so long as it is inert to the reaction. Examples include carboxylic acid amides such as N,N-dimethylformamide, or N,N-dimethylacetamide; halogenated hydrocarbons such as dichloromethane, chloroform, carbon tetrachloride, or chlorobenzene; ketones such as acetone; cyclic ethers such as tetrahydrofuran or 1,4-dioxane; esters such as ethyl acetate; and nitriles such as acetonitrile. These solvents may be used individually or by mixing two or more of them.

The reaction temperature differs depending on the type of solvent, base, and such. Production can be carried out by performing the reaction, for example, between 0° C. and the boiling point of the solvent, or preferably between room temperature and the boiling point of the solvent. The reaction time differs depending on the reaction temperature, and is usually about 10 minutes to 100 hours, and preferably about 30 minutes to 24 hours.

4) General Procedure-4

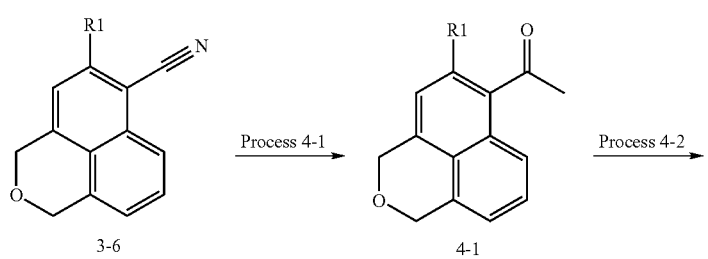

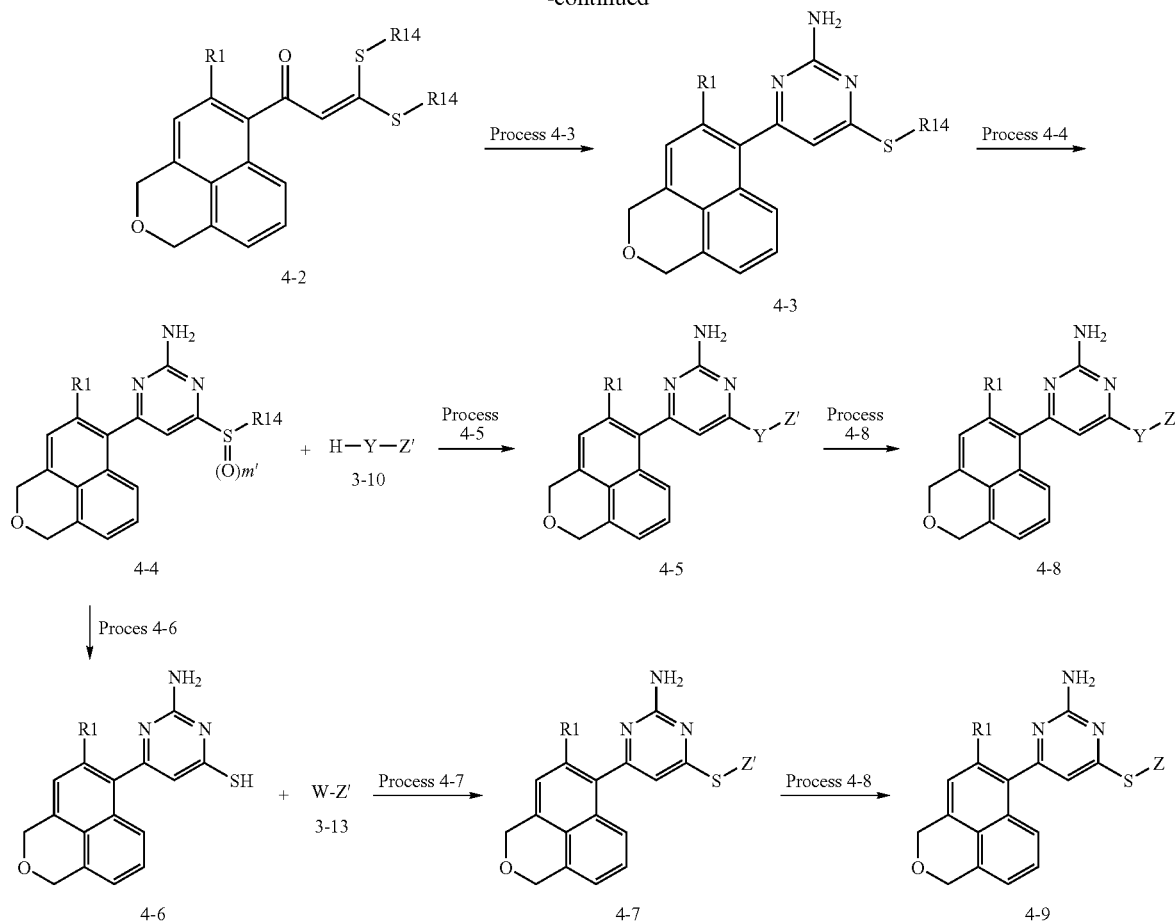

(In the formulas, Y, Z, and $R_1$ are the same as those defined in formula (1), and Z' is as defined previously. $R_{14}$ is the same as that defined for Z. m' is an integer from 1 to 2, and W represents a leaving group.)

The "leaving group" is as defined in Process 1.

(Process 4-1)

Compound 4-1 can be obtained by reacting compound 3-6 obtained in Process 3-5 with trimethylaluminum (one equivalent to a large excess, or preferably one to five equivalents), in a solvent that is inert to the reaction to produce an imine, and then preferably hydrolyzing this imine under acidic conditions.

The solvent to be used for the reaction of converting the cyano group in compound 3-6 to an acetyl group is not particularly limited, and may be any solvent so long as it is inert to the reaction. For example, toluene, xylene, benzene, hexane, 1,2-dichloroethane, and such may be used individually or in combination, and of them, toluene is preferred. The reaction temperature differs depending on the type of solvent, base, and such. Production can be carried out by performing the reaction, for example, between 0° C. and the boiling point of the solvent, or preferably between room temperature and the boiling point of the solvent. The reaction time differs depending on the reaction temperature, and is usually about 30 minutes to 100 hours, and preferably about 12 hours to 48 hours.

Furthermore, the solvent to be used for the hydrolysis of imine under acidic conditions is not particularly limited, and may be any solvent so long as it is inert to the reaction. For example, tetrahydrofuran, 1,4-dioxane, diethyl ether, 1,2-dimethoxyethane, ethyl acetate, toluene, benzene, methanol, ethanol, isopropanol, or water, may be used individually or as a mixture thereof, and preferred examples include tetrahydrofuran, 1,4-dioxane, 1,2-dimethoxyethane, or such individually, or as a mixture thereof. Examples of the acid include organic acids such as trifluoroacetic acid, methanesulfonic acid, or p-toluenesulfonic acid, and inorganic acids such as hydrochloric acid, or sulfuric acid, and a preferred example is hydrochloric acid. The reaction temperature differs depending on the type of solvent or acid, or the concentration of the acid. Production can be carried out by performing the reaction, for example, between 0° C. and the boiling point of the solvent, or preferably between room temperature and the boiling point of the solvent. The reaction time differs depending on the reaction temperature, and is usually about 30 minutes to 100 hours, and preferably about 10 hours to 48 hours.

(Process 4-2)

Compound 4-2 can be obtained by reacting compound 4-1 obtained in Process 4-1 with a base (one equivalent to a large excess or preferably one to five equivalent), in a solvent that is inert to the reaction to produce an enolate, and then trapping this enolate with carbon disulfide (one equivalent to a large excess, or preferably one to 20 equivalents) and an alkylating agent (two equivalents to a large excess, or preferably two to ten equivalents).

The solvent to be used for the reaction is not particularly limited and may be any solvent so long as it is inert to the reaction, and examples include tetrahydrofuran, 1,4-dioxane, diethyl ether, and 1,2-dimethoxyethane. These solvents may be used individually or as a mixture of two or more solvents.

Examples of a suitable base include lithium hydride, sodium hydride, potassium hydride, potassium bistrimethylsilylamide, sodium bistrimethylsilylamide, lithium bistrimethylsilylamide, and lithium diisopropylamide. A preferred example is sodium hydride.

Examples of a suitable alkylating agent include methyl iodide, benzyl bromide, and allyl bromide, and a preferred example is methyl iodide.

The reaction temperature differs depending on the type of solvent, base, and such. Production can be carried out by performing the reaction, for example, between 0° C. and the boiling point of the solvent, or preferably between 0° C. and room temperature. The reaction time differs depending on the reaction temperature, and such, and is usually about 10 minutes to 100 hours, and preferably about 30 minutes to 24 hours.

(Process 4-3)

Compound 4-3 can be obtained by reacting compound 4-2 obtained in Process 4-2 with guanidine (one equivalent to a large excess, or preferably one to five equivalents), in a solvent that is inert to the reaction. When guanidine is a salt such as hydrochloride, nitrate or the like, an equivalent amount of a base is preferably added for neutralization. Furthermore, in this reaction, one equivalent of a thiol is formed as a byproduct; therefore, addition of a thiol trapping agent is preferred depending on the substrate.

Examples of a suitable base include metal hydrides such as lithium hydride, sodium hydride, or potassium hydride; and metal alkoxides such as sodium methoxide, sodium ethoxide, or potassium tert-butoxide. A preferred example is sodium hydride.

Examples of a suitable thiol trapping agent include 1-bromo-2,4-difluorobenzene, 1-bromo-2,4,6-trifluorobenzene, and 1-bromo-2,3,5,6-tetrafluorobenzene. A particularly preferred example is 1-bromo-2,4,6-trifluorobenzene.

The solvent to be used for the reaction is not particularly limited and may be any solvent so long as it is inert to the reaction. Preferred examples include amide type solvents such as N,N-dimethylformamide, N,N-dimethylacetamide, or N-methylpyrrolidone. When metal alkoxides are used as a base, an alcohol type solvent such as methanol, ethanol, or tert-butanol is also used in addition to the above-mentioned solvent.

The reaction temperature differs depending on the type of solvent, base, and such. Production can be carried out by performing the reaction, for example, between 0° C. and the boiling point of the solvent, or preferably between room temperature and 150° C. The reaction time differs depending on the reaction temperature, and is usually about 10 minutes to 24 hours, and preferably about 30 minutes to 5 hours.

(Process 4-4)

Compound 4-4 can be obtained by reacting compound 4-3 obtained in Process 4-3 with an oxidizing agent (one equivalent to a large excess, or preferably one to two equivalents), in a solvent that is inert to the reaction. Reaction conditions described above for Process 3-8 can be applied herein.

(Process 4-5)

Compound 4-5 can be obtained by reacting compound 4-4 obtained in Process 4-4 with compound 3-10 (one equivalent to a large excess, or preferably three to five equivalents), in the presence or absence of a base, in a solvent that is inert to the reaction. Reaction conditions described above for Process 3-9 can be applied herein.

(Process 4-6)

Compound 4-6 can be obtained by reacting compound 4-4 obtained in Process 4-4 with a thiol source (one equivalent to a large excess, or preferably 3-5 equivalents), in a solvent that is inert to the reaction. Examples of a thiol source that may be used include potassium thioacetate, thiourea, thioacetamide, hydrogen sulfide, and sodium hydrosulfide. Of them, the use of sodium hydrosulfide under acidic conditions is preferred.

The solvent used for the reaction is not particularly limited and may be any solvent so long as it is inert to the reaction. N,N-dimethylformamide, N,N-dimethylacetamide, N-methyl-2-pyrrolidinone, tetrahydrofuran, 1,4-dioxane, 1,2-dimethoxyethane, dichloromethane, 1,2-dichloroethane, chloroform, methanol, ethanol, water, toluene, hexane, and such may be used individually or in combination, and of them, N,N-dimethylformamide is preferred.

Examples of a suitable acid for generating hydrogen sulfide from sodium hydrosulfide are organic acids such as trifluoroacetic acid, methanesulfonic acid, or p-toluenesulfonic acid, and inorganic acids such as hydrochloric acid or sulfuric acid. Of them, hydrochloric acid is preferred. In the reaction between compound 4-4 and the generated hydrogen sulfide, triethylamine or N,N-diisopropylethylamine is preferably used as a base.

The reaction temperature for generating hydrogen sulfide from sodium hydrosulfide under acidic conditions is for example, 0° C. to the boiling point of the solvent, or preferably 0° C. to room temperature. When compound 4-4 is reacted with the generated hydrogen sulfide, the temperature is, for example, 0° C. to the boiling point of the solvent, or preferably room temperature to approximately 100° C.

The reaction time differs depending on the reaction temperature and such. For generating hydrogen sulfide, the reaction time is usually about 5 minutes to 24 hours, or preferably about 10 minutes to 5 hours. For the reaction between hydrogen sulfide and compound 4-4, the reaction time is usually about 10 minutes to 24 hours, or preferably about 30 minutes to 5 hours.

(Process 4-7)

Compound 3-14 can be obtained by reacting compound 4-6 obtained in Process 4-6 with compound 3-13 (one equivalent to a large excess, or preferably one to three equivalents), in the presence of a base, in a solvent that is inert to the reaction. Reaction conditions described above for Process 3-11 can be applied herein.

(Process 4-8)

Compounds 4-8 and 4-9 can be obtained by performing a simple chemical modification to compounds 4-5 and 4-7 obtained in Processes 4-5 and 4-7, when Z' has a substituent such as a hydroxyl group, amino group, or carboxyl group. Reaction conditions described above for Process 3-12 can be applied herein.

All prior art documents cited herein are incorporated herein by reference.

EXAMPLES

Herein below, the present invention will be specifically described with reference to Examples, but it is not to be construed as being limited thereto.

NMR analyses were carried out using JNM-EX270 (270 MHz), JNM-GSX400 (400 MHz), or JNM-A500 (500 MHz), all of which are manufactured by JEOL. NMR data are shown in ppm (parts per million) (6) and were referenced to the deuterium lock signal from the sample solvent. Mass spectral data were obtained using JMS-DX303 or JMS-SX/SX102A manufactured by JEOL. Meanwhile, data of high performance liquid chromatography/mass spectrometry were obtained using Micromass ZMD equipped with a Waters 996-600E gradient high performance liquid chromatography

Example 1

Synthesis of {5-[4-amino-6-(2-methoxy-phenylsulfanyl)-[1,3,5]triazin-2-yl]-2,4-dichlorophenoxy}-acetonitrile Step 1: Synthesis of tert-butyl-(2,4-dichloro-5-iodophenoxy)-dimethyl-silane

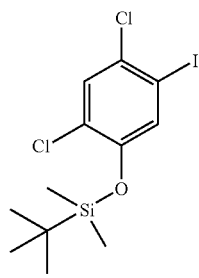

TBDMSCl (5.22 g) was added to a dimethylformamide solution (50 mL) of imidazole (2.83 g) and 2,4-dichloro-5-iodophenol (10 g), which was synthesized according to the production method described in WO 2001/027088. The mixture was stirred at room temperature for 4 hours. Water (150 mL) was added and extracted with hexane (200 mL). The extract was then washed in succession twice with water (100 mL) and once with brine (100 mL), and was pre-dried over anhydrous sodium sulfate, and then filtered. The solvent was distilled off, and the resulting residue was purified by silica gel column chromatography (developing solvent: hexane) to give tert-butyl-(2,4-dichloro-5-iodophenoxy)-dimethyl-silane as pale yellow oil (11.39 g).

Physicochemical properties of tert-butyl-(2,4-dichloro-5-iodophenoxy)-dimethyl-silane EI: m/z=402(M+)
$^1$H-NMR (270 MHz, in CDCl$_3$) chemical shifts δ: 0.23 (6H, s), 1.01 (9H, s), 7.33 (1H, s), 7.44 (1H, s).

Step 2: Synthesis of 2-[5-(tert-butyl-dimethyl-silanyloxy)-2,4-dichloro-phenyl]-5,5-dimethyl-[1,3,2]dioxaborinane

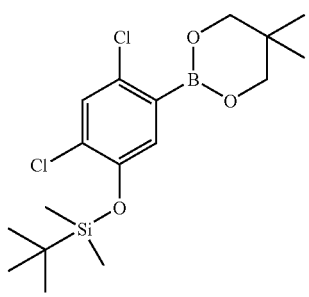

A solution of tert-Butyl-(2,4-dichloro-5-iodophenoxy)-dimethyl-silane (857 mg), obtained in Step 1, in tetrahydrofuran (1 mL) and toluene (4 mL) is prepared under nitrogen atmosphere, and cooled to −78° C. (dry ice-acetone). After addition of triisopropyl borate (0.6 mL), n-butyl lithium (1.6 N hexane solution; 1.62 mL) was added dropwise over 5 minutes. The resulting mixture was stirred at the same temperature for 30 minutes. The cooling bath was then removed and the mixture was allowed to warm. When the internal temperature reached 0° C., 2,2-dimethyl-propan-1,3-diol (0.27 g) was added. The mixture was then allowed to warm to room temperature. After the mixture was stirred at room temperature for 8 hours, water (20 mL) was added thereto and extracted with ethyl acetate (20 mL). The extract was washed in succession with a half-saturated aqueous ammonium chloride solution (15 mL), water (15 mL), and brine (10 mL), and then pre-dried over anhydrous sodium sulfate and filtered. The solvent was distilled off. The resulting residue was purified by silica gel column chromatography (developing solvent: hexane:ethyl acetate=20:1 to 9:1) to give 2-[5-(tert-butyl-dimethylsilanyloxy)-2,4-dichlorophenyl]-5,5-dimethyl-[1,3,2]dioxaborinane as pale yellow oil (547 mg).

Physicochemical properties of 2-[5-(tert-butyl-dimethylsilanyloxy)-2,4-dichlorophenyl]-5,5-dimethyl-[1,3,2]dioxaborinane EI: m/z=388(M+)
$^1$H-NMR (270 MHz, in CDCl$_3$) chemical shifts δ: 0.21 (6H, s), 1.02 (9H, s), 1.05 (6H, s), 3.78 (4H, s), 7.14 (1H, s), 7.33 (1H, s).

Step 3: Synthesis of 4-benzylsulfanyl-6-chloro-4-[1,3,5]triazin-2-ylamine

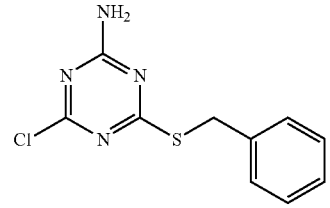

Dimethylformamide (120 mL) solution of 4,6-dichloro-[1,3,5]triazin-2-yl amine (10 g), which was synthesized according to the production method described in Japanese Patent Application Kokai Publication No. (JP-A) S60-208968 (unexamined, published Japanese patent application), was cooled to 0° C. in an ice bath. Triethylamine (11 mL) was added to the solution, and benzyl mercaptan (6.4 mL) was added dropwise over 5 minutes. The resulting mixture was allowed to gradually warm to room temperature. After the mixture was stirred for 8 hours, water (400 mL) was added thereto and extracted with ethyl acetate (400 mL). The extract was washed in succession twice with water (400 mL) and once with brine (200 mL). The extract was then pre-dried over anhydrous sodium sulfate, and then filtered. The solvent was distilled off. The resulting residue was recrystallized from dichloromethane to give 4-benzylsulfanyl-6-chloro-4-[1,3,5]triazin-2-ylamine as white solid (5.27 g).

Physicochemical properties of 4-benzylsulfanyl-6-chloro-4-[1,3,5]triazin-2-ylamine ESI (LC/MS positive mode) m/z=255/253(M+H+)
$^1$H-NMR (270 MHz, in DMSO-d$_6$) chemical shifts δ: 4.34 (2H, s), 7.24-7.34 (3H, m), 7.42-7.44 (2H, m), 8.12 (2H, s).

Step 4: Synthesis of 5-(4-amino-6-benzylsulfanyl-[1,3,5]triazin-2-yl)-2,4-dichloro-phenol

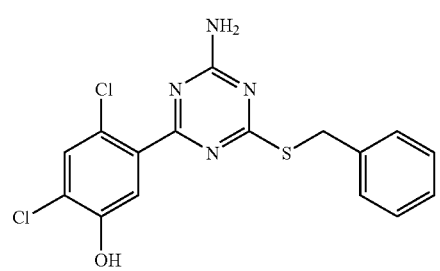

2-[5-(tert-Butyl-dimethyl-silanyloxy)-2,4-dichlorophenyl]-5,5-dimethyl-[1,3,2]dioxaborinane (0.5 g) and 4-benzylsulfanyl-6-chloro-4-[1,3,5]triazin-2-ylamine (0.32 g), respectively obtained in Steps 2 and 3 described above, were dissolved in 1,2-dimethoxyethane (15.5 mL). Aqueous sodium bicarbonate solution (1N; 2.57 mL) and tetrakis(triphenylphosphine)palladium (0.3 g) were added in succession to the mixture. After three cycles of nitrogen replacement using a vacuum pump, the mixture was stirred in an oil bath at 80° C. for 4 hours. After cooling to room temperature, water (50 mL) was added to the mixture. The resulting mixture was extracted with ethyl acetate (70 mL). The extract was washed with a saturated aqueous ammonium chloride solution (50 mL). The extract was then pre-dried over anhydrous sodium sulfate and filtered. The solvent was distilled off. The resulting residue was purified by silica gel column chromatography (developing solvent: hexane:ethyl acetate=7:3) to give 5-(4-amino-6-benzylsulfanyl-[1,3,5]triazin-2-yl)-2,4-dichlorophenol as pale yellow solid (379 mg).

Physicochemical properties of 5-(4-amino-6-benzylsulfanyl-[1,3,5]triazin-2-yl)-2,4-dichlorophenol ESI (LC/MS positive mode) m/z=381/379(M+H$^+$)
$^1$H-NMR (270 MHz, CDCl$_3$) chemical shifts δ: 4.43 (2H, s), 5.41 (2H, brs), 7.22-7.49 (7H, m).

Step 5: Synthesis of [5-(4-amino-6-benzylsulfanyl-[1,3,5]triazin-2-yl)-2,4-dichlorophenoxy]-acetonitrile

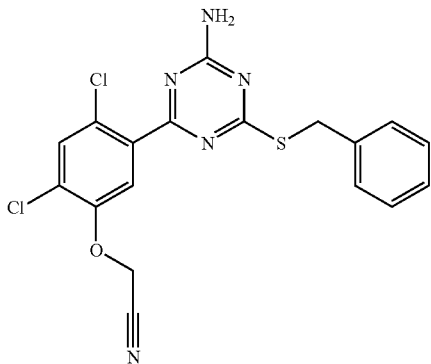

Cesium carbonate (12 mg) was added to a dimethylformamide solution (1 mL) of 5-(4-amino-6-benzylsulfanyl-[1,3,5]triazin-2-yl)-2,4-dichlorophenol (11 mg) obtained in Step 4 described above. A solution of α-bromoacetonitrile (3.6 mg) in dimethylformamide (0.2 mL) was added, and the resulting mixture was stirred at room temperature for 3 hours. After dilution with ethyl acetate (7 mL), the mixture was washed in succession twice with water (6 mL) and once with brine (3 mL). The mixture was then pre-dried over anhydrous sodium sulfate and filtered. The solvent was distilled off. The resulting residue was purified by silica gel column chromatography (developing solvent: hexane:ethyl acetate=8:2) to give [5-(4-amino-6-benzylsulfanyl-[1,3,5]triazin-2-yl)-2,4-dichlorophenoxy]-acetonitrile (11 mg) as white solid.

Physicochemical properties of [5-(4-amino-6-benzylsulfanyl-[1,3,5]triazin-2-yl)-2,4-dichlorophenoxy]-acetonitrile ESI (LC/MS positive mode) m/z=420/418(M+H$^+$)
$^1$H-NMR (270 MHz, in DMSO-d$_6$) chemical shifts δ: 4.40 (2H, s), 5.33 (2H, s), 7.22-7.46 (5H, m), 7.59 (1H, s), 7.83 (1H, s), 7.88 (2H, s).

Step 6: Synthesis of [5-(4-amino-6-phenylmethanesulfinyl-[1,3,5]triazin-2-yl)-2,4-dichlorophenoxy]-acetonitrile

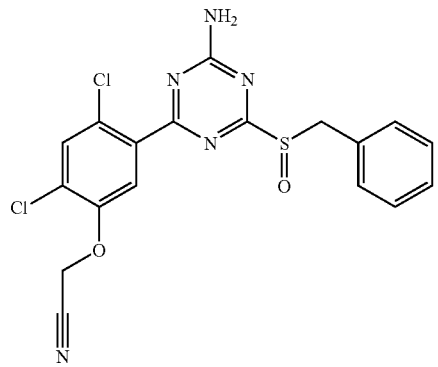

A dichloromethane solution (100 mL) of [5-(4-amino-6-benzylsulfanyl-[1,3,5]triazin-2-yl)-2,4-dichlorophenoxy]-acetonitrile (3 g) obtained in Step 5 was cooled to 0° C. in an ice bath. m-Perbenzoic acid (2 g) was added, and the mixture was stirred at the same temperature for 5 minutes and then at room temperature for 6 hours. After dilution with hexane (50 mL), the solid material was collected by filtration. Further, the solid material was washed with a dichloromethane-hexane (1:1) mixture (20 mL), and dried under reduced pressure to give the title compound [5-(4-amino-6-phenylmethanesulfinyl-[1,3,5]triazin-2-yl)-2,4-dichlorophenoxy]-acetonitrile as pale yellow solid (2.37 g).

Physicochemical properties of [5-(4-amino-6-phenylmethanesulfinyl-[1,3,5]triazin-2-yl)-2,4-dichlorophenoxy]-acetonitrile ESI (LC/MS positive mode) m/z=436/434(M+H$^+$)
$^1$H-NMR (270 MHz, in DMSO-d$_6$) chemical shifts δ: 4.29 (1H, d, J=13 Hz), 4.51 (1H, d, J=13 Hz), 5.36 (2H, s), 7.17-7.22 (2H, m), 7.29-7.35 (3H, m), 7.61 (1H, s), 7.89 (1H, s), 8.36 (1H, brs), 8.51 (1H, brs).

Step 7: Synthesis of {5-[4-amino-6-(2-methoxyphenylsulfanyl)-[1,3,5]triazin-2-yl]-2,4-dichlorophenoxy}-acetonitrile

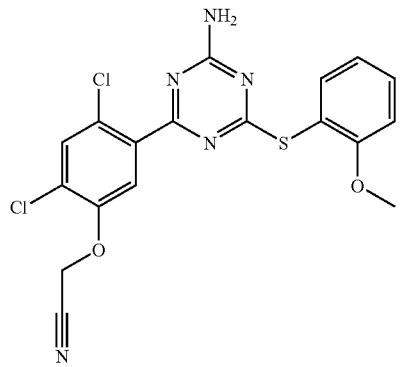

Triethylamine (12 μL) and 2-methoxybenzenethiol (12 mg) were added in succession to a solution of the above-described [5-(4-amino-6-phenylmethanesulfinyl-[1,3,5]triazin-2-yl)-2,4-dichlorophenoxy]-acetonitrile (12 mg) in dimethylformamide (0.5 mL). The mixture was stirred at room temperature for 8 hours. After dilution with ethyl acetate (7 mL), the mixture was washed twice with water and once with brine. The mixture was pre-dried over anhydrous sodium sulfate, and filtered. The solvent was distilled off. The resulting residue was purified by silica gel column chromatography (developing solvent: hexane:ethyl acetate=7:3) to give {5-[4-amino-6-(2-methoxy-phenylsulfanyl)-[1,3,5]triazin-2-yl]-2,4-dichlorophenoxy}-acetonitrile as white solid (10 mg).

Physicochemical properties of {5-[4-amino-6-(2-methoxy-phenylsulfanyl)-[1,3,5]triazin-2-yl]-2,4-dichlorophenoxy}-acetonitrile ESI (LC/MS positive mode) m/z=436/434(M+H$^+$)
$^1$H-NMR (270 MHz, in DMSO-d$_6$) chemical shifts δ: 3.79 (3H, s), 5.29 (2H, s), 7.00 (1H, td, J=8, 1 Hz), 7.13 (1H, dd, J=8, 1 Hz), 7.43-7.50 (2H, m), 7.55 (1H, dd, J=8, 2 Hz), 7.70 (1H, brs), 7.74 (1H, brs), 7.76 (1H, s).

Example 2

Synthesis of 5-(4-amino-6-benzylsulfanyl-[1,3,5]triazin-2-yl)-2,4-dichloro-N-(2-hydroxyethyl)-benzamide Step 1: Synthesis of 2,4-dichloro-5-iodobenzoic acid methyl ester

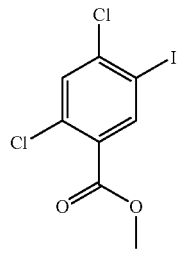

Sodium iodate (4.4 g) and iodine (11.1 g) were added to 90% sulfuric acid (330 mL), and stirred at room temperature for 8 hours. 2,4-Dichlorobenzoic acid (21 g) commercially available was added and stirred at the same temperature for 24 hours. The reaction solution was poured into ice water (3 L), and the precipitated solid material was collected by filtration. Further, the solid material was washed with water, and dried under reduced pressure. 2,4-Dichloro-5-iodobenzoic acid (16.8 g) was obtained by recrystallization (acetic acid-water). The resulting 2,4-dichloro-5-iodobenzoic acid (2 g) was dissolved in a mixture of dichloromethane (20 mL) and methanol (20 mL). Trimethylsilyldiazomethane (hexane solution, 2 M) was added dropwise until the solution became yellow. A small amount of acetic acid was added, and then the resulting mixture was concentrated under reduced pressure. The resulting residue was recrystallized using hexane to give the title compound 2,4-dichloro-5-iodobenzoic acid methyl ester as white solid (2 g).

Physicochemical properties of 2,4-dichloro-5-iodobenzoic acid methyl ester

ESI (LC/MS positive mode) m/z=333/331(M+H$^+$)
$^1$H-NMR (270 MHz, in DMSO-d$_6$) chemical shifts δ: 3.86 (3H, s), 7.91 (1H, s), 8.31 (1H, s).

Step 2: Synthesis of 5-(4-amino-6-benzylsulfanyl-[1,3,5]triazin-2-yl)-2,4-dichlorobenzoic acid methyl ester

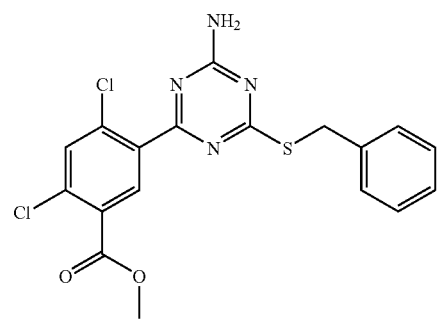

Under nitrogen atmosphere, dimethylsulfoxide (3.8 mL) was added to a mixture of [1,1'-bis(diphenylphosphino)ferrocene]dichloropalladium (II) dichloromethane adduct (41 mg), bis(pinacolato)diboron (176 mg), potassium acetate (185 mg), and 2,4-dichloro-5-iodobenzoic acid methyl ester (0.21 g) obtained in Step 1 described above. The resulting mixture was stirred at 80° C. overnight. After cooling, the mixture was diluted with ethyl acetate (30 mL), and washed three times with water (20 mL) and then with brine (15 mL). The mixture was pre-dried over anhydrous sodium sulfate, and then filtered. The solvent was distilled off. 4-Benzylsulfanyl-6-chloro-4-[1,3,5]triazin-2-yl amine (159 mg) was added to the resulting residue, and dissolved in 1,2-dimethoxyethane (6 mL). Aqueous sodium bicarbonate solution (1N, 6 mL) and tetrakis(triphenylphosphine)palladium (108 mg) were added in succession. After three cycles of nitrogen replacement using a vacuum pump, the mixture was stirred at 85° C. for 4 hours. After cooling to room temperature, water (40 mL) was added, and the resulting mixture was extracted with ethyl acetate (50 mL). The extract was washed with brine (20 mL), and pre-dried over anhydrous sodium sulfate and filtered. The solvent was distilled off. The resulting residue was purified by silica gel column chromatography (developing solvent: hexane:ethyl acetate=9:1 to 4:1) to give 5-(4-amino-6-benzylsulfanyl-[1,3,5]triazin-2-yl)-2,4-dichlorobenzoic acid methyl ester as white solid (379 mg).

Physicochemical properties of 5-(4-amino-6-benzylsulfanyl-[1,3,5]triazin-2-yl)-2,4-dichlorobenzoic acid methyl ester ESI (LC/MS positive mode) m/z=423/421(M+H$^+$)
$^1$H-NMR (270 MHz, in DMSO-d$_6$) chemical shifts δ: 3.88 (3H, s), 4.40 (2H, s), 7.22-7.47 (5H, m), 7.89 (1H, brs), 7.90 (1H, brs), 7.93 (1H, s), 8.20 (1H, s).

Step 3: Synthesis of 5-(4-amino-6-benzylsulfanyl-[1,3,5]triazin-2-yl)-2,4-dichloro-N-(2-hydroxyethyl)benzamide

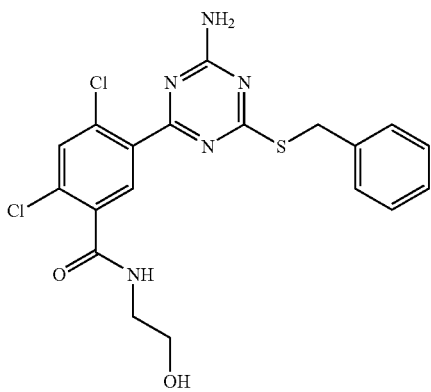

A solution of tetrahydrofuran (6 mL) and methanol (6 mL) mixed with 5-(4-amino-6-benzylsulfanyl-[1,3,5]triazin-2-yl)-2,4-dichlorobenzoic acid methyl ester (64 mg) obtained in Step 2 described above was cooled to 0° C. in an ice bath. An aqueous solution of lithium hydroxide (0.2 mM, 1 mL) was added, and the resulting mixture was allowed to gradually warm to room temperature. The mixture was stirred for 10 hours, and then diluted with ethyl acetate (15 mL). The mixture was washed in succession with an aqueous solution of 10% citric acid (10 mL), water (10 mL), and brine (5 mL). The solution was pre-dried over anhydrous sodium sulfate, and then filtered. The solvent was distilled off. The resulting residue was dissolved in dimethylformamide (7 mL). 1-Hydroxybenzotriazole (0.28 g), N-ethyldiisopropylamine (0.53 mL), 2-amino-ethanol (280 mg), and 1-(3-dimethylaminopropyl)-3-ethyl carbodiimide hydrochloride (0.7 g) were added in succession to the solution, and stirred at room temperature for 24 hours. The mixture was diluted with ethyl acetate (30 mL), and washed in succession three times with water (30 mL) and once with brine. The solution was pre-dried over anhydrous sodium sulfate and filtered. The solvent was distilled off. The resulting residue was purified by silica gel column chromatography (developing solvent: dichloromethane:methanol=20:1 to 15:1) to give 5-(4-amino-6-benzylsulfanyl-[1,3,5]triazin-2-yl)-2,4-dichloro-N-(2-hydroxyethyl)benzamide (42 mg) as white solid.

Physicochemical properties of 5-(4-amino-6-benzylsulfanyl-[1,3,5]triazin-2-yl)-2,4-dichloro-N-(2-hydroxyethyl)benzamide ESI (LC/MS positive mode) m/z=452/450(M+H$^+$)
$^1$H-NMR (270 MHz, in DMSO-d$_6$) chemical shifts δ: 3.22-3.54 (4H, m), 4.39 (2H, s), 4.74 (1H, t, J=6 Hz), 7.21-7.48 (5H, m), 7.75 (1H, s), 7.81 (1H, s), 7.86 (2H, s), 8.57 (1H, t, J=5 Hz).

The compounds described in Examples 3 to 70 below were synthesized according to the method described in Example 1 or 2 above.

Example 3

4-(2,4-Dichlorophenyl)-6-(2,5-dimethoxyphenylsulfanyl)-[1,3,5]triazin-2-ylamine

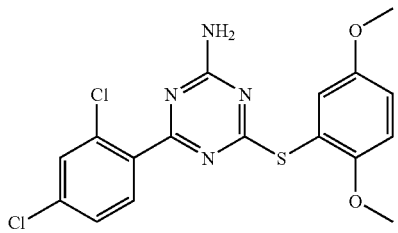

ESI (LC/MS positive mode) m/z=411/409(M+H$^+$)
$^1$H-NMR (270 MHz, in CDCl$_3$) chemical shifts δ: 3.79 (3H, s), 3.80 (3H, s), 5.39 (2H, brs), 6.91 (1H, d, J=9 Hz), 6.99 (1H, dd, J=9, 3 Hz), 7.16 (1H, d, J=3 Hz), 7.26-7.30 (1H, m), 7.43 (1H, d, J=2 Hz), 7.69 (1H, d, J=8 Hz).

Example 4

4-(5-Benzyloxy-2,4-dichlorophenyl)-6-benzylsulfanyl-[1,3,5]triazin-2-ylamine

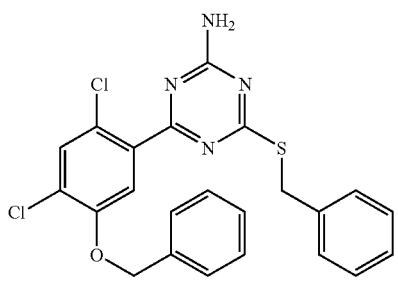

ESI (LC/MS positive mode) m/z=471/469(M+H$^+$)
$^1$H-NMR (270 MHz, in CDCl$_3$) chemical shifts δ: 4.41 (2H, s), 5.14 (2H, s), 5.59 (2H, brs), 7.22-7.47 (11H, m), 7.51 (1H, s).

Example 5

4-Benzylsulfanyl-6-(2,4-dichlorophenyl)-[1,3,5]triazin-2-ylamine

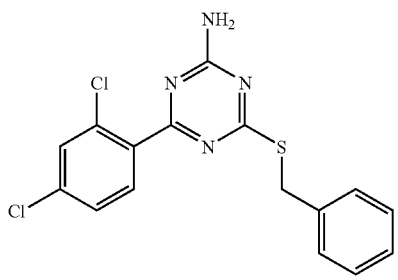

ESI (LC/MS positive mode) m/z=364/362(M+H$^+$)
$^1$H-NMR (270 MHz, in CDCl$_3$) chemical shifts δ: 4.43 (2H, s), 5.43 (2H, brs), 7.22-7.44 (6H, m), 7.50 (1H, d, J=2 Hz), 7.71 (1H, d, J=8 Hz).

Example 6

4-(2,4-Dichlorophenyl)-6-(2-methoxyphenylsulfanyl)-[1,3,5]triazin-2-ylamine

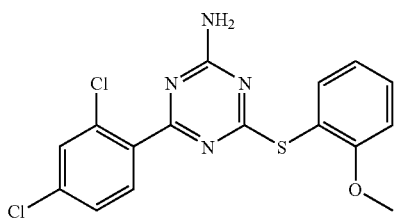

ESI (LC/MS positive mode) m/z=381/379(M+H$^+$)

$^1$H-NMR (270 MHz, in CDCl$_3$) chemical shifts δ: 3.84 (3H, s), 5.57 (2H, brs), 6.95-7.03 (2H, m), 7.27 (1H, dd, J=8, 2 Hz), 7.41-7.48 (2H, m), 7.58 (1H, dd, J=8, 2 Hz), 7.66 (1H, d, J=8 Hz).

Example 7

4-(2-Aminophenylsulfanyl)-6-(2,4-dichlorophenyl)-[1,3,5]triazin-2-ylamine

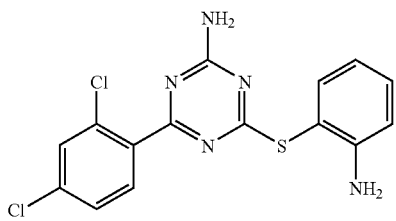

ESI (LC/MS positive mode) m/z=366/364(M+H$^+$)

$^1$H-NMR (270 MHz, in CDCl$_3$) chemical shifts δ: 4.31 (2H, brs), 5.68 (2H, brs), 6.74-6.83 (2H, m), 7.23-7.32 (1H, m), 7.41-7.47 (2H, m), 7.69 (1H, d, J=8 Hz).

Example 8

{5-[4-Amino-6-(2,5-dimethoxyphenylsulfanyl)-[1,3,5]triazin-2-yl]-2,4-dichlorophenoxy}-acetonitrile

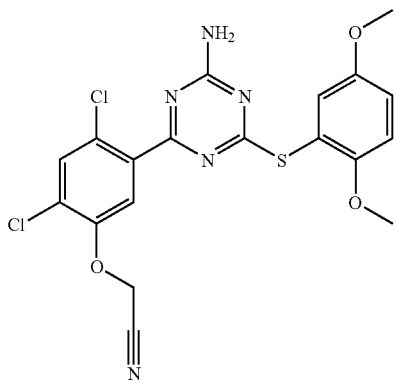

ESI (LC/MS positive mode) m/z=466/464(M+H$^+$)

$^1$H-NMR (270 MHz, in DMSO-d$_6$) chemical shifts δ: 3.72 (3H, s), 3.74 (3H, s), 5.30 (2H, s), 7.01-7.16 (3H, m), 7.49 (1H, s), 7.75 (2H, brs), 7.79 (1H, s).

Example 9

[5-(4-Amino-6-phenylsulfanyl-[1,3,5]triazin-2-yl)-2,4-dichlorophenoxy]-acetonitrile

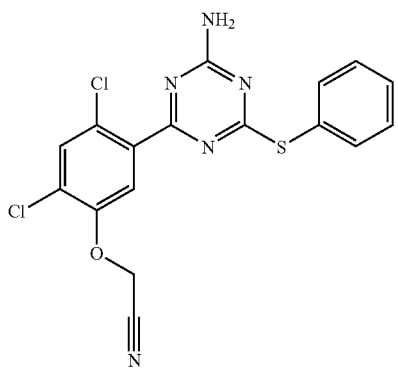

ESI (LC/MS positive mode) m/z=406/404(M+H$^+$)

$^1$H-NMR (270 MHz, in DMSO-d$_6$) chemical shifts δ: 5.29 (2H, s), 7.42-7.50 (3H, m), 7.51 (1H, s), 7.60-7.67 (2H, m), 7.75-7.81 (2H, m), 7.85 (1H, brs).

Example 10

{5-[4-Amino-6-(pyrimidin-2-ylsulfanyl)-[1,3,5]triazin-2-yl]-2,4-dichlorophenoxy}-acetonitrile

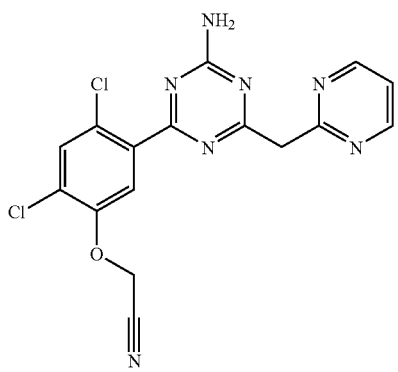

ESI (LC/MS positive mode) m/z=408/406(M+H$^+$)

$^1$H-NMR (270 MHz, in DMSO-d$_6$) chemical shifts δ: 5.31 (2H, s), 7.50 (1H, s), 7.51 (1H, t, J=5 Hz), 7.79 (1H, s), 7.91 (1H, brs), 7.98 (1H, brs), 8.85 (1H, d, J=5 Hz).

Example 11

{5-[4-Amino-6-(5-methyl-[1,3,4]thiadiazol-2-ylsulfanyl)-[1,3,5]triazin-2-yl]-2,4-dichlorophenoxy}-acetonitrile

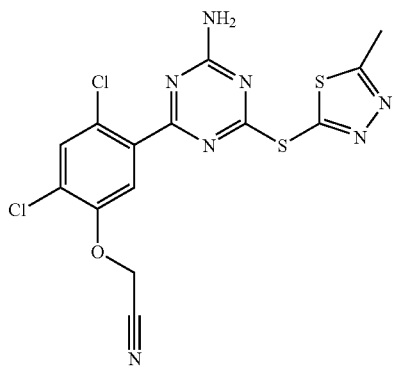

ESI (LC/MS positive mode) m/z=428/426(M+H$^+$)

$^1$H-NMR (270 MHz, in DMSO-d$_6$) chemical shifts δ: 2.74 (3H, s), 5.34 (2H, s), 7.62 (1H, s), 7.86 (1H, s), 8.21 (1H, brs), 8.26 (1H, brs).

Example 12

{5-[4-Amino-6-(1H-benzoimidazole-2-ylsulfanyl)-[1,3,5]triazin-2-yl]-2,4-dichlorophenoxy}-acetonitrile

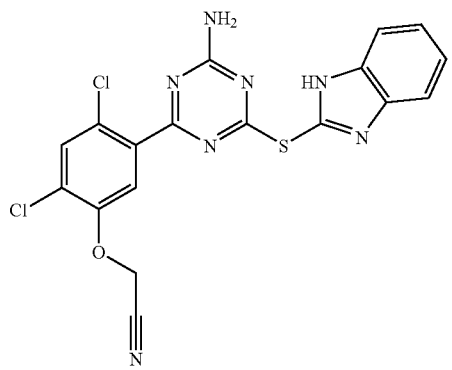

ESI (LC/MS positive mode) m/z=446/444(M+H$^+$)

$^1$H-NMR (270 MHz, in DMSO-d$_6$) chemical shifts δ: 5.24 (2H, s), 7.10-7.40 (2H, m), 7.50-7.59 (2H, m), 7.67 (1H, d, J=8 Hz), 7.79 (1H, s), 8.00 (1H, brs), 8.04 (1H, brs), 13.12 (1H, s).

Example 13

{5-[4-Amino-6-(benzothiazol-2-ylsulfanyl)-[1,3,5]triazin-2-yl]-2,4-dichlorophenoxy}-acetonitrile

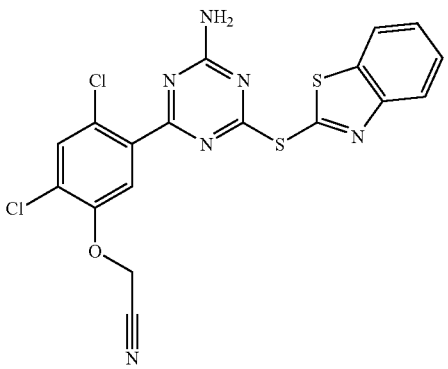

ESI (LC/MS positive mode) m/z=463/461 (M+H$^+$)

$^1$H-NMR (270 MHz, in acetone-d$_6$) chemical shifts δ: 5.17 (2H, s), 7.30-7.46 (4H, m), 7.57 (1H, s), 7.65 (1H, s), 7.84-7.88 (1H, m), 7.92-7.96 (1H, m).

Example 14

[5-(4-Amino-6-cyclopropylmethylsulfanyl-[1,3,5]triazin-2-yl)-2,4-dichlorophenoxy]-acetonitrile

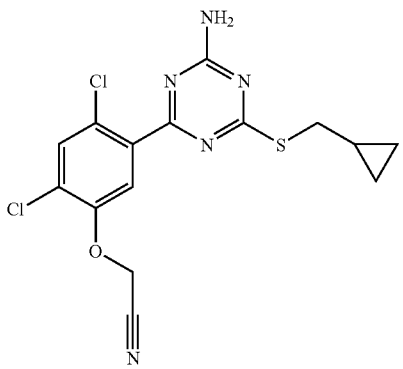

ESI (LC/MS positive mode) m/z=384/382(M+H$^+$)

$^1$H-NMR (270 MHz, in CDCl$_3$) chemical shifts δ: 0.29-0.37 (2H, m), 0.58-0.67 (2H, m), 1.13-1.28 (1H, m), 3.13 (2H, d, J=7 Hz), 4.88 (2H, s), 5.40 (2H, brs), 7.55 (1H, s), 7.56 (1H, s).

Example 15

(5-{4-Amino-6-[2-methoxy-4-(4-methyl-piperazine-1-carbonyl)-phenylsulfanyl]-[1,3,5]triazin-2-yl}-2,4-dichlorophenoxy)-acetonitrile

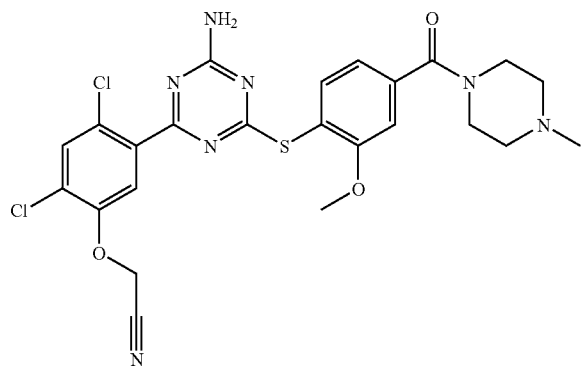

ESI (LC/MS positive mode) m/z=562/560(M+H$^+$)

$^1$H-NMR (270 MHz, in DMSO-d$_6$) chemical shifts δ: 2.14-2.43 (7H, m), 3.25-3.68 (4H, m), 3.81 (3H, s), 5.29 (2H, s), 6.97 (1H, dd, J=8, 2 Hz), 7.09 (1H, d, J=2 Hz), 7.49 (1H, s), 7.62 (1H, d, J=8 Hz), 7.75-7.83 (3H, m).

Example 17

(5-{4-Amino-6-[4-(4-methyl-piperazine-1-carbonyl)-phenylsulfanyl]-[1,3,5]triazin-2-yl}-2,4-dichlorophenoxy)-acetonitrile

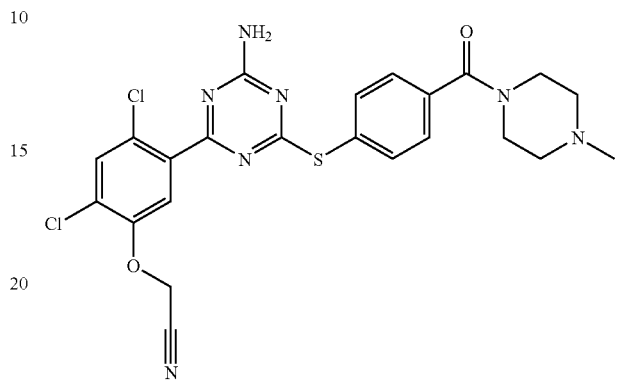

ESI (LC/MS positive mode) m/z=532/530(M+H$^+$)

$^1$H-NMR (270 MHz, in DMSO-d$_6$) chemical shifts δ: 2.20 (3H, s), 2.21-2.42 (4H, m), 3.18-3.22 (4H, m), 5.76 (2H, s), 7.44 (2H, d, J=8 Hz), 7.52 (1H, s), 7.70 (2H, d, J=8 Hz), 7.78 (1H, s), 7.85 (1H, s), 7.89 (1H, s).

Example 16

4-[4-Amino-6-(2,4-dichloro-5-cyanomethoxyphenyl)-[1,3,5]triazin-2-ylsulfanyl]-N-(2,3-dihydroxypropyl)-3-methoxybenzamide

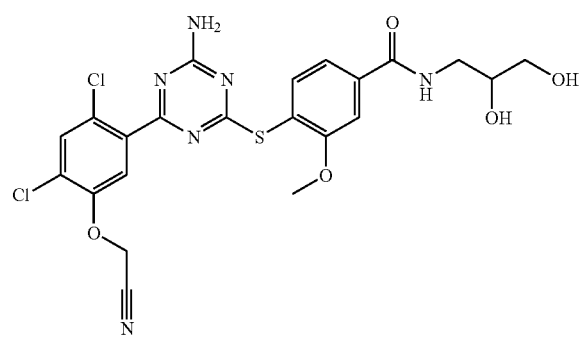

ESI (LC/MS positive mode) m/z=553/551(M+H$^+$)

$^1$H-NMR (270 MHz, in DMSO-d$_6$) chemical shifts δ: 3.12-3.49 (3H, m), 3.58-3.71 (1H, m), 3.86 (3H, s), 4.60 (1H, t, J=6 Hz), 4.85 (1H, d, J=5 Hz), 5.29 (2H, s), 7.46-7.51 (2H, m), 7.55-7.58 (1H, m), 7.66 (1H, d, J=9 Hz), 7.74 (1H, brs), 7.78 (1H, s), 7.80 (1H, brs), 8.57 (1H, t, J=6 Hz).

Example 18

(5-{4-Amino-6-[4-(piperazine-1-carbonyl)-phenylsulfanyl]-[1,3,5]triazin-2-yl}-2,4-dichlorophenoxy)-acetonitrile

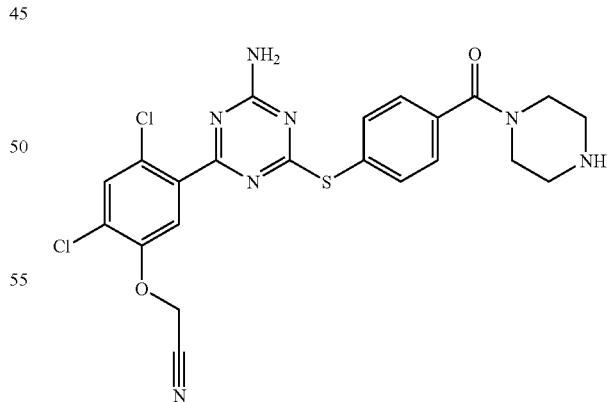

ESI (LC/MS positive mode) m/z=518/516 (M+H$^+$)

$^1$H-NMR (270 MHz, in DMSO-d$_6$) chemical shifts δ: 2.57-2.79 (4H, m), 3.18-3.62 (4H, m), 5.29 (2H, s), 7.44 (2H, d, J=8 Hz), 7.52 (1H, s), 7.69 (2H, d, J=8 Hz), 7.78 (1H, s), 7.85 (1H, s), 7.89 (1H, s).

Example 19

4-[4-Amino-6-(2,4-dichloro-5-cyanomethoxyphenyl)-[1,3,5]triazin-2-ylsulfanyl]-N-(2,3-dihydroxypropyl)-benzamide

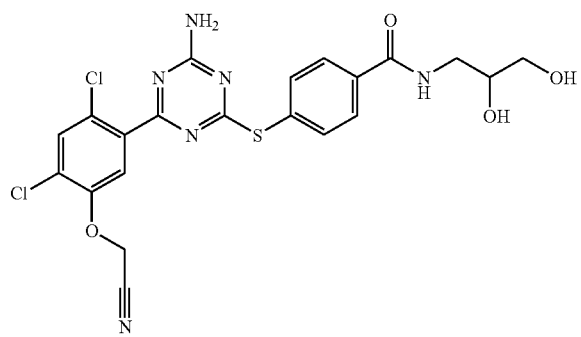

ESI (LC/MS positive mode) m/z=523/521(M+H$^+$)

$^1$H-NMR (270 MHz, in DMSO-d$_6$) chemical shifts δ: 3.13-3.69 (4H, m), 4.58 (1H, t, J=6 Hz), 4.82 (1H, d, J=5 Hz), 5.29 (2H, s), 7.51 (1H, s), 7.72 (2H, d, J=9 Hz), 7.79 (1H, s), 7.82 (1H, s), 7.86-7.95 (3H, m), 8.51 (1H, t, J=6 Hz).

Example 20

4-[4-Amino-6-(2,4-dichloro-5-cyanomethoxyphenyl)-[1,3,5]triazin-2-ylsulfanyl]-N-(2-hydroxy-1-hydroxymethyl-ethyl)-benzamide

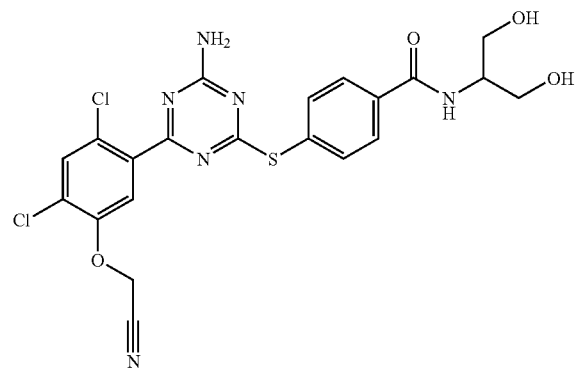

ESI (LC/MS positive mode) m/z=523/521(M+H$^+$)

$^1$H-NMR (270 MHz, in DMSO-d$_6$) chemical shifts δ: 3.51 (4H, dd, J=6, 6 Hz), 3.91-4.04 (1H, m), 4.67 (2H, t, J=6 Hz), 5.29 (2H, s), 7.51 (1H, s), 7.72 (2H, d, J=8 Hz), 7.79 (1H, s), 7.81 (1H, s), 7.88 (1H, s), 7.93 (2H, d, J=8 Hz), 8.08 (1H, d, J=8 Hz).

Example 21

(5-{4-Amino-6-[2-methoxy-4-(piperazine-1-carbonyl)-phenylsulfanyl]-[1,3,5]triazin-2-yl}-2,4-dichlorophenoxy)-acetonitrile

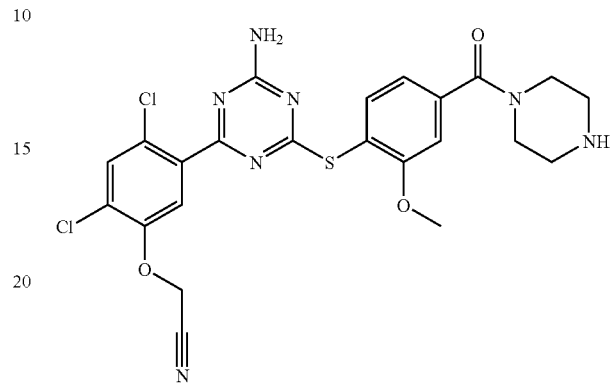

ESI (LC/MS positive mode) m/z=548/546(M+H$^+$)

$^1$H-NMR (270 MHz, in chloroform-d) chemical shifts δ: 2.76-3.06 (4H, m), 3.33-3.84 (4H, m), 3.87 (3H, s), 4.78 (2H, s), 5.43 (2H, s), 6.99 (1H, dd, J=2, 8 Hz), 7.05 (1H, d, J=2 Hz), 7.43 (1H, s), 7.47 (1H, s), 7.63 (1H, d, J=8 Hz).

Example 22

4-[4-Amino-6-(2,4-dichloro-5-cyanomethoxyphenyl)-[1,3,5]triazin-2-ylsulfanyl]-3-methoxy-N-(1-methyl-piperidin-4-yl)-benzamide

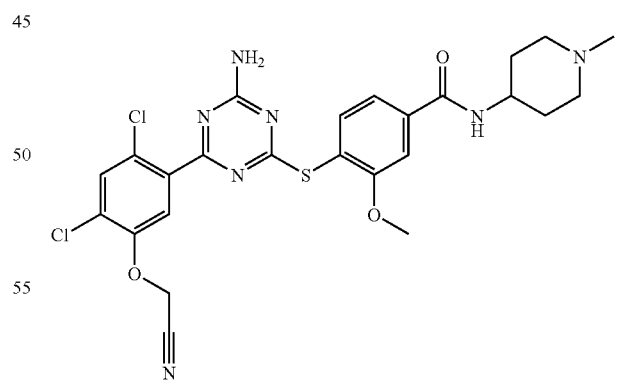

ESI (LC/MS positive mode) m/z=575/574(M+H$^+$)

$^1$H-NMR (270 MHz, in DMSO-d$_6$) chemical shifts δ: 1.55-1.88 (4H, m), 2.31 (3H, s), 2.40-2.63 (3H, m), 2.85-3.01 (2H, m), 3.86 (3H, s), 5.29 (2H, s), 7.46-7.53 (3H, m), 7.66 (1H, d, J=8 Hz), 7.73 (1H, brs), 7.78 (1H, s), 7.80 (1H, brs), 8.40 (1H, d, J=7 Hz).

Example 23

4-[4-Amino-6-(2,4-dichloro-5-cyanomethoxyphenyl)-[1,3,5]triazin-2-ylsulfanyl]-3-methoxy-N-(1-methyl-piperidin-4-yl)-benzamide

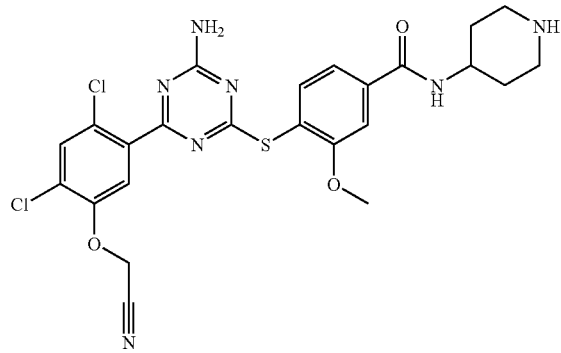

ESI (LC/MS positive mode) m/z=562/560(M+H$^+$)

$^1$H-NMR (270 MHz, in DMSO-d$_6$) chemical shifts δ: 1.36-1.50 (2H, m), 1.69-1.79 (2H, m), 2.44-2.59 (3H, m), 2.91-3.01 (2H, m), 3.86 (3H, s), 5.29 (2H, s), 7.45-7.54 (3H, m), 7.65 (1H, d, J=8 Hz), 7.73 (1H, brs), 7.78 (1H, s), 7.80 (1H, brs), 8.36 (1H, d, J=8 Hz).

Example 24

4-(2,4-Dichloro-5-pyrimidin-2-yl-phenyl)-6-methylsulfanyl-[1,3,5]triazin-2-ylamine

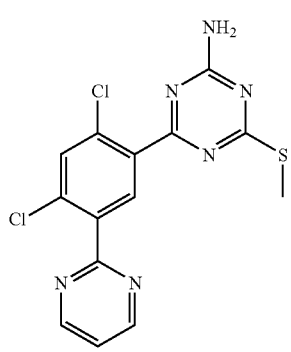

ESI (LC/MS positive mode) m/z=367/365(M+H$^+$)

$^1$H-NMR (270 MHz, in DMSO-d$_6$) chemical shifts δ: 3.23 (3H, s), 7.59 (1H, t, J=5 Hz), 7.73 (1H, s), 7.79 (1H, s), 7.90 (1H, s), 8.15 (1H, s), 8.99 (2H, d, J=5 Hz).

Example 25

N-{2-[4-Amino-6-(2,4-dichloro-5-pyrimidin-2-yl-phenyl)-[1,3,5]triazin-2-ylsulfanyl]-ethyl}-acetamide

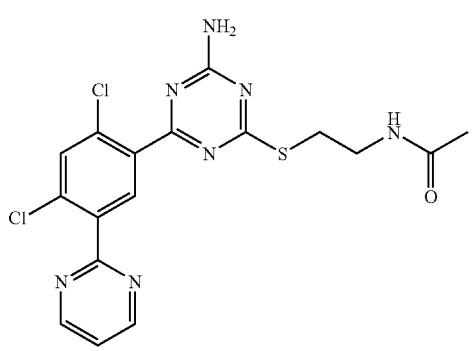

ESI (LC/MS positive mode) m/z=438/436(M+H$^+$)

$^1$H-NMR (270 MHz, in DMSO-d$_6$) chemical shifts δ: 1.79 (3H, s), 3.17 (2H, t, J=6 Hz), 3.19-3.39 (2H, m), 7.59 (1H, t, J=5 Hz), 7.76 (1H, s), 7.84 (1H, s), 7.92 (1H, s), 8.08 (1H, brs), 8.15 (1H, s), 8.99 (2H, d, J=5 Hz).

Example 26

5-(4-Amino-6-benzylsulfanyl-[1,3,5]triazin-2-yl)-2,4-dichlorobenzamide

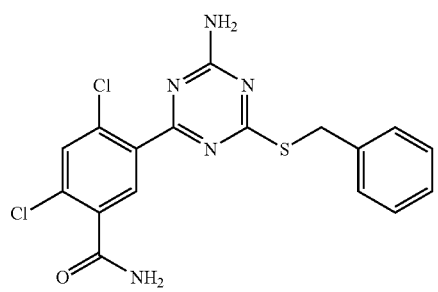

ESI (LC/MS positive mode) m/z=408/406(M+H$^+$)

$^1$H-NMR (270 MHz, in DMSO-d$_6$) chemical shifts δ: 4.39 (2H, s), 7.21-7.37 (3H, m), 7.41-7.48 (2H, m), 7.74-7.88 (5H, m), 8.03 (1H, s).

Example 27

5-(4-Amino-6-benzylsulfanyl-[1,3,5]triazin-2-yl)-2,4-dichloro-N-(2,3-dihydroxypropyl)-benzamide

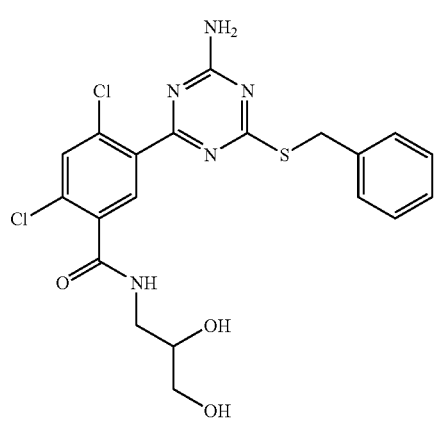

ESI (LC/MS positive mode) m/z=482/480(M+H$^+$)

$^1$H-NMR (270 MHz, in DMSO-d$_6$) chemical shifts δ: 3.08-3.66 (5H, m), 4.39 (2H, s), 4.61 (1H, brs), 4.86 (1H, brs), 7.21-7.48 (5H, m), 7.77 (1H, s), 7.83 (1H, s), 7.90 (2H, s), 8.57 (1H, t, J=6 Hz).

Example 28

5-(4-Amino-6-benzylsulfanyl-[1,3,5]triazin-2-yl)-2,4-dichloro-N-(2-hydroxy-1-hydroxymethyl-ethyl)-benzamide

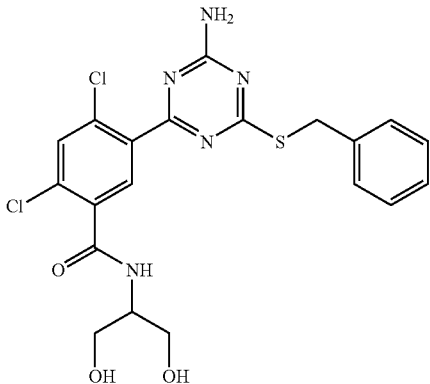

ESI (LC/MS positive mode) m/z=482/480(M+H$^+$)

$^1$H-NMR (270 MHz, in DMSO-d$_6$) chemical shifts δ: 3.48 (4H, dd, J=6, 6 Hz), 3.83-3.96 (1H, m), 4.39 (2H, s), 4.69 (2H, d, J=6 Hz), 7.21-7.48 (5H, m), 7.76 (1H, s), 7.80 (1H, s), 7.87 (2H, s), 8.29 (1H, d, J=8 Hz).

Example 29

5-(4-Amino-6-benzylsulfanyl-[1,3,5]triazin-2-yl)-2,4-dichloro-N-(1-methyl-piperidin-4-yl)-benzamide

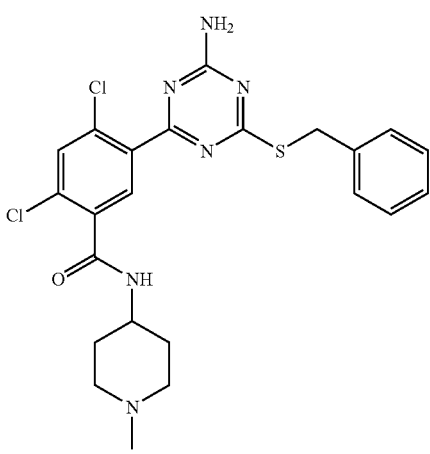

ESI (LC/MS positive mode) m/z=505/503(M+H$^+$)

$^1$H-NMR (270 MHz, in DMSO-d$_6$) chemical shifts δ: 1.39-1.57 (2H, m), 1.72-1.83 (2H, m), 1.89-2.02 (2H, m), 2.14 (3H, s), 2.66-2.78 (2H, m), 3.60-3.76 (1H, m), 4.39 (2H, s), 7.21-7.48 (5H, m), 7.69 (1H, s), 7.81 (1H, s), 7.85 (2H, s), 8.51 (1H, d, J=8 Hz).

Example 30

[5-(4-Amino-6-benzylsulfanyl-[1,3,5]triazin-2-yl)-2,4-dichlorophenyl]-(4-methyl-piperazin-1-yl)-methanone

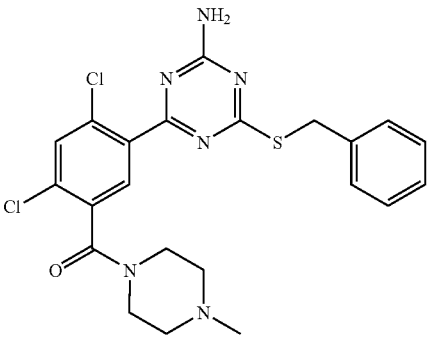

ESI (LC/MS positive mode) m/z=491/489(M+H$^+$)

$^1$H-NMR (270 MHz, in DMSO-d$_6$) chemical shifts δ: 2.17 (3H, s), 2.22-2.57 (4H, m), 3.11-3.19 (2H, m), 3.57-3.70 (2H, m), 4.39 (2H, s), 7.21-7.48 (5H, m), 7.68 (1H, s), 7.82-7.89 (3H, m).

Example 31

[5-(4-Amino-6-benzylsulfanyl-[1,3,5]triazin-2-yl)-2,4-dichlorophenyl]-morpholin-4-yl-methanone

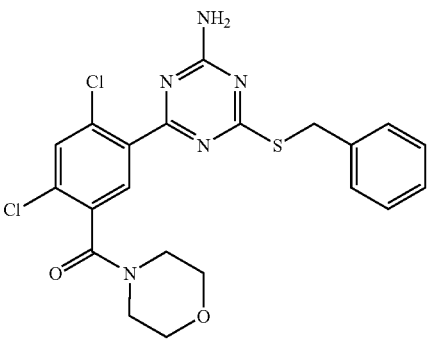

ESI (LC/MS positive mode) m/z=478/476(M+H$^+$)

$^1$H-NMR (270 MHz, in DMSO-d$_6$) chemical shifts δ: 3.13-3.21 (2H, m), 3.48-3.73 (6H, m), 4.39 (2H, s), 7.21-7.48 (5H, m), 7.72 (1H, s), 7.81-7.90 (3H, m).

Example 32

5-(4-Amino-6-benzylsulfanyl-[1,3,5]triazin-2-yl)-2,4-dimethylbenzoic acid methyl ester

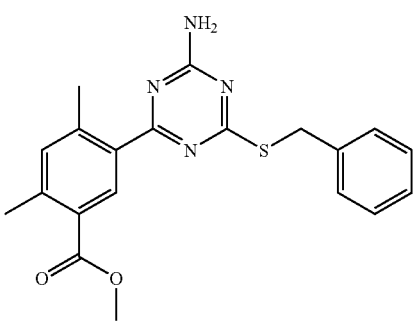

ESI (LC/MS positive mode) m/z=381 (M+H$^+$)
$^1$H-NMR (270 MHz, in DMSO-d$_6$) chemical shifts δ: 2.55 (3H, s), 2.57 (3H, s), 3.83 (3H, s), 4.40 (2H, s), 7.22-7.48 (6H, m), 7.69 (1H, s), 7.72 (1H, s), 8.40 (1H, s).

Example 33

5-[4-Amino-6-(2-methoxyphenylsulfanyl)-[1,3,5]triazin-2-yl]-2,4-dimethylbenzoic acid methyl ester

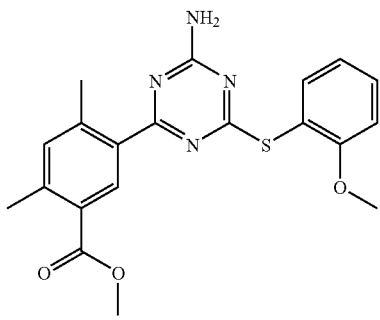

ESI (LC/MS positive mode) m/z=397(M+H$^+$)
$^1$H-NMR (270 MHz, in DMSO-d$_6$) chemical shifts δ: 2.22 (3H, s), 2.51 (3H, s), 3.78 (3H, s), 3.82 (3H, s), 6.96-7.03 (1H, m), 7.11-7.18 (2H, m), 7.45-7.67 (4H, m), 8.32 (1H, s).

Example 34

5-[4-Amino-6-(2,5-dimethoxyphenylsulfanyl)-[1,3,5]triazin-2-yl]-2,4-dimethylbenzoic acid methyl ester

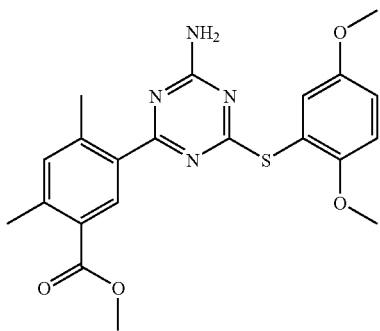

ESI (LC/MS positive mode) m/z=427(M+H$^+$)
$^1$H-NMR (270 MHz, in DMSO-d$_6$) chemical shifts δ: 2.26 (3H, s), 2.52 (3H, s), 3.71 (3H, s), 3.72 (3H, s), 3.82 (3H, s), 7.04-7.16 (3H, m), 7.11-7.17 (2H, m), 7.18 (1H, s), 7.59 (1H, s), 7.66 (1H, s), 8.32 (1H, s).

Example 35

5-[4-Amino-6-(2-hydroxyethylsulfanyl)-[1,3,5]triazin-2-yl]-2,4-dimethylbenzoic acid methyl ester

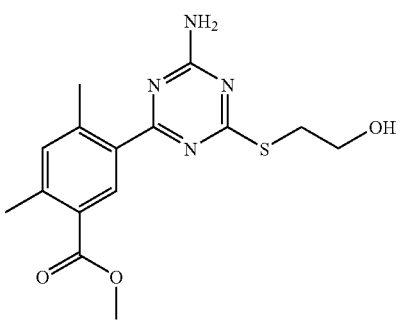

ESI (LC/MS positive mode) m/z=335(M+H$^+$)
$^1$H-NMR (270 MHz, in DMSO-d$_6$) chemical shifts δ: 2.55 (3H, s), 2.58 (3H, s), 3.19 (2H, t, J=6 Hz), 3.60-3.69 (2H, m), 4.99 (1H, t, J=5 Hz), 7.29 (1H, s), 7.60 (1H, s), 7.67 (1H, s), 8.38 (1H, s).

Example 36

5-[4-Amino-6-(3-hydroxypropylsulfanyl)-[1,3,5]triazin-2-yl]-2,4-dimethylbenzoic acid methyl ester

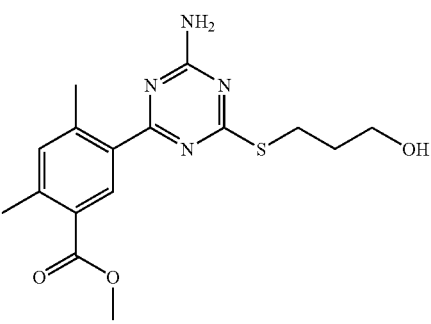

ESI (LC/MS positive mode) m/z=349(M+H$^+$)
$^1$H-NMR (270 MHz, in DMSO-d$_6$) chemical shifts δ: 1.75-1.87 (2H, m), 2.55 (3H, s), 2.60 (3H, s), 3.13 (2H, t, J=7 Hz), 3.47-3.55 (2H, m), 3.83 (3H, s), 4.57 (1H, t, J=5 Hz), 7.29 (1H, s), 7.59 (1H, s), 7.65 (1H, s), 8.40 (1H, s).

Example 37

5-[4-Amino-6-(2,3-dihydroxypropylsulfanyl)-[1,3,5]triazin-2-yl]-2,4-dimethylbenzoic acid methyl ester

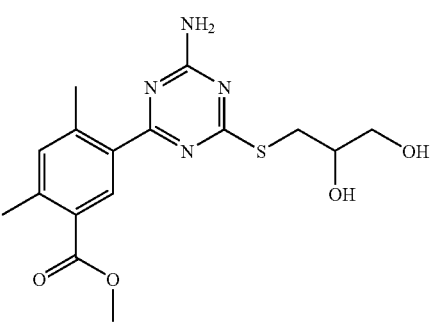

ESI (LC/MS positive mode) m/z=365(M+H)
$^1$H-NMR (270 MHz, in DMSO-d$_6$) chemical shifts δ: 2.55 (3H, s), 2.59 (3H, s), 3.05 (1H, dd, J=8, 13 Hz), 3.29-3.44 (3H, m), 3.64-3.73 (1H, m), 3.83 (3H, s), 4.69 (1H, t, J=6 Hz), 5.03 (1H, d, J=5 Hz), 7.28 (1H, s), 7.59 (1H, s), 7.65 (1H, s), 8.38 (1H, s).

Example 38

5-[4-Amino-6-(2-methoxyphenylsulfanyl)-[1,3,5]triazin-2-yl]-2,4-dichloro-N-(2-hydroxyethyl)-benzamide

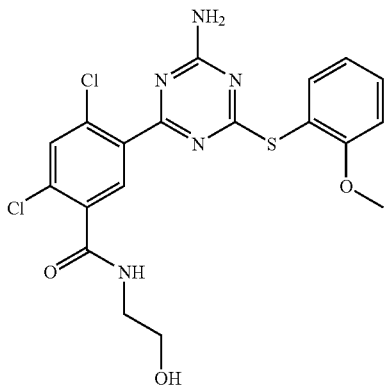

ESI (LC/MS positive mode) m/z=468/466(M+H$^+$)
$^1$H-NMR (270 MHz, in methanol d$_4$) chemical shifts δ: 3.48 (2H, t, J=6 Hz), 3.71 (12H, t, J=6 Hz), 3.83 (3H, s), 1.73 (3H, s), 6.99 (1H, td, J=1, 8 Hz), 7.09 (1H, d, J=7 Hz), 7.46 (1H, dt, J=4, 11 Hz), 7.52 (1H, dd, J=2, 7 Hz), 7.62 (1H, s), 7.81 (1H, s).

Example 39

4-(2,4-Dichlorophenyl)-6-(2,5-dimethoxyphenylsulfanyl)-pyrimidin-2-ylamine

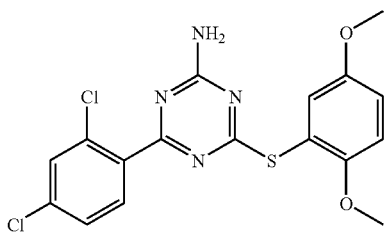

ESI (LC/MS positive mode) m/z=410/408(M+H$^+$)
$^1$H-NMR (270 MHz, in CDCl$_3$) chemical shifts δ: 3.78 (3H, s), 3.79 (3H, s), 5.12 (2H, brs), 6.35 (1H, s), 6.93 (1H, d, J=9 Hz), 7.01 (1H, dd, J=9, 3 Hz), 7.16 (1H, d, J=3 Hz), 7.28 (1H, dd, J=8, 2 Hz), 7.39 (1H, d, J=2 Hz), 7.46 (1H, d, J=8 Hz).

Example 40

4-(2,5-Dimethoxyphenylsulfanyl)-6-naphthalen-1-yl-pyrimidin-2-ylamine

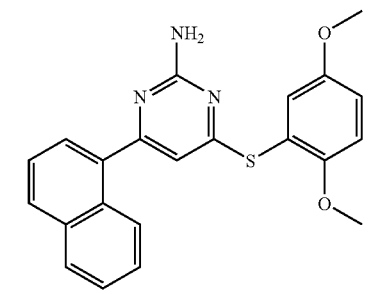

ESI (LC/MS positive mode) m/z=390(M+H$^+$)
$^1$H-NMR (270 MHz, in CDCl$_3$) chemical shifts δ: 3.76 (3H, s), 3.84 (3H, s), 5.17 (2H, brs), 6.33 (1H, s), 6.86-6.97 (2H, m), 7.18 (1H, d, J=3 Hz), 7.40-7.52 (4H, m), 7.82-7.91 (2H, m), 7.99-8.06 (1H, m).

Example 41

4-(2,5-Dimethoxyphenylsulfanyl)-6-(2,5-dimethylphenyl)-pyrimidin-2-ylamine

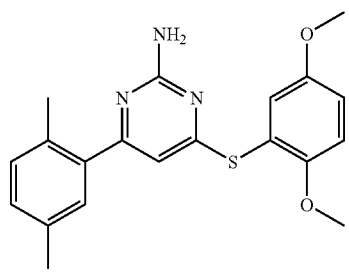

ESI (LC/MS positive mode) m/z=368(M+H$^+$)
$^1$H-NMR (270 MHz, in CDCl$_3$) chemical shifts δ: 2.17 (3H, s), 2.30 (3H, s), 3.77 (3H, s), 3.80 (3H, s), 5.11 (2H, brs), 6.13 (1H, s), 6.91 (1H, d, J=9 Hz), 6.99 (1H, dd, J=9, 3 Hz), 7.06-7.08 (2H, m), 7.11 (1H, s), 7.16 (1H, d, J=3 Hz).

Example 42

4-(2,5-Dimethoxyphenylsulfanyl)-6-(2,4,5-trimethylphenyl)-pyrimidin-2-ylamine

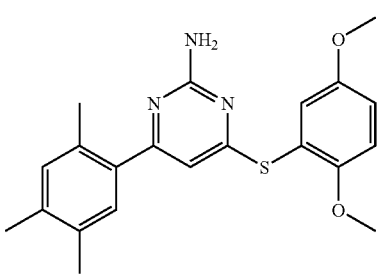

ESI (LC/MS positive mode) m/z=382(M+H$^+$)
$^1$H-NMR (270 MHz, in CDCl$_3$) chemical shifts δ: 2.15 (3H, s), 2.21 (3H, s), 2.21 (3H, s), 3.76 (3H, s), 3.79 (3H, s), 5.14 (2H, brs), 6.09 (1H, s), 6.88-7.01 (3H, m), 7.09 (1H, s), 7.15 (1H, d, J=3 Hz).

Example 43

4-[2-Amino-6-(2,5-dimethoxyphenylsulfanyl)-pyrimidin-4-yl]-3-methylphenol

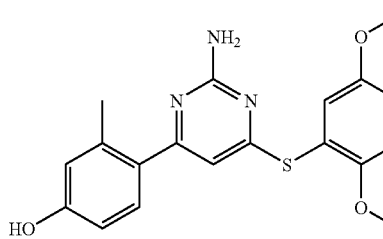

ESI (LC/MS positive mode) m/z=370(M+H⁺)
¹H-NMR (270 MHz, in CDCl₃) chemical shifts δ: 2.16 (3H, s), 3.77 (3H, s), 3.80 (3H, s), 5.18 (2H, brs), 6.08 (1H, s), 6.53-6.59 (2H, m), 6.92 (1H, d, J=9 Hz), 7.00 (1H, dd, J=9, 3 Hz), 7.13-7.18 (2H, m).

Example 44

3-{4-[2-Amino-6-(2,5-dimethoxyphenylsulfanyl)-pyrimidin-4-yl]-3-methylphenoxy}-propan-1-ol

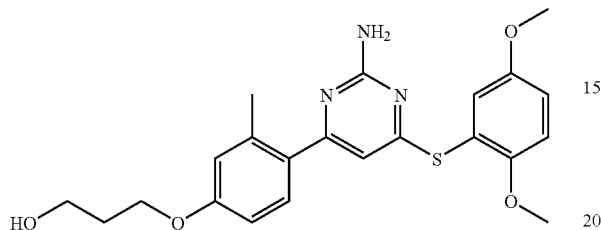

ESI (LC/MS positive mode) m/z=428(M+H⁺)
¹H-NMR (270 MHz, in CDCl₃) chemical shifts δ: 1.97-2.08 (2H, m), 2.22 (3H, s), 3.77 (3H, s), 3.80 (3H, s), 3.85 (2H, t, J=6 Hz), 4.11 (2H, t, J=6 Hz), 5.02 (2H, brs), 6.09 (1H, s), 6.70-6.77 (2H, m), 6.92 (1H, d, J=9 Hz), 6.99 (1H, dd, J=9, 3 Hz), 7.16 (1H, d, J=3 Hz), 7.22-7.28 (1H, m).

Example 45

{4-[2-Amino-6-(2,5-dimethoxyphenylsulfanyl)-pyrimidin-4-yl]-3-methylphenoxy}-acetonitrile

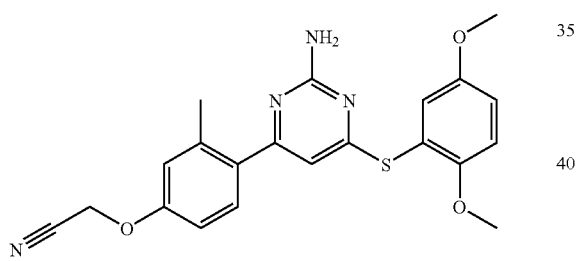

ESI (LC/MS positive mode) m/z=409(M+H⁺)
¹H-NMR (270 MHz, in DMSO-d₆) chemical shifts δ: 2.19 (3H, s), 3.73 (3H, s), 3.75 (3H, s), 5.16 (2H, s), 5.82 (1H, s), 6.74 (2H, brs), 6.89-6.96 (2H, m), 7.06-7.18 (3H, m), 7.24-7.30 (1H, m).

Example 46

2-{4-[2-Amino-6-(2,5-dimethoxyphenylsulfanyl)-pyrimidin-4-yl]-3-methylphenoxy}-acetamide

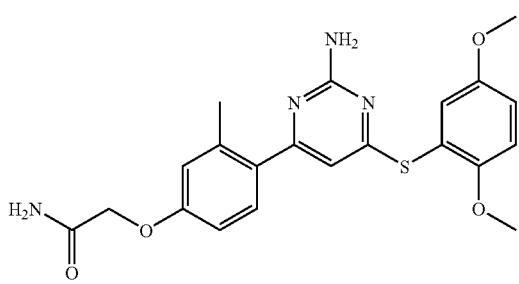

ESI (LC/MS positive mode) m/z=427(M+H⁺)
¹H-NMR (270 MHz, in CDCl₃) chemical shifts δ: 2.24 (3H, s), 3.77 (3H, s), 3.80 (3H, s), 4.49 (2H, s), 5.07 (2H, brs), 5.68 (1H, brs), 6.10 (1H, s), 6.47 (1H, brs), 6.73-6.79 (2H, m), 6.93 (1H, d, J=9 Hz), 7.00 (1H, dd, J=9, 3 Hz), 7.16 (1H, d, J=3 Hz), 7.26-7.30 (1H, m).

Example 47

2-{4-[2-Amino-6-(2,5-dimethoxyphenylsulfanyl)-pyrimidin-4-yl]-3-methylphenoxy}-ethanol

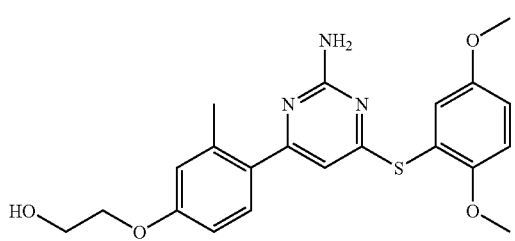

ESI (LC/MS positive mode) m/z=414(M+H⁺)
¹H-NMR (270 MHz, in CDCl₃) chemical shifts δ: 2.23 (3H, s), 3.77 (3H, s), 3.80 (3H, s), 3.91-3.97 (2H, m), 4.04-4.09 (2H, m), 5.12 (2H, brs), 6.10 (1H, s), 6.72-6.79 (2H, m), 6.93 (1H, d, J=9 Hz), 7.00 (1H, dd, J=9, 3 Hz), 7.16 (1H, d, J=3 Hz), 7.26-7.30 (1H, m).

Example 48

4-(5-Benzyloxy-2,4-dichlorophenyl)-6-(2,5-dimethoxyphenylsulfanyl)-pyrimidin-2-ylamine

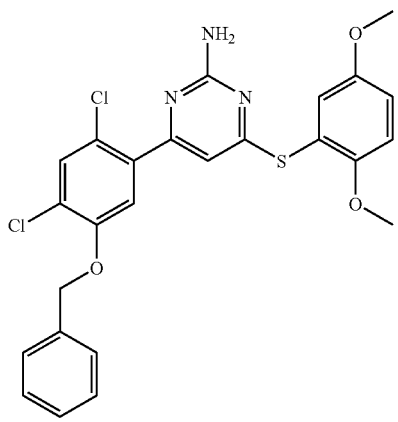

ESI (LC/MS positive mode) m/z=516/514(M+H⁺)
¹H-NMR (270 MHz, in CDCl₃) chemical shifts δ: 1.77 (3H, s), 3.78 (3H, s), 5.07 (2H, brs), 5.13 (2H, s), 6.39 (1H, s), 6.93 (1H, d, J=9 Hz), 7.01 (1H, dd, J=9, 3 Hz), 7.15 (1H, d, J=3 Hz), 7.20 (1H, s), 7.30-7.40 (6H, m).

Example 49

4-(2,5-Dimethoxyphenylsulfanyl)-6-(2,4,6-trimethylphenyl)-pyrimidin-2-ylamine

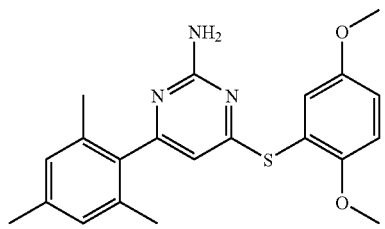

ESI (LC/MS positive mode) m/z=382(M+H⁺)

¹H-NMR (270 MHz, in CDCl₃) chemical shifts δ: 2.03 (6H, s), 2.25 (3H, s), 3.76 (3H, s), 3.77 (3H, s), 5.06 (2H, brs), 5.99 (1H, s), 6.82-6.89 (3H, m), 6.95 (1H, dd, J=9, 3 Hz), 7.15 (1H, d, J=3 Hz).

Example 50

5-[2-Amino-6-(2,5-dimethoxyphenylsulfanyl)-pyrimidin-4-yl]-2,4-dichlorophenol

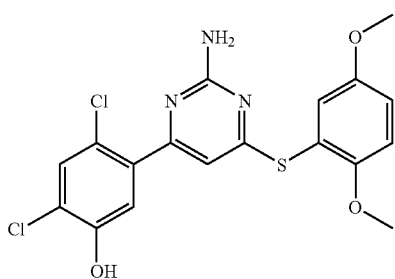

ESI (LC/MS positive mode) m/z=426/424(M+H⁺)

¹H-NMR (270 MHz, in CDCl₃) chemical shifts δ: 3.77 (3H, s), 3.79 (3H, s), 5.12 (2H, brs), 6.33 (1H, s), 6.93 (1H, d, J=9 Hz), 7.01 (1H, dd, J=9, 3 Hz), 7.15 (1H, d, J=3 Hz), 7.16 (1H, s), 7.33 (1H, s).

Example 51

4-(2,5-Dimethoxyphenylsulfanyl)-6-(2-methyl-4-prop-2-ynyloxy-phenyl)-pyrimidin-2-ylamine

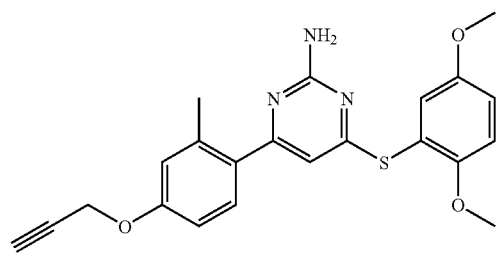

ESI (LC/MS positive mode) m/z=408(M+H⁺)

¹H-NMR (270 MHz, in CDCl₃) chemical shifts δ: 2.24 (3H, s), 2.50 (1H, t, J=2 Hz), 3.77 (3H, s), 3.84 (3H, s), 4.68 (2H, d, J=2 Hz), 5.08 (2H, s), 6.10 (1H, s), 6.77-6.85 (2H, m), 6.93 (1H, d, J=9 Hz), 7.00 (1H, dd, J=9, 3 Hz), 7.16 (1H, d, J=3 Hz), 7.28 (1H, d, J=8 Hz).

Example 52

{5-[2-Amino-6-(2,5-dimethoxyphenylsulfanyl)-pyrimidin-4-yl]-2,4-dichlorophenoxy}-acetonitrile

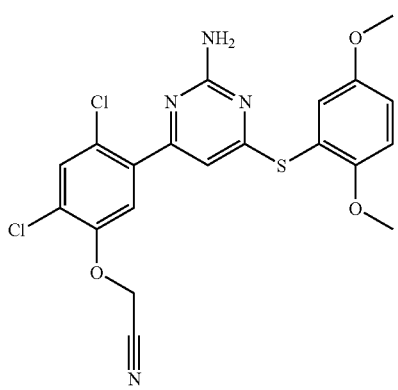

ESI (LC/MS positive mode) m/z=465/463(M+H⁺)

¹H-NMR (270 MHz, in CDCl₃) chemical shifts δ: 3.78 (3H, s), 3.80 (3H, s), 4.85 (2H, s), 5.15 (2H, brs), 6.41 (1H, s), 6.94 (1H, d, J=9 Hz), 7.02 (1H, dd, J=9, 3 Hz), 7.16 (1H, d, J=3 Hz), 7.28 (1H, s), 7.45 (1H, s).

Example 53

{5-[2-Amino-6-(2-aminophenylsulfanyl)-pyrimidin-4-yl]-2,4-dichlorophenoxy}-acetonitrile

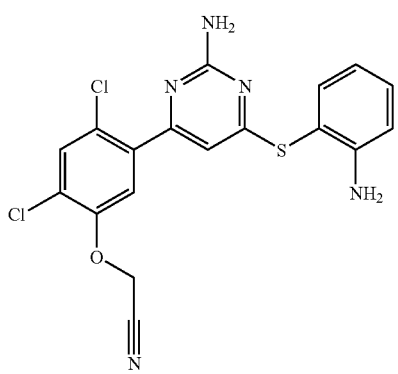

ESI (LC/MS positive mode) m/z=420/418(M+H⁺)

¹H-NMR (270 MHz, in DMSO-d₆) chemical shifts δ: 5.28 (2H, s), 5.51 (2H, brs), 6.03 (1H, s), 6.55-6.62 (1H, m), 6.79-6.83 (1H, m), 6.92 (2H, brs), 7.15-7.23 (1H, m), 7.27-7.32 (1H, m), 7.36 (1H, s), 7.73 (1H, s).

Example 54

{5-[2-Amino-6-(1H-benzimidazol-2-ylsulfanyl)-pyrimidin-4-yl]-2,4-dichlorophenoxy}-acetonitrile

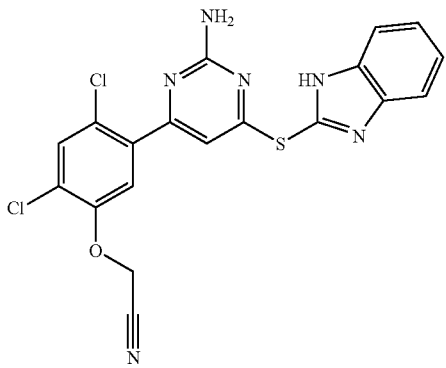

ESI (LC/MS positive mode) m/z=445/443(M+H$^+$)
$^1$H-NMR (270 MHz, in DMSO-d$_6$) chemical shifts δ: 5.30 (2H, s), 6.52 (1H, s), 7.11 (2H, s), 7.18-7.25 (2H, m), 7.39 (1H, s), 7.54-7.61 (2H, m), 7.75 (1H, s).

Example 55

2-[2-Amino-6-(2,4-dichloro-5-cyanomethoxyphenyl)-pyrimidin-4-ylsulfanyl]-3H-imidazole 4-carboxylic acid ethyl ester

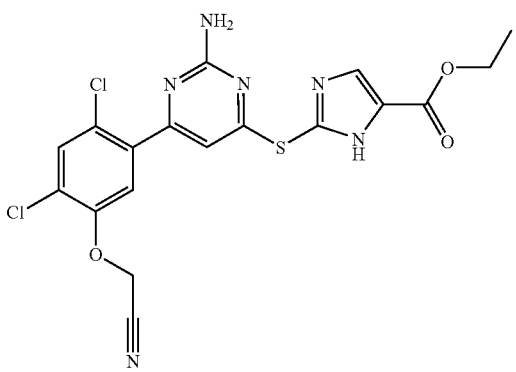

ESI (LC/MS positive mode) m/z=467/465(M+H$^+$)
$^1$H-NMR (270 MHz, in DMSO-d$_6$) chemical shifts δ: 1.27 (3H, t, J=7 Hz), 4.23 (2H, q, J=7 Hz), 5.30 (2H, s), 6.16 (1H, s), 7.06 (2H, s), 7.38 (1H, s), 7.78 (1H, s), 8.11 (1H, s), 13.57 (1H, s).

Example 56

{5-[2-Amino-6-(1-methyl-1H-imidazol-2-ylsulfanyl)-pyrimidin-4-yl]-2,4-dichlorophenoxy}-acetonitrile

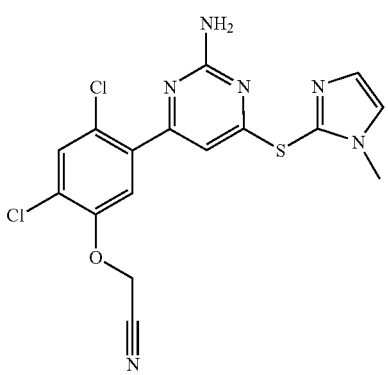

ESI (LC/MS positive mode) m/z=409/407(M+H$^+$)
$^1$H-NMR (270 MHz, in CDCl$_3$) chemical shifts δ: 1.75 (3H, s), 4.86 (2H, s), 5.12 (2H, s), 6.39 (1H, s), 7.18-7.27 (2H, m), 7.29 (1H, s), 7.49 (1H, s).

Example 57

3-[4-Amino-6-(2,4-dichloro-5-cyanomethoxyphenyl)-[1,3,5]triazin-2-ylsulfanyl]-propionic acid methyl ester

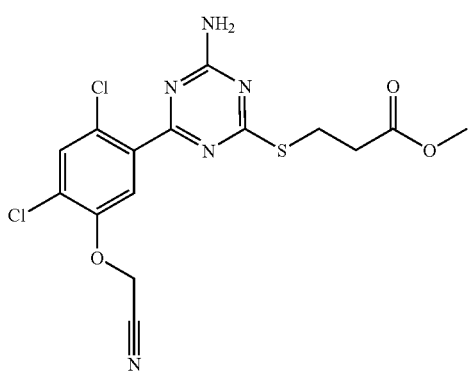

ESI (LC/MS positive mode) m/z=414/416(M+H$^+$)
$^1$H-NMR (270 MHz, in DMSO-d$_6$) chemical shifts δ: 2.80 (2H, t, J=6.9 Hz), 3.28 (2H, t, J=6.9 Hz), 3.61 (3H, s), 5.34 (2H, s), 7.59 (1H, s), 7.83 (1H, s), 7.85 (2H, brs).

Example 58

{5-[4-Amino-6-(3-hydroxypropylsulfanyl)-[1,3,5]triazin-2-yl]-2,4-dichlorophenoxy}-acetonitrile

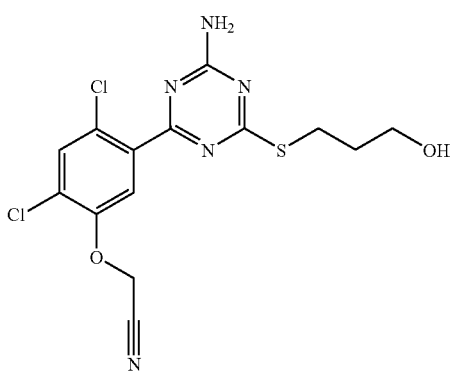

ESI (LC/MS positive mode) m/z=386/388(M+H$^+$)
$^1$H-NMR (270 MHz, in DMSO-d$_6$) chemical shifts δ: 1.80 (2H, tt (like qui), J=7.3, 6.6 Hz), 3.13 (2H, t, J=7.1 Hz), 3.49 (2H, brtd (like brq), J=ca. 5 Hz), 4.56 (1H, brt, J=ca. 5 Hz), 5.34 (2H, s), 7.58 (1H, s), 7.78 (2H, brs), 7.82 (1H, s).

Example 59

N-{2-[4-Amino-6-(2,4-dichloro-5-cyanomethoxyphenyl)-[1,3,5]triazin-2-ylsulfanyl]-ethyl}-acetamide

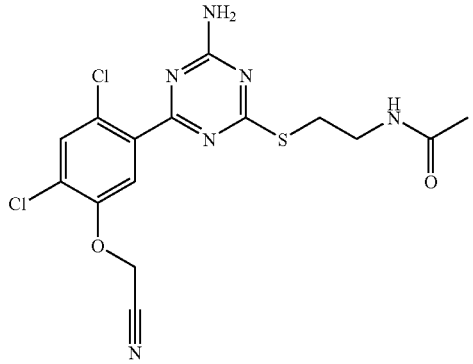

ESI (LC/MS positive mode) m/z=413/415(M+H$^+$)
$^1$H-NMR (270 MHz, in DMSO-d$_6$) chemical shifts δ: 1.79 (3H, s), 3.12 (2H, t, J=6.1 Hz), 3.35 (2H, td, J=6.4, 4.6 Hz), 5.36 (2H, s), 7.60 (1H, s), 7.80 (2H, brs), 7.83 (1H, s), 8.09 (1H, brt, J=5.0 Hz).

Example 60

3-[4-Amino-6-(2,4-dichloro-5-cyanomethoxyphenyl)-[1,3,5]triazin-2-ylsulfanyl]-N-methyl-propionamide

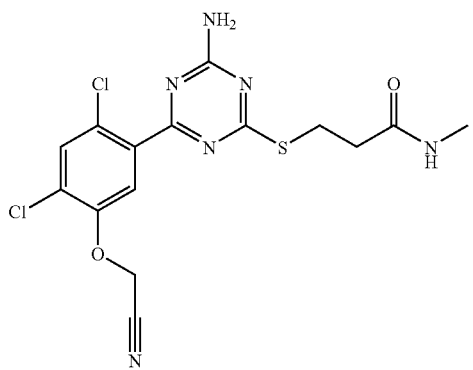

ESI (LC/MS positive mode) m/z=413/415(M+H$^+$)
$^1$H-NMR (270 MHz, in DMSO-d$_6$) chemical shifts δ: 2.50-2.55 (2H), 2.57 (3H, d, J=4.6 Hz), 3.27 (2H, t, J=6.9 Hz), 5.35 (2H, s), 7.60 (1H, s), 7.81 (2H, brs), 7.82 (1H, s), 7.75-7.90 (1H).

Example 61

3-[4-Amino-6-(2,4-dichloro-5-cyanomethoxyphenyl)-[1,3,5]triazin-2-ylsulfanyl]-N-(2-hydroxyethyl)-propionamide

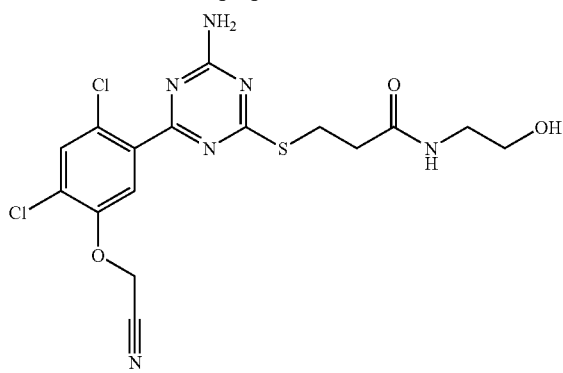

ESI (LC/MS positive mode) m/z=443/445(M+H$^+$)
$^1$H-NMR (270 MHz, in DMSO-d$_6$) chemical shifts δ: 2.54 (2H, t, J=6.8 Hz), 3.12 (2H, td (like q)), J=5.8, 5.8 Hz), 3.27 (2H, t, J=6.8 Hz), 3.38 (2H, td (like q), J=5.8, 5.8 Hz), 4.67 (1H, brt, J=5.6 Hz), 5.35 (2H, s), 7.60 (1H, s), 7.81 (2H, brs), 7.82 (1H, s), 7.92 (1H, brt, J=5.8 Hz).

Example 62

3-[4-Amino-6-(2,4-dichloro-5-cyanomethoxyphenyl)-[1,3,5]triazin-2-ylsulfanyl]-propionamide

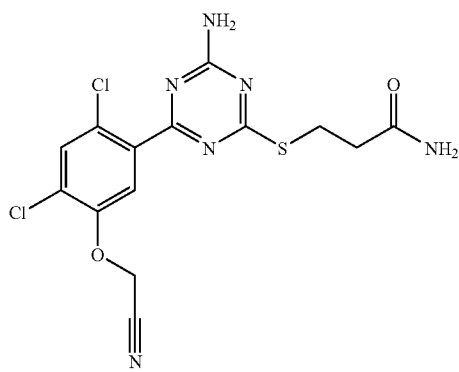

ESI (LC/MS positive mode) m/z=399/401(M+H$^+$)
$^1$H-NMR (270 MHz, in DMSO-d$_6$) chemical shifts δ: 2.50-2.54 (2H), 3.24 (2H, t, J=6.8 Hz), 5.34 (2H, s), 6.93 (1H, brs), 7.36 (1H, brs), 7.59 (1H, s), 7.82 (2H, brs), 7.82 (1H, s).

Example 63

{5-[4-Amino-6-(3-morpholin-4-yl-3-oxo-propylsulfanyl)-[1,3,5]triazin-2-yl]-2,4-dichlorophenoxy}-acetonitrile

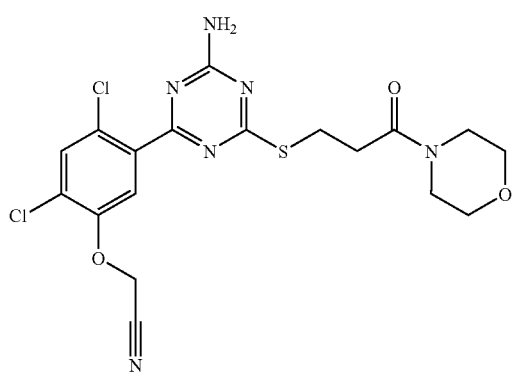

ESI (LC/MS positive mode) m/z=469/471 (M+H$^+$)
$^1$H-NMR (270 MHz, in DMSO-d$_6$) chemical shifts δ: 2.78 (2H, t, J=6.8 Hz), 3.27 (2H, t, J=6.9 Hz), 3.39-3.52 (8H, m), 5.34 (2H, s), 7.60 (1H, s), 7.82 (2H, brs), 7.84 (1H, s).

Example 64

3-[4-Amino-6-(2,4-dichloro-5-cyanomethoxyphenyl)-[1,3,5]triazin-2-ylsulfanyl]-N-(2-hydroxyethoxy)-propionamide

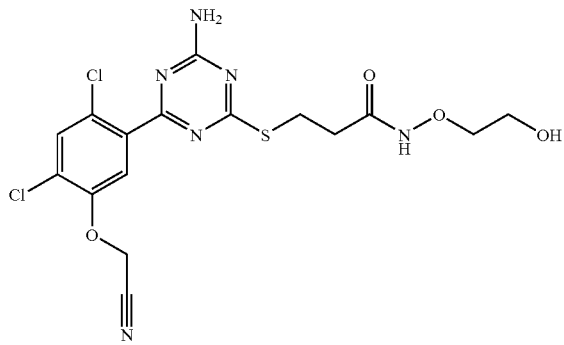

ESI (LC/MS positive mode) m/z=459/461(M+H$^+$)

$^1$H-NMR (270 MHz, in DMSO-d$_6$) chemical shifts δ: 2.46 (2H, t, J=6.6 Hz), 3.28 (2H, t, J=6.4 Hz), 3.52 (2H, t, J=4.6 Hz), 3.77 (2H, t, J=4.6 Hz), 4.74 (1H, brs), 5.34 (2H, s), 7.60 (1H, s), 7.82 (2H, brs), 7.82 (1H, s).

Example 65

3-[4-Amino-6-(2,4-dichloro-5-cyanomethoxyphenyl)-[1,3,5]triazin-2-ylsulfanyl]-N-pyridin-4-ylmethyl-propionamide

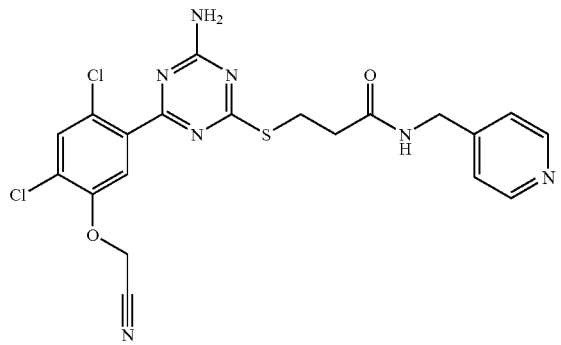

ESI (LC/MS positive mode) m/z=490/492(M+H$^+$)

$^1$H-NMR (270 MHz, in DMSO-d$_6$) chemical shifts δ: 2.67 (2H, t, J=6.8 Hz), 3.30-3.35 (2H), 4.31 (1H, d, J=5.8 Hz), 5.34 (2H, s), 7.24 (2H, d, J=5.1 Hz), 7.61 (1H, s), 7.83 (2H, brs), 7.83 (1H, s), 8.49 (2H, d, J=5.3 Hz), 8.54 (1H, brt, J=5.6 Hz).

Example 66

3-[4-Amino-6-(2,4-dichloro-5-cyanomethoxyphenyl)-[1,3,5]triazin-2-ylsulfanyl]-N-pyridin-4-yl-propionamide

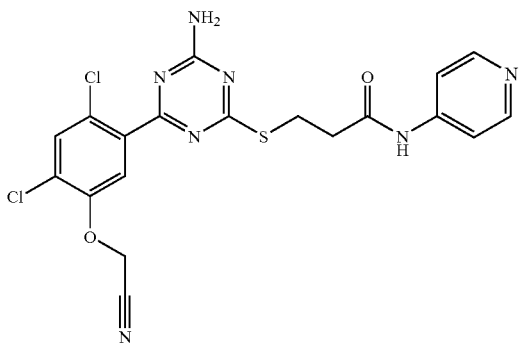

ESI (LC/MS positive mode) m/z=476/478(M+H$^+$)

$^1$H-NMR (270 MHz, in DMSO-d$_6$) chemical shifts δ: 2.87 (2H, t, J=6.6 Hz), 3.30-3.45 (2H), 5.35 (2H, s), 7.54 (2H, d, J=6.4 Hz), 7.61 (1H, s), 7.82 (1H, s), 7.85 (2H, brs), 8.41 (2H, d, J=6.4 Hz), 10.39 (1H, brs).

Example 67

3-[4-Amino-6-(2,4-dichloro-5-cyanomethoxyphenyl)-[1,3,5]triazin-2-ylsulfanyl]-N-(2-dimethylaminoethyl)-propionamide

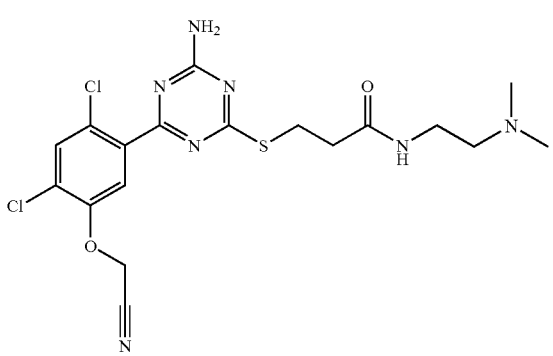

ESI (LC/MS positive mode) m/z=470/472(M+H$^+$)

$^1$H-NMR (270 MHz, in DMSO-d$_6$) chemical shifts δ: 2.12 (6H, s), 2.24 (2H, t, J=6.6 Hz), 2.53 (2H, t, J=6.6 Hz), 3.13 (2H, td (like q), J=6.3, 6.3 Hz), 3.27 (2H, t, J=6.9 Hz), 5.35 (2H, s), 7.60 (1H, s), 7.81 (2H, brs), 7.82 (1H, s), 7.83 (1H, brt, J=ca. 6 Hz).

Example 68

3-[4-Amino-6-(2,4-dichloro-5-cyanomethoxyphenyl)-[1,3,5]triazin-2-ylsulfanyl]-N-(2-morpholin-4-yl-ethyl)-propionamide

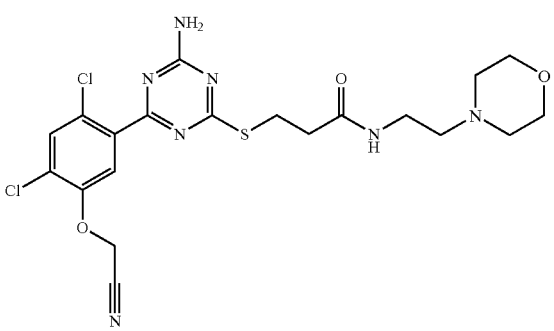

ESI (LC/MS positive mode) m/z=512/514(M+H$^+$)

$^1$H-NMR (270 MHz, in DMSO-d$_6$) chemical shifts δ: 2.31 (2H, t, J=6.4 Hz), 2.35 (4H, t, J=4.5 Hz), 2.53 (2H, t, J=6.9 Hz), 3.17 (2H, dt (like q), J=6.4, 6.4 Hz), 3.27 (2H, t, J=6.3 Hz), 3.55 (4H, t, J=4.6 Hz), 5.35 (2H, s), 7.60 (1H, s), 7.81 (2H, brs), 7.82 (1H, s), 7.85 (1H, brt, J=ca. 6 Hz).

Example 69

3-[4-Amino-6-(2,4-dichloro-5-cyanomethoxyphenyl)-[1,3,5]triazin-2-ylsulfanyl]-N-thiazole-2-yl-propionamide

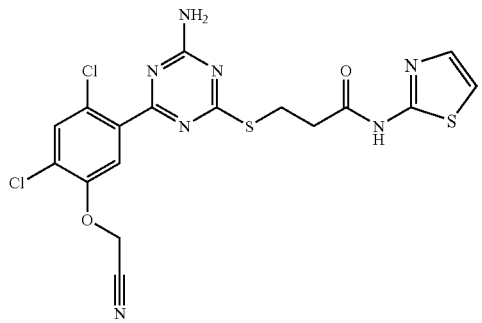

ESI (LC/MS positive mode) m/z=482/484(M+H$^+$)
$^1$H-NMR (270 MHz, in DMSO-d$_6$) chemical shifts δ: 2.93 (2H, t, J=6.6 Hz), 3.37 (2H, t, J=6.6 Hz), 5.34 (2H, s), 7.21 (1H, d, J=3.5 Hz), 7.46 (1H, d, J=3.5 Hz), 7.60 (1H, s), 7.82 (1H, s), 7.84 (2H, brs), 12.17 (1H, brs).

Example 70

2-[4-Amino-6-(2,4-dichloro-5-cyanomethoxyphenyl)-[1,3,5]triazin-2-ylsulfanyl]-N-methyl-acetamide

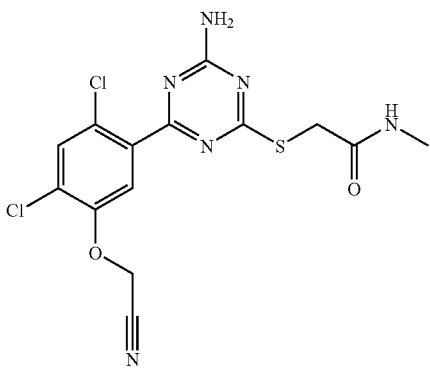

ESI (LC/MS positive mode) m/z=399/401(M+H$^+$)
$^1$H-NMR (270 MHz, in DMSO-d$_6$) chemical shifts δ: 2.59 (3H, d, J=4.6 Hz), 3.82 (2H, s), 5.35 (2H, s), 7.59 (1H, s), 7.83 (1H, s), 7.87 (2H, brs), 7.98 (1H, brq, J=ca. 4 Hz).

Example 71

4-(5-Chloro-1H,3H-benzo[de]isochromen-6-yl)-6-(2-methoxyphenylsulfanyl)-[1,3,5]triazin-2-yl amine Step 1: Synthesis of 3-nitro-4-bromo-1,8-naphthalic anhydride

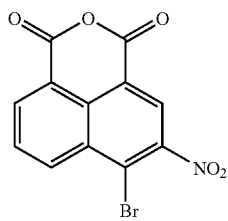

4-Bromo-1,8-naphthalic anhydride (50.0 g, 180 mmol) was dissolved in sulfuric acid (150 mL). The reaction vessel was cooled in an ice bath, and a mixed solution of fuming nitric acid (26.0 ml, 612 mmol) and sulfuric acid (34.0 ml, 684 mmol) was added dropwise while the internal temperature was kept below 4° C. Then, the reaction solution was stirred for 2 hours while keeping the internal temperature below 4° C. Ice water (500 mL) was slowly added to the reaction solution, and stirred at room temperature for 30 minutes. Water (500 mL) was added, and the resulting precipitate was filtered. The precipitate was suspended in acetonitrile (300 mL). The suspension was stirred at room temperature for 4 hours, and filtered. After washing with acetonitrile, the resulting precipitate was again suspended in acetonitrile (200 mL). The same treatment was repeated, and the precipitate was dried under reduced pressure to give the title compound as pale yellow solid (42.5 g, 73%).
$^1$H-NMR (300 MHz, in DMSO-d$_6$) chemical shifts δ: 8.19 (1H, dd, J=8.8, 7.2 Hz), 8.74 (1H, d, J=8.8 Hz), 8.83 (1H, d, J=7.2 Hz), 8.92 (1H, s).

Step 2:
5-Nitro-6-bromo-1H,3H-benzo[de]isochromene

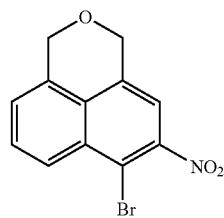

Tetrahydrofuran (800 mL) was added to 3-nitro-4-bromo-1,8-naphthalic anhydride (30.0 g, 93.1 mmol), and stirred thoroughly to prepare a suspension. Trifluoroborane ether complex (35.4 ml, 279 mmol) and lithium borohydride (4.05 g, 186 mmol) were added to the suspension at room temperature. The resulting reaction mixture was stirred at 40 to 50° C. for 2 hours. The mixture was allowed to return to room temperature, and then water was added and extracted twice with ethyl acetate. The organic layer was washed with brine, dried over anhydrous sodium sulfate, and then concentrated under reduced pressure. The crude product was suspended in a mixed solvent of n-hexane and ethyl acetate (5:1). The mixture was stirred at room temperature for 4 hours, and filtered. After washing with n-hexane-ethyl acetate (5:1), the mixture was dried under reduced pressure to give the title compound as pale yellow solid (23.0 g, 84%).
$^1$H-NMR (300 MHz, in DMSO-d$_6$) chemical shifts δ: 5.05 (2H, s), 5.08 (2H, s), 7.59 (1H, d, J=7.0 Hz), 7.81-7.86 (2H, m), 8.24 (1H, d, J=8.3 Hz).

Step 3: 5-Nitro-6-cyano-1H,3H benzo[de]isochromene

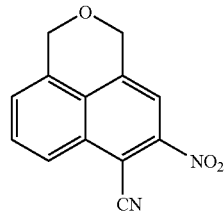

5-Nitro-6-bromo-1H,3H-benzo[de]isochromene (23.0 g, 78.2 mmol) was dissolved in anhydrous DMF (500 mL). Then, copper (I) cyanide (10.5 g, 117 mmol) was added to the mixture at room temperature. The mixture was stirred at the internal temperature of 140° C. for 3 hours, and then cooled to 70° C. The resulting insoluble material was separated by filtration. The filtrate was poured into water (1500 mL), and stirred at room temperature for 2 hours. The resulting precipitate was collected by filtration, washed with acetonitrile, and air-dried. The title compound was obtained as yellow solid (15.9 g, 85%).

$^1$H-NMR (300 MHz, in $CDCl_3$) chemical shifts δ: 5.13 (2H, s), 5.16 (2H, s), 7.53 (1H, d, J=7.4 Hz), 7.84 (1H, dd, J=8.3, 7.4 Hz), 8.15 (1H, s), 8.42 (1H, d, J=8.3 Hz).

Step 4: 5-Amino-6-cyano-1H,3H benzo[de]isochromene

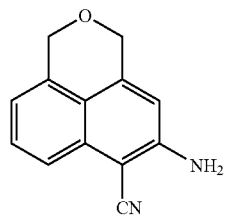

5-Nitro-6-cyano-1H,3H benzo[de]isochromene (14.3 g, 59.5 mmol) was dissolved in diglyme (297 mL). The reaction vessel was cooled in an ice bath, and a mixed solution of tin (I) chloride (45.1 g, 238 mmol) and concentrated hydrochloric acid (159 mL) was added slowly while the internal temperature was kept below 5° C. The reaction solution was stirred at 5° C. for 2 hours, and then added to a mixture of 50% aqueous sodium hydroxide solution (476 mL) and ice (1400 mL) while stirring vigorously. The precipitate was collected by filtration, and then dissolved in ethyl acetate. The solution was washed with brine, dried over anhydrous sodium sulfate, and concentrated under reduced pressure. The resulting crude product was purified by silica gel column chromatography using ethyl acetate, and dried under reduced pressure. The title compound was obtained as pale yellow solid (6.7 g, 53%).

$^1$H-NMR (300 MHz, in $CDCl_3$) chemical shifts δ: 4.75 (2H, brs), 4.93 (2H, s), 4.99 (2H, s), 6.60 (1H, s), 7.02 (1H, d, J=7.2 Hz), 7.50 (1H, dd, J=8.4, 7.2 Hz), 7.79 (1H, d, J=8.4 Hz).

Step 5: 5-Chloro-6-cyano-1H,3H benzo[de]isochromene

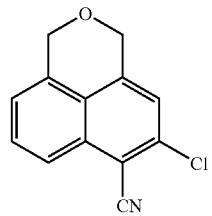

tert-Butyl nitrite (27.5 ml, 208 mmol) was added to a suspension of copper (II) chloride (22.5 g, 167 mmol) in anhydrous acetonitrile (500 mL) at room temperature under nitrogen atmosphere. The resulting dark green suspension was heated to the internal temperature of 65° C., and a solution of 5-amino-6-cyano-1H,3H benzo[de]isochromene (29.2 g, 139 mmol) in anhydrous acetonitrile (1000 mL) was added thereto. The reaction solution was stirred at 65° C. for 30 minutes, and then allowed to return to room temperature. The reaction solution was diluted with methylene chloride. The mixture was washed in succession with 1N aqueous hydrochloric acid solution and brine, dried over anhydrous magnesium sulfate, and concentrated under reduced pressure. The resulting crude product was purified by silica gel column chromatography using methylene chloride, and dried under reduced pressure. The title compound was obtained as yellow solid material (27.7 g, 87%).

$^1$H-NMR (300 MHz, in $CDCl_3$) chemical shifts δ: 5.05 (2H, s), 5.07 (2H, s), 7.27 (1H, s), 7.32 (1H, d, J=7.2 Hz), 7.68 (1H, dd, J=8.7, 7.2 Hz), 8.07 (1H, d, J=8.7 Hz).

Step 6: 5-Chloro-6-cyano-1H,3H benzo[de]isochromene-6-carboxyamidine

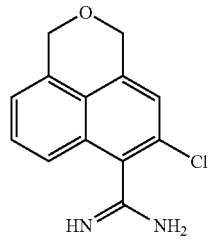

A solution of 2N trimethylaluminum in toluene (2400 ml, 4.80 mmol) was added to a suspension of ammonium chloride (257 g, 4.80 mmol) in toluene (1200 mL) while the internal temperature was kept 5° C. by cooling with ice. The solution was stirred at the internal temperature of 5° C. for 30 minutes and then allowed to return to room temperature, and 5-chloro-6-cyano-1H,3H benzo[de]isochromene (28.8 g, 125 mmol) was added thereto. The reaction solution was stirred while heating under reflux for 30 hours, and then cooled to room temperature. A saturated aqueous potassium sodium tartrate solution and an aqueous 3N sodium hydroxide solution were added to the reaction solution, and then extracted twice with ethyl acetate. The organic layer was washed with brine, dried over anhydrous magnesium sulfate, and concentrated under reduced pressure. The title compound was obtained as brown solid (31.3 g, quantitative).

$^1$H-NMR (300 MHz, in DMSO-$d_6$) chemical shifts δ: 5.01 (4H, s), 6.65-6.90 (3H, brs), 7.32 (1H, d, J=7.4 Hz), 7.36 (1H, s), 7.57 (1H, dd, J=8.3, 7.4 Hz), 7.79 (1H, d, J=8.3 Hz).

Step 7: 4-(5-Chloro-6-cyano-1H,3H benzo[de]isochromen-6-yl)-6-methylsulfamyl-[1,3,5]triazin-2-ylamine

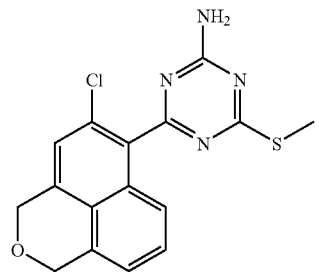

Dimethyl cyanodithioiminocarbonate (15.6 g, 107 mmol) and diisopropylethylamine (33.8 ml, 194 mmol) were added to a solution of 5-chloro-6-cyano-1H,3H benzo[de]isochromene-6-carboxyamidine (23.9 g, 96.9 mmol) in ethanol (240 mL) at room temperature. The resulting reaction mixture was stirred while heating under reflux for 3 hours. The mixture was cooled to 4° C. in an ice bath. After 3 hours, the precipitated crystals were collected by filtration. After washing with cold ethanol, the crystals were dried under reduced pressure. The title compound was obtained as light brown solid (32.9 g, 96%).

ESI (LC/MS positive mode) m/z=345/347(M+H$^+$)

$^1$H-NMR (300 MHz, in DMSO-d$_6$) chemical shifts δ: 2.45 (3H, s), 5.04 (2H, s), 5.05 (2H, s), 7.34 (1H, d, J=6.9 Hz), 7.40 (1H, d, J=8.4 Hz), 7.44 (1H, s), 7.52 (1H, dd, J=8.4, 6.9 Hz), 7.79 (2H, brs).

Step 8: 4-(5-Chloro-6-cyano-1H,3H benzo[de]isochromen-6-yl)-6-methylsulfinyl-[1,3,5]triazin-2-ylamine

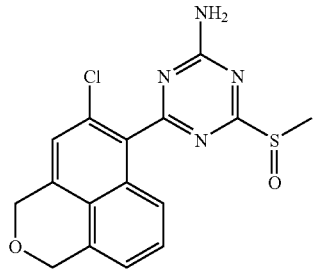

m-Chloroperbenzoic acid (7.10 g, 31.9 mmol) was added to a solution of 4-(5-chloro-6-cyano-1H,3H benzo[de]isochromen-6-yl)-6-methylsulfamyl-[1,3,5]triazin-2-ylamine (10.0 g, 29.0 mmol) in methylene chloride (100 mL) at room temperature. After the reaction solution was stirred at room temperature for 15 hours, the precipitate was collected by filtration. The resulting precipitate was suspended in methylene chloride, and stirred at room temperature for 3 hours. The insoluble material was collected by filtration, washed with methylene chloride, and dried under reduced pressure. The title compound was obtained as light brown solid (8.34 g, 79%).

ESI m/z=361/363(M+H$^+$)

$^1$H-NMR (300 MHz, in DMSO-d$_6$) chemical shifts δ: 2.88 (3H, s), 5.05 (2H, s), 5.06 (2H, s), 7.32-7.40 (1H, m), 7.49-7.58 (3H, m), 8.38 (1H, brs), 8.53 (1H, brs).

Step 9: 4-(5-Chloro-6-cyano-1H,3H benzo[de]isochromen-6-yl)-6-methylsulfinyl-[1,3,5]triazine-2-thiol

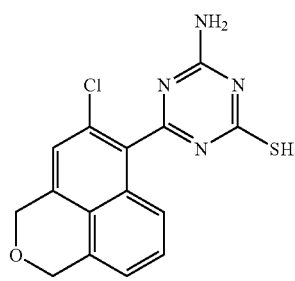

Potassium thioacetate (2.54 g, 22.2 mmol) was added to a suspension of 4-(5-chloro-6-cyano-1H,3H benzo[de]isochromen-6-yl)-6-methylsulfinyl-[1,3,5]triazin-2-ylamine (4.00 g, 11.1 mmol) in N,N-dimethylformamide (100 mL) at room temperature. After the mixture was stirred at room temperature for 6 hours, an 2N aqueous sodium hydroxide solution (100 mL) was added thereto. After the reaction solution was stirred at room temperature for 30 minutes, the pH was adjusted to 5 to 6 with 1N hydrochloric acid. Water (200 mL) was further added to the solution, and the precipitate was collected by filtration. The precipitate was washed in succession with water and diethyl ether, and then dried under reduced pressure. The title compound was obtained as brown solid (3.25 g, 88%).

ESI (positive mode) m/z=331(M+H$^+$); 353/355(M+Na$^+$)

$^1$H-NMR (300 MHz, in DMSO-d$_6$) chemical shifts δ: 5.03 (2H, s), 5.06 (2H, s), 7.39 (1H, d, J=5.8 Hz), 7.50 (1H, s), 7.55-7.64 (2H, m), 8.11 (1H, brs), 8.23 (1H, brs), 13.43 (1H, brs).

Step 10: Synthesis of 4-(5-chloro-6-cyano-1H,3H benzo[de]isochromen-6-yl)-6-(2-methoxyphenylsulfanyl)-[1,3,5]triazin-2-ylamine

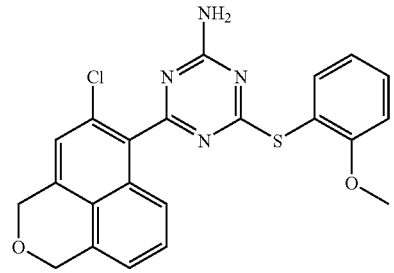

2-Methoxythiophenol (39 mg, 0.278 mmol) was added to a suspension of potassium carbonate (95.7 mg, 0.692 mmol) and 4-(5-chloro-6-cyano-1H,3H benzo[de]isochromen-6-yl)-6-methylsulfinyl-[1,3,5]triazin-2-ylamine (50 mg, 0.139 mmol) in N,N-dimethylformamide (2.5 mL) at room temperature under argon atmosphere. The reaction solution was stirred at 85° C. for 12 hours, and then allowed to return to room temperature. The reaction solution was diluted with ethyl acetate, and then water was added. The organic layer was separated, washed with brine, dried over anhydrous magnesium sulfate, and concentrated under reduced pressure. The resulting crude product was purified by silica gel column chromatography using methylene chloride-ethyl acetate (mixing ratio=7:1 to 4:1) and dried under reduced pressure to give the title compound (34 mg, 56%).

ESI (positive mode) m/z=437/439(M+H$^+$)

$^1$H-NMR (300 MHz, in CDCl$_3$) chemical shifts δ: 3.87 (3H, s), 5.02 (2H, s), 5.04 (2H, s), 5.48 (2H, brd), 6.94 (1H, d, J=8.3 Hz), 6.97 (1H, dt, J=7.7, 1.3 Hz), 7.16 (1H, dd, J=6.5, 1.3 Hz), 7.20 (1H, s), 7.40-7.48 (3H, m), 7.59 (1H, dd, J=7.7, 1.7 Hz).

The compounds described below in Examples 72 to 145 were synthesized according to the method described above in Example 71.

Example 72

4-(5-Chloro-1H,3H-benzo[de]isochromen-6-yl)-6-(2-methoxyphenylsulfanyl)-[1,3,5]triazin-2-ylamine

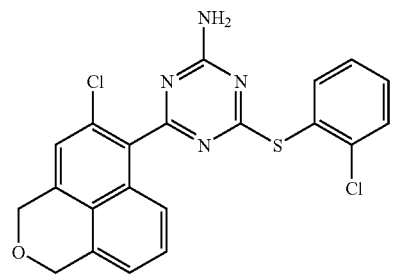

ESI (positive mode) m/z=441/443(M+H⁺)
¹H-NMR (300 MHz, in CDCl₃) chemical shifts δ: 5.02 (2H, s), 5.04 (2H, s), 5.50 (2H, brd), 7.17 (1H, d, J=6.5 Hz), 7.20 (1H, s), 7.29 (1H, dd, J=7.6, 1.4 Hz), 7.20 (1H, dt, J=7.6, 1.9 Hz), 7.40-7.50 (3H, m), 7.73 (1H, dd, J=7.6, 1.9 Hz).

Example 73

4-(5-Chloro-1H,3H-benzo[de]isochromen-6-yl)-6-(3-chlorophenylsulfanyl)-[1,3,5]triazin-2-ylamine

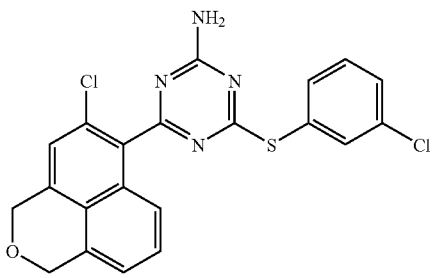

ESI (positive mode) m/z=441/443(M+H⁺)
¹H-NMR (300 MHz, in DMSO-d₆) chemical shifts δ: 5.03 (4H, s), 7.32-7.62 (7H, m), 7.75 (1H, s), 7.82 (1H, brs), 7.89 (1H, brs).

Example 74

4-(5-Chloro-1H,3H-benzo[de]isochromen-6-yl)-6-(4-chlorophenylsulfanyl)-[1,3,5]triazin-2-ylamine

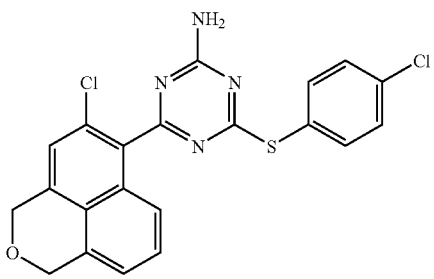

ESI (positive mode) m/z=441/443(M+H⁺)
¹H-NMR (300 MHz, in DMSO-d₆) chemical shifts δ: 5.03 (4H, s), 7.34 (1H, d, J=6.5 Hz), 7.42-7.56 (5H, m), 7.66 (2H, d, J=8.8 Hz), 7.79 (1H, brs), 7.86 (1H, brs).

Example 75

4-(5-Chloro-1H,3H-benzo[de]isochromen-6-yl)-6-(4-methylsulfanyl-phenylsulfanyl)-[1,3,5]triazin-2-ylamine

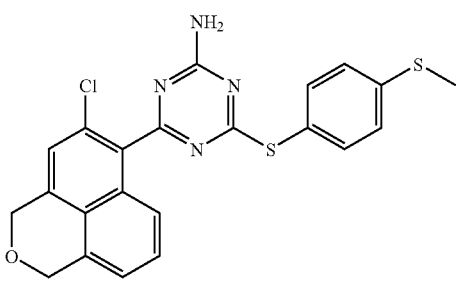

ESI (positive mode) m/z=453/455(M+H⁺)
¹H-NMR (300 MHz, in CDCl₃+methanol d₄) chemical shifts δ: 2.52 (3H, s), 5.07 (2H, s), 5.08 (2H, s), 7.21-7.32 (4H, m), 7.44-7.49 (2H, m), 7.55 (2H, d, J=8.3 Hz).

Example 76

4-(5-Chloro-1H,3H-benzo[de]isochromen-6-yl)-6-(3-methoxyphenylsulfanyl)-[1,3,5]triazin-2-ylamine

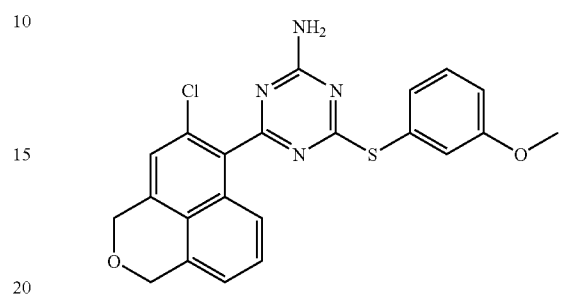

ESI (positive mode) m/z=437/439(M+H⁺)
¹H-NMR (300 MHz, in CDCl₃+methanol d₄) chemical shifts δ: 3.84 (3H, s), 5.07 (2H, s), 5.08 (2H, s), 6.98-7.02 (1H, m), 7.21-7.26 (3H, m), 7.38 (1H, d, J=8.0 Hz), 7.40 (1H, s), 7.47-7.50 (2H, m).

Example 77

4-(5-Chloro-1H,3H-benzo[de]isochromen-6-yl)-6-(4-methoxyphenylsulfanyl)-[1,3,5]triazin-2-ylamine

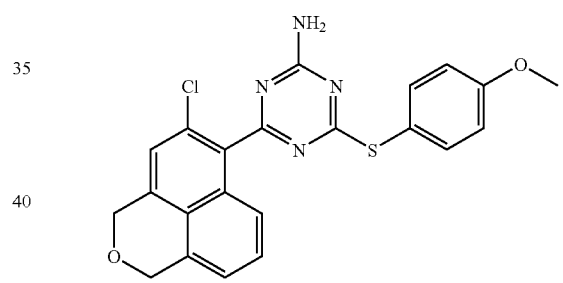

ESI (positive mode) m/z=437/439(M+H⁺)
¹H-NMR (300 MHz, in DMSO-d₆) chemical shifts δ: 3.76 (3H, s), 5.03 (4H, s), 6.97 (2H, d, J=9.0 Hz), 7.33 (1H, d, J=6.7 Hz), 7.41-7.44 (2H, m), 7.50-7.55 (3H, m), 7.71 (1H, brs), 7.76 (1H, brs).

Example 78

4-(5-Chloro-1H,3H-benzo[de]isochromen-6-yl)-6-(2,5-difluorophenylsulfanyl)-[1,3,5]triazin-2-ylamine

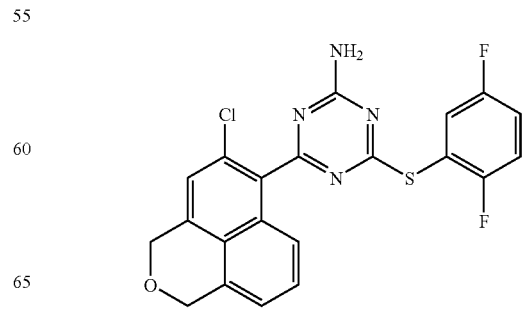

ESI (positive mode) m/z=443/445(M+H⁺)
¹H-NMR (300 MHz, in CDCl₃+methanol d₄) chemical shifts δ: 5.06 (2H, s), 5.08 (2H, s), 6.91-7.00 (2H, m), 7.20-7.25 (2H, m), 7.46 (1H, s), 7.48 (1H, s), 7.58-7.66 (1H, m).

Example 79

4-(5-Chloro-1H,3H-benzo[de]isochromen-6-yl)-6-(2-fluorophenylsulfanyl)-[1,3,5]triazin-2-ylamine

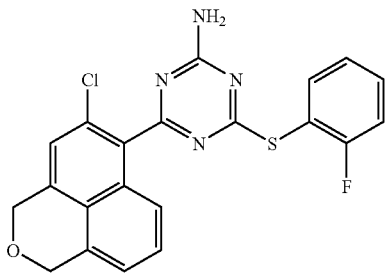

ESI (positive mode) m/z=425/427(M+H⁺)
¹H-NMR (300 MHz, in CDCl₃+methanol d₄) chemical shifts δ: 5.06 (2H, s), 5.07 (2H, s), 7.14-7.27 (4H, m), 7.43-7.53 (3H, m), 7.62-7.67 (1H, m).

Example 80

4-(5-Chloro-1H,3H-benzo[de]isochromen-6-yl)-6-(4-fluorophenylsulfanyl)-[1,3,5]triazin-2-ylamine

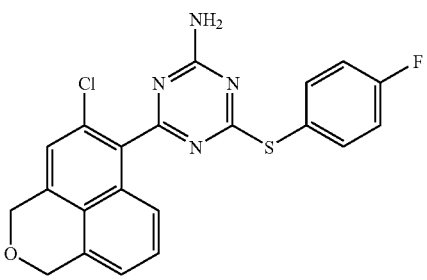

ESI (positive mode) m/z=425/427(M+H⁺)
¹H-NMR (300 MHz, in CDCl₃+methanol d₄) chemical shifts δ: 5.07 (2H, s), 5.08 (2H, s), 7.09-7.18 (2H, m), 7.21-7.27 (2H, m), 7.43-7.52 (2H, m), 7.61-7.68 (2H, m).

Example 81

4-(2-Bromphenoxy)-6-(5-chloro-1H,3H-benzo[de]isochromen-6-yl)-[1,3,5]triazin-2-ylamine

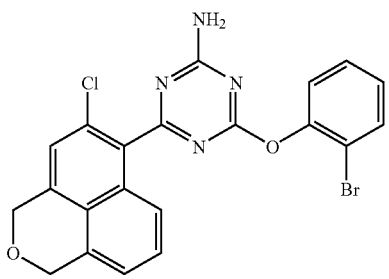

ESI (positive mode) m/z=469/471/473(M+H⁺)
¹H-NMR (300 MHz, in DMSO-d₆) chemical shifts δ: 5.03 (4H, s), 7.19 (1H, m), 7.34 (1H, d, J=6.5 Hz), 7.42-7.46 (4H, m), 7.53 (1H, dd, J=8.3, 6.5 Hz), 7.69 (1H, d, J=7.6 Hz), 7.95 (2H, brd).

Example 82

4-(5-Chloro-1H,3H-benzo[de]isochromen-6-yl)-6-(3,4-dimethoxyphenoxy)-[1,3,5]triazin-2-ylamine

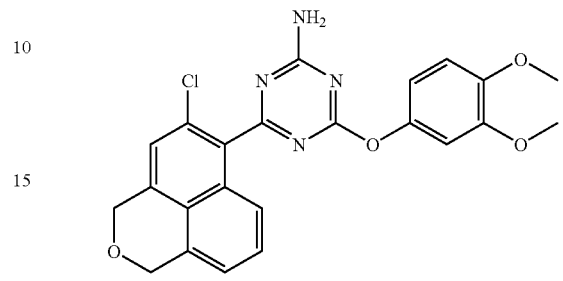

ESI (positive mode) m/z=451/453(M+H⁺)
¹H-NMR (300 MHz, in DMSO-d₆) chemical shifts δ: 3.74 (6H, s), 5.05 (4H, s), 6.77 (1H, dd, J=8.5, 2.5 Hz), 6.92-6.97 (2H, m), 7.31-7.58 (4H, m), 7.86 (2H, brs).

Example 83

4-(5-Chloro-1H,3H-benzo[de]isochromen-6-yl)-6-(3,5-dimethoxyphenoxy)-[1,3,5]triazin-2-ylamine

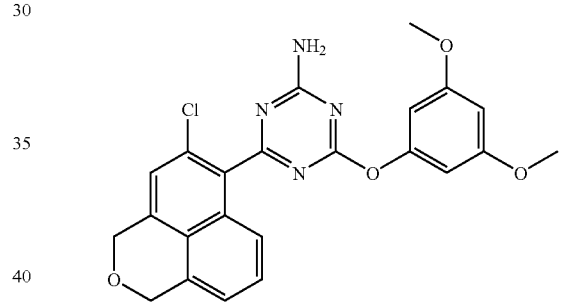

ESI (positive mode) m/z=451/453(M+H⁺)
¹H-NMR (300 MHz, in DMSO-d₆) chemical shifts δ: 3.73 (6H, s), 5.05 (4H, s), 6.34-6.37 (1H, m), 6.50 (2H, d, J=2.4 Hz), 7.33-7.37 (1H, m), 7.45 (1H, s), 7.52-7.55 (2H, m), 7.80 (1H, brs), 7.93 (1H, brs).

Example 84

4-(5-Chloro-1H,3H-benzo[de]isochromen-6-yl)-6-(1H-imidazol-2-ylsulfanyl)-[1,3,5]triazin-2-ylamine

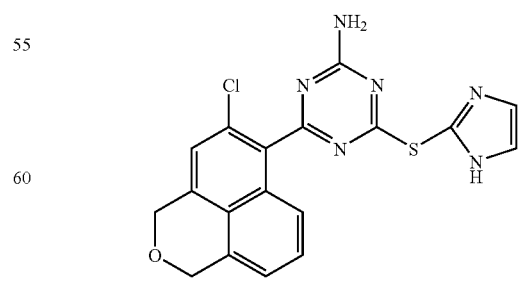

ESI (positive mode) m/z=397/399(M+H⁺)
¹H-NMR (300 MHz, in methanol d₄) chemical shifts δ: 5.08 (4H, s), 7.26-7.36 (4H, m), 7.42-7.54 (2H, m).

Example 85

4-(5-Chloro-1H,3H-benzo[de]isochromen-6-yl)-6-(naphthalen-1-ylsulfanyl)-[1,3,5]triazin-2-ylamine

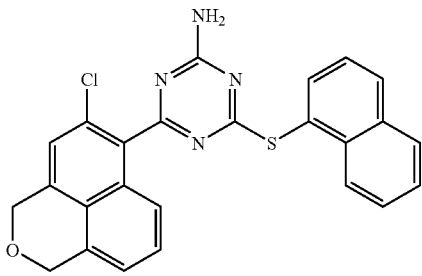

ESI (positive mode) m/z=457/459(M+H⁺)
$^1$H-NMR (300 MHz, in DMSO-$d_6$) chemical shifts δ: 4.98 (4H, s), 7.27-7.45 (4H, m), 7.51-7.63 (2H, m), 7.67-7.80 (3H, m), 7.94-7.98 (2H, m), 8.04 (1H, d, J=8.5 Hz), 8.29 (1H, d, J=8.5 Hz).

Example 86

4-(5-Chloro-1H,3H-benzo[de]isochromen-6-yl)-6-(naphthalen-2-ylsulfanyl)-[1,3,5]triazin-2-ylamine

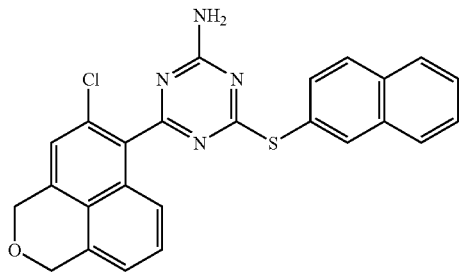

ESI (positive mode) m/z=457/459(M+H⁺)
$^1$H-NMR (300 MHz, in DMSO-$d_6$) chemical shifts δ: 5.02 (4H, s), 7.34 (1H, d, J=6.4 Hz), 7.42 (1H, s), 7.47-7.61 (4H, m), 7.70 (1H, dd, J=8.2, 1.5 Hz), 7.78 (1H, brs), 7.93 (1H, brs), 7.92-7.98 (3H, m), 8.27 (1H, s).

Example 87

4-(5-Chloro-1H,3H-benzo[de]isochromen-6-yl)-6-(3,4-dimethoxyphenylsulfanyl)-[1,3,5]triazin-2-ylamine

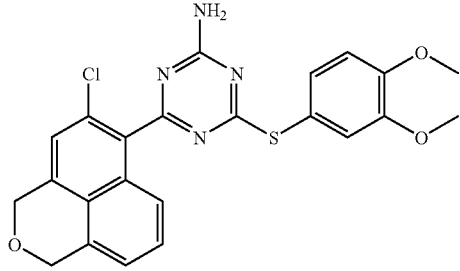

ESI (positive mode) m/z=467/469(M+H⁺)
$^1$H-NMR (300 MHz, in DMSO-$d_6$) chemical shifts δ: 3.71 (3H, s), 3.74 (3H, s), 5.03 (4H, s), 6.96 (1H, d, J=8.4 Hz), 7.13 (1H, dd, J=8.4, 2.0 Hz), 7.19 (1H, d, J=2.0 Hz), 7.33 (1H, d, J=6.6 Hz), 7.42 (1H, s), 7.44 (1H, d, J=8.7 Hz), 7.52 (1H, dd, J=8.7, 6.6 Hz), 7.76 (2H, brd).

Example 88

4-(5-Chloro-1H,3H-benzo[de]isochromen-6-yl)-6-(3-trifluoromethoxyphenylsulfanyl)-[1,3,5]triazin-2-ylamine

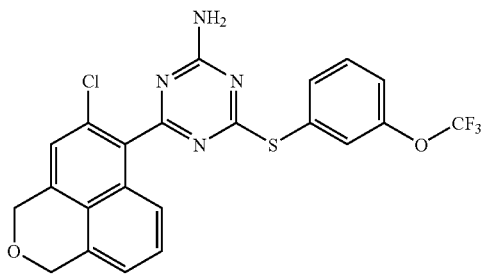

ESI (positive mode) m/z=491/493(M+H⁺)
$^1$H-NMR (300 MHz, in DMSO-$d_6$) chemical shifts δ: 5.03 (4H, s), 7.33 (1H, dd, J=6.3, 1.3 Hz), 7.40 (1H, d, J=10.3 Hz), 7.42 (1H, s), 7.45-7.57 (3H, m), 7.67 (2H, m), 7.84 (1H, brd), 7.90 (1H, brd).

Example 89

4-(5-Chloro-1H,3H-benzo[de]isochromen-6-yl)-6-(4-trifluoromethoxyphenylsulfanyl)-[1,3,5]triazin-2-ylamine

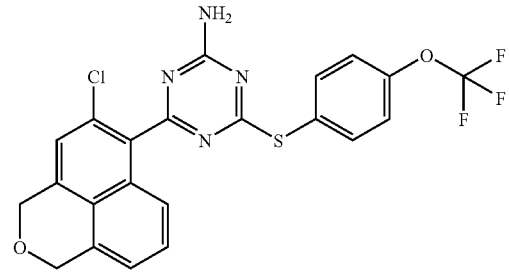

ESI (positive mode) m/z=491/493(M+H⁺)
$^1$H-NMR (300 MHz, in DMSO-$d_6$) chemical shifts δ: 5.03 (4H, s), 7.33 (1H, d, J=6.4 Hz), 7.41 (2H, d, J=8.8 Hz), 7.42 (1H, s), 7.46 (1H, d, J=8.8 Hz), 7.53 (1H, dd, J=8.8, 6.4 Hz), 7.80 (2H, d, J=8.8 Hz), 7.80 (1H, s, brd), 7.88 (1H, s, brd).

Example 90

4-(5-Chloro-1H,3H-benzo[de]isochromen-6-yl)-6-(2,5-dichlorophenylsulfanyl)-[1,3,5]triazin-2-ylamine

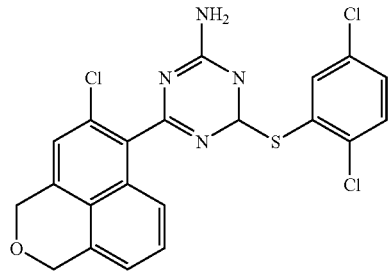

ESI (positive mode) m/z=477/479(M+H⁺)
$^1$H-NMR (300 MHz, in CDCl₃+methanol $d_4$) chemical shifts δ: 5.06 (2H, s), 5.07 (2H, s), 7.20-7.25 (2H, m), 7.33-7.37 (2H, m), 7.47-7.49 (2H, m), 7.76 (1H, d, J=2.2 Hz).

Example 91

4-(2-Bromophenylsulfanyl)-6-(5-chloro-1H,3H-benzo[de]isochromen-6-yl)-[1,3,5]triazin-2-ylamine

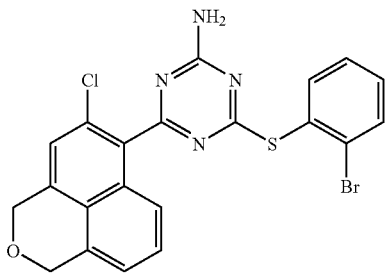

ESI (positive mode) m/z=485/487/489(M+H⁺)

$^1$H-NMR (300 MHz in DMSO-$d_6$) chemical shifts δ: 5.02 (4H, s), 7.30-7.44 (5H, m), 7.52 (1H, dd, J=8.8, 6.9 Hz), 7.74 (1H, dd, J=8.0, 1.6 Hz), 7.82 (1H, dd, J=7.6, 1.6 Hz), 7.81 (1H, brd), 7.86 (1H, brd).

Example 92

4-(5-Chloro-1H,3H-benzo[de]isochromen-6-yl)-6-cyclohexylsulfanyl-[1,3,5]triazin-2-ylamine

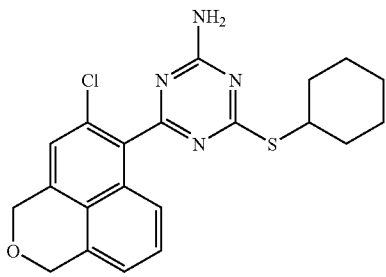

ESI (positive mode) m/z=413(M+H⁺), 435/437(M+Na⁺)

$^1$H-NMR (300 MHz, in DMSO-$d_6$) chemical shifts δ: 1.27-1.53 (6H, m), 1.65 (2H, brd), 2.00 (2H, m), 3.74 (1H, brd), 5.04 (2H, s), 5.05 (2H, s), 7.34 (1H, d, J=7.0 Hz), 7.41 (1H, d, J=8.7 Hz), 7.44 (1H, s), 7.52 (2H, dd, J=8.7, 7.0 Hz), 7.74 (2H, brd).

Example 93

4-(5-Chloro-1H,3H-benzo[de]isochromen-6-yl)-6-isobutylsulfanyl-[1,3,5]triazin-2-ylamine

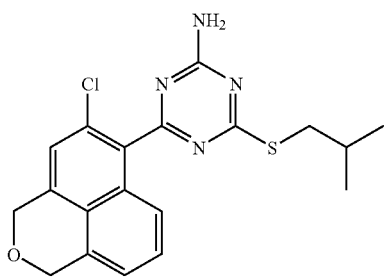

ESI (positive mode) m/z=387(M+H⁺), 409/411(M+Na⁺)

$^1$H-NMR (300 MHz, in DMSO-$d_6$) chemical shifts δ: 0.96 (6H, d, J=6.9 Hz), 1.9 (1H, m), 2.99 (2H, d, J=6.4 Hz), 5.04 (2H, s), 5.05 (2H, s), 7.34 (1H, d, J=6.9 Hz), 7.39 (1H, d, J=8.1 Hz), 7.44 (1H, s), 7.52 (2H, dd, J=8.1, 6.9 Hz), 7.76 (2H, brd).

Example 94

4-(5-Chloro-1H,3H-benzo[de]isochromen-6-yl)-6-isopropylsulfanyl-[1,3,5]triazin-2-ylamine

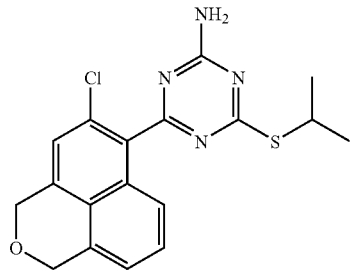

ESI (positive mode) m/z=373(M+H⁺), 395/397(M+Na⁺)

$^1$H-NMR (300 MHz, in DMSO-$d_6$) chemical shifts δ: 1.33 (6H, d, J=6.9 Hz), 3.81 (1H, m), 5.04 (2H, s), 5.05 (2H, s), 7.34 (1H, d, J=6.9 Hz), 7.40 (1H, d, J=8.0 Hz), 7.44 (1H, s), 7.52 (2H, dd, J=8.0, 6.9 Hz), 7.76 (2H, brd).

Example 95

N-{4-[4-Amino-6-(5-chloro-1H,3H-benzo[de]isochromen-6-yl)-[1,3,5]triazin-2-ylsulfanyl]-phenyl}-acetamide

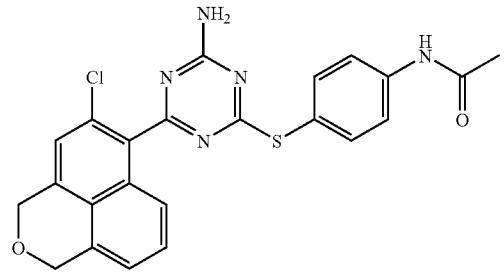

ESI (positive mode) m/z=464(M+H⁺), 486/488(M+Na⁺)

$^1$H-NMR (300 MHz, in DMSO-$d_6$) chemical shifts δ: 2.04 (3H, s), 5.03 (4H, s), 7.33 (1H, d, J=6.6 Hz), 7.41-7.63 (7H, m), 7.73 (1H, brs), 7.78 (1H, brs), 10.06 (1H, s).

Example 96

4-(5-Chloro-1H,3H-benzo[de]isochromen-6-yl)-6-(4-methoxybenzylsulfanyl)-[1,3,5]triazin-2-ylamine

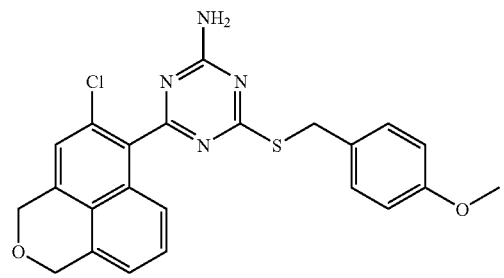

ESI (positive mode) m/z=451/453(M+H⁺)

$^1$H-NMR (300 MHz, in DMSO-$d_6$) chemical shifts δ: 3.73 (3H, s), 4.29 (2H, s), 5.04 (2H, s), 5.05 (2H, s), 6.83 (2H, d, J=8.4 Hz), 7.33 (2H, d, J=8.4 Hz), 7.34 (1H, s), 7.39 (1H, d, J=6.9 Hz), 7.45 (1H, s), 7.52 (1H, dd, J=8.4, 6.9 Hz), 7.85 (2H, brd).

Example 97

4-(5-Chloro-1H,3H-benzo[de]isochromen-6-yl)-6-(3-chlorobenzyloxy)-[1,3,5]triazin-2-ylamine

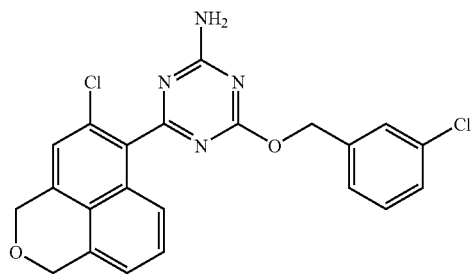

ESI (positive mode) m/z=439/441(M+H$^+$)

$^1$H-NMR (300 MHz, in DMSO-d$_6$) chemical shifts δ: 5.04 (2H, s), 5.05 (2H, s), 5.38 (2H, s), 7.33 (1H, d, J=7.2 Hz), 7.36-7.44 (5H, m), 7.46-7.52 (2H, m), 7.80 (2H, brd).

Example 98

4-(5-Chloro-1H,3H-benzo[de]isochromen-6-yl)-6-(3-methoxyphenoxy)-[1,3,5]triazin-2-ylamine

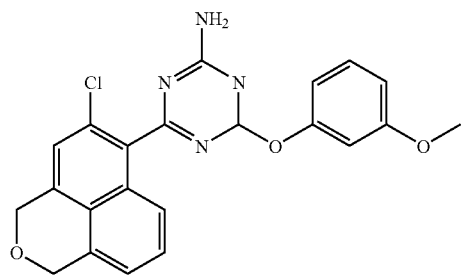

ESI (positive mode) m/z=421(M+H$^+$), 443/445(M+Na$^+$)

$^1$H-NMR (300 MHz, in DMSO-d$_6$) chemical shifts δ: 3.76 (3H, s), 5.05 (4H, s), 6.78-6.87 (2H, m), 6.92 (1H, t, J=2.3 Hz), 7.28-7.37 (2H, m), 7.45 (1H, s), 7.54 (2H, d, J=4.3 Hz), 7.90 (2H, brs).

Example 99

{4-[4-Amino-6-(5-chloro-1H,3H-benzo[de]isochromen-6-yl)-[1,3,5]triazin-2-yloxy]-phenyl}-methanol

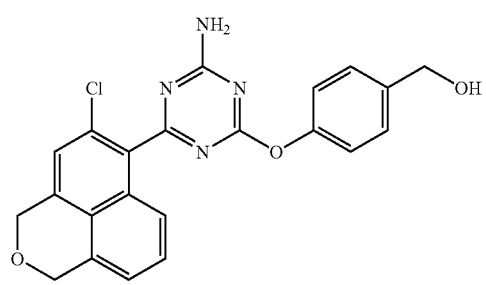

ESI (positive mode) m/z=421/423(M+H$^+$)

$^1$H-NMR (300 MHz, in DMSO-d$_6$) chemical shifts δ: 4.47 (2H, d, J=6.2 Hz), 5.04 (4H, s), 5.17 (1H, t, J=6.2 Hz), 7.21 (1H, d, J=8.8 Hz), 7.22 (1H, s), 7.33 (3H, m), 7.43 (1H, s), 7.48-7.56 (2H, m), 7.86 (2H, brd).

Example 100

4-(5-Chloro-1H,3H-benzo[de]isochromen-6-yl)-6-(4-methoxyphenoxy)-[1,3,5]triazin-2-ylamine

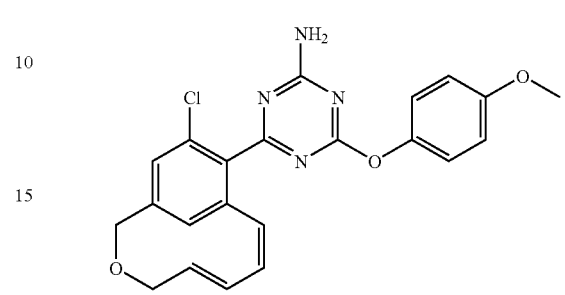

ESI (positive mode) m/z=421(M+H$^+$), 443/445(M+Na$^+$)

$^1$H-NMR (300 MHz, in DMSO-d$_6$) chemical shifts δ: 3.73 (3H, s), 5.04 (4H, s), 6.90-6.96 (2H, m), 7.15-7.21 (2H, m), 7.34 (1H, d, J=5.3 Hz), 7.43 (1H, s), 7.49-7.56 (2H, m), 7.83 (2H, brs).

Example 101

4-(5-Chloro-1H,3H-benzo[de]isochromen-6-yl)-6-(2-methoxyphenoxy)-[1,3,5]triazin-2-ylamine

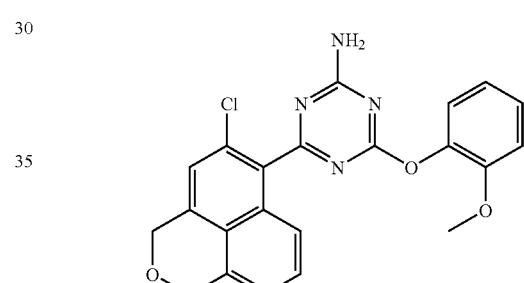

ESI (positive mode) m/z=421/423(M+H$^+$)

$^1$H-NMR (300 MHz, in DMSO-d$_6$) chemical shifts δ: 3.77 (3H, s), 5.02 (4H, s), 6.89-6.96 (1H, m), 7.06-7.10 (1H, m), 7.14-7.22 (2H, m), 7.31-7.42 (3H, m), 7.50-7.57 (1H, m), 7.83 (2H, brs).

Example 102

N-{3-[4-Amino-6-(5-chloro-1H,3H-benzo[de]isochromen-6-yl)-[1,3,5]triazin-2-yloxy]-phenyl}-acetamide

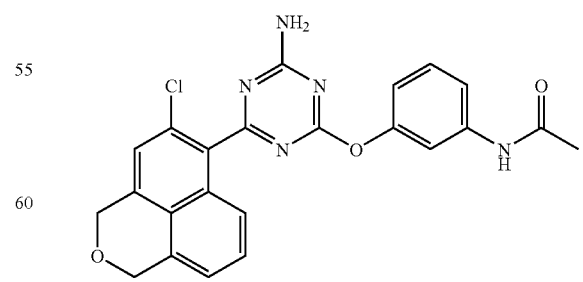

ESI (positive mode) m/z=448(M+H$^+$), 470/472(M+Na$^+$)

$^1$H-NMR (300 MHz, in DMSO-d$_6$) chemical shifts δ: 2.05 (3H, s), 5.05 (4H, s), 6.92-6.97 (1H, m), 7.29-7.37 (3H, m), 7.44-7.60 (4H, m), 7.89 (2H, s), 10.05 (1H, s).

Example 103

2-{3-[4-Amino-6-(5-chloro-1H,3H-benzo[de]isochromen-6-yl)-[1,3,5]triazin-2-yloxy]-phenyl}-ethanol

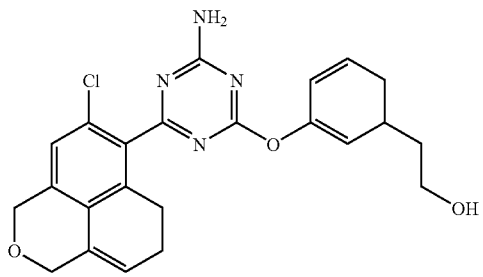

ESI (positive mode) m/z=435(M+H$^+$), 457/459(M+Na$^+$)
$^1$H-NMR (300 MHz, in DMSO-d$_6$) chemical shifts δ: 2.73 (2H, t, J=6.9 Hz), 3.55-3.65 (2H, m), 4.63 (1H, t, J=4.9 Hz), 5.04 (4H, s), 7.05-7.13 (3H, m), 7.29-7.35 (2H, m), 7.43 (1H, s), 7.48-7.57 (2H, m), 7.87 (2H, brs).

Example 104

{3-[4-Amino-6-(5-chloro-1H,3H-benzo[de]isochromen-6-yl)-[1,3,5]triazin-2-yloxy]-phenyl}-urea

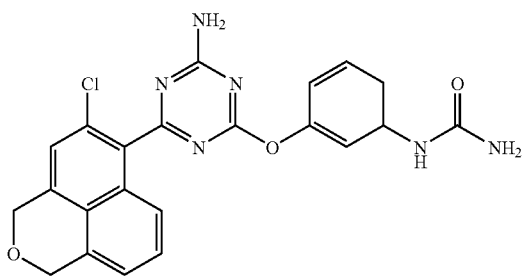

ESI (positive mode) m/z=449(M+H$^+$), 471/473(M+Na$^+$)
$^1$H-NMR (300 MHz, in DMSO-d$_6$) chemical shifts δ: 5.04 (4H, s), 5.92 (2H, s), 6.78 (1H, d, J=8.0 Hz), 7.08-7.12 (1H, m), 7.20-7.25 (1H, m), 7.35-7.31 (1H, m), 7.42-7.58 (4H, m), 7.85-7.93 (2H, brm), 8.72 (1H, s).

Example 105

4-[4-Amino-6-(5-chloro-1H,3H-benzo[de]isochromen-6-yl)-[1,3,5]triazin-2-ylsulfanyl]-phenol

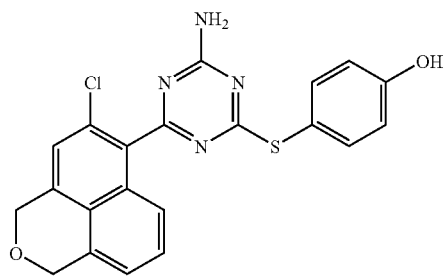

ESI (positive mode) m/z=423/425(M+H$^+$)
$^1$H-NMR (300 MHz, in DMSO-d$_6$) chemical shifts δ: 5.03 (4H, s), 6.78 (2H, d, J=8.5 Hz), 7.33 (1H, d, J=6.9 Hz), 7.38-7.43 (4H, m), 7.52 (1H, dd, J=8.4, 6.9 Hz), 7.68 (1H, brd), 7.74 (1H, brd), 9.83 (1H, s).

Example 106

4-(5-Chloro-1H,3H-benzo[de]isochromen-6-yl)-6-(4-nitrophenylsulfanyl)-[1,3,5]triazin-2-ylamine

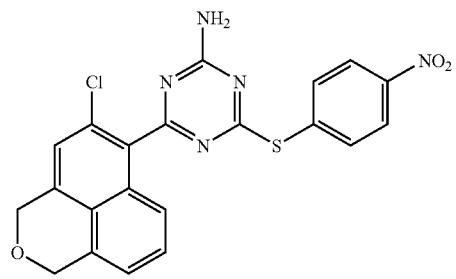

ESI (positive mode) m/z=450/452(M+H$^+$)
$^1$H-NMR (300 MHz, in DMSO-d$_6$) chemical shifts δ: 5.03 (4H, s), 7.34 (1H, d, J=6.2 Hz), 7.41 (1H, s), 7.46-7.58 (2H, m), 7.87-8.00 (4H, m), 8.20 (1H, s), 8.23 (1H, s).

Example 107

4-(5-Chloro-1H,3H-benzo[de]isochromen-6-yl)-6-(2-methyl-furan-3-ylsulfanyl)-[1,3,5]triazin-2-ylamine

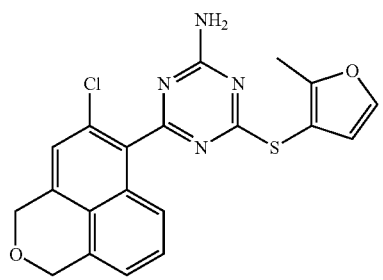

ESI (positive mode) m/z=411/413(M+H$^+$)
$^1$H-NMR (300 MHz, in DMSO-d$_6$) chemical shifts δ: 2.30 (3H, s), 5.04 (4H, s), 6.57 (1H, d, J=1.9 Hz), 7.34 (1H, d, J=6.6 Hz), 7.39-7.55 (3H, m), 7.59 (1H, d, J=1.9 Hz), 7.82 (2H, brs).

Example 108

4-(5-Chloro-1H,3H-benzo[de]isochromen-6-yl)-6-(2,5-dimethoxyphenoxy)-[1,3,5]triazin-2-ylamine

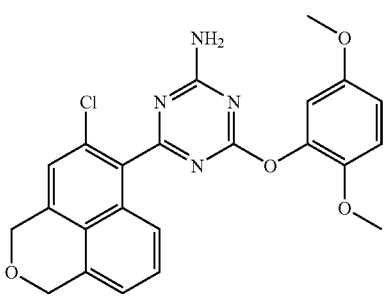

ESI (positive mode) m/z=451/453(M+H$^+$)
$^1$H-NMR (300 MHz, in CDCl$_3$+methanol d$_4$) chemical shifts δ: 3.77 (3H, s), 3.79 (3H, s), 5.05 (2H, s), 5.06 (2H, s), 6.75 (1H, dd, J=9.0, 2.2 Hz), 6.82 (1H, d, J=2.2 Hz), 6.92 (1H, d, J=9.0 Hz), 7.21 (1H, d, J=6.6 Hz), 7.25 (1H, s), 7.4-7.48 (2H, m).

Example 109

4-(3-Aminophenylsulfanyl)-6-(5-chloro-1H,3H-benzo[de]isochromen-6-yl)-[1,3,5]triazin-2-ylamine

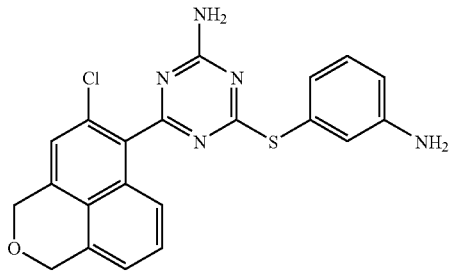

ESI (positive mode) m/z=422/424(M+H$^+$)
$^1$H-NMR (300 MHz, in DMSO-d$_6$) chemical shifts δ: 5.03 (4H, s), 5.22 (2H, s), 6.57 (1H, dd, J=8.1, 2.3 Hz), 6.73 (1H, dd, J=7.6, 1.9 Hz), 6.81 (1H, t, J=2.3, 1.9 Hz), 7.03 (1H, dd, J=8.1, 7.6 Hz), 7.33 (1H, d, J=6.9 Hz), 7.42 (1H, d, J=8.4 Hz), 7.43 (1H, s), 7.54 (1H, dd, J=8.4, 6.9 Hz), 7.74 (2H, brd).

Example 110

4-(5-Chloro-1H,3H-benzo[de]isochromen-6-yl)-6-propylsulfanyl-[1,3,5]triazin-2-ylamine

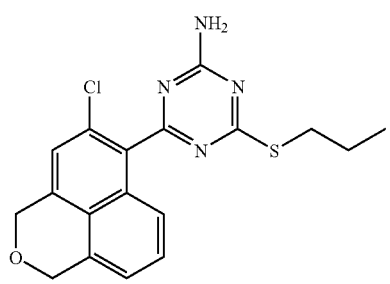

ESI (positive mode) m/z=373/375(M+H$^+$)
$^1$H-NMR (300 MHz, in DMSO-d$_6$) chemical shifts δ: 0.94 (3H, t, J=7.3 Hz), 1.66 (2H, m), 3.03 (2H, t, J=7.3 Hz), 5.04 (2H, s), 5.05 (2H, s), 7.34 (1H, d, J=6.6 Hz), 7.40 (1H, d, J=8.0 Hz), 7.44 (1H, s), 7.52 (1H, dd, J=8.0, 6.6 Hz), 7.76 (2H, brd).

Example 111

[4-Amino-6-(5-chloro-1H,3H-benzo[de]isochromen-6-yl)-[1,3,5]triazin-2-ylsulfanyl]-acetic acid methyl ester

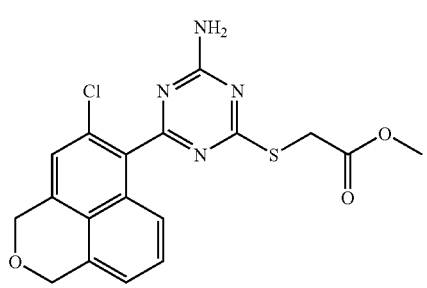

ESI (positive mode) m/z=403(M+H$^+$), 425(M+Na$^+$)
$^1$H-NMR (300 MHz, in DMSO-d$_6$) chemical shifts δ: 3.56 (3H, s), 3.97 (2H, s), 5.04 (2H, s), 5.05 (2H, s), 7.34-7.37 (2H, m), 7.44 (1H, s), 7.52 (1H, dd, J=8.4, 6.6 Hz), 7.82 (1H, brd), 7.86 (1H, brd).

Example 112

[4-Amino-6-(5-chloro-1H,3H-benzo[de]isochromen-6-yl)-[1,3,5]triazin-2-ylsulfanyl]-acetic acid

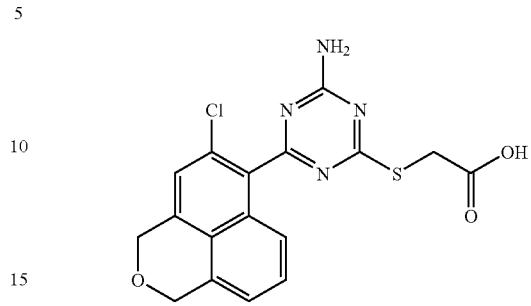

ESI (positive mode) m/z=389/391(M+H$^+$)
$^1$H-NMR (300 MHz, in DMSO-d$_6$) chemical shifts δ: 3.92 (2H, s), 5.04 (2H, s), 5.05 (2H, s), 7.34 (1H, d, J=7.1 Hz), 7.38 (1H, d, J=8.1 Hz), 7.44 (1H, s), 7.52 (1H, dd, J=8.1, 7.1 Hz), 7.82 (1H, brd), 7.85 (1H, brd), 12.7 (1H, brd).

Example 113

N-{2-[4-Amino-6-(5-chloro-1H,3H-benzo[de]isochromen-6-yl)-[1,3,5]triazin-2-ylsulfanyl]-ethyl}-acetamide

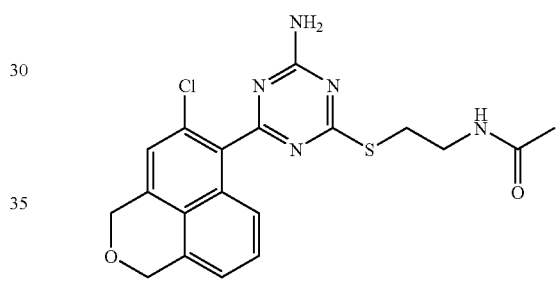

ESI (positive mode) m/z=416/418(M+H$^+$)
$^1$H-NMR (300 MHz, in DMSO-d$_6$) chemical shifts δ: 1.77 (3H, s), 3.10 (2H, t, J=6.6 Hz), 3.31 (2H, m), 5.04 (2H, s), 5.05 (2H, s), 7.34 (1H, d, J=6.5 Hz), 7.41 (1H, d, J=8.4 Hz), 7.45 (1H, s), 7.52 (1H, dd, J=8.4, 6.5 Hz), 7.81 (1H, brd), 7.83 (1H, brd), 8.07 (1H, t, J=6.2 Hz).

Example 114

4-(5-Chloro-1H,3H-benzo[de]isochromen-6-yl)-6-(2-dimethylamino-ethylsulfanyl)-[1,3,5]triazin-2-ylamine

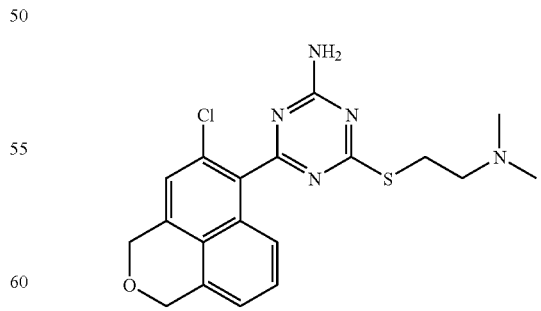

ESI (positive mode) m/z=402/404(M+H$^+$)
$^1$H-NMR (300 MHz, in DMSO-d$_6$) chemical shifts δ: 2.91 (6H, s), 5.03 (4H, s), 6.69 (2H, d, J=8.7 Hz), 7.33 (1H, d, J=6.9 Hz), 7.36 (2H, d, J=8.7 Hz), 7.40 (1H, d, J=8.7 Hz), 7.41 (1H, s), 7.52 (1H, dd, J=8.7, 6.9 Hz), 7.67 (1H, brd), 7.70 (1H, brd).

Example 115

3-[4-Amino-6-(5-chloro-1H,3H-benzo[de]isochromen-6-yl)-[1,3,5]triazin-2-ylsulfanyl]-propan-1-ol

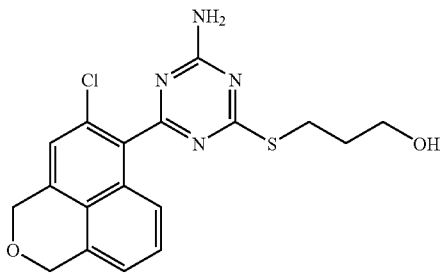

ESI (positive mode) m/z=389/391(M+H$^+$)
$^1$H-NMR (300 MHz, in DMSO-d$_6$) chemical shifts δ: 1.78 (2H, tt, J=6.9 Hz), 3.08 (2H, t, J=6.9 Hz), 3.47 (2H, dt, J=6.9, 5.0 Hz), 4.53 (1H, t, J=5.0 Hz), 5.04 (2H, s), 5.05 (2H, s), 7.34 (1H, d, J=6.9 Hz), 7.40 (1H, d, J=8.3 Hz), 7.45 (1H, s), 7.52 (1H, dd, J=8.3, 6.9 Hz), 7.80 (2H, brd).

Example 116

1-(4-{3-[4-Amino-6-(5-chloro-1H,3H-benzo[de]isochromen-6-yl)-[1,3,5]triazin-2-yloxy]-phenyl}-piperazin-1-yl)-ethanone

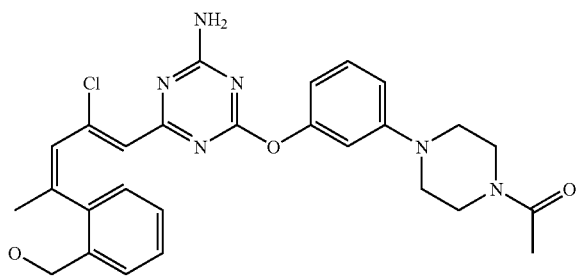

ESI (positive mode) m/z=539/541(M+H$^+$)
$^1$H-NMR (300 MHz, in DMSO-d$_6$) chemical shifts δ: 2.03 (3H, s), 3.05-3.23 (4H, m), 3.50-3.62 (4H, m), 5.04 (4H, s), 6.67 (1H, dd, J=7.9, 2.1 Hz), 6.78 (1H, d, J=7.9, 2.1 Hz), 6.89 (1H, d, J=1.9 Hz), 7.22 (1H, t, J=7.9 Hz), 7.34 (1H, t, J=4.0 Hz), 7.43 (1H, s), 7.52 (2H, d, J=4.0 Hz), 7.84 (1H, brs), 7.86 (1H, brs).

Example 117

2-[4-Amino-6-(5-chloro-1H,3H-benzo[de]isochromen-6-yl)-[1,3,5]triazin-2-ylsulfanyl]-phenol

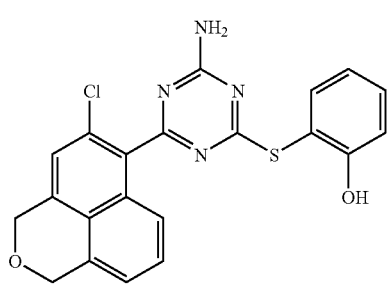

ESI (positive mode) m/z=423/425(M+H$^+$)
$^1$H-NMR (300 MHz, in DMSO-d$_6$) chemical shifts δ: 5.03 (4H, s), 6.79 (1H, t, J=7.9 Hz), 6.91 (1H, d, J=7.9 Hz), 7.23 (1H, t, J=7.9 Hz), 7.33 (1H, d, J=7.0 Hz), 7.41 (1H, s), 7.42-7.48 (2H, m), 7.54 (1H, dd, J=8.6, 7.0 Hz), 7.68 (1H, brd), 7.70 (1H, brd), 10.0 (1H, s).

Example 118

4-(5-Chloro-1H,3H-benzo[de]isochromen-6-yl)-6-o-tolylsulfanyl-[1,3,5]triazin-2-ylamine

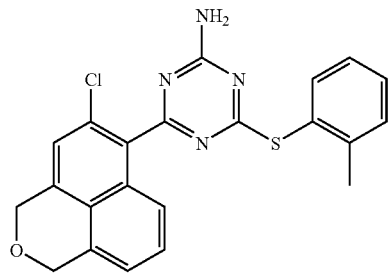

ESI (positive mode) m/z=421/423(M+H$^+$)
$^1$H-NMR (300 MHz, in DMSO-d$_6$) chemical shifts δ: 2.40 (3H, s), 5.02 (4H, s), 7.20 (1H, m), 7.31-7.34 (3H, m), 7.38 (1H, d, J=8.5 Hz), 7.40 (1H, s), 7.54 (1H, dd, J=8.5, 6.8 Hz), 7.59 (1H, d, J=6.8 Hz), 7.75 (1H, brd), 7.78 (1H, brd).

Example 119

2-[4-Amino-6-(5-chloro-1H,3H-benzo[de]isochromen-6-yl)-[1,3,5]triazin-2-ylsulfanyl]-acetamide

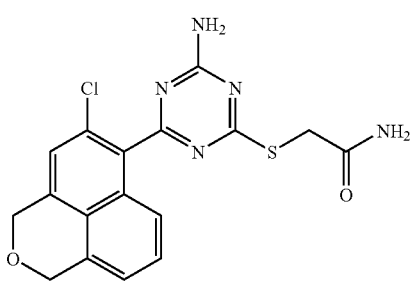

ESI (positive mode) m/z=388/390(M+H$^+$)
$^1$H-NMR (300 MHz, in DMSO-d$_6$) chemical shifts δ: 3.78 (2H, s), 5.04 (2H, s), 5.05 (2H, s), 7.12 (1H, brd), 7.34 (1H, d, J=7.7 Hz), 7.41 (1H, d, J=8.5 Hz), 7.44 (1H, s), 7.44 (1H, brd), 7.52 (1H, dd, J=8.5, 7.7 Hz), 7.81 (1H, brd), 7.83 (1H, brd).

Example 120

4-(5-Chloro-1H,3H-benzo[de]isochromen-6-yl)-6-(2-methoxybenzyloxy)-[1,3,5]triazin-2-ylamine

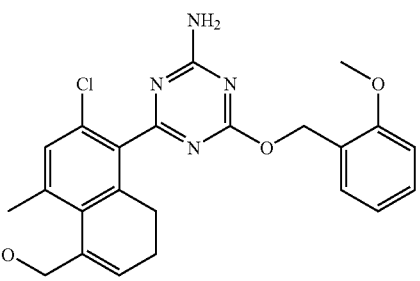

ESI (positive mode) m/z=435/437(M+H$^+$)
$^1$H-NMR (300 MHz, in DMSO-d$_6$) chemical shifts δ: 3.80 (3H, s), 5.05 (4H, s), 5.36 (2H, s), 6.96 (1H, t, J=7.4 Hz), 7.04 (1H, d, J=8.3 Hz), 7.30-7.53 (6H, m), 7.76 (2H, brs).

Example 121

4-(5-Chloro-1H,3H-benzo[de]isochromen-6-yl)-6-(3-methoxybenzyloxy)-[1,3,5]triazin-2-ylamine

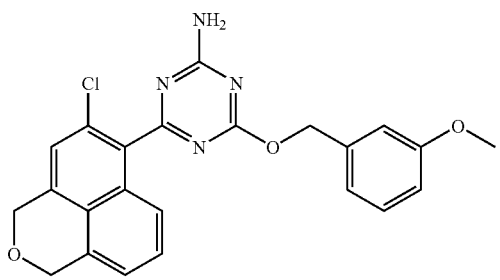

ESI (positive mode) m/z=435/437(M+H$^+$)
$^1$H-NMR (300 MHz, in DMSO-d$_6$) chemical shifts δ: 3.74 (3H, s), 5.05 (4H, s), 5.35 (2H, s), 6.91 (1H, dd, J=8.0, 2.4 Hz), 6.98-7.05 (2H, m), 7.27-7.53 (5H, m), 7.77 (1H, brs), 7.79 (1H, brs).

Example 122

4-(5-Chloro-1H,3H-benzo[de]isochromen-6-yl)-6-(4-methoxybenzyloxy)-[1,3,5]triazin-2-ylamine

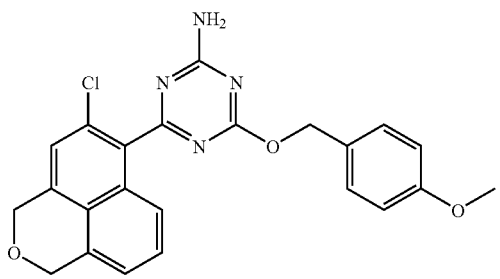

ESI (positive mode) m/z=435/437(M+H$^+$)
$^1$H-NMR (300 MHz, in DMSO-d$_6$) chemical shifts δ: 3.76 (3H, s), 5.05 (4H, s), 5.30 (2H, s), 6.91-6.96 (2H, m), 7.31-7.45 (5H, m), 7.50 (1H, dd, J=8.9, 6.9 Hz), 7.75 (2H, brs).

Example 123

4-(5-Chloro-1H,3H-benzo[de]isochromen-6-yl)-6-(4-dimethylaminophenylsulfanyl)-[1,3,5]triazin-2-ylamine

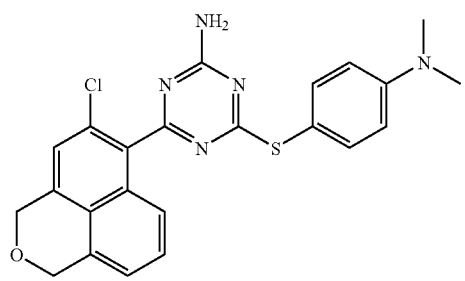

ESI (positive mode) m/z=450/452(M+H$^+$)
$^1$H-NMR (300 MHz, in DMSO-d$_6$) chemical shifts δ: 2.91 (6H, s), 5.03 (4H, s), 6.69 (2H, d, J=8.7 Hz), 7.32-7.39 (3H, m), 7.42 (1H, s), 7.40 (1H, s), 7.52 (1H, dd, J=8.7, 6.9 Hz), 7.67 (1H, brd), 7.70 (1H, brd).

Example 124

3-[4-Amino-6-(5-chloro-1H,3H-benzo[de]isochromen-6-yl)-[1,3,5]triazin-2-ylsulfanyl]-propionic acid methyl ester

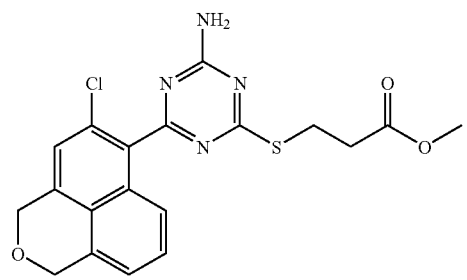

ESI (positive mode) m/z=417(M+H$^+$), 439/441(M+Na$^+$)
$^1$H-NMR (300 MHz, in DMSO-d$_6$) chemical shifts δ: 2.78 (2H, t, J=6.9 Hz), 3.22 (2H, t, J=6.9 Hz), 3.60 (3H, s), 5.04 (2H, s), 5.05 (2H, s), 7.34 (1H, d, J=6.8 Hz), 7.42 (1H, d, J=7.9 Hz), 7.45 (1H, s), 7.52 (1H, dd, J=7.9, 6.8 Hz), 7.87 (2H, brd).

Example 125

3-[4-amino-6-(5-chloro-1H,3H-benzo[de]isochromen-6-yl)-[1,3,5]triazin-2-ylsulfanyl]-propionamide

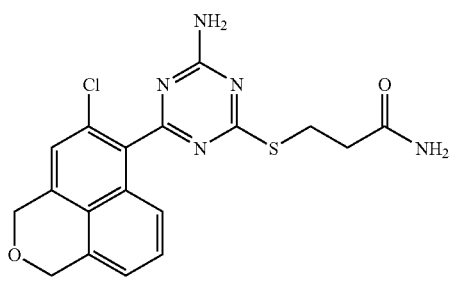

ESI (positive mode) m/z=402/404(M+H$^+$)
$^1$H-NMR (300 MHz, in DMSO-d$_6$) chemical shifts δ: 2.49 (2H, t, J=6.9 Hz), 3.21 (2H, t, J=6.9 Hz), 5.05 (4H, s), 6.96 (1H, brd), 7.35 (1H, d, J=6.9 Hz), 7.38 (1H, brd), 7.42 (1H, d, J=7.7 Hz), 7.46 (1H, s), 7.52 (1H, dd, J=7.7, 6.9 Hz), 7.85-7.87 (2H, brd).

Example 126

3-[4-Amino-6-(5-chloro-1H,3H-benzo[de]isochromen-6-yl)-[1,3,5]triazin-2-ylsulfanyl]-propionic acid

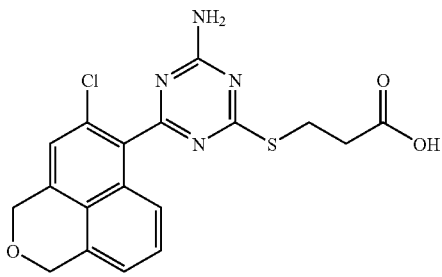

ESI (positive mode) m/z=403/405(M+H⁺)

¹H-NMR (300 MHz, in DMSO-d$_6$) chemical shifts δ: 2.68 (2H, t, J=6.9 Hz), 3.18 (2H, t, J=6.9 Hz), 5.04 (2H, s), 5.05 (2H, s), 7.34 (1H, d, J=6.9 Hz), 7.42 (1H, d, J=8.0 Hz), 7.45 (1H, s), 7.52 (1H, dd, J=8.0, 6.9 Hz), 7.85-7.89 (2H, brd), 12.40 (1H, brd).

Example 127

N-{2-[4-Amino-6-(5-chloro-1H,3H-benzo[de]isochromen-6-yl)-[1,3,5]triazin-2-yloxymethyl]-phenyl}-acetamide

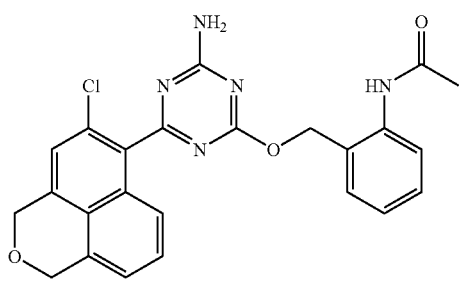

ESI (positive mode) m/z=462(M+H⁺), 484/486(M+Na⁺)

¹H-NMR (300 MHz, in DMSO-d$_6$) chemical shifts δ: 1.95 (3H, s), 5.05 (4H, s), 5.36 (2H, s), 7.21 (1H, t, J=7.8 Hz), 7.26-7.55 (7H, m), 7.76 (1H, brs), 7.79 (1H, brs), 9.55 (1H, s).

Example 128

N-{4-[4-Amino-6-(5-chloro-1H,3H-benzo[de]isochromen-6-yl)-[1,3,5]triazin-2-yloxymethyl]-phenyl}-acetamide

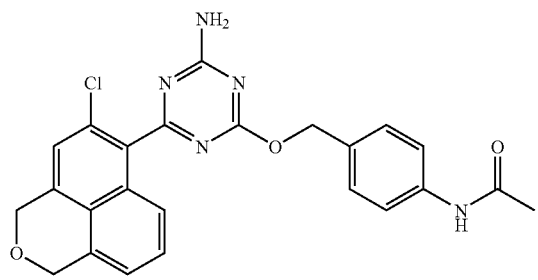

ESI (positive mode) m/z=462(M+H⁺), 484/486(M+Na⁺)

¹H-NMR (300 MHz, in DMSO-d$_6$) chemical shifts δ: 2.04 (3H, s), 5.05 (4H, s), 5.29 (2H, s), 7.32-7.58 (8H, m), 7.74-7.78 (2H, brm), 9.95 (1H, s).

Example 129

N-{3-[4-Amino-6-(5-chloro-1H,3H-benzo[de]isochromen-6-yl)-[1,3,5]triazin-2-yloxymethyl]-phenyl}-acetamide

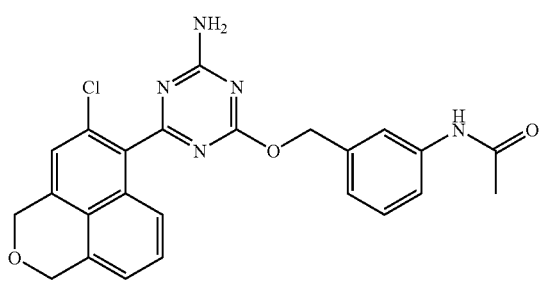

ESI (positive mode) m/z=462(M+H⁺), 484/486(M+Na⁺)

¹H-NMR (300 MHz, in DMSO-d$_6$) chemical shifts δ: 2.03 (3H, s), 5.05 (4H, s), 5.35 (2H, s), 7.08 (1H, d, J=7.6 Hz), 7.23-7.58 (6H, m), 7.65 (1H, s), 7.76 (1H, brs), 7.79 (1H, brs), 9.96 (1H, s).

Example 130

(R)-2-[4-Amino-6-(5-chloro-1H,3H-benzo[de]isochromen-6-yl)-[1,3,5]triazin-2-ylsulfanylmethyl]-4-oxo-pentanoic acid

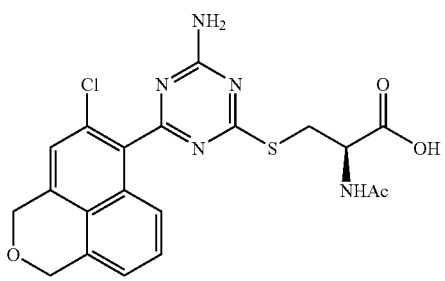

ESI (positive mode) m/z=460/462(M+H⁺)

¹H-NMR (300 MHz, in DMSO-d$_6$) chemical shifts δ: 1.83 (3H, s), 3.24 (1H, dd, J=13.7, 9.2 Hz), 3.63 (1H, dd, J=13.7, 5.1 Hz), 4.51 (1H, m), 5.05 (2H, s), 5.06 (2H, s), 7.34 (1H, d, J=6.2 Hz), 7.43 (1H, d, J=8.1 Hz), 7.45 (1H, s), 7.52 (1H, dd, J=8.1, 6.2 Hz), 7.80-7.83 (2H, brd), 8.29 (1H, d, J=8.0 Hz), 12.77 (1H, brd).

Example 131

3-[4-Amino-6-(5-chloro-1H,3H-benzo[de]isochromen-6-yl)-[1,3,5]triazin-2-ylsulfanyl]-2-methyl-propionic acid

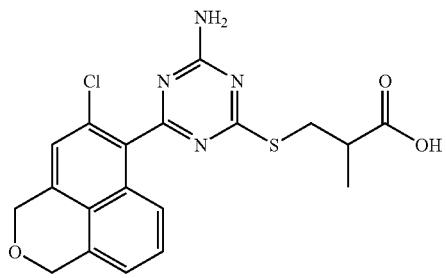

ESI (positive mode) m/z=417(M+H$^+$), 439/441(M+Na$^+$)
$^1$H-NMR (300 MHz, in DMSO-d$_6$) chemical shifts δ: 1.16 (3H, d, J=7.8 Hz), 2.74 (1H, m), 3.22 (2H, dd, J=7.8, 6.2 Hz), 5.04 (2H, s), 5.05 (2H, s), 7.34 (1H, d, J=6.8 Hz), 7.41 (1H, d, J=7.7 Hz), 7.44 (1H, s), 7.52 (1H, dd, J=7.7, 6.8 Hz), 7.80 (2H, brd), 12.40 (1H, brd).

Example 132

2-[4-Amino-6-(5-chloro-1H,3H-benzo[de]isochromen-6-yl)-[1,3,5]triazin-2-ylsulfanyl]-ethanol

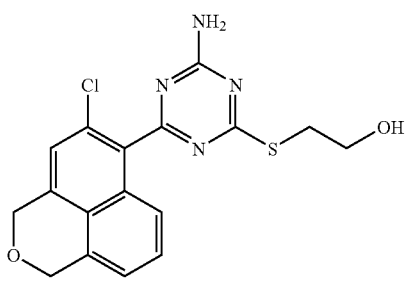

ESI (positive mode) m/z=375/377(M+H$^+$)
$^1$H-NMR (300 MHz, in DMSO-d$_6$) chemical shifts δ: 3.14 (2H, d, J=6.5 Hz), 3.62 (2H, dt, J=6.5, 5.5 Hz), 4.91 (1H, t, J=5.5 Hz), 5.04 (2H, s), 5.05 (2H, s), 7.34 (1H, d, J=7.8 Hz), 7.40 (1H, d, J=8.0 Hz), 7.44 (1H, s), 7.52 (1H, dd, J=8.0, 7.8 Hz), 7.78 (2H, brd).

Example 133

{2-[4-Amino-6-(5-chloro-1H,3H-benzo[de]isochromen-6-yl)-[1,3,5]triazin-2-ylsulfanyl]-ethyl}-carbamic acid tert-butyl ester

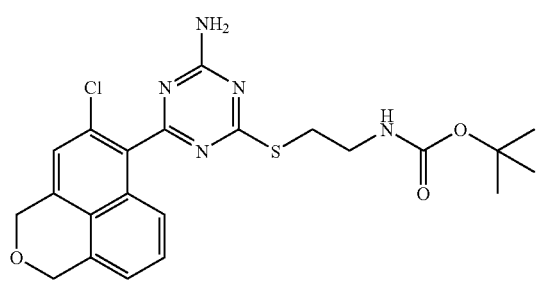

ESI (positive mode) m/z=474/476(M+H$^+$)
$^1$H-NMR (300 MHz, in DMSO-d$_6$) chemical shifts δ: 1.36 (9H, s), 3.11 (2H, t, J=6.1 Hz), 3.24 (2H, dt, J=8.0, 6.1 Hz), 5.04 (2H, s), 5.05 (2H, s), 6.95 (1H, brd), 7.34 (1H, d, J=7.3 Hz), 7.42 (1H, d, J=7.9 Hz), 7.44 (1H, s), 7.52 (1H, dd, J=7.9, 7.3 Hz), 7.78 (2H, brd).

Example 134

4-(5-Chloro-1H,3H-benzo[de]isochromen-6-yl)-6-(3-dimethylaminophenylsulfanyl)-[1,3,5]triazin-2-ylamine

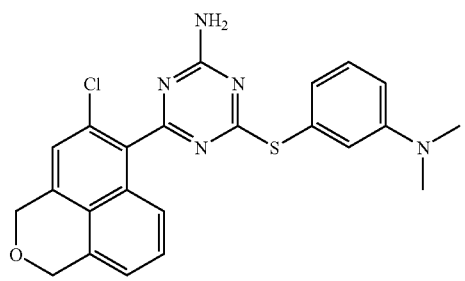

ESI (positive mode) m/z=450/452(M+H$^+$)
$^1$H-NMR (300 MHz, in DMSO-d$_6$) chemical shifts δ: 2.85 (6H, s), 6.71 (1H, dd, J=8.6, 2.6 Hz), 6.86 (1H, d, J=8.0 Hz), 6.94 (1H, s), 7.18 (1H, t, J=8.0 Hz), 7.33 (1H, d, J=6.8 Hz), 7.42-7.58 (3H, m), 7.78 (2H, brs).

Example 135

3-[4-Amino-6-(5-chloro-1H,3H-benzo[de]isochromen-6-yl)-[1,3,5]triazin-2-ylsulfanyl]-2-methyl-propionic acid methyl ester

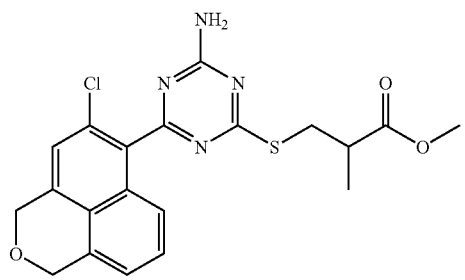

ESI (positive mode) m/z=431/433(M+H$^+$)
$^1$H-NMR (300 MHz, in DMSO-d$_6$) chemical shifts δ: 1.17 (3H, d, J=7.4 Hz), 2.88 (1H, m), 3.26 (2H, d, J=6.9 Hz), 3.60 (3H, s), 5.04 (2H, s), 5.05 (2H, s), 7.34 (1H, d, J=6.8 Hz), 7.41 (1H, d, J=7.5 Hz), 7.45 (1H, s), 7.52 (1H, dd, J=7.5, 6.8 Hz), 7.81 (2H, brd).

Example 136

(R)-2-Acetylamino-3-[4-amino-6-(5-chloro-1H,3H-benzo[de]isochromen-6-yl)-[1,3,5]triazin-2-ylsulfanyl]-propionic acid methyl ester

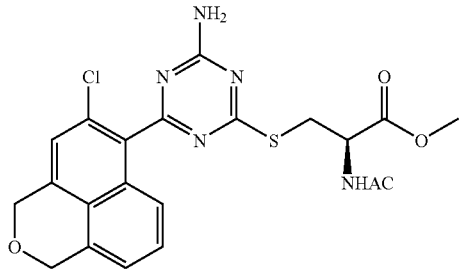

ESI (positive mode) m/z=474(M+H$^+$), 496/498(M+Na$^+$)
$^1$H-NMR (300 MHz, in DMSO-d$_6$) chemical shifts δ: 1.83 (3H, s), 3.27 (1H, m), 3.58 (3H, s), 3.60 (1H, m), 4.58 (1H, m), 5.04 (2H, s), 5.05 (2H, s), 7.34 (1H, d, J=6.4 Hz), 7.43 (1H, d, J=8.5 Hz), 7.45 (1H, s), 7.52 (1H, dd, J=8.5, 6.4 Hz), 7.80 (1H, brd), 7.86 (1H, brd), 8.44 (1H, d, J=7.7 Hz).

Example 137

4-(4-Amino-phenylsulfanyl)-6-(5-chloro-1H,3H-benzo[de]isochromen-6-yl)-[1,3,5]triazin-2-ylamine

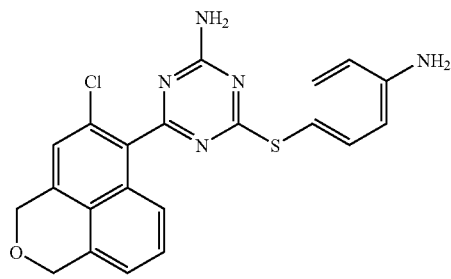

ESI (positive mode) m/z=422(M+H$^+$), 444/446(M+Na$^+$)
$^1$H-NMR (300 MHz, in DMSO-d$_6$) chemical shifts δ: 5.04 (4H, s), 5.47 (2H, s), 6.56 (2H, d, J=8.4 Hz), 7.22 (2H, d, J=8.4 Hz), 7.34 (1H, d, J=7.0 Hz), 7.40-7.43 (2H, m), 7.51-7.56 (1H, m), 7.69 (1H, brs), 7.70 (1H, brs).

Example 138

4-(5-Chloro-1H,3H-benzo[de]isochromen-6-yl)-6-(3-chloropropylsulfanyl)-[1,3,5]triazin-2-ylamine

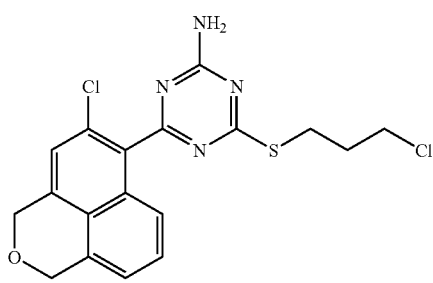

ESI (positive mode) m/z=407/409(M+H$^+$)
$^1$H-NMR (300 MHz, in DMSO-d$_6$) chemical shifts δ: 2.11 (2H, tt, J=6.4, 7.0 Hz), 3.14 (2H, t, J=7.0 Hz), 3.70 (2H, t, J=6.4 Hz), 5.04 (2H, s), 5.05 (2H, s), 7.34 (1H, d, J=6.1 Hz), 7.41 (1H, d, J=8.4 Hz), 7.44 (1H, s), 7.52 (1H, dd, J=8.4, 6.1 Hz), 7.80 (2H, brd).

Example 139

4-[4-(N,N-Dimethylaminosulfonyl)amino-phenylsulfanyl]-6-(5-chloro-1H,3H-benzo[de]isochromen-6-yl)-[1,3,5]triazin-2-ylamine

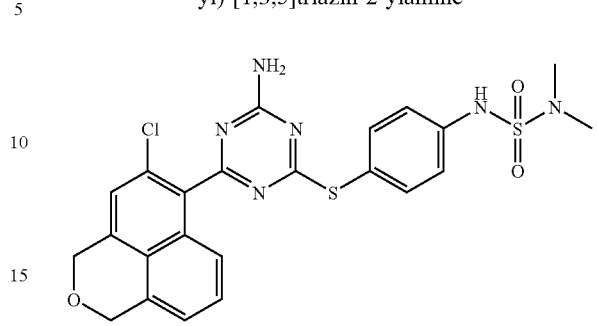

ESI (positive mode) m/z=529(M+H$^+$), 551/553(M+Na$^+$)
$^1$H-NMR (300 MHz, in DMSO-d$_6$) chemical shifts δ: 2.64 (6H, s), 5.03 (4H, s), 7.18 (2H, d, J=8.7 Hz), 7.33 (1H, d, J=6.8 Hz), 7.41 (1H, s), 7.43 (1H, d, J=7.8 Hz), 7.49-7.55 (3H, m), 7.75 (1H, brs), 7.80 (1H, brs), 10.11 (1H, s).

Example 140

N-{4-[4-Amino-6-(5-chloro-1H,3H-benzo[de]isochromen-6-yl)-[1,3,5]triazin-2-ylsulfanylmethyl]-phenyl}-acetamide

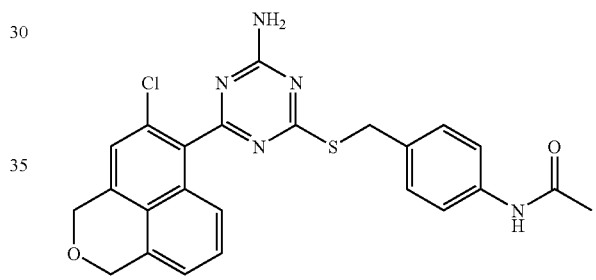

ESI (positive mode) m/z=478(M+H$^+$), 500/502(M+Na$^+$)
$^1$H-NMR (300 MHz, in DMSO-d$_6$) chemical shifts δ: 2.02 (3H, s), 4.28 (2H, s), 5.05 (4H, s), 7.31-7.40 (4H, m), 7.45-7.55 (4H, m), 7.86 (2H, brs), 9.90 (1H, s).

Example 141

4-(5-Chloro-1H,3H-benzo[de]isochromen-6-yl)-6-(3-dimethylaminopropylsulfanyl)-[1,3,5]triazin-2-ylamine

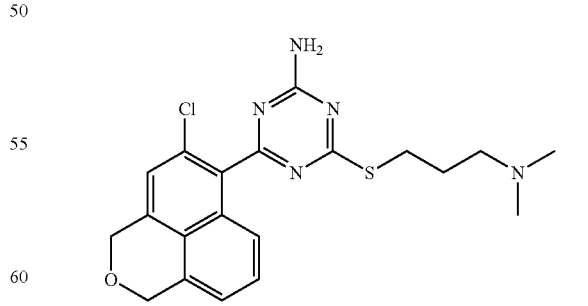

ESI (positive mode) m/z=416/418(M+H$^+$)
$^1$H-NMR (300 MHz, in DMSO-d$_6$) chemical shifts δ: 1.80 (2H, tt, J=7.7, 6.4 Hz), 2.14 (6H, s), 2.37 (2H, t, J=6.4 Hz), 3.04 (2H, t, J=7.7 Hz), 5.04 (2H, s), 5.05 (2H, s), 7.34 (1H, d, J=6.8 Hz), 7.40 (1H, d, J=8.1 Hz), 7.44 (1H, s), 7.52 (1H, dd, J=8.1, 6.8 Hz), 7.75 (2H, brd).

Example 142

4-(4-Aminosulfonyl)amino-phenylsulfanyl-6-(5-chloro-1H,3H-benzo[de]isochromen-6-yl)-[1,3,5]triazin-2-ylamine

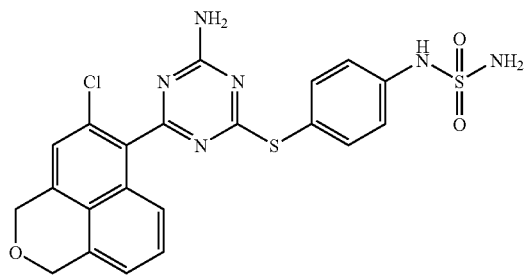

ESI (negative mode) m/z=499/501(M⁻)
¹H-NMR (300 MHz, in DMSO-d₆) chemical shifts δ: 5.03 (4H, s), 7.14 (2H, d, J=8.4 Hz), 7.18 (2H, s), 7.34 (1H, d, J=7.1 Hz), 7.42-7.56 (5H, m), 7.76 (2H, brs), 9.81 (1H, s).

Example 143

N-{2-[4-Amino-6-(5-chloro-1H,3H-benzo[de]isochromen-6-yl)-[1,3,5]triazin-2-ylsulfanylmethyl]-phenyl}-acetamide

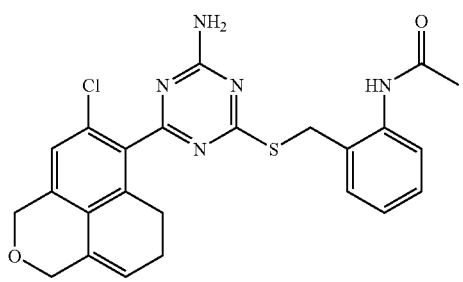

ESI (positive mode) m/z=478(M+H⁺), 500/502(M+H⁺)
¹H-NMR (300 MHz, in DMSO-d₆) chemical shifts δ: 1.94 (3H, s), 4.35 (2H, s), 5.06 (4H, s), 7.10 (1H, dd, J=7.7, 7.2 Hz), 7.24 (1H, dd, J=8.1, 7.2 Hz), 7.33-7.39 (3H, m), 7.49-7.54 (3H, m), 7.85 (2H, brs), 9.43 (1H, s).

Example 144

N-{3-[4-Amino-6-(5-chloro-1H,3H-benzo[de]isochromen-6-yl)-[1,3,5]triazin-2-ylsulfanylmethyl]-phenyl}-acetamide

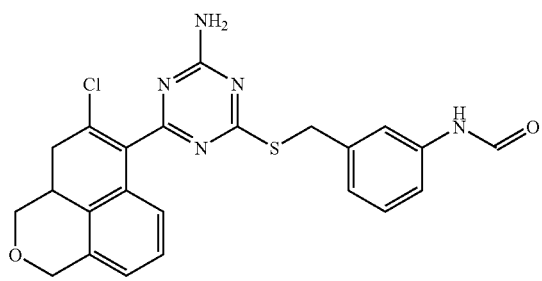

ESI (positive mode) m/z=478(M+H⁺), 500/502(M+H⁺)
¹H-NMR (300 MHz, in DMSO-d₆) chemical shifts δ: 2.03 (3H, s), 4.32 (2H, s), 5.05 (4H, s), 7.07 (1H, d, J=7.6 Hz), 7.20 (1H, t, J=7.6 Hz), 7.34-7.53 (5H, m), 7.63 (1H, s), 7.83 (1H, s), 7.86 (1H, s), 9.90 (1H, s).

Example 145

4-(5-Chloro-1H,3H-benzo[de]isochromen-6-yl)-6-(2,5-dimethoxyphenylsulfanyl)-[1,3,5]triazin-2-ylamine

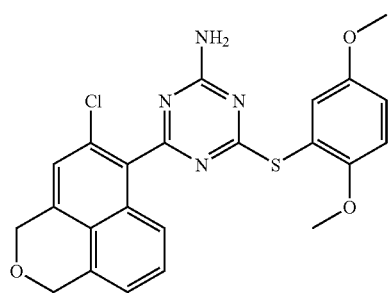

ESI (positive mode) m/z=467,469(M+H⁺)
¹H-NMR (270 MHz, in DMSO-d₆) chemical shifts δ: 3.67 (3H, s), 3.74 (3H, s), 5.02 (4H, s), 6.94 (1H, dd, J=8.8, 2.9 Hz), 6.99 (1H, d, J=8.8 Hz), 7.16 (1H, d, J=2.9 Hz), 7.33 (1H, d, J=6.9 Hz), 7.38 (1H, d, J=8.3 Hz), 7.41 (1H, s), 7.52 (1H, dd, J=8.3, 6.9 Hz), 7.75 (2H, brs).

Example 146

4-(7-Chloro-isochroman-6-yl)-6-methylsulfanyl-[1,3,5]triazin-2-ylamine

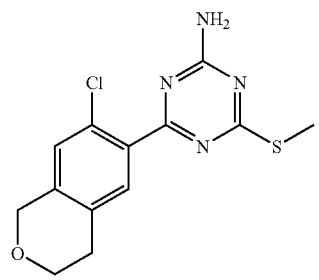

Step 1: Dimethyl 2-(2-carboxy-5-nitrophenyl)malonate

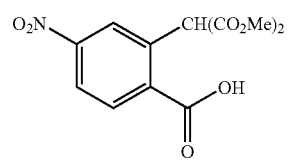

2-Chloro-4-nitrobenzoic acid (7.5 g, 37.2 mmol) was dissolved in deaerated dimethyl malonate (90 mL). Copper (I) bromide (0.54 g, 3.7 mmol) and sodium methoxide (4.83 g, 89.4 mmol) were added to the solution. The mixture was stirred at room temperature for 15 minutes, and then stirred at 70 to 75° C. overnight. After the reaction solution was allowed to return to room temperature, water was added thereto and extracted with ethyl acetate. The organic layer was washed with brine, dried over anhydrous magnesium sulfate, and concentrated under reduced pressure to give the title compound (7.0 g, 68%).

$^1$H-NMR (300 MHz, in CDCl$_3$) chemical shifts δ: 1.29 (3H, s), 1.31 (3H, s), 5.75 (1H, s), 8.16 (1H, s), 8.20 (1H, d, J=6.5 Hz), 8.30 (1H, d, J=6.5 Hz).

Step 2: 2-Carboxymethyl-4-nitrobenzoic acid

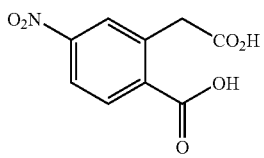

A solution of sodium hydroxide (5.0 g, 125 mmol) in water (60 mL) was added to a solution of dimethyl 2-(2-carboxy-5-nitrophenyl)malonate (7.0 g, 21.5 mmol) in methanol (60 mL) at room temperature. After the reaction solution was stirred at room temperature for 3 hours, methanol was distilled off. The resulting residue was acidified using 1N hydrochloric acid (11 mL). The suspension was extracted with ethyl acetate. The organic layer was washed with brine, dried over anhydrous magnesium sulfate, and concentrated under reduced pressure to give a crude product. After the crude product was stirred in ethyl acetate (20 mL) at 70 to 80° C. overnight, the temperature was allowed to return to room temperature. The precipitate was collected by filtration, and dried under reduced pressure to give the title compound (1.13 g, 23%).

$^1$H-NMR (300 MHz, in CDCl$_3$+methanol d$_4$) chemical shifts δ: 4.12 (2H, s), 8.15 (1H, s), 8.20 (2H, m).

Step 3: Methyl 2-methoxycarbonylmethyl-4-nitrobenzoate

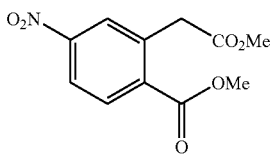

Sulfuric acid was added in excess to a solution of 2-carboxymethyl-4-nitrobenzoic acid (3.00 g, 13.68 mmol) in methanol (30 mL). The reaction solution was stirred overnight while heating under reflux. After the solution was cooled to room temperature, water was added thereto and extracted with ethyl acetate. The organic layer was washed with saturated aqueous sodium bicarbonate, and then with brine. The organic layer was dried over anhydrous magnesium sulfate, and concentrated under reduced pressure. The title compound was obtained as colorless oily material (1.74 g, 50%).

$^1$H-NMR (300 MHz, in CDCl$_3$) chemical shifts δ: 3.72 (3H, s), 3.93 (3H, s), 4.12 (2H, s), 8.14-8.23 (3H, m).

Step 4: Methyl 2-methoxycarbonylmethyl-4-aminobenzoate

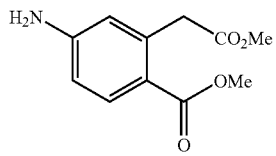

Methyl 2-methoxycarbonylmethyl-4-nitrobenzoate (1.74 g, 6.87 mmol) was dissolved in a mixed solvent of ethyl acetate and methanol under nitrogen atmosphere, and then 10% palladium ddcarbon (30 w/w %) was added thereto. After replacing nitrogen gas with hydrogen gas, the reaction solution was stirred at room temperature overnight. The palladium catalyst was removed by Celite filtration, followed by washing with ethyl acetate. The filtrate and washing solution were combined together, and concentrated under reduced pressure to give the title compound (1.30 g, 84%).

$^1$H-NMR (300 MHz, in CDCl$_3$) chemical shifts δ: 3.70 (3H, s), 3.80 (3H, s), 3.92 (2H, s), 4.04 (2H, brd), 6.46 (1H, d, J=2.4 Hz), 6.56 (1H, dd, J=8.5, 2.4 Hz), 7.88 (1H, d, J=8.5 Hz).

Step 5: Methyl 2-methoxycarbonylmethyl-4-amino-5-chlorobenzoate

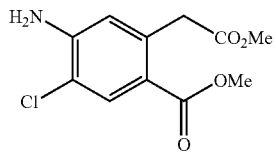

N-Chlorosuccinimide (1.0 g, 7.3 mmol) was added to a solution of methyl 2-methoxycarbonylmethyl-4-aminobenzoate (1.5 g, 6.6 mmol) in acetonitrile (10 mL). The mixture was stirred while heating under reflux for 1 hour. After the reaction solution was cooled to room temperature, water was added thereto and extracted with ethyl acetate. The organic layer was dried over anhydrous magnesium sulfate, and concentrated under reduced pressure. Then, the resulting solid was washed with ethyl acetate to give a 0.9:1 mixture of the title compound and methyl 2-methoxycarbonylmethyl-4-amino-3-chlorobenzoate (1.5 g, 88%).

Methyl 2-methoxycarbonylmethyl-4-amino-5-chlorobenzoate $^1$H-NMR (300 MHz, in CDCl$_3$) chemical shifts δ: 3.70 (3H, s), 3.82 (3H, s), 3.91 (2H, s), 4.47 (2H, brd), 6.57 (1H, s), 7.99 (1H, s).

Methyl 2-methoxycarbonylmethyl-4-amino-3-chlorobenzoate $^1$H-NMR (300 MHz, in CDCl$_3$) chemical shifts δ: 3.72 (3H, s), 3.80 (3H, s), 4.31 (2H, s), 4.47 (2H, brd), 6.69 (1H, d, J=8.7 Hz), 7.81 (1H, d, J=8.7 Hz).

Step 6: Methyl 2-methoxycarbonylmethyl-4-cyano-5-chlorobenzoate

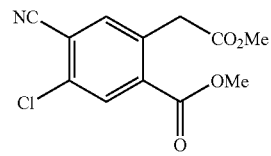

A solution of sodium nitrite (40 mg, 0.6 mmol) in water (0.25 mL) was added to a solution of a mixture (100 mg, 0.39 mmol) of methyl 2-methoxycarbonylmethyl-4-amino-5-chlorobenzoate and methyl 2-methoxycarbonylmethyl-4-amino-3-chlorobenzoate in 2N hydrochloric acid (0.5 mL) under the ice cold condition. The reaction solution was stirred at 0° C. for 1.5 hour. The resulting suspension was dissolved by adding water (0.1 mL) and ethyl acetate (0.2 mL). This solution was added to a suspension of copper (I) cyanide (45 mg, 0.5 mmol) and potassium cyanide (38 mg, 0.6 mmol) in a mixture of water (0.4 mL) and ethyl acetate (0.8 mL) at 0° C. The reaction solution was stirred at 0° C. for 1 hour. The resulting insoluble material was collected by Celite filtration, and washed with a mixed solvent of water and ethyl acetate (1:2). The filtrate and washing solution were combined together. The organic layer was separated, and dried over anhydrous magnesium sulfate, and concentrated under reduced pressure to give crude product. The crude product was purified by silica gel column chromatography using n-hexane-ethyl acetate (mixing ratio 10:1), and dried under reduced pressure to give a 0.7:1 mixture (30 mg, 29%) of the title compound and methyl 2-methoxycarbonylmethyl-4-cyano-3-chlorobenzoate.

Methyl 2-methoxycarbonylmethyl-4-cyano-5-chlorobenzoate $^1$H-NMR (300 MHz, in CDCl$_3$) chemical shifts δ: 3.71 (3H, s), 3.91 (3H s), 4.01 (2H, s), 7.57 (1H, s), 8.12 (1H, s).

Methyl 2-methoxycarbonylmethyl-4-cyano-3-chlorobenzoate $^1$H-NMR (300 MHz, in CDCl$_3$) chemical shifts δ: 3.73 (3H, s), 3.92 (3H, s), 4.30 (2H, s), 7.69 (1H, d, J=8.2 Hz), 7.96 (1H, d, J=8.2 Hz).

Step 7: 2-Chloro-5-(2-hydroxyethyl)-4-hydroxymethylbenzonitrile

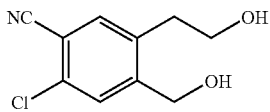

Calcium chloride (0.33 g, 3 mmol) and sodium borohydride (0.23 g, 6 mmol) were added to a mixture (0.80 g, 3 mmol) of methyl 2-methoxycarbonylmethyl-4-cyano-5-chlorobenzoate and methyl 2-methoxycarbonylmethyl-4-cyano-3-chlorobenzoate in a mixed solution (1:1, 10 mL) of ethanol and tetrahydrofuran. The resulting mixture was stirred at room temperature overnight. Water was added to the reaction solution, and extracted with ethyl acetate. The organic layer was dried over anhydrous magnesium sulfate, and concentrated under reduced pressure to give a 0.6:1 mixture (0.57 g, 89%) of the title compound and 2-chloro-3-(2-hydroxyethyl)-4-hydroxymethylbenzonitrile.

2-Chloro-5-(2-hydroxyethyl)-4-hydroxymethylbenzonitrile $^1$H-NMR (300 MHz, in CDCl$_3$) chemical shifts δ: 2.90 (2H, t, J=5.6 Hz), 3.90 (2H, t, J=5.6 Hz), 4.68 (2H, s), 7.53 (1H, s), 7.56 (1H, s).

2-Chloro-3-(2-hydroxyethyl)-4-hydroxymethylbenzonitrile $^1$H-NMR (300 MHz, in CDCl$_3$) chemical shifts δ: 3.16 (2H, t, J=6.8 Hz), 3.99 (2H, t, J=6.8 Hz), 4.70 (2H, s), 7.41 (1.5H, d, J=7.9 Hz), 7.58 (1.5H, d, J=7.9 Hz).

Step 8: 7-Chloroisochromane-6-carbonitrile

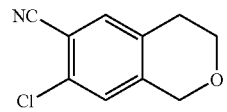

p-Toluene sulfonic acid (0.76 g, 5.4 mmol) was added to a solution of a mixture (0.57 g, 2.7 mmol) of 2-chloro-5-(2-hydroxyethyl)-4-hydroxymethylbenzonitrile and 2-chloro-3-(2-hydroxyethyl)-4-hydroxymethylbenzonitrile in toluene (10 mL). The mixture was stirred while heating under reflux overnight. The reaction solution was cooled to room temperature, and water was added thereto. The mixture was extracted with ethyl acetate. The organic layer was dried over anhydrous magnesium sulfate, and concentrated under reduced pressure to give crude product. The resulting crude product was purified by silica gel column chromatography using n-hexane-ethyl acetate (mixing ratio=2:1), and dried under reduced pressure to give a 1:0.1 mixture (0.4 g, 79%) of the title compound and 5-chloroisochromane-6-carbonitrile.

7-Chloroisochromane-6-carbonitrile $^1$H-NMR (300 MHz, in CDCl$_3$) chemical shifts δ: 2.86 (2H, t, J=5.7 Hz), 4.01 (2H, t, J=5.7 Hz), 4.75 (2H, s), 7.15 (1H, s), 7.44 (1H, s).

5-Chloroisochromane-6-carbonitrile $^1$H-NMR (300 MHz, in CDCl$_3$) chemical shifts δ: 2.88 (2H, t, J=5.7 Hz), 4.01 (2H, t, J=5.7 Hz), 4.76 (2H, s), 7.03 (1H, d, J=8.1 Hz), 7.48 (1H, d, J=8.1 Hz).

Step 9: 7-Chloroisochromane-6-carboxamidine

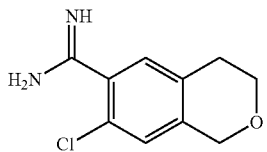

A solution of trimethyl amine in toluene (5 ml, 9.8 mmol) was added to a solution of ammonium chloride (0.6 g, 11.1 mmol) in toluene (3 mL) at 0 to 5° C. After the mixture was stirred at room temperature for 1 hour, a mixture (50 mg, 0.26 mmol) of 7-chloroisochromane-6-carbonitrile and 5-chloroisochromane-6-carbonitrile was added thereto. The reaction solution was stirred while heating under reflux overnight. After the reaction solution was cooled to room temperature, an aqueous solution of 2N sodium hydroxide was added and extracted with ethyl acetate. The organic layer was dried over anhydrous magnesium sulfate, and concentrated under reduced pressure to give a 1:0.5 mixture (44 mg, 81%) of the title compound and 5-chloroisochromane-6-carboxamidine.

7-Chloroisochromane-6-carboxamidine

¹H-NMR (300 MHz, in DMSO-d₆) chemical shifts δ: 2.74 (2H, t, J=5.8 Hz), 3.30 (1H, brd), 3.86 (2H, t, J=5.8 Hz), 4.66 (2H, s), 6.72 (2H, brd), 7.06 (1H, s), 7.18 (1H, s).

5-Chloroisochromane-6-carboxamidine

¹H-NMR (300 MHz, in DMSO-d₆) chemical shifts δ: 2.74 (2H, t, J=5.7 Hz), 3.30 (1H, brd), 3.92 (2H, t, J=5.7 Hz), 4.67 (2H, s), 6.73 (2H, brd), 7.06 (1H, d, J=8.0 Hz), 7.20 (1H, d, J=8.0 Hz).

Step 10: 4-(7-Chloroisochroman-6-yl)-6-methylsulfanyl-[1,3,5]triazin-2-ylamine

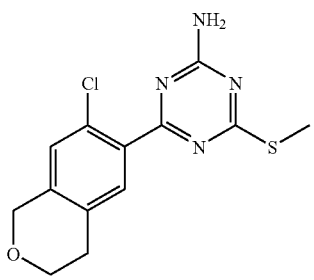

Dimethyl cyanodithioiminocarbonate (0.28 mg, 0.19 mmol) and diisopropylethyl amine (66 μl, 0.38 mmol) were added to a solution of a mixture (40 mg, 0.19 mmol) of 7-chloroisochromane-6-carboxamidine and 5-chloroisochromane-6-carboxamidine in ethanol (3 mL) at room temperature. The reaction solution was stirred while heating under reflux for 3 hours. After the reaction solution was cooled to room temperature, the precipitated crystals were collected by filtration. The crystals were washed with ethanol and dried under reduced pressure to give a yellow solid material (28.7 mg, 49%) mainly including 4-(5-chloroisochroman-6-yl)-6-methylsulfanyl-[1,3,5]triazin-2-ylamine. The filtrate and washing solution were combined together, and concentrated to give a yellow solid material (28.8 mg, 49%) mainly including the title compound. This was purified by thin layer silica gel chromatography using methylene chloride-methanol (mixing ratio=30:1). The title compound was obtained as pale yellow solid (15.7 mg, 27%).

4-(7-Chloroisochroman-6-yl)-6-methylsulfanyl-[1,3,5]triazin-2-ylamine

ESI (positive mode) m/z=309, 311(M⁺)
¹H-NMR (300 MHz, in DMSO-d₆) chemical shifts δ: 2.55 (3H, s), 2.86 (2H, t, J=5.7 Hz), 3.96 (2H, t, J=5.7), 4.76 (2H, s), 5.52 (2H, brs), 7.10 (1H, s), 7.53 (1H, s).

4-(5-Chloroisochroman-6-yl)-6-methylsulfanyl-[1,3,5]triazin-2-ylamine

ESI (positive mode) m/z=309/311(M+H⁺)
¹H-NMR (300 MHz, in DMSO-d₆) chemical shifts δ: 2.46 (3H, s), 2.78 (2H, t), 3.95 (2H, t), 4.72 (2H, s), 7.14 (1H, d, J=8.0 Hz), 7.44 (1H, d, J=8.2 Hz), 7.65 (2H, brs).

The compounds described in Examples 147 and 148 below were synthesized according to Steps 8 and 10 of Example 71 using as a starting material the compound of Example 146 above.

Example 147

4-(5-Chloro-isochroman-6-yl)-6-(2,5-dimethoxyphenylsulfanyl)-pyrimidin-2-ylamine

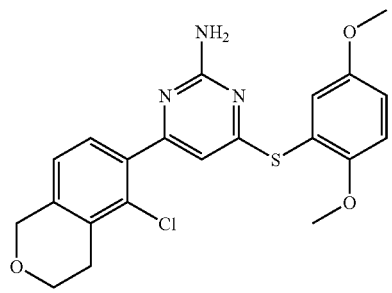

ESI (LC/MS positive mode) 431 (M+H⁺)
¹H-NMR (in DMSO-d₆) chemical shifts δ: 2.74 (2H, t, J=5.8 Hz), 3.72 (3H, s), 3.73 (3H, s), 3.93 (2H, t, J=5.8 Hz), 4.70 (2H, s), 7.01 (1H, dd, J=9.0, 2.9 Hz), 7.06 (1H, d, J=9.0 Hz), 7.10 (1H, d, J=7.8 Hz), 7.15 (1H, d, J=2.9 Hz), 7.36 (1H, d, J=7.8 Hz), 7.59-7.62 (2H, brm).

Example 148

4-(7-Chloro-isochroman-6-yl)-6-(2,5-dimethoxyphenylsulfanyl)-pyrimidin-2-ylamine

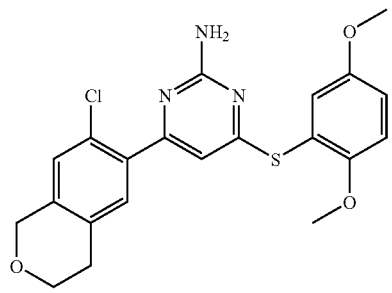

ESI (LC/MS positive mode) 431 (M+H⁺)
¹H-NMR (300 MHz, in DMSO-d₆) chemical shifts δ: 2.73 (2H, t, J=5.6 Hz), 3.69 (3H, s), 3.70 (3H, s), 3.84 (2H, t, J=5.6 Hz), 4.65 (2H, s), 6.99 (1H, dd, J=9.1, 3.0 Hz), 7.03 (1H, d, J=9.1 Hz), 7.12 (1H, d, J=3.0 Hz), 7.17 (1H, s), 7.38 (1H, s), 7.57-7.61 (2H, brm).

Example 149

Preparation of N-{3-[4-amino-6-(5-chloro-1H,3H-benzo[de]isochromen-6-yl)-[1,3,5]triazin-2-ylsulfanyl]-propyl}-acetamide

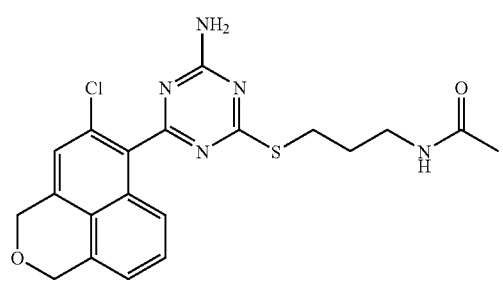

4-Amino-6-(5-chloro-1H,3H-benzo[de]isochromen-6-yl)-[1,3,5]triazine-2-thiol (1.80 g), which was obtained in Step 9 at Example 71, was dissolved in N,N-dimethylformamide (50 ml) under nitrogen atmosphere. To the mixture were added to 3-chloropropylacetamide (1.02 g, 7.53 mmol) and N-ethyldiisopropylamine (2.6 ml, 14.9 mmol) at room temperature. The resulting mixture was stirred at 70° C. for 15.5 hours. After cooling the reaction mixture to room temperature, the mixture was purified by HPLC (column; ODS, mobile phase; 0.05% TFA in water: 0.05% TFA in acetonitrile=60:40). The fractions containing the desired product were collected, and neutralized by saturated aqueous sodium bicarbonate. The acetonitrile was removed by evaporation and the resulting aqueous solution was extracted with ethyl acetate (300 m, 3 times). The extracts were combined, washed with brine (300 ml), dried over anhydrous sodium sulfate, and filtered. The filtrate was concentrated by evaporation following exposure to an oil pump vacuum to give N-{3-[4-amino-6-(5-chloro-1H,3H-benzo[de]isochromen-6-yl)-[1,3,5]triazin-2-ylsulfanyl]-propyl}-acetamide (1.58 g, 74%) as an off-white amorphous.

ESI (LC/MS positive mode): m/z=430, 432(M+H$^+$).

$^1$H-NMR (400 MHz, DMSO-d$_6$) chemical shifts δ: 1.74 (3H, s), 1.70-1.80 (2H, m), 3.04 (2H, t, J=6.8 Hz), 3.11 (2H, dt, J=5.9 Hz and 6.8 Hz), 5.04 (2H, s), 5.05 (2H, s), 7.34 (1H, d, J=6.8 Hz), 7.41 (1H, d, J=8.3 Hz), 7.44 (1H, s), 7.52 (1H, dd, J=6.8 Hz and 8.3 Hz), 7.78 (3H, brs).

Example 175

Preparation of {2-[4-amino-6-(5-chloro-1H,3H-benzo[de]isochromen-6-yl)-[1,3,5]triazin-2-ylsulfanyl]-ethyl}-urea

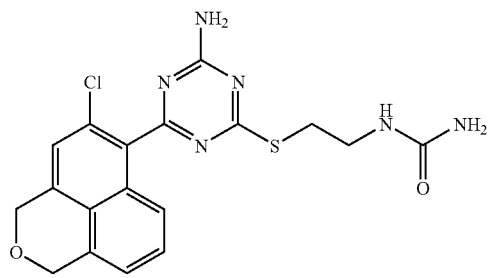

Proceeding in the same manner as Example 149 and replacing 3-chloropropylacetamide by (2-chloroethyl)urea (14 mg), there was obtained {2-[4-amino-6-(5-chloro-1H,3H-benzo[de]isochromen-6-yl)-[1,3,5]triazin-2-ylsulfanyl]-ethyl}-urea (20 mg) as a pale yellow solid from 4-amino-6-(5-chloro-1H,3H-benzo[de]isochromen-6-yl)-[1,3,5]triazine-2-thiol (25 mg).

ESI (LC/MS positive mode): m/z=417, 419(M+H$^+$).

$^1$H-NMR (400 MHz, DMSO-d$_6$) chemical shifts δ: 3.10 (2H, t, J=6.4 Hz), 3.25 (2H, m), 5.04 (2H, brs), 5.05 (2H, brs), 5.48 (2H, brs), 6.18 (1H, t, J=5.5 Hz), 7.34 (1H, d, J=6.9 Hz), 7.42 (1H, d, J=8.2 Hz), 7.45 (1H, s), 7.52 (1H, m), 7.82 (2H, brs).

Example 178

Preparation of N-{2-[4-amino-6-(5-chloro-1H,3H-benzo[de]isochromen-6-yl)-[1,3,5]triazin-2-yl sulfanyl]-ethyl}-methanesulfonamide

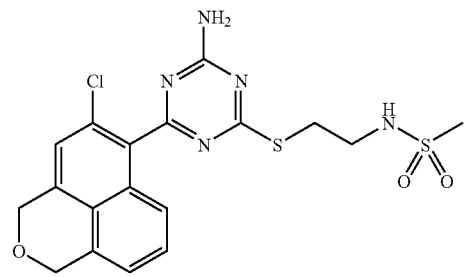

Proceeding in the same manner as Example 149 and replacing 3-chloropropylacetamide by N-(2-chloroethyl) methanesulfonamide (380 mg), there was obtained N-{2-[4-amino-6-(5-chloro-1H,3H-benzo[de]isochromen-6-yl)-[1,3,5]triazin-2-yl sulfanyl]-ethyl}-methanesulfonamide (383 mg) as a white solid from 4-amino-6-(5-chloro-1H,3H-benzo[de]isochromen-6-yl)-[1,3,5]triazine-2-thiol (399 mg).

ESI (LC/MS positive mode): m/z=452, 454(M+H$^+$).

$^1$H-NMR (270 MHz, DMSO-d$_6$) chemical shifts δ: 2.84 (3H, s), 3.16 (2H, t, J=6.6 Hz), 3.24-3.28 (2H, m), 5.04 (2H, brs), 5.05 (2H, brs), 7.21 (1H, brs), 7.34 (1H, d, J=6.8 Hz), 7.42 (1H, d, J=8.3 Hz), 7.45 (1H, s), 7.52 (1H, dd, J=8.3, 6.8 Hz), 7.78 (1H, brs), 7.83 (1H, brs).

Example 205

Preparation of 3-[4-amino-6-(5-chloro-1H,3H-benzo[de]isochromen-6-yl)-[1,3,5]triazin-2-ylsulfanyl]-N-methyl-propionamide

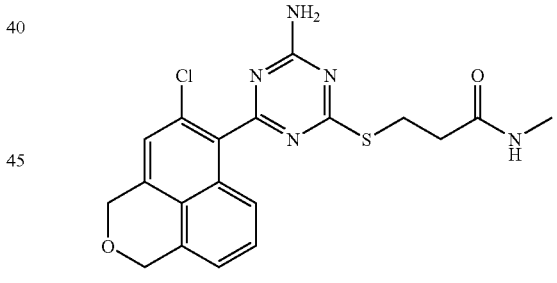

Step 1: Preparation of 3-[4-amino-6-(5-chloro-1H,3H-benzo[de]isochromen-6-yl)-[1,3,5]triazin-2-ylsulfanyl]-propionic acid

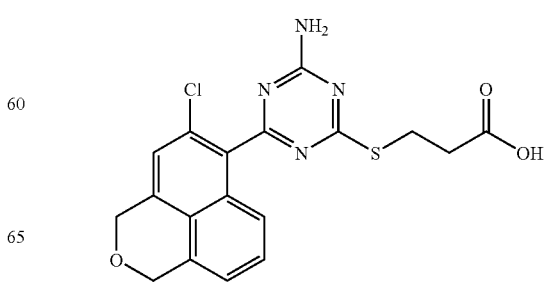

4-(5-Chloro-1H,3H-benzo[de]isochromen-6-yl)-6-methanesulfinyl-[1,3,5]triazin-2-ylamine (6.063 g), which was obtained in Step 8 at Example 71, was dissolved in N,N-dimethylformamide (60 ml) under nitrogen atmosphere. To the mixture were added 3-mercaptopropionic acid (3.66 ml, 42 mmol) and N-ethyldiisopropylamine (8.484 ml, 49.56 mmol) successively at room temperature. The mixture was stirred for 8 hours at the same temperature. The reaction was quenched by adding aqueous potassium hydrogen sulfate (0.5N, 250 ml), and the mixture was diluted with water (250 ml). The mixture was stirred for an additional 2 hours. The resulting precipitates were collected by filtration. The cake was washed with water (100 ml, twice) and dried in vacuo to give 3-[4-amino-6-(5-chloro-1H,3H-benzo[de]isochromen-6-yl)-[1,3,5]triazin-2-ylsulfanyl]-propionic acid (7.0 g, quantitative yield) as a pale yellowish solid.

ESI (LC/MS positive mode): m/z=403, 405(M+H$^+$).

$^1$H-NMR (270 MHz, DMSO-d$_6$) chemical shifts δ: 2.68 (2H, t, J=6.8 Hz), 3.19 (2H, t, J=6.8 Hz), 5.05 (4H, s), 7.35 (1H, d, J=7.3 Hz), 7.42 (1H, d, J=8.4 Hz), 7.45 (1H, s), 7.53 (1H, dd, J=7.3 Hz, 8.4 Hz), 7.85 (2H, brs), 12.37 (1H, brs).

Step 2: Preparation of 3-[4-amino-6-(5-chloro-1H,3H-benzo[de]isochromen-6-yl)-[1,3,5]triazin-2-yl-sulfanyl]-N-methyl-propionamide

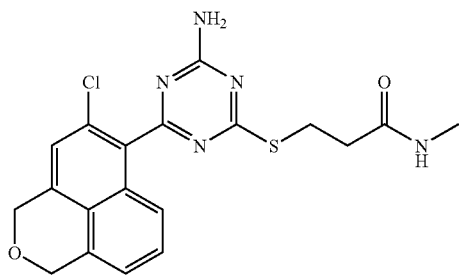

3-[4-Amino-6-(5-chloro-1H,3H-benzo[de]isochromen-6-yl)-[1,3,5]triazin-2-ylsulfanyl]-propionic acid (1.1 g), which was obtained at Step 1 described above, and 1-hydroxybenzotriazole (1.258 g, 8.2 mmol) were dissolved in N,N-dimethylformamide (30 ml). To this mixture were added N-ethyldiisopropylamine (3.76 ml, 21.8 mmol) and methylamine hydrochloride (553 mg, 8.2 mmol) and 1-ethyl-3-(3-dimethylaminopropyl)carbodiimide (1.57 g, 8.2 mmol) successively at room temperature. The mixture was stirred for 10 hours at the same temperature. The reaction was quenched by adding water (400 ml) and extracted with ethyl acetate (400 ml). The separated organic layer was washed with water (400 ml) and saturated aqueous sodium bicarbonate (250 ml) successively. The organic layer was dried over anhydrous sodium sulfate and concentrated to its dryness after removal of inorganic salts. The resulting residue was purified by silica gel column chromatography (developing solvent: dichloromethane:methanol=30:1) to give 3-[4-amino-6-(5-chloro-1H,3H-benzo[de]isochromen-6-yl)-[1,3,5]triazin-2-ylsulfanyl]-N-methyl-propionamide (887 mg, 78% yield) as a white solid.

ESI (LC/MS positive mode): m/z=416, 418(M+H$^+$).

$^1$H-NMR (270 MHz, DMSO-d$_6$) chemical shifts δ: 2.49 (2H, t, J=6.8 Hz), 2.56 (3H, d, J=4.5 Hz), 3.22 (2H, t, J=6.8 Hz), 5.05 (4H, s), 7.35 (1H, d, J=7.1 Hz), 7.42 (1H, d, J=8.2 Hz), 7.45 (1H, s), 7.53 (1H, dd, J=7.1 Hz, 8.2 Hz), 7.78-7.88 (3H, brs).

Example 234

Preparation of 3-[4-amino-6-(5-chloro-1H,3H-benzo[de]isochromen-6-yl)-[1,3,5]triazin-2-ylsulfanyl]-N-(2-hydroxy-ethyl)-propionamide

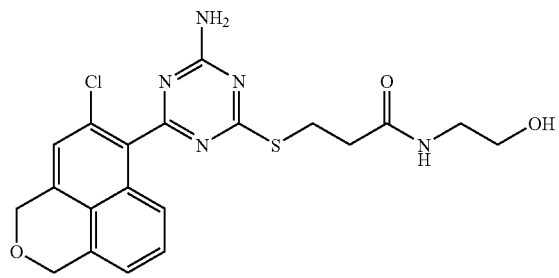

Proceeding in the same manner as in Step 2 of Example 205 and replacing N-methylamine hydrochloride by 2-aminoethanol (1.063 g), and omitting addition of N-ethyldiisopropylamine, there was obtained 3-[4-amino-6-(5-chloro-1H,3H-benzo[de]isochromen-6-yl)-[1,3,5]triazin-2-ylsulfanyl]-N-(2-hydroxyethyl)propionamide (1.40 g, 90%) as a white solid from 3-[4-amino-6-(5-chloro-1H,3H-benzo[de]isochromen-6-yl)-[1,3,5]triazin-2-ylsulfanyl]-propionic acid (1.40 g).

ESI (LC/MS positive mode): m/z=446, 448(M+H$^+$).

$^1$H-NMR (270 MHz, CDCl$_3$) chemical shifts δ: 2.66 (2H, t, J=7.2 Hz), 3.25-3.39 (4H, m), 3.61 (2H, t, J=4.9 Hz), 5.03-5.10 (4H, m), 5.82 (1H, brs), 6.03 (1H, brs), 6.25-6.38 (1H, m), 7.19-7.26 (2H, m), 7.44-7.49 (2H, m).

Example 270

Preparation of Carbamic Acid 2-[4-amino-6-(5-chloro-1H,3H-benzo[de]isochromen-6-yl)-[1,3,5]triazin-2-yl sulfanyl]-ethyl ester

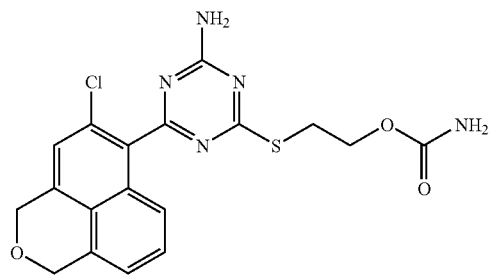

Proceeding in the same manner as Example 149 and replacing 3-chloropropylacetamide by carbamic acid 2-bromo-ethyl ester (5.42 g), there was obtained carbamic acid 2-[4-amino-6-(5-chloro-1H,3H-benzo[de]isochromen-6-yl)-[1,3,5]triazin-2-yl sulfanyl]-ethyl ester (3.19 g) as a pale orange solid from 4-amino-6-(5-chloro-1H,3H-benzo[de]isochromen-6-yl)-[1,3,5]triazine-2-thiol (2.9 g).

ESI (LC/MS positive mode): m/z=418, 420(M+H$^+$).

$^1$H-NMR (270 MHz, DMSO-d$_6$) chemical shifts δ: 3.27 (2H, t, J=6.4 Hz), 4.13 (2H, t, J=6.4 Hz), 5.05 (4H, brs), 6.55 (2H, brs), 7.33-7.55 (4H, m), 7.86 (2H, brs).

Example 314

Production of 2-[2-amino-6-(5-chloro-1H,3H-benzo[de]isochromen-6-yl)-pyrimidin-4-ylsulfanyl]-acetamide (compound 314)

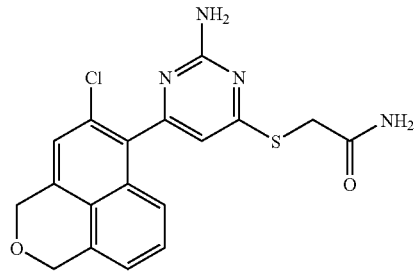

Step 1: Synthesis of 1-(5-chloro-1H,3H-benzo[de]isochromen-6-yl)-ethylidene-amine

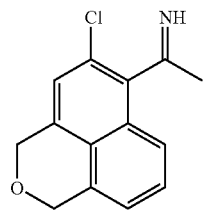

5-Chloro-1H,3H-benzo[de]isochromen-6-carbonitrile (20 g, 87.08 mmol) obtained in Step 5 of Example 71 was suspended in anhydrous toluene (100 mL) under nitrogen atmosphere, and 2 M trimethyl aluminum-toluene solution (218 mL, 435 mmol) was added at room temperature. The obtained solution was stirred while heating in a 105° C. oil bath for 12 hours. The reaction solution was cooled to room temperature, and then slowly poured into an aqueous solution of potassium sodium (+)-tartarate tetrahydrate (184 g). 2 N aqueous sodium hydroxide solution (250 mL) was additionally added, and after stirring for 30 minutes, this was extracted with ethyl acetate (500 mL). The separated organic layer was washed with water (300 mL) and brine, then dried over anhydrous sodium sulfate, filtered, concentrated, and thus, 1-(5-chloro-1H,3H-benzo[de]isochromen-6-yl)-ethylidene-amine (22 g) was obtained as an orange-colored oil like substance.

Physicochemical properties of 1-(5-chloro-1H,3H-benzo[de]isochromen-6-yl)-ethylidene-amine ESI (LC/MS positive mode) m/z=246/249 (M+H$^+$).
$^1$H-NMR (270 MHz, in deuterated chloroform) chemical shifts δ: 2.49 (3H, s), 4.95-5.10 (4H, m), 7.16-7.27 (2H, m), 7.50 (1H, dd, J=8.5 Hz, J=6.8 Hz), 7.62 (1H, d, J=8.5 Hz), 9.38 (1H, brs).

Step 2: Synthesis of 1-(5-chloro-1H,3H-benzo[de]isochromen-6-yl)-ethanone

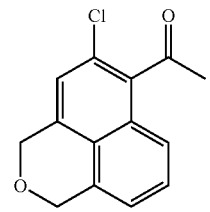

1-(5-Chloro-1H,3H-benzo[de]isochromen-6-yl)-ethylidene-amine (22 g) obtained in Step 1 described above was dissolved in tetrahydrofuran (200 mL), 5 N aqueous hydrochloric acid solution (200 mL) was added, and this was stirred while heating at 80° C. for 48 hours. After cooling the mixture to room temperature, the solvent was removed by using a rotary evaporator. The obtained residue was dissolved in ethyl acetate (400 mL), then washed with water (300 mL) and saturated sodium hydrogen carbonate solution successively, and then dried over sodium sulfate. A residue obtained after filtration and concentration was purified by silica gel column chromatography (developing solvent; n-hexane:dichloromethane:ethyl acetate=10:10:1), and thus, 1-(5-chloro-1H,3H-benzo[de]isochromen-6-yl)-ethanone (19.2 g) was obtained as a white solid.

Physicochemical properties of 1-(5-chloro-1H,3H-benzo[de]isochromen-6-yl)-ethanone ESI (LC/MS positive mode) m/z=247/249 (M+H$^+$).
$^1$H-NMR (270 MHz, in dimethylsulfoxide-d$_6$) chemical shifts δ: 2.66 (3H, s), 5.00-5.03 (4H, m), 7.34-7.44 (2H, m), 7.51 (1H, d, J=8.5 Hz), 7.60 (1H, dd, J=8.5 Hz, J=6.8 Hz).

Step 3: Synthesis of 1-(5-chloro-1H,3H-benzo[de]isochromen-6-yl)-3,3-bis-methylsulfanyl-propenone

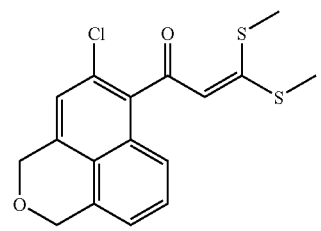

1-(5-Chloro-1H,3H-benzo[de]isochromen-6-yl)-ethanone (1 g) obtained in Step 2 described above was dissolved in anhydrous tetrahydrofuran (20 mL), and sodium hydride (60% suspension in oil, 810 mg) was added. After stirring at room temperature for 45 minutes, carbon disulfide (2.443 mL) was added to the mixture, and this was stirred at room temperature for 10 hours. Methyl iodide (1.51 mL) was slowly added to the obtained mixture, and this was stirred at the same temperature for five hours. The reaction solution was poured into water (200 mL), and then extracted with ethyl acetate (200 mL). The separated organic layer was washed with water and brine, and then dried over anhydrous sodium sulfate. The yellow solid obtained after filtration and concentration was dissolved in dichloromethane (12 mL), and n-hexane (35 mL) was added slowly. The mixture was left to stand at room temperature, the produced pale yellow crystals were collected by filtration, washed with n-hexane, then dried under reduced pressure, and thus, 1-(5-chloro-1H,3H-benzo[de]isochromen-6-yl)-3,3-bis-methylsulfanyl-propenone (1.115 g) was obtained.

Physicochemical properties of 1-(5-chloro-1H,3H-benzo[de]isochromen-6-yl)-3,3-bis-methylsulfanyl-propenone ESI (LC/MS positive mode) m/z=351/353 (M+H$^+$).
$^1$H-NMR (270 MHz, in dimethylsulfoxide-d$_6$) chemical shifts δ: 2.42 (3H, s), 2.59 (3H, s), 5.02-5.08, (4H, m), 6.29 (1H, s), 7.16-7.22 (2H, m), 7.46 (1H, dd, J=7.1 Hz, 8.6 Hz), 7.69 (1H, d, J=8.6 Hz).

Step 4: Synthesis of 4-(5-chloro-1H,3H-benzo[de]isochromen-6-yl)-6-methylsulfanyl-pyrimidin-2-ylamine

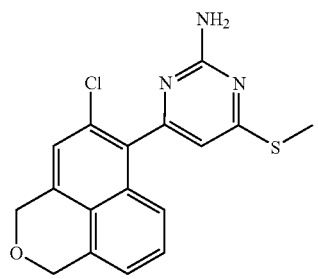

1-(5-Chloro-1H,3H-benzo[de]isochromen-6-yl)-3,3-bis-methylsulfanyl-propenone (10.345 g) obtained in Step 3 described above, guanidine hydrochloride salt (11.266 g), and sodium hydride (60% suspension in oil, 4.717 g) were placed into a reaction vessel, and N,N-dimethylacetamide (207 mL) was added under nitrogen atmosphere. 1-bromo-2,4,6-trifluorobenzene (6.95 mL) was added to this mixture and this was stirred while heating at 100° C. for two hours. The reaction solution was cooled to room temperature, diluted with ethyl acetate (700 mL), and then washed with water (500 mL) and the separated aqueous layer was extracted again with ethyl acetate (500 mL). The combined organic layers were washed with water (500 mL×2) and brine successively. The washed organic layer was dried over anhydrous sodium sulfate and filtered, and then the filtrate was concentrated under reduced pressure. The obtained residue was purified by silica gel column chromatography (developing solvent; dichloromethane:ethyl acetate=9:1 to 4:1), and thus, 4-(5-chloro-1H,3H-benzo[de]isochromen-6-yl)-6-methylsulfanyl-pyrimidin-2-ylamine (9.223 g) was obtained as a white solid.

Physicochemical properties of 4-(5-chloro-1H,3H-benzo[de]isochromen-6-yl)-6-methylsulfanyl-pyrimidin-2-ylamine ESI (LC/MS positive mode) m/z=344/346 (M+H$^+$).
$^1$H-NMR (270 MHz, in deuterated chloroform) chemical shifts δ: 2.55 (3H, s), 5.04-5.08 (4H, m), 5.12 (2H, brs), 6.64 (1H, s), 7.16-7.22 (1H, m), 7.24-7.26 (1H, m), 7.41-7.44 (2H, m).

Step 5: Synthesis of 4-(5-chloro-1H,3H-benzo[de]isochromen-6-yl)-6-methanesulfinyl-pyrimidin-2-ylamine

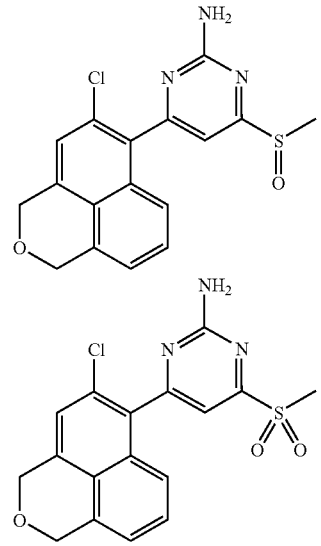

4-(5-Chloro-1H,3H-benzo[de]isochromen-6-yl)-6-methylsulfanyl-pyrimidin-2-ylamine (910 mg) obtained in Step 4 described above was dissolved in dichloromethane (50 mL), and cooled to 0° C. in an ice bath. m-Chloroperbenzoic acid (840 mg) was added and was stirred at the same temperature for 15 minutes and then the temperature was raised to room temperature and stirred for another one hour. The obtained mixture was concentrated, and the resulting residue was dissolved in ethyl acetate (70 mL), and this solution was washed with saturated aqueous sodium hydrogen carbonate solution (40 mL×3). After drying over anhydrous sodium sulfate, the solution was filtered and concentrated, and thus, a mixture of 4-(5-chloro-1H,3H-benzo[de]isochromen-6-yl)-6-methanesulfinyl-pyrimidin-2-ylamine and 4-(5-chloro-1H,3H-benzo[de]isochromen-6-yl)-6-methanesulfonyl-pyrimidin-2-ylamine (980 mg) was obtained as a yellow solid. Analysis samples were obtained by purifying the mixture mentioned above by silica gel thin layer chromatography (developing solvent; n-hexane:ethyl acetate=3:2).

Physicochemical properties of 4-(5-chloro-1H,3H-benzo[de]isochromen-6-yl)-6-methanesulfinyl-pyrimidin-2-ylamine ESI (LC/MS positive mode) m/z=360/362 (M+H$^+$).
$^1$H-NMR (270 MHz, in deuterated chloroform) chemical shifts δ: 2.95 (3H, s), 5.05-5.10 (4H, m), 5.39 (2H, brs), 7.21 (1H, dd, J=6.8 Hz, J=1.2 Hz), 7.25-7.46 (4H, m).

Physicochemical properties of 4-(5-chloro-1H,3H-benzo[de]isochromen-6-yl)-6-methanesulfonyl-pyrimidin-2-ylamine ESI (LC/MS positive mode) m/z=376/378 (M+H$^+$).
$^1$H-NMR (270 MHz, in deuterated chloroform) chemical shifts δ: 3.27 (3H, s), 5.04-5.13 (4H, m), 5.62 (2H, brs), 7.23 (1H, dd, J=6.9 Hz, J=1.0 Hz), 7.25-7.35 (2H, m), 7.40-7.48 (2H, m).

Step 6: Synthesis of 2-[2-amino-6-(5-chloro-1H,3H-benzo[de]isochromen-6-yl)-pyrimidin-4-ylsulfanyl]-acetamide (compound 314)

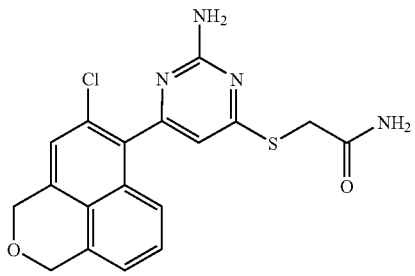

Partially purified 4-(5-chloro-1H,3H-benzo[de]isochromen-6-yl)-6-methanesulfinyl-pyrimidin-2-ylamine (100 mg) obtained in Step 5 described above was dissolved in N,N-dimethylformamide (1 mL), mercapto acetic acid (0.058 mL) and N,N-diisopropylethylamine (0.192 mL) were added, and this was stirred under nitrogen atmosphere at 80° C. for one hour. After cooling the obtained mixture to room temperature, N,N-dimethylformamide (2 mL), ammonium chloride (134 mg), 1-hydroxybenzotriazole hydrate (422 mg), 1-ethyl-3-(3'-dimethylaminopropyl)carbodiimide hydrochloride salt (480 mg), and N,N-diisopropylethylamine (0.432 mL) were added, and this was stirred at room temperature for 13 hours. The reaction solution was diluted with ethyl acetate (30 mL), then washed with aqueous ammonium chloride solution (20 mL×2), water (30 mL×2), and saturated aqueous sodium hydrogen carbonate solution (20 mL×2) successively, and then dried over anhydrous sodium sulfate. The residue obtained after filtration and concentration was purified by silica gel thin layer chromatography (developing solvent; dichloromethane:methanol=9:1), and thus, 2-[2-amino-6-(5-chloro-1H,3H-benzo[de]isochromen-6-yl)-pyrimidin-4-ylsulfanyl]-acetamide (compound 314) (62 mg) was obtained as a white solid.

Physicochemical properties of 2-[2-amino-6-(5-chloro-1H,3H-benzo[de]isochromen-6-yl)-pyrimidin-4-ylsulfanyl]-acetamide (compound 314)

ESI (LC/MS positive mode) m/z=387/389 (M+H$^+$).
$^1$H-NMR (270 MHz, in dimethylsulfoxide-d$_6$) chemical shifts δ: 3.79 (2H, s), 5.00-5.08 (4H, m), 6.59 (1H, s), 6.92 (2H, brs), 7.20 (1H, brs), 7.28-7.37 (2H, m), 7.41-7.57 (3H, m).

Example 315

Production of 2-[2-amino-6-(5-chloro-1H,3H-benzo[de]isochromen-6-yl)-pyrimidin-4-ylsulfanyl]-N-cyanomethyl-acetamide (compound 315)

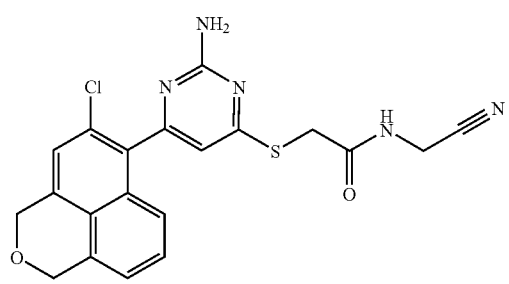

2-[2-Amino-6-(5-chloro-1H,3H-benzo[de]isochromen-6-yl)-pyrimidin-4-ylsulfanyl]-N-cyanomethyl-acetamide (compound 315) (103 mg) was obtained from partially purified 4-(5-chloro-1H,3H-benzo[de]isochromen-6-yl)-6-methanesulfinyl-pyrimidin-2-ylamine (100 mg) obtained in Step 5 of Example 314 by performing a reaction using the same operation as the production method described in Step 6 of Example 314 with amino acetonitrile hydrochloride salt (232 mg) instead of ammonium chloride.

Physicochemical properties of 2-[2-amino-6-(5-chloro-1H,3H-benzo[de]isochromen-6-yl)-pyrimidin-4-ylsulfanyl]-N-cyanomethyl-acetamide (compound 315)

ESI (LC/MS positive mode) m/z=426/428 (M+H$^+$).
$^1$H-NMR (270 MHz, in dimethylsulfoxide-d$_6$) chemical shifts δ: 3.92 (2H, s), 4.16-4.20 (2H, m), 5.01-5.09 (4H, m), 6.61 (1H, s), 6.93 (2H, brs), 7.31-7.34 (2H, m), 7.45-7.53 (2H, m), 8.77 (1H, t, J=5.7 Hz).

Example 316

Production of 3-[2-amino-6-(5-chloro-1H,3H-benzo[de]isochromen-6-yl)-pyrimidin-4-ylsulfanyl]-propionamide (compound 316)

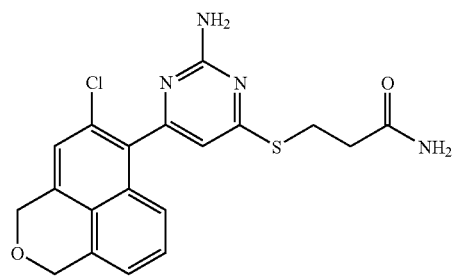

3-[2-amino-6-(5-chloro-1H,3H-benzo[de]isochromen-6-yl)-pyrimidin-4-ylsulfanyl]-propionic acid (90.0 mg) was obtained by performing reaction of partially purified 4-(5-chloro-1H,3H-benzo[de]isochromen-6-yl)-6-methanesulfinyl-pyrimidin-2-ylamine (98.1 mg) obtained in Step 5 of Example 314 with 3-mercaptopropionic acid (71.3 µL) instead of mercaptoacetic acid, using the same operation as the production method described in Step 6 of Example 314. Furthermore, the obtained 3-[2-amino-6-(5-chloro-1H,3H-benzo[de]isochromen-6-yl)-pyrimidin-4-ylsulfanyl]-propionic acid (32.0 mg) and ammonium chloride (12.7 mg) were reacted using the same operation as the production method described in Step 6 of Example 314, and thus, 3-[2-amino-6-(5-chloro-1H,3H-benzo[de]isochromen-6-yl)-pyrimidin-4-ylsulfanyl]-propionamide (compound 316) (22.0 mg) was obtained as a white solid.

Physicochemical properties of 3-[2-amino-6-(5-chloro-1H,3H-benzo[de]isochromen-6-yl)-pyrimidin-4-ylsulfanyl]-propionamide (compound 316)

ESI (LC/MS positive mode) m/z=401/403 (M+H$^+$).
$^1$H-NMR (400 MHz, in dimethylsulfoxide-d$_6$) chemical shifts δ: 2.51-2.54 (2H, m), 3.31 (2H, t, J=7.09 Hz), 5.04 (2H, s), 5.05 (2H, s), 6.55 (1H, s), 6.90 (2H, brs), 7.33 (1H, d, J=7.70 Hz), 7.35 (1H, d, J=7.78 Hz), 7.39 (2H, brs), 7.45 (1H, s), 7.50 (1H, t, J=7.78 Hz).

Example 317

Production of 3-[2-amino-6-(5-chloro-1H,3H-benzo[de]isochromen-6-yl)-pyrimidin-4-ylsulfanyl]-N-(2-hydroxy-ethyl)-propionamide (compound 317)

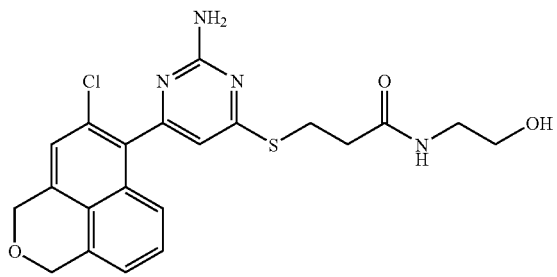

3-[2-Amino-6-(5-chloro-1H,3H-benzo[de]isochromen-6-yl)-pyrimidin-4-ylsulfanyl]-propionic acid (14.0 mg) obtained in Example 316 was reacted with 2-aminoethanol (6.4 mg) instead of ammonium chloride using the same operation as the production method described in Step 6 of Example 314, and thus, 3-[2-amino-6-(5-chloro-1H,3H-benzo[de]isochromen-6-yl)-pyrimidin-4-ylsulfanyl]-N-(2-hydroxy-ethyl)-propionamide (compound 317) (11.5 mg) was obtained as a white solid.

Physicochemical properties of 3-[2-amino-6-(5-chloro-1H,3H-benzo[de]isochromen-6-yl)-pyrimidin-4-ylsulfanyl]-N-(2-hydroxy-ethyl)-propionamide (compound 317)

ESI (LC/MS positive mode) m/z=445/447 (M+H$^+$).
$^1$H-NMR (400 MHz, in dimethylsulfoxide-d$_6$) chemical shifts δ: 2.55 (2H, t, J=7.09 Hz), 3.13 (2H, q, J=5.95 Hz), 3.30-3.33 (2H, m), 3.40 (2H, q, J=5.95 Hz), 4.66 (1H, t, J=5.49 Hz), 5.04 (2H, s), 5.05 (2H, s), 6.54 (1H, s), 6.89 (2H, brs), 7.33 (1H, d, J=7.70 Hz), 7.35 (1H, d, J=7.78 Hz), 7.45 (1H, s), 7.51 (1H, t, J=7.78 Hz), 7.95 (1H, t, J=5.49 Hz).

Example 318

3-[2-amino-6-(5-chloro-1H,3H-benzo[de]isochromen-6-yl)-pyrimidin-4-ylsulfanyl]-N-methyl-propionamide (compound 318)

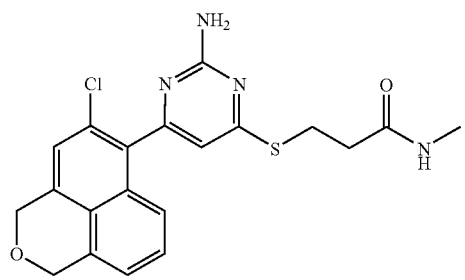

3-[2-Amino-6-(5-chloro-1H,3H-benzo[de]isochromen-6-yl)-pyrimidin-4-ylsulfanyl]-propionic acid (14.0 mg) obtained in Example 316 was reacted with methylamine hydrochloride salt (7.1 mg) instead of ammonium chloride using the same operation as the production method described in Step 6 of Example 314, and thus, 3-[2-amino-6-(5-chloro-1H,3H-benzo[de]isochromen-6-yl)-pyrimidin-4-ylsulfanyl]-N-methyl-propionamide (compound 318) (12.4 mg) was obtained as a white solid.

Physicochemical properties of 3-[2-amino-6-(5-chloro-1H,3H-benzo[de]isochromen-6-yl)-pyrimidin-4-ylsulfanyl]-N-methyl-propionamide (compound 318)

ESI (LC/MS positive mode) m/z=415/417 (M+H$^+$).
$^1$H-NMR (400 MHz, in dimethylsulfoxide-d$_6$) chemical shifts δ: 2.54 (2H, t, J=7.32 Hz), 2.60 (3H, d, J=4.12 Hz), 3.32 (2H, t, J=6.87 Hz), 5.04 (2H, s), 5.05 (2H, s), 6.55 (1H, s), 6.89 (2H, s), 7.33 (1H, d, J=7.70 Hz), 7.35 (1H, d, J=7.78 Hz), 7.45 (1H, s), 7.50 (1H, t, J=7.78 Hz), 7.87 (1H, d, J=4.12 Hz).

Example 319

Production of 3-[2-amino-6-(5-chloro-1H,3H-benzo[de]isochromen-6-yl)-pyrimidin-4-ylsulfanyl]-N-(2-methoxy-ethyl)-propionamide (compound 319)

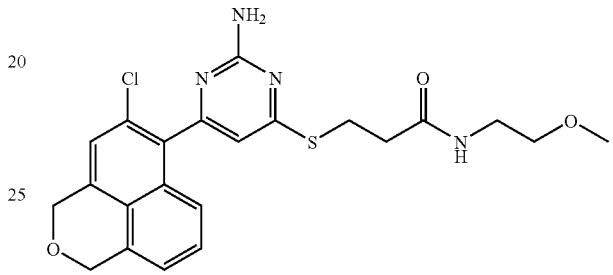

3-[2-Amino-6-(5-chloro-1H,3H-benzo[de]isochromen-6-yl)-pyrimidin-4-ylsulfanyl]-propionic acid (14.0 mg) obtained in Example 316 was reacted with 2-methoxyethylamine (7.8 mg) instead of ammonium chloride using the same operation as the production method described in Step 6 of Example 314, and thus, 3-[2-amino-6-(5-chloro-1H,3H-benzo[de]isochromen-6-yl)-pyrimidin-4-ylsulfanyl]-N-(2-methoxy-ethyl)-propionamide (compound 319) (10.2 mg) was obtained as a white solid.

Physicochemical properties of 3-[2-amino-6-(5-chloro-1H,3H-benzo[de]isochromen-6-yl)-pyrimidin-4-ylsulfanyl]-N-(2-methoxy-ethyl)-propionamide (compound 319)

ESI (LC/MS positive mode) m/z=459/461 (M+H$^+$).
$^1$H-NMR (400 MHz, in dimethylsulfoxide-d$_6$) chemical shifts δ: 2.56 (2H, t, J=7.09 Hz), 3.21-3.36 (9H, m), 5.04 (2H, s), 5.05 (2H, s), 6.55 (1H, s), 6.90 (2H, s), 7.33 (1H, d, J=7.70 Hz), 7.35 (1H, d, J=7.78 Hz), 7.45 (1H, s), 7.50 (1H, t, J=7.78 Hz), 8.03 (1H, t, J=5.26 Hz).

Example 320

Production of 3-[2-amino-6-(5-chloro-1H,3H-benzo[de]isochromen-6-yl)-pyrimidin-4-ylsulfanyl]-N—((R)-2,3-dihydroxy-propyl)-propionamide (compound 320)

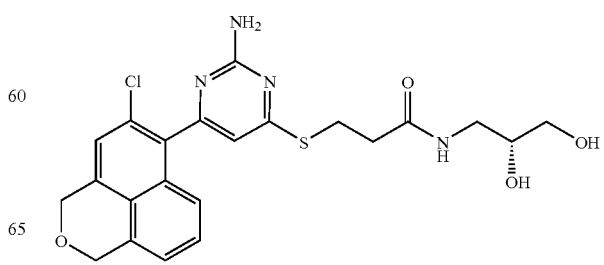

3-[2-Amino-6-(5-chloro-1H,3H-benzo[de]isochromen-6-yl)-pyrimidin-4-ylsulfanyl]-propionic acid (14.0 mg) obtained in Example 316 was reacted with (R)-3-amino-propane-1,2-diol (9.5 mg) instead of ammonium chloride using the same operation as the production method described in Step 6 of Example 314, and thus, 3-[2-amino-6-(5-chloro-1H,3H-benzo[de]isochromen-6-yl)-pyrimidin-4-ylsulfanyl]-N—((R)-2,3-dihydroxy-propyl)-propionamide (compound 320) (12.7 mg) was obtained as a white solid.

Physicochemical properties of 3-[2-amino-6-(5-chloro-1H,3H-benzo[de]isochromen-6-yl)-pyrimidin-4-ylsulfanyl]-N—((R)-2,3-dihydroxy-propyl)-propionamide (compound 320)

ESI (LC/MS positive mode) m/z=475/477 (M+H$^+$).
$^1$H-NMR (400 MHz, in dimethylsulfoxide-d$_6$) chemical shifts δ: 2.58 (2H, t, J=7.09 Hz), 2.96-3.02 (1H, m), 3.20-3.31 (5H, m), 3.49 (1H, s), 4.52 (1H, brs), 4.74 (1H, brs), 5.04 (2H, s), 5.05 (2H, s), 6.55 (1H, s), 6.89 (2H, s), 7.33 (1H, d, J=7.70 Hz), 7.35 (1H, d, J=7.78 Hz), 7.45 (1H, s), 7.50 (1H, t, J=7.78 Hz), 7.94 (1H, t, J=5.72 Hz).

Example 321

Production of 3-[2-amino-6-(5-chloro-1H,3H-benzo[de]isochromen-6-yl)-pyrimidin-4-ylsulfanyl]-2-methyl-propionamide (compound 321)

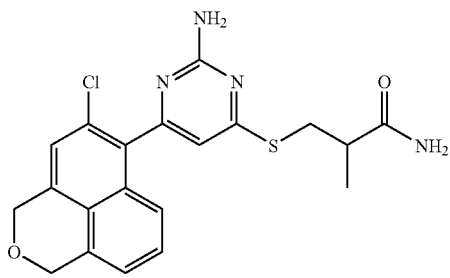

Partially purified 4-(5-chloro-1H,3H-benzo[de]isochromen-6-yl)-6-methanesulfinyl-pyrimidin-2-ylamine (99.9 mg) obtained in Step 5 of Example 314 was reacted with 3-mercapto-2-methylpropionic acid (133.0 mg) instead of mercaptoacetic acid using the same operation as the production method described in Step 6 of Example 314, and thus, 3-[2-amino-6-(5-chloro-1H,3H-benzo[de]isochromen-6-yl)-pyrimidin-4-ylsulfanyl]-2-methyl-propionic acid (115.4 mg) was obtained. Then, the obtained 3-[2-amino-6-(5-chloro-1H,3H-benzo[de]isochromen-6-yl)-pyrimidin-4-ylsulfanyl]-2-methyl-propionic acid (58 mg) was reacted with ammonium chloride (37.9 mg) using the same operation as the production method described in Step 6 of Example 314, and thus, 3-[2-amino-6-(5-chloro-1H,3H-benzo[de]isochromen-6-yl)-pyrimidin-4-ylsulfanyl]-2-methyl-propionamide (compound 321) (41.4 mg) was obtained as a white solid.

Physicochemical properties of 3-[2-amino-6-(5-chloro-1H,3H-benzo[de]isochromen-6-yl)-pyrimidin-4-ylsulfanyl]-2-methyl-propionamide (compound 321)

ESI (LC/MS positive mode) m/z=415/417 (M+H$^+$).
$^1$H-NMR (400 MHz, in dimethylsulfoxide-d$_6$) chemical shifts δ: 1.16 (3H, d, J=7.0 Hz), 2.57-2.65 (1H, m), 3.18-3.23 (2H, m), 5.04 (4H, s), 6.54 (1H, s), 6.89 (2H, brs), 7.25-7.53 (4H, m).

Example 322

Production of 3-[2-amino-6-(5-chloro-1H,3H-benzo[de]isochromen-6-yl)-pyrimidin-4-ylsulfanyl]-2,N-dimethyl-propionamide (compound 322)

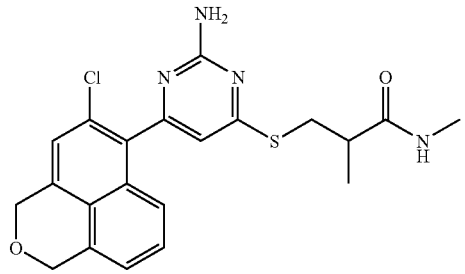

3-[2-Amino-6-(5-chloro-1H,3H-benzo[de]isochromen-6-yl)-pyrimidin-4-ylsulfanyl]-2-methyl-propionic acid (57.3 mg) was reacted with methylamine hydrochloride salt (93.3 mg) instead of ammonium chloride using the same operation as the production method described in Step 6 of Example 314, and thus, 3-[2-amino-6-(5-chloro-1H,3H-benzo[de]isochromen-6-yl)-pyrimidin-4-ylsulfanyl]-2,N-dimethyl-propionamide (compound 322) (47.2 mg) was obtained as a white solid.

Physicochemical properties of 3-[2-amino-6-(5-chloro-1H,3H-benzo[de]isochromen-6-yl)-pyrimidin-4-ylsulfanyl]-2,N-dimethyl-propionamide (compound 322)

ESI (LC/MS positive mode) m/z=429/430 (M+H$^+$).
$^1$H-NMR (400 MHz, in dimethylsulfoxide-d$_6$) chemical shifts δ: 1.13 (3H, d, J=7.0 Hz), 2.57-2.65 (4H, m), 3.15-3.30 (2H, m), 5.04 (4H, s), 6.54 (1H, s), 6.89 (2H, brs), 7.30-7.55 (4H, m), 7.88 (1H, m).

Example 323

Production of 3-[2-amino-6-(5-chloro-1H,3H-benzo[de]isochromen-6-yl)-pyrimidin-4-ylsulfanyl]-N-(2-hydroxy-ethyl)-2-methyl-propionamide (compound 323)

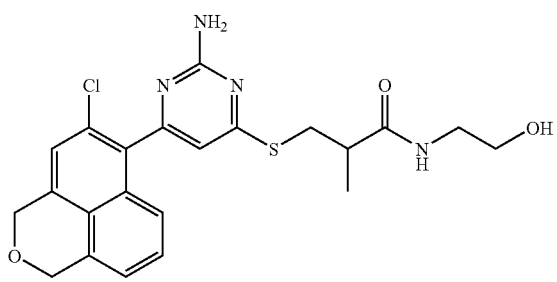

3-[2-Amino-6-(5-chloro-1H,3H-benzo[de]isochromen-6-yl)-pyrimidin-4-ylsulfanyl]-2-methyl-propionic acid (59.1 mg) was reacted with 2-aminoethanol (81.2 μL) instead of ammonium chloride and benzotriazol-1-yloxytris(dimethylamino)phosphoniumhexafluoro-phosphate (125.9 mg) instead of 1-ethyl-3-(3'-dimethylaminopropyl)carbodiimide hydrochloride salt using the same operation as the production method described in Step 6 of Example 314, and thus, 3-[2-amino-6-(5-chloro-1H,3H-benzo[de]isochromen-6-yl)-pyrimidin-4-ylsulfanyl]-N-(2-hydroxy-ethyl)-2-methyl-propionamide (compound 323) (36.0 mg) was obtained as a white solid.

Physicochemical properties of 3-[2-amino-6-(5-chloro-1H,3H-benzo[de]isochromen-6-yl)-pyrimidin-4-ylsulfanyl]-N-(2-hydroxy-ethyl)-2-methyl-propionamide (compound 323)

ESI (LC/MS positive mode) m/z=459/461 (M+H+).
$^1$H-NMR (400 MHz, in dimethylsulfoxide-$d_6$) chemical shifts δ: 1.51 (3H, d, J=7.0 Hz), 2.60-2.70 (1H, m), 3.10-3.47 (6H, m), 4.68 (1H, dd, J=5.1 Hz, J=5.7 Hz), 5.04 (4H, s), 6.54 (1H, s), 6.89 (2H, brs), 7.30-7.55 (4H, m), 7.96 (1H, t, J=5.4 Hz).

Example 324

Production of 4-[2-amino-6-(5-chloro-1H,3H-benzo[de]isochromen-6-yl)-pyrimidin-4-ylsulfanyl]-butylamide (compound 324)

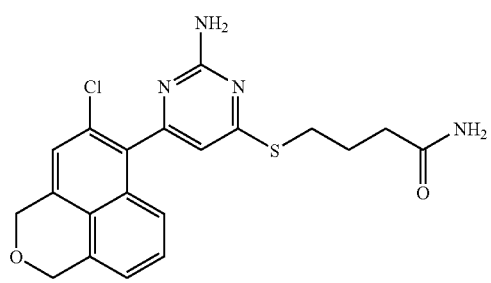

4,4'-Dithiodibutyric acid (53 mg) was dissolved in N,N-dimethylformamide (1.8 mL) and water (0.2 mL), then n-butylphosphine (0.054 mL) was added under nitrogen atmosphere, and this was stirred at room temperature for 2 hours. Partially purified 4-(5-chloro-1H,3H-benzo[de]isochromen-6-yl)-6-methanesulfinyl-pyrimidin-2-ylamine (40 mg) obtained in Step 5 of Example 314 and N,N-diisopropylethylamine (0.08 mL) were added to the obtained mixture, and this was stirred under nitrogen atmosphere at 80° C. for 1.5 hours. The reaction solution was cooled to room temperature, then diluted with ethyl acetate (5 mL), and then dried over anhydrous sodium sulfate. To the residue obtained after filtration and concentration, N,N-dimethylformamide (2 mL), ammonium chloride (72 mg), 1-hydroxybenzotriazole hydrate (226 mg), 1-ethyl-3-(3-dimethylaminopropyl)carbodiimide hydrochloride (256 mg), and N,N-diisopropylethylamine (0.23 mL) were added, and this was stirred at room temperature for 13 hours. The reaction solution was diluted with ethyl acetate (15 mL), then washed with aqueous ammonium chloride solution (10 mL×2), water (10 mL×2), and saturated aqueous sodium hydrogen carbonate solution (10 mL×2) successively, and then dried over anhydrous sodium sulfate. The residue obtained after filtration and concentration was purified by silica gel thin layer chromatography (developing solvent: dichloromethane:methanol=9:1), and thus, 4-[2-amino-6-(5-chloro-1H,3H-benzo[de]isochromen-6-yl)-pyrimidin-4-ylsulfanyl]-butylamide (compound 324) (34 mg) was obtained as a white solid.

Physicochemical properties of 4-[2-amino-6-(5-chloro-1H,3H-benzo[de]isochromen-6-yl)-pyrimidin-4-ylsulfanyl]-butylamide (compound 324)

ESI (LC/MS positive mode) m/z=415/417 (M+H+).
$^1$H-NMR (270 MHz, in dimethylsulfoxide-$d_6$) chemical shifts δ: 1.81-1.92: (2H, m), 2.21 (2H, t, J=7.3 Hz), 3.11 (2H, t, J=7.2 Hz), 5.01-5.09 (4H, m), 6.57 (1H, s), 6.79 (1H, brs), 6.86 (2H, brs), 7.28-7.37 (3H, m), 7.44 (1H, s), 7.50 (1H, dd, J=8.7, 6.8 Hz).

Example 325

Production of carbamic acid 2-[2-amino-6-(5-chloro-1H,3H-benzo[de]isochromen-6-yl)-pyrimidin-4-ylsulfanyl]-ethyl ester (compound 325)

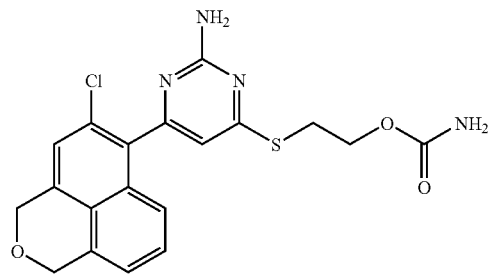

Carbamic acid 2-(2-carbamoyloxy-ethyldisulfanyl)-ethyl ester (205.9 mg, 0.857 mmol) was dissolved in a mixed solution of N,N-dimethylformamide (4.5 mL) and water (0.5 mL), tri-n-butylphosphine (189 μL, 0.759 mmol) was added, and this was stirred at room temperature for 1.5 hours. Additional tri n-butylphosphine (10 μL, 0.040 mmol) was added, and this was stirred at room temperature for 50 minutes. 1 mL of this reaction solution was sampled and added to the partially purified 4-(5-chloro-1H,3H-benzo[de]isochromen-6-yl)-6-methanesulfinyl-pyrimidin-2-ylamine (28.1 mg) obtained in Step 5 of Example 314, N,N-diisopropylethylamine (105 μL, 0.603 mmol) was further added, and this was stirred at 80° C. for 1 hour. The reaction solution was cooled to room temperature, water (10 mL) and 1 N hydrochloric acid (1 mL) were added, and this was extracted with ethyl acetate (15 mL, 10 mL). The organic layers were combined, and then washed with 0.01 N hydrochloric acid (8 mL), water (8 mL), and brine (8 mL), then dried over anhydrous sodium sulfate, and then concentrated under reduced pressure. The obtained residue was purified by silica gel thin layer chromatography (developing solvent; methylene chloride:methanol=20:1), and thus, carbamic acid 2-[2-amino-6-(5-chloro-1H,3H-benzo[de]isochromen-6-yl)-pyrimidin-4-ylsulfanyl]-ethyl ester (compound 325) (14.1 mg) was obtained.

Physicochemical properties of carbamic acid 2-[2-amino-6-(5-chloro-1H,3H-benzo[de]isochromen-6-yl)-pyrimidin-4-ylsulfanyl]-ethyl ester (compound 325)

ESI (LC/MS positive mode) m/z=417/419 (M+H+).
$^1$H-NMR (270 MHz, in dimethylsulfoxide-$d_6$) chemical shifts δ: 3.37 (2H, t, J=6.6 Hz), 4.16 (2H, t, J=6.6 Hz), 5.05 (4H, brs), 6.40-6.75 (2H, brs), 6.61 (1H, s), 6.92 (2H, brs, NH$_2$), 7.33 (1H, d, J=6.9 Hz), 7.35 (1H, d, J=8.3 Hz), 7.45 (1H, s), 7.50 (1H, dd, J=8.3 Hz, 6.9 Hz).

Example 326

Production of 3-[2-amino-6-(5-chloro-1H,3H-benzo[de]isochromen-6-yl)-pyrimidin-4-ylsulfanyl]-propan-1-ol (compound 326)

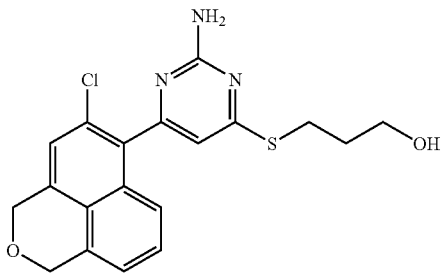

Partially purified 4-(5-chloro-1H,3H-benzo[de]isochromen-6-yl)-6-methanesulfinyl-pyrimidin-2-ylamine (29.1 mg) obtained in Step 5 of Example 314 was dissolved in N,N-dimethylformamide (1 mL), 3-mercapto-1-propanol (17 μL, 0.197 mmol) and N,N-diisopropylethylamine (55 μL, 0.316 mmol) were added, and this was stirred at 80° C. Four hours later, 3-mercapto-1-propanol (8 μL, 0.093 mmol) and N,N-diisopropylethylamine (23 μL, 0.132 mmol) were added, and this was stirred at 80° C. for another eleven hours. The reaction solution was cooled to room temperature, water (10 mL) and 1 N hydrochloric acid (1 mL) were added, and this was extracted with ethyl acetate (15 mL, 10 mL). The organic layers were combined, and then washed with 0.01 N hydrochloric acid (8 mL), water (8 mL), and brine (8 mL), then dried over anhydrous sodium sulfate, and then concentrated under reduced pressure. The obtained residue was purified by silica gel thin layer chromatography (developing solvent; methylene chloride:methanol=20:1), and thus, 3-[2-amino-6-(5-chloro-1H,3H-benzo[de]isochromen-6-yl)-pyrimidin-4-ylsulfanyl]-propan-1-ol (compound 326) (13.4 mg) was obtained.

Physicochemical properties of 3-[2-amino-6-(5-chloro-1H,3H-benzo[de]isochromen-6-yl)-pyrimidin-4-ylsulfanyl]-propan-1-ol (compound 326)

ESI (LC/MS positive mode) m/z=388/390 (M+H$^+$).
$^1$H-NMR (270 MHz, in dimethylsulfoxide-d$_6$) chemical shifts δ: 1.80 (2H, dddd (like qui), J=7.3 Hz, 7.3 Hz, 6.4 Hz, 6.4 Hz), 3.15 (2H, dd (like t), J=7.3 Hz, 7.3 Hz), 3.51 (2H, ddd (like q), J=6.4 Hz, 6.4 Hz, 5.4 Hz), 4.57 (1H, dd (like t), J=5.4 Hz, 5.4 Hz, OH), 5.04 (4H, brs), 6.54 (1H, s), 6.87 (2H, brs, NH$_2$), 7.33 (1H, d, J=6.6 Hz), 7.35 (1H, d, J=8.9 Hz), 7.44 (1H, s), 7.50 (1H, dd, J=8.9 Hz, 6.6 Hz).

Example 327

Production of N-{2-[2-amino-6-(5-chloro-1H,3H-benzo[de]isochromen-6-yl)-pyrimidin-4-ylsulfanyl]-ethyl}-acetamide (compound 327)

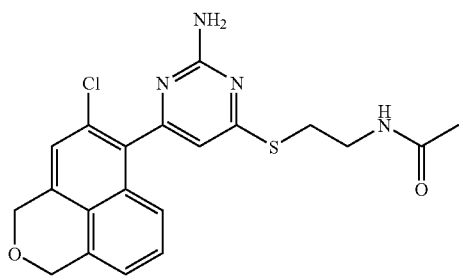

N-{2-[2-amino-6-(5-chloro-1H,3H-benzo[de]isochromen-6-yl)-pyrimidin-4-ylsulfanyl]-ethyl}-acetamide (compound 327) (32.1 mg) was obtained from partially purified 4-(5-chloro-1H,3H-benzo[de]isochromen-6-yl)-6-methanesulfinyl-pyrimidin-2-ylamine (35.1 mg) obtained in Step 5 of Example 314 by performing a reaction using the same operation as the production method described in Example 326 with N-(2-mercaptoethyl)acetamide (54.5 μL) instead of 3-mercapto-1-propanol.

Physicochemical properties of N-{2-[2-amino-6-(5-chloro-1H,3H-benzo[de]isochromen-6-yl)-pyrimidin-4-ylsulfanyl]-ethyl}-acetamide (compound 327)

ESI (LC/MS positive mode) m/z=415/417 (M+H$^+$).
$^1$H-NMR (270 MHz, in deuterated chloroform) chemical shifts δ: 2.00 (3H, s), 3.35-3.39 (2H, m), 3.63 (2H, dt, J=5.9 Hz, 5.9 Hz), 5.06 (4H, d, J=3.0 Hz), 5.23 (2H, brs), 6.28 (1H, brs), 6.66 (1H, s), 7.19 (1H, t, J=4.0 Hz), 7.25 (1H, s), 7.42 (2H, d, J=4.0 Hz).

Example 328

Production of N-{3-[2-amino-6-(5-chloro-1H,3H-benzo[de]isochromen-6-yl)-pyrimidin-4-ylsulfanyl]-propyl}-acetamide (compound 328)

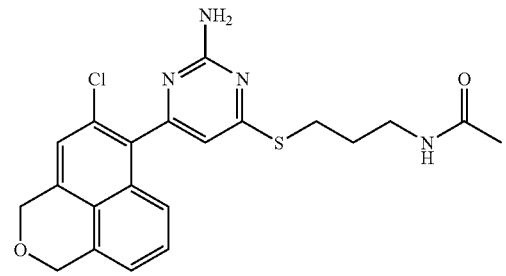

N-{3-[2-amino-6-(5-chloro-1H,3H-benzo[de]isochromen-6-yl)-pyrimidin-4-ylsulfanyl]-propyl}-acetamide (compound 328) (7.9 mg) was obtained from partially purified 4-(5-chloro-1H,3H-benzo[de]isochromen-6-yl)-6-methanesulfinyl-pyrimidin-2-ylamine (26.0 mg) obtained in Step 5 of Example 314 by performing a reaction using the same operation as the production method described in Example 326 with N-(2-mercaptopropyl)acetamide instead of 3-mercapto-1-propanol.

Physicochemical properties of N-{3-[2-amino-6-(5-chloro-1H,3H-benzo[de]isochromen-6-yl)-pyrimidin-4-ylsulfanyl]-propyl}-acetamide (compound 328)

ESI (LC/MS positive mode) m/z=429/431 (M+H$^+$).
$^1$H-NMR (270 MHz, in dimethylsulfoxide-d$_6$) chemical shifts δ: 3.20-3.45 (4H, m), 5.05 (4H, brs), 5.54 (2H, brs), 6.21 (1H, t, J=5.4 Hz), 6.63 (1H, s), 6.88 (2H, brs, NH$_2$), 7.33 (1H, d, J=6.9 Hz), 7.34 (1H, d, J=8.3 Hz), 7.45 (1H, s), 7.51 (1H, dd, J=8.3 Hz, 6.9 Hz).

Example 329

Production of N-{2-[2-amino-6-(5-chloro-1H,3H-benzo[de]isochromen-6-yl)-pyrimidin-4-ylsulfanyl]-ethyl}-methanesulfonamide (compound 329)

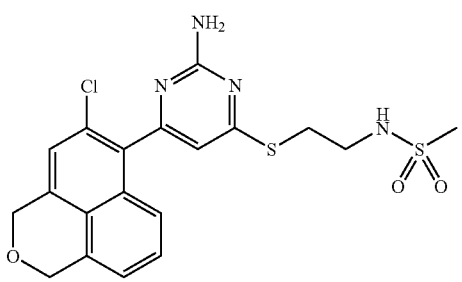

Partially purified 4-(5-chloro-1H,3H-benzo[de]isochromen-6-yl)-6-methanesulfinyl-pyrimidin-2-ylamine (94.7 mg) obtained in Step 5 of Example 314 was dissolved in N,N-dimethylformamide (3 mL), sodium hydrosulfide (29.9 mg) and water (100 µL) were added, and this was stirred at room temperature for 10 minutes. Water was added to the reaction solution, and this was extracted using ethyl acetate. This ethyl acetate solution was washed with water, 1 N hydrochloric acid, water, and brine successively, and then dried over anhydrous magnesium sulfate. Anhydrous magnesium sulfate was filtered off, and the filtrate was concentrated under reduced pressure. The obtained residue was dissolved in N,N-dimethylformamide (6 mL), and then N-(2-chloroethyl)methanesulfonamide (58.8 mg) and N,N-diisopropylethylamine (86.7 µL) were added and stirred at 110° C. for 14 hours. The reaction solution was cooled to room temperature, and then diluted with ethyl acetate. This ethyl acetate solution was washed with water and brine successively, and then dried over anhydrous sodium sulfate. Anhydrous sodium sulfate was removed by filtration, and the filtrate was concentrated under reduced pressure. The obtained residue was purified by silica gel thin layer chromatography (developing solvent; methylene chloride:methanol=9:1), and thus, N-{2-[2-amino-6-(5-chloro-1H,3H-benzo[de]isochromen-6-yl)-pyrimidin-4-ylsulfanyl]-ethyl}-m ethanesulfonamide (compound 329) (58.1 mg) was obtained.

Physicochemical properties of N-{2-[2-amino-6-(5-chloro-1H,3H-benzo[de]isochromen-6-yl)-pyrimidin-4-ylsulfanyl]-ethyl}-m ethanesulfonamide (compound 329)

ESI (LC/MS positive mode) m/z=451/453 (M+H$^+$).
$^1$H-NMR (400 MHz, in dimethylsulfoxide-d$_6$) chemical shifts δ: 2.93 (3H, s), 3.25-3.27 (4H, s), 5.04 (4H, d, J=4.1 Hz), 6.59 (1H, s), 6.86 (2H, brs), 7.27-7.30 (1H, m), 7.32 (1H, d, J=6.4 Hz), 7.34 (1H, d, J=7.8 Hz), 7.44 (1H, s), 7.49 (1H, m).

Example 330

Production of 5-[2-amino-6-(5-chloro-1H,3H-benzo[de]isochromen-6-yl)-pyrimidin-4-ylsulfanylmethyl]-oxazolidin-2-one (compound 330)

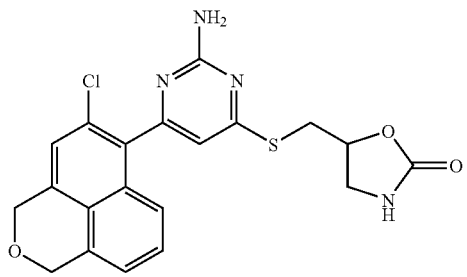

5-[2-amino-6-(5-chloro-1H,3H-benzo[de]isochromen-6-yl)-pyrimidin-4-ylsulfanylmeth yl]-oxazolidin-2-one (compound 330) (25.7 mg) was obtained from partially purified 4-(5-chloro-1H,3H-benzo[de]isochromen-6-yl)-6-methanesulfinyl-pyrimidin-2-ylamine (87.5 mg) obtained in Step 5 of Example 314 by performing a reaction using the same operation as the production method described in Example 329 with 5-chloromethyloxazolidin-2-one (65.6 mg) instead of N-(2-chloroethyl)methanesulfonamide.

Physicochemical properties of 5-[2-amino-6-(5-chloro-1H,3H-benzo[de]isochromen-6-yl)-pyrimidin-4-ylsulfanylmethyl]-oxazolidin-2-one (compound 330)

ESI (LC/MS positive mode) m/z=429/431 (M+H$^+$).
$^1$H-NMR (270 MHz, in deuterated chloroform) chemical shifts δ: 3.20-3.37 (2H, m), 3.52 (1H, dd, J=8.3 Hz, 8.3 Hz), 3.73 (1H, dd, J=4.9 Hz, 14.1 Hz), 4.93 (1H, m), 5.07 (4H, s), 5.52 (2H, brs), 6.33 (1H, brs), 6.63 (1H, s), 7.20-7.21 (1H, m), 7.25 (1H, s), 7.42-7.43 (2H, m).

Example 331

Production of N-{2-[2-amino-6-(5-chloro-1H,3H-benzo[de]isochromen-6-yl)-pyrimidin-4-ylsulfanyl]-ethyl}-2-hydroxy-acetamide (compound 331)

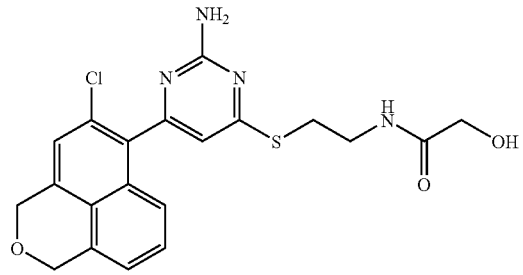

Partially purified acetic acid {2-[2-amino-6-(5-chloro-1H,3H-benzo[de]isochromen-6-yl)-pyrimidin-4-ylsulfanyl]-ethylcarbamoyl}-methylester was obtained from partially purified 4-(5-chloro-1H,3H-benzo[de]isochromen-6-yl)-6-methanesulfinyl-pyrimidin-2-ylamine (87.5 mg) obtained in Step 5 of Example 314 using the same operation as the production method described in Example 329 with acetic acid (2-chloroethylcarbamoyl)methylester (52.2 mg) instead of N-(2-chloroethyl)methane sulfonamide. This partially purified product was dissolved in tetrahydrofuran (5 mL), 1 N aqueous sodium hydroxide (0.8 mL) was added at room temperature, and the obtained mixture was stirred at room temperature for 30 minutes. 1 N hydrochloric acid (0.8 mL) was added to the reaction solution, and then this was extracted with ethyl acetate. The organic layer was washed with water and brine successively, and then dried over anhydrous sodium sulfate. After filtering off the anhydrous sodium sulfate, the filtrate was concentrated under reduced pressure. The obtained residue was purified by preparative high-performance liquid chromatography (column packing material: ODS; mobile phase: aqueous solution containing 0.05% trifluoroacetic acid: acetonitrile solution containing 0.05% trifluoacetic acid=10:90 to 95:5 (gradient)), and thus, N-{2-[2-amino-6-(5-chloro-1H,3H-benzo[de]isochromen-6-yl)-pyrimidin-4-ylsulfanyl]-ethyl}-2-hydroxy-acetamide (compound 331) (20.6 mg) was obtained.

Physicochemical properties of N-{2-[2-amino-6-(5-chloro-1H,3H-benzo[de]isochromen-6-yl)-pyrimidin-4-ylsulfanyl]-ethyl}-2-hydroxy-acetamide (compound 331)

ESI (LC/MS positive mode) m/z=431/433 (M+H$^+$).
$^1$H-NMR (270 MHz, in deuterated chloroform) chemical shifts δ: 3.37 (2H, t, J=5.9 Hz), 3.68 (2H, t, J=5.9 Hz), 4.06 (2H, s), 5.08 (4H, s), 6.63 (1H, s), 7.20-7.23 (1H, m), 7.23 (1H, s), 7.43 (2H, d, J=5.6 Hz), 8.19 (1H, brs).

Example 332

Production of {2-[2-amino-6-(5-chloro-1H,3H-benzo[de]isochromen-6-yl)-pyrimidin-4-ylsulfanyl]-ethyl}-urea (compound 332)

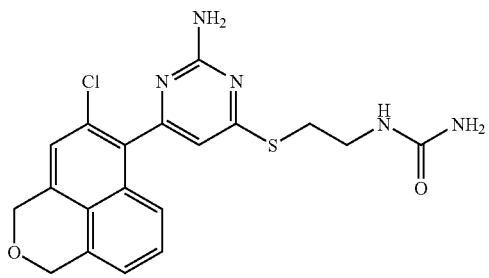

Sodium hydrogen sulfide (1.07 g) was dissolved in N,N-dimethylformamide (25 ml). To the mixture was added 4N hydrogen chloride in ethylacetate (13.3 ml) at room temperature. After stirring for approximately 30 minutes at the same temperature, to the resulting mixture were added 4-(5-chloro-1H,3H-benzo[de]isochromen-6-yl)-6-methanesulfinyl-pyrimidin-2-ylamine (1.20 g) obtained in Step 5 of Example 314 and N,N-diisopropylethylamine (2.9 ml) successively. The mixture was stirred at 80° C. for four hours, and then the mixture was allowed to cool to room temperature. To the mixture were added to 2-chloro-ethylurea (3.20 g), N,N-diisopropylethylamine (5.8 ml) and N,N-dimethylformamide (15 ml) successively. The reaction mixture was stirred at 80° C. for 14 hours and then allowed to cool to room temperature. The reaction was quenched by adding water and extracted with ethyl acetate. The organic layer was separated, washed with water and brine subsequently, dried over anhydrous sodium sulfate. After removal of inorganic salts, the solution was concentrated by evaporation. The resulting residue was purified by HPLC (column; ODS, mobile phase; 0.05% TFA in water: 0.05% TFA in acetonitrile=65:35) to give {2-[2-amino-6-(5-chloro-1H,3H-benzo[de]isochromen-6-yl)-pyrimidin-4-ylsulfanyl]-ethyl}-urea (0.93 g).

Physicochemical properties of {2-[2-amino-6-(5-chloro-1H,3H-benzo[de]isochromen-6-yl)-pyrimidin-4-ylsulfanyl]-ethyl}-urea (compound 332)

ESI (LC/MS positive mode) m/z=416/418 (M+H⁺).
¹H-NMR (270 MHz, in dimethylsulfoxide-$d_6$) chemical shifts δ: 1.78 (2H, qui, J=6.9 Hz), 3.05-3.20 (4H, m), 5.05 (4H, brs), 6.54 (1H, s), 6.88 (2H, brs, $NH_2$), 7.33 (1H, d, J=6.9 Hz), 7.34 (1H, d, J=8.7 Hz), 7.45 (1H, s), 7.51 (1H, dd, J=8.7 Hz, 6.9 Hz), 7.89 (1H, brt, J=ca. 5 Hz).

Example 333

Preparation of 2-[4-amino-6-(5-chloro-1H,3H-benzo[de]isochromen-6-yl)-[1,3,5]triazin-2-ylsulfanyl]-N-cyano methyl-acetamide Step 1: Preparation of [4-amino-6-(5-chloro-1H,3H-benzo[de]isochromen-6-yl)-[1,3,5]triazin-2-ylsulfanyl]-acetic acid Proceeding in the same manner as in Step 1 of Example 205 and replacing 3-mercaptopropionic acid by thioglycolic acid (4.8 ml, 69 mmol), there was obtained [4-amino-6-(5-chloro-1H,3H-benzo[de]isochromen-6-yl)-[1,3,5]triazin-2-ylsulfanyl]-acetic acid (10.49 g, 98%) as a white solid from 4-(5-chloro-1H,3H-benzo[de]isochromen-6-yl)-6-methanesulfinyl-[1,3,5]triazin-2-ylamine (9.96 g).

ESI (LC/MS positive mode): m/z=389, 401(M+H⁺).
¹H-NMR (270 MHz, DMSO-$d_6$) chemical shifts δ: 3.93 (2H, s), 5.05 (4H, brs), 7.35 (1H, d, J=6.9 Hz), 7.39 (1H, d, J=8.6 Hz), 7.45 (1H, s), 7.52 (1H, dd, J=8.6 Hz, J=6.9 Hz), 7.85 (1H, brs), 7.88 (1H, brs), 12.75 (1H, brs).

Step 2: Preparation of 2-[4-amino-6-(5-chloro-1H,3H-benzo[de]isochromen-6-yl)-[1,3,5]triazin-2-ylsulfanyl]-N-cyano methyl-acetamide Proceeding in the same manner as in Step 2 of Example 205 and replacing N-methylamine hydrochloride and 3-[4-amino-6-(5-chloro-1H,3H-benzo[de]isochromen-6-yl)-[1,3,5]triazin-2-ylsulfanyl]-propionic acid by aminoacetonitrile hydrochloride (1.91 g, 20.6 mmol) and [4-amino-6-(5-chloro-1H,3H-benzo[de]isochromen-6-yl)-[1,3,5]triazin-2-ylsulfanyl]-acetic acid (2.0 g, 5.16 mmol) respectively, there was obtained 2-[4-amino-6-(5-chloro-1H,3H-benzo[de]isochromen-6-yl)-[1,3,5]triazin-2-ylsulfanyl]-N-cyano methyl-acetamide (1.22 g, 55%) as a white solid from [4-amino-6-(5-chloro-1H,3H-benzo[de]isochromen-6-yl)-[1,3,5]triazin-2-ylsulfanyl]-acetic acid (2.0 g).

ESI (LC/MS positive mode): m/z=427, 428(M+H⁺).
¹H-NMR (270 MHz, DMSO-$d_6$) chemical shifts δ: 3.87 (2H, s), 4.10 (2H, d, J=5.6 Hz), 5.05 (4H, brs), 7.34 (1H, d, J=7.1 Hz), 7.38 (1H, d, J=8.9 Hz), 7.45 (1H, s), 7.53 (1H, dd, J=8.9 Hz, J=7.1 Hz), 7.83 (1H, brs), 7.91 (1H, brs), 8.71 (1H, t, J=5.6 Hz).

Example 334

Preparation of 3-[4-amino-6-(5-chloro-1H,3H-benzo[de]isochromen-6-yl)-[1,3,5]triazin-2-ylsulfanyl]-N-(2-methoxy-ethyl)-propionamide

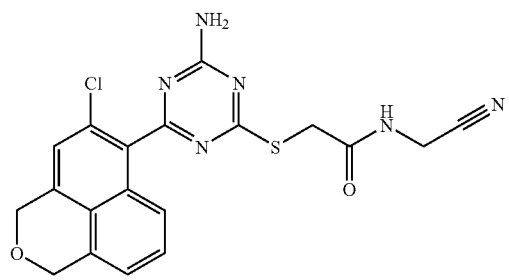

Proceeding in the same manner as in Step 2 of Example 205 and replacing N-methylamine hydrochloride by 2-methoxy-ethylamine (0.71 ml), there was obtained 3-[4-amino-6-(5-chloro-1H,3H-benzo[de]isochromen-6-yl)-[1,3,5]triazin-2-ylsulfanyl]-N-(2-methoxy-ethyl)-propionamide (969 mg, 77%) as a white solid from 3-[4-amino-6-(5-chloro-1H,3H-benzo[de]isochromen-6-yl)-[1,3,5]triazin-2-ylsulfanyl]-propionic acid (1.10 g).

ESI (LC/MS positive mode): m/z=460, 462(M+H⁺).

¹H-NMR (270 MHz, DMSO-d₆) chemical shifts δ: 2.48-2.55 (2H, m), 3.15-3.33 (9H, m), 5.05 (4H, brs), 7.34 (1H, d, J=6.9 Hz), 7.42 (1H, d, J=8.4 Hz), 7.45 (1H, s), 7.53 (1H, dd, J=8.4 Hz, J=6.9 Hz), 7.83 (2H, brs), 7.99 (1H, t, J=5.5 Hz).

Example 335

Preparation of 3-[4-amino-6-(5-chloro-1H,3H-benzo[de]isochromen-6-yl)-[1,3,5]triazin-2-ylsulfanyl]-N—((R)-2,3-dihydroxy-propyl)-propionamide

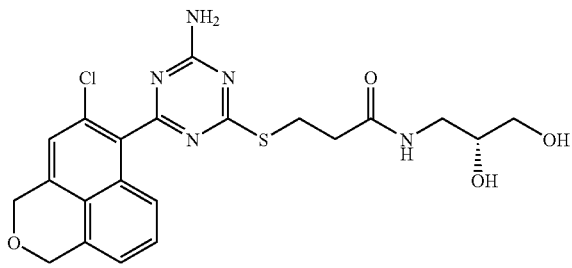

Proceeding in the same manner as in Step 2 of Example 205 and replacing N-methylamine hydrochloride by (R)-(+)-3-amino-1,2-propanediol (1.358 g), and omitting addition of N-ethyldiisopropylamine, there was obtained 3-[4-amino-6-(5-chloro-1H,3H-benzo[de]isochromen-6-yl)-[1,3,5]triazin-2-ylsulfanyl]-N—((R)-2,3-dihydroxy-propyl)propionamide (2.03 g, 86%) as a white solid from 3-[4-amino-6-(5-chloro-1H,3H-benzo[de]isochromen-6-yl)-[1,3,5]triazin-2-ylsulfanyl]-propionic acid (2.0 g).

ESI (LC/MS positive mode): m/z=476, 478(M+H⁺).

¹H-NMR (270 MHz, DMSO-d₆) chemical shifts δ: 2.54 (2H, t, J=6.8 Hz), 2.91-3.02 (1H, m), 3.12-3.44 (7H, m), 4.51 (1H, t, J=5.9 Hz), 4.73 (1H, d, J=4.9 Hz), 5.05 (4H, brs), 7.34 (1H, d, J=6.6 Hz), 7.42 (1H, d, J=8.6 Hz), 7.45 (1H, s), 7.53 (1H, dd, J=8.6 Hz, J=6.6 Hz), 7.83 (2H, brs), 7.90 (1H, t, J=5.4 Hz).

Example 336

Preparation of 3-[4-amino-6-(5-chloro-1H,3H-benzo[de]isochromen-6-yl)-[1,3,5]triazin-2-ylsulfanyl]-2-methyl-propionamide

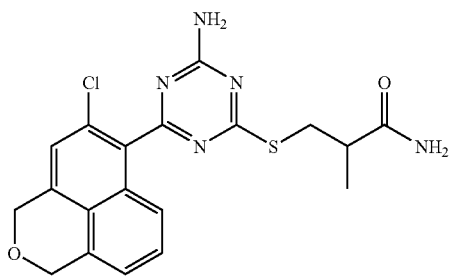

Step 1: Preparation of 3-[4-amino-6-(5-chloro-1H,3H-benzo[de]isochromen-6-yl)-[1,3,5]triazin-2-ylsulfanyl]-2-methyl-propionic acid

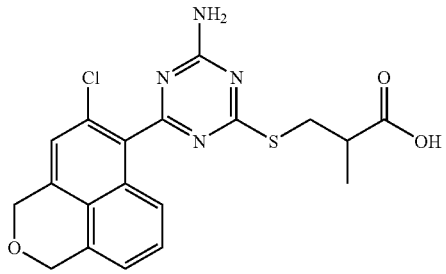

Proceeding in the same manner as in Step 1 of Example 205 and replacing 3-mercaptopropionic acid by 3-mercaptoisobutyric acid (5.08 g, 42 mmol), there was obtained [4-amino-6-(5-chloro-1H,3H-benzo[de]isochromen-6-yl)-[1,3,5]triazin-2-ylsulfanyl]-acetic acid (6.18 g, 88%) as a pale yellow solid from 4-(5-chloro-1H,3H-benzo[de]isochromen-6-yl)-6-methanesulfinyl-[1,3,5]triazin-2-ylamine (6.1 g).

ESI (LC/MS positive mode): m/z=417, 419(M+H⁺).

¹H-NMR (270 MHz, DMSO-d₆) chemical shifts δ: 1.16 (3H, d, J=7.3 Hz), 2.70-2.81 (1H, m), 3.19-3.26 (2H, m), 5.06 (4H, brs), 7.35 (1H, d, J=7.1 Hz), 7.41 (1H, d, J=8.2 Hz), 7.46 (1H, s), 7.53 (1H, dd, J=8.2 Hz, J=7.1 Hz), 7.85 (2H, brs), 12.44 (1H, brs).

Step 2: Preparation of 3-[4-amino-6-(5-chloro-1H,3H-benzo[de]isochromen-6-yl)-[1,3,5]triazin-2-ylsulfanyl]-2-methyl-propionamide Proceeding in the same manner as in Step 2 of Example 205 and replacing N-methylamine hydrochloride and 3-[4-amino-6-(5-chloro-1H,3H-benzo[de]isochromen-6-yl)-[1,3,5]triazin-2-ylsulfanyl]-propionic acid by ammonium chloride (963 mg, 18 mmol) and 3-[4-amino-6-(5-chloro-1H,3H-benzo[de]isochromen-6-yl)-[1,3,5]triazin-2-ylsulfanyl]-2-methyl-propionic acid (1.5 g, 3.6 mmol) respectively, there was obtained 3-[4-amino-6-(5-chloro-1H,3H-benzo[de]isochromen-6-yl)-[1,3,5]triazin-2-ylsulfanyl]-2-methyl-propionamide (978 mg, 65%) as a white solid.

ESI (LC/MS positive mode): m/z=416, 418(M+H⁺).

¹H-NMR (270 MHz, DMSO-d₆) chemical shifts δ: 1.09 (3H, d, J=6.6 Hz), 2.55-2.65 (1H, m), 3.08-3.20 (2H, m), 5.05 (4H, brs), 6.89 (1H, brs), 7.32-7.46 (3H, m), 7.53 (1H, dd, J=8.7 Hz, 6.8 Hz), 7.82 (2H, brs).

Example 337

Preparation of 3-[4-amino-6-(5-chloro-1H,3H-benzo[de]isochromen-6-yl)-[1,3,5]triazin-2-ylsulfanyl]-2,N-dimethyl-propionamide

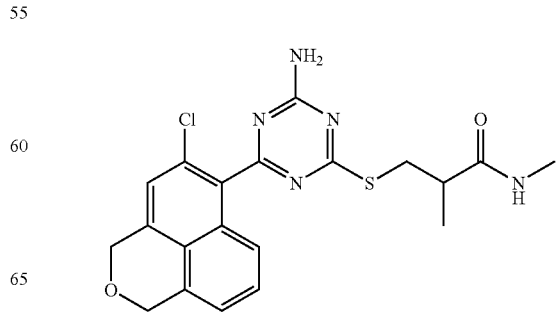

Proceeding in the same manner as in Step 2 of Example 336 and replacing ammonium chloride by N-methylamine hydrochloride (12 mg), there was obtained 3-[4-amino-6-(5-chloro-1H,3H-benzo[de]isochromen-6-yl)-[1,3,5]triazin-2-ylsulfanyl]-2,N-dimethyl-propionamide (13.7 mg, 86%) as a white solid from 3-[4-amino-6-(5-chloro-1H,3H-benzo[de]isochromen-6-yl)-[1,3,5]triazin-2-ylsulfanyl]-2-methyl-propionic acid (15 mg).

ESI (LC/MS positive mode): m/z=430, 432(M+H$^+$).

$^1$H-NMR (270 MHz, CDCl$_3$) chemical shifts δ: 1.21 (3H, d, J=6.9 Hz), 2.48 (3H, d, J=4.8 Hz), 2.53-2.66 (1H, m), 2.88-2.97 (1H, m), 3.44 (1H, dd, J=5.6 Hz, J=14 Hz), 5.04-5.11 (4H, m), 5.79-6.05 (3H, m), 7.19-7.26 (2H, m), 7.45-7.49 (2H, m).

Example 338

Preparation of 3-[4-amino-6-(5-chloro-1H,3H-benzo[de]isochromen-6-yl)-[1,3,5]triazin-2-ylsulfanyl]-N-(2-hydroxy-ethyl)-2-methyl-propionamide

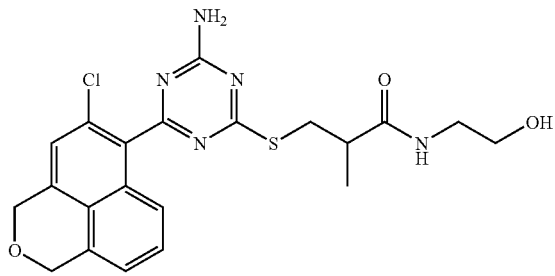

Proceeding in the same manner as in Step 2 of Example 336 and replacing ammonium chloride by 2-hydroxyethylamine (1.1 g, 18 mmol), there was obtained 3-[4-amino-6-(5-chloro-1H,3H-benzo[de]isochromen-6-yl)-[1,3,5]triazin-2-ylsulfanyl]-N-(2-hydroxyethyl)-2-methyl-propionamide (1.073 g, 65%) as a white solid from 3-[4-amino-6-(5-chloro-1H,3H-benzo[de]isochromen-6-yl)-[1,3,5]triazin-2-ylsulfanyl]-2-methyl-propionic acid (1.5 g).

ESI (LC/MS positive mode): m/z=460, 462(M+H$^+$).

$^1$H-NMR (270 MHz, DMSO-d$_6$) chemical shifts δ: 1.08 (3H, d, J=6.9 Hz), 2.57-2.69 (1H, m), 3.07-3.22 (4H, m), 3.33-3.40 (2H, m), 4.65 (1H, t, J=5.4 Hz), 5.05 (4H, brs), 7.35 (1H, d, J=6.8 Hz), 7.41-7.45 (2H, m), 7.53 (1H, dd, J=8.6 Hz, J=6.8 Hz), 7.81 (2H, brs), 7.91 (1H, t, J=5.5 Hz).

Example 339

Preparation of 4-[4-amino-6-(5-chloro-1H,3H-benzo[de]isochromen-6-yl)-[1,3,5]triazin-2-ylsulfanyl]-butyramide

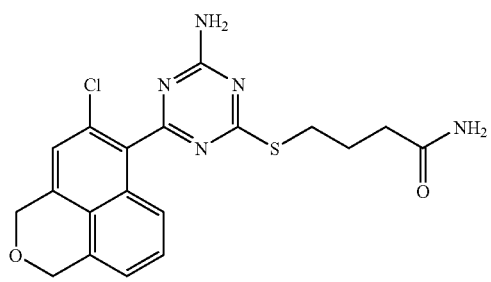

4,4-dithiobutyric acid (1.49 g, 6.24 mmol) was dissolved in N,N-dimethylformamide (16 ml) and water (1.78 ml) under nitrogen atmosphere. Tri-n-butylphosphine (1.45 ml, 5.82 mmol) was added to the solution and the resulting mixture was stirred for 1.5 hours at room temperature. To the obtained mixture were added 4-(5-chloro-1H,3H-benzo[de]isochromen-6-yl)-6-methanesulfinyl-[1,3,5]triazin-2-ylamine (1.5 g, 4.16 mmol), N-ethyldiisopropylamine (2.15 ml, 12.47 mmol) and N,N-dimethylformamide (8 ml) successively, and stirring was continued overnight. The mixture was diluted with water (100 ml), and extracted with ethyl acetate (100 ml). The separated organic layer was washed with water (100 ml) and brine successively, and then dried over anhydrous sodium sulfate. After removal of inorganic salts by filtration, the filtrate was concentrated in vacuo giving crude 4-[4-amino-6-(5-chloro-1H,3H-benzo[de]isochromen-6-yl)-[1,3,5]triazin-2-ylsulfanyl]-butyric acid as a yellow oil [ESI (LC/MS positive mode): m/z=417, 419(M+H$^+$)].

The obtained crude product was dissolved in N,N-dimethylformamide (50 ml). To the solution were added ammonium chloride (2.22 g, 41 mmol), 1-hydroxybenzotriazole (7.00 g, 41 mmol), N-ethyldiisopropylamine (7 ml, 41 mmol) and 1-ethyl-3-(3-dimethylaminopropyl)carbodiimide (8.00 g, 41 mmol) successively at room temperature. The mixture was stirred for 10 hours at the same temperature. Work-up and purification was carried out in the same manner of Step 2 of Example 205, giving 4-[4-amino-6-(5-chloro-1H,3H-benzo[de]isochromen-6-yl)-[1,3,5]triazin-2-ylsulfanyl]-butyramide (1.522 g, 88% in 2 steps) as a white solid.

ESI (LC/MS positive mode): m/z=416, 418(M+H$^+$).

$^1$H-NMR (270 MHz, CDCl$_3$) chemical shifts δ: 2.04-2.14 (2H, m), 2.36 (2H, t, J=6.9 Hz), 3.11-3.18 (2H, m), 4.94 (1H, brs), 5.04-5.11 (4H, m), 5.52 (2H, brs), 5.92 (1H, brs), 7.18-7.30 (2H, m), 7.44-7.47 (2H, m).

Example 340

Preparation of 3-[4-amino-6-(5-chloro-1H,3H-benzo[de]isochromen-6-yl)-[1,3,5]triazin-2-ylsulfanyl]-propan-1-ol (the same compound as that of Example 115)

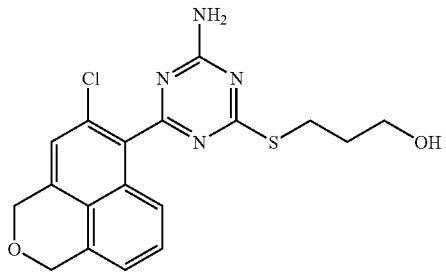

Proceeding in the same manner as Example 149 and replacing 3-chloropropylacetamide by 3-mercaptopropan-1-ol (38 mg), there was obtained 3-[4-amino-6-(5-chloro-1H,3H-benzo[de]isochromen-6-yl)-[1,3,5]triazin-2-ylsulfanyl]-propan-1-ol (21 mg) (the same compound as that of Example 115) as a pale yellow solid from 4-amino-6-(5-chloro-1H,3H-benzo[de]isochromen-6-yl)-[1,3,5]triazine-2-thiol (50 mg).

ESI (LC/MS positive mode): m/z=389, 391(M+H$^+$).

$^1$H-NMR (400 MHz, DMSO-d$_6$) chemical shifts δ: 1.78 (2H, m), 3.08 (2H, t, J=7.1 Hz), 3.47 (2H, m), 4.53 (1H, t, J=5.0 Hz), 5.04 (2H, brs), 5.05 (2H, brs), 7.34 (1H, d, J=6.9 Hz), 7.40 (1H, d, J=8.7 Hz), 7.45 (1H, s), 7.52 (1H, dd, J=8.7, 6.9 Hz), 7.79 (2H, brs).

Example 341

Preparation of 5-[4-amino-6-(5-chloro-1H,3H-benzo[de]isochromen-6-yl)-[1,3,5]triazin-2-ylsulfanylmethyl]-oxazolidin-2-one

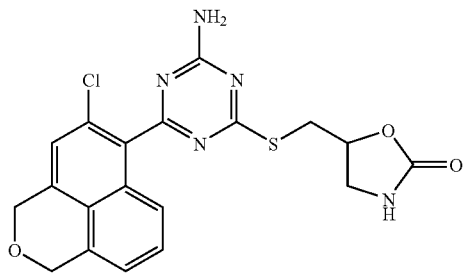

Proceeding in the same manner as Example 149 and replacing 3-chloropropylacetamide by 5-chloromethyl-oxazolidin-2-one (1.59 g), there was obtained 5-[4-amino-6-(5-chloro-1H,3H-benzo[de]isochromen-6-yl)-[1,3,5]triazin-2-ylsulfanylmethyl]-oxazolidin-2-one (1.32 g, 79%) as a white solid from 4-amino-6-(5-chloro-1H,3H-benzo[de]isochromen-6-yl)-[1,3,5]triazine-2-thiol (1.50 g).

ESI (LC/MS positive mode): m/z=430,432(M+H$^+$).

$^1$H-NMR (400 MHz, DMSO-d$_6$) chemical shifts δ: 3.26 (1H, dd, J=5.9 Hz and 8.8 Hz), 3.39 (1H, dd, J=5.9 Hz and 14.2 Hz), 3.48 (1H, dd, J=5.9 Hz and 14.2 Hz), 3.57 (1H, dd, J=8.8 Hz and 8.8 Hz), 4.79-4.86 (1H, m), 5.04 (2H, s), 5.05 (2H, s), 7.35 (1H, d, J=6.8 Hz), 7.43 (1H, d, J=8.3 Hz), 7.52 (1H, dd, J=6.8 Hz and 8.3 Hz), 7.54 (1H, s), 7.87 (2H, s).

Example 342

Preparation of N-{2-[4-amino-6-(5-chloro-1H,3H-benzo[de]isochromen-6-yl)-[1,3,5]triazin-2-ylsulfanyl]-ethyl}-2-hydroxy-acetamide

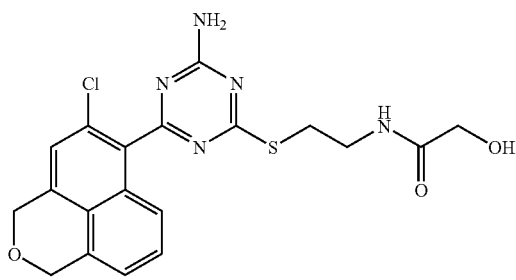

Proceeding in the same manner as Example 149 and replacing 3-chloropropylacetamide by acetic acid (2-chloroethylcarbamoyl)-methyl ester (3.15 g), there was obtained acetic acid {2-[4-amino-6-(5-chloro-1H,3H-benzo[de]isochromen-6-yl)-[1,3,5]triazin-2-ylsulfanyl]-ethylcarbamoyl}-methyl ester from 4-amino-6-(5-chloro-1H,3H-benzo[de]isochromen-6-yl)-[1,3,5]triazine-2-thiol (1.71 g). Then the product was hydrolyzed by 1.0N sodium hydroxide solution (50 ml) to give N-{2-[4-amino-6-(5-chloro-1H,3H-benzo[de]isochromen-6-yl)-[1,3,5]triazin-2-ylsulfanyl]-ethyl}-2-hydroxy-acetamide (1.33 g) as a white solid ESI (LC/MS positive mode): m/z=432, 434 (M+H$^+$).

$^1$H-NMR (270 MHz, DMSO-d$_6$) chemical shifts δ: 3.18 (2H, t, J=6.4 Hz), 4.44 (2H, m), 3.80 (2H, d, J=5.8 Hz), 5.04 (2H, brs), 5.05 (2H, brs), 5.49 (1H, t, J=5.8 Hz), 7.34 (1H, d, J=6.8 Hz), 7.43 (1H, d, J=8.6 Hz), 7.45 (1H, s), 7.52 (1H, dd, J=8.6, 6.8 Hz), 7.81 (2H, m), 7.95 (1H, t, J=5.7 Hz).

Example 343

Preparation of 4-[4-amino-6-(5-chloro-1H,3H-2-thia-phenalen-6-yl)-[1,3,5]triazin-2-ylsulfanyl]-butyramide

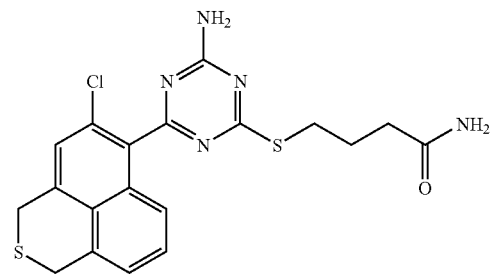

4-[4-amino-6-(5-chloro-1H,3H-benzo[de]isochromen-6-yl)-[1,3,5]triazin-2-ylsulfanyl]-butyramide (100 mg, 0.24 mmol) obtained in Example 339 was dissolved in dichloromethane (4 ml) at room temperature. To the solution was added boron tribromide (1.0M in dichloromethane, 0.96 ml) and the resulted suspension was stirred overnight. The mixture was concentrated followed by dilution with N,N-dimethylformamide (6 ml). To the mixture were added sodium sulfide nonahydrate (220 mg, 2.46 mmol) and N-ethyldiisopropylamine (0.2 ml) successively at room temperature for 6 hours. The mixture was diluted with ethyl acetate (100 ml), and washed with water (50 ml, 3 times), brine successively, and then dried over anhydrous sodium sulfate. After removal of inorganic salts by filtration, the filtrate was concentrated. The resulting residue was purified by silica gel thin layer chromatography (developing solvent; dichloromethane/methanol=9:1) to give 4-[4-amino-6-(5-chloro-1H,3H-2-thia-phenalen-6-yl)-[1,3,5]triazin-2-ylsulfanyl]-butyramide (52 mg, 49%) as a yellow solid.

ESI (LC/MS positive mode): m/z=432, 434(M+H$^+$)

$^1$H-NMR (270 MHz, CDCl$_3$) chemical shifts δ: 2.02-2.12 (2H, m), 2.34 (2H, t, J=6.9 Hz), 3.13 (2H, t, J=7.3 Hz), 4.12-4.19 (4H, m), 5.07 (1H, brs), 5.67 (2H, brs), 5.92 (1H, brs), 7.29-7.46 (4H, m).

Examples 150-174, 176-177, 179-204, 206-233, 235-269 and 271-313

The compounds described below can be synthesized by the same methods as described above.

TABLE 1

| | | |
|---|---|---|
| 150 | | N-{4-[4-amino-6-(5-chloro-1H,3H-benzo[de]isochromen-6-yl)-[1,3,5]triazin-2-ylsulfanyl]-butyl}-acetamide |
| 151 | | N-{2-[4-amino-6-(5-chloro-1H,3H-benzo[de]isochromen-6-yl)-[1,3,5]triazin-2-ylsulfanyl]-ethyl}-propionamide |
| 152 | | N-{2-[4-amino-6-(5-chloro-1H,3H-benzo[de]isochromen-6-yl)-[1,3,5]triazin-2-ylsulfanyl]-ethyl}-butylamide |
| 153 | | N-{2-[4-amino-6-(5-chloro-1H,3H-benzo[de]isochromen-6-yl)-[1,3,5]triazin-2-ylsulfanyl]-ethyl}-isobutylamide |
| 154 | | cyclopropane carboxylic acid {2-[4-amino-6-(5-chloro-1H,3H-benzo[de]isochromen-6-yl)-[1,3,5]triazin-2-ylsulfanyl]-ethyl}-amide |

| | | |
|---|---|---|
| 155 | 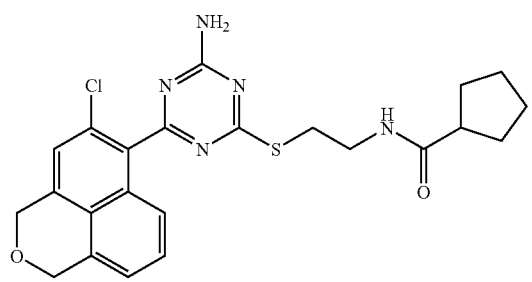 | cyclopentane carboxylic acid {2-[4-amino-6-(5-chloro-1H,3H-benzo[de]isochromen-6-yl)-[1,3,5]triazin-2-ylsulfanyl]-ethyl}-amide |
| 156 | 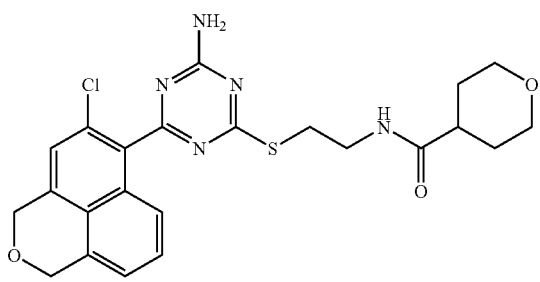 | tetrahydro-pyran-4-carboxylic acid {2-[4-amino-6-(5-chloro-1H,3H-benzo[de]isochromen-6-yl)-[1,3,5]triazin-2-ylsulfanyl]-ethyl}-amide |
| 157 | 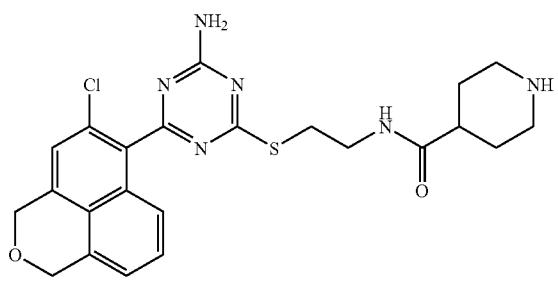 | piperidine-4-carboxylic acid {2-[4-amino-6-(5-chloro-1H,3H-benzo[de]isochromen-6-yl)-[1,3,5]triazin-2-ylsulfanyl]-ethyl}-amide |
| 158 | 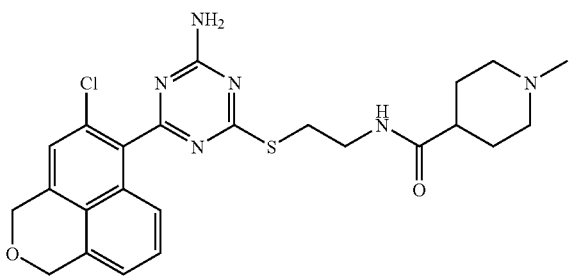 | 1-methyl-piperidine-4-carboxylic acid {2-[4-amino-6-(5-chloro-1H,3H-benzo[de]isochromen-6-yl)-[1,3,5]triazin-2-ylsulfanyl]-ethyl}-amide |
| 159 | 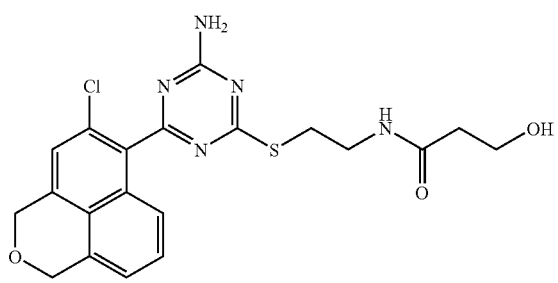 | N-{2-[4-amino-6-(5-chloro-1H,3H-benzo[de]isochromen-6-yl)-[1,3,5]triazin-2-ylsulfanyl]-ethyl}-3-hydroxypropionamide |

TABLE 1-continued

| # | Structure | Name |
|---|---|---|
| 160 | 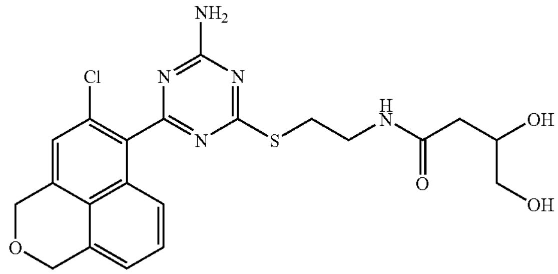 | N-{2-[4-amino-6-(5-chloro-1H,3H-benzo[de]isochromen-6-yl)-[1,3,5]triazin-2-ylsulfanyl]-ethyl}-3,4-dihydroxybutylamide |
| 161 | 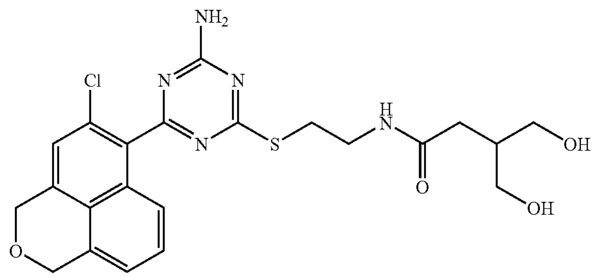 | N-{2-[4-amino-6-(5-chloro-1H,3H-benzo[de]isochromen-6-yl)-[1,3,5]triazin-2-ylsulfanyl]-ethyl}-4-hydroxy-3-hydroxymethylbutylamide |
| 162 | 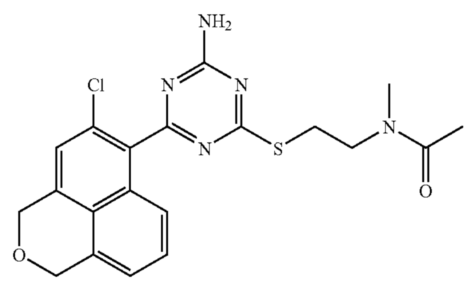 | N-{2-[4-amino-6-(5-chloro-1H,3H-benzo[de]isochromen-6-yl)-[1,3,5]triazin-2-ylsulfanyl]-ethyl}-N-methyl-acetamide |
| 163 | 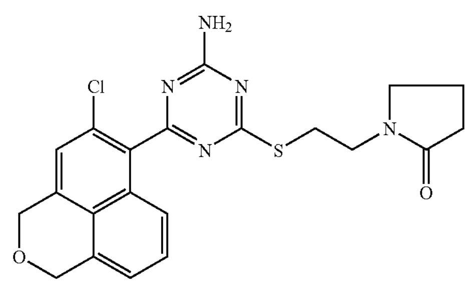 | 1-{2-[4-amino-6-(5-chloro-1H,3H-benzo[de]isochromen-6-yl)-[1,3,5]triazin-2-ylsulfanyl]-ethyl}-pyrrolidin-2-one |
| 164 | 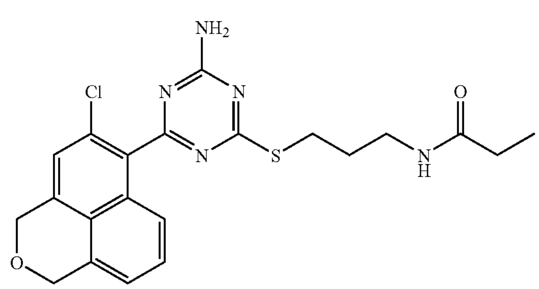 | N-{3-[4-amino-6-(5-chloro-1H,3H-benzo[de]isochromen-6-yl)-[1,3,5]triazin-2-ylsulfanyl]-propyl}-propionamide |

| | | |
|---|---|---|
| 165 | 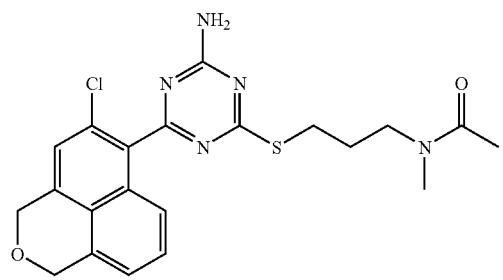 | N-{3-[4-amino-6-(5-chloro-1H,3H-benzo[de]isochromen-6-yl)-[1,3,5]triazin-2-ylsulfanyl]-propyl}-N-methyl-acetamide |
| 166 | 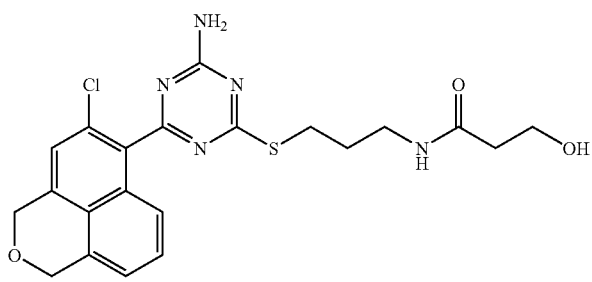 | N-{3-[4-amino-6-(5-chloro-1H,3H-benzo[de]isochromen-6-yl)-[1,3,5]triazin-2-ylsulfanyl]-propyl}-3-hydroxypropionamide |
| 167 | 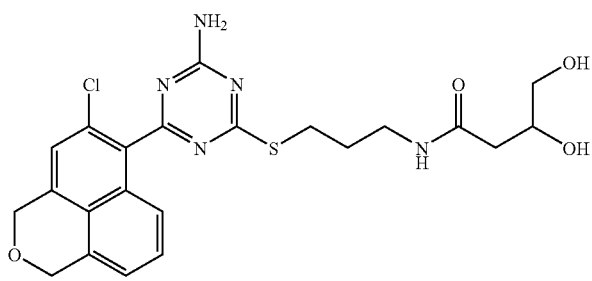 | N-{3-[4-amino-6-(5-chloro-1H,3H-benzo[de]isochromen-6-yl)-[1,3,5]triazin-2-ylsulfanyl]-propyl}-3,4-dihydroxybutylamide |
| 168 | 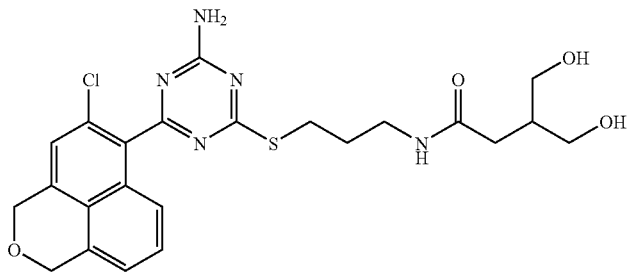 | N-{3-[4-amino-6-(5-chloro-1H,3H-benzo[de]isochromen-6-yl)-[1,3,5]triazin-2-ylsulfanyl]-propyl}-4-hydroxy-3-hydroxymethyl-butylamide |
| 169 | 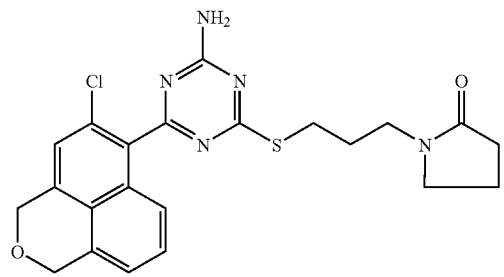 | 1-{3-[4-amino-6-(5-chloro-1H,3H-benzo[de]isochromen-6-yl)-[1,3,5]triazin-2-ylsulfanyl]-propyl}-pyrrolidin-2-one |

TABLE 1-continued

| | | |
|---|---|---|
| 170 | 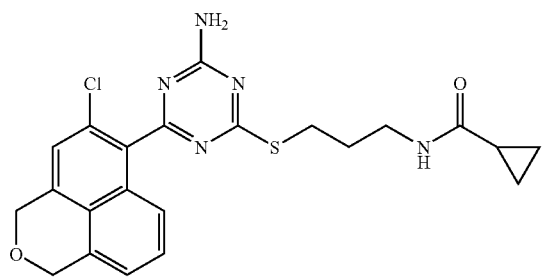 | cyclopropane carboxylic acid {3-[4-amino-6-(5-chloro-1H,3H-benzo[de]isochromen-6-yl)-[1,3,5]triazin-2-ylsulfanyl]-propyl}-amide |
| 171 | 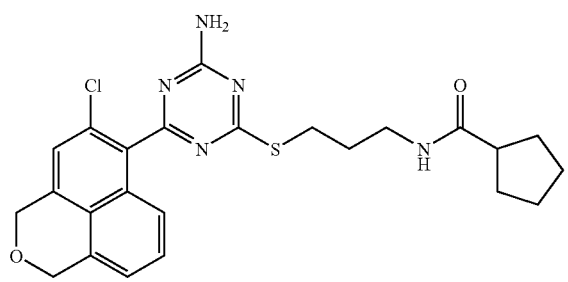 | cyclopentane carboxylic acid {3-[4-amino-6-(5-chloro-1H,3H-benzo[de]isochromen-6-yl)-[1,3,5]triazin-2-ylsulfanyl]-propyl}-amide |
| 172 | 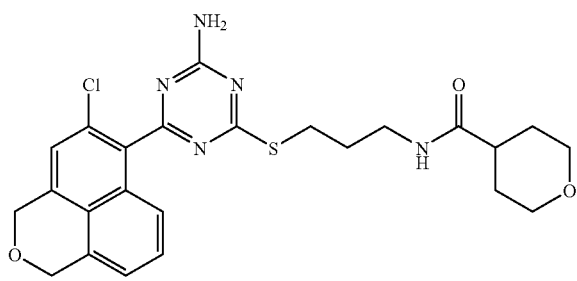 | tetrahydro-pyran-4-carboxylic acid {3-[4-amino-6-(5-chloro-1H,3H-benzo[de]isochromen-6-yl)-[1,3,5]triazin-2-ylsulfanyl]-propyl}-amide |
| 173 | 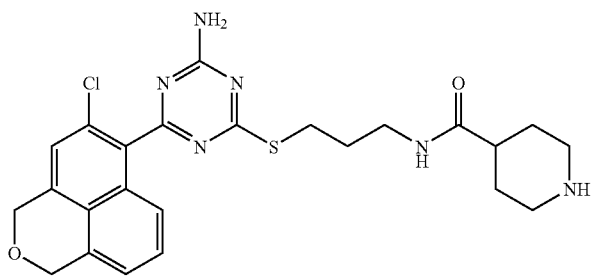 | piperidin-4-carboxylic acid {3-[4-amino-6-(5-chloro-1H,3H-benzo[de]isochromen-6-yl)-[1,3,5]triazin-2-ylsulfanyl]-propyl}-amide |
| 174 | 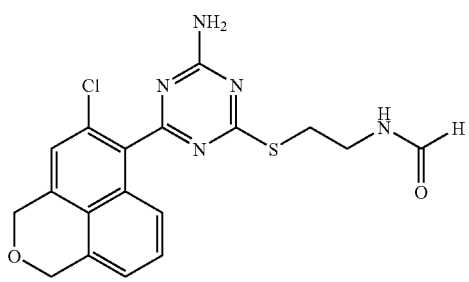 | N-{2-[4-amino-6-(5-chloro-1H,3H-benzo[de]isochromen-6-yl)-[1,3,5]triazin-2-ylsulfanyl]-ethyl}-formamide |

TABLE 1-continued

| | | |
|---|---|---|
| 176 | 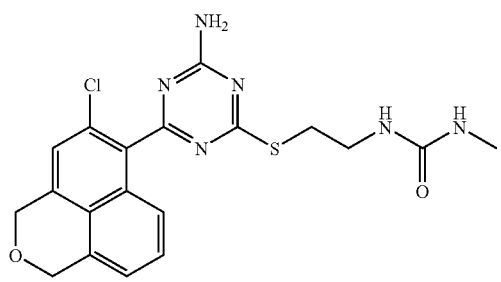 | 1-{2-[4-amino-6-(5-chloro-1H,3H-benzo[de]isochromen-6-yl)-[1,3,5]triazin-2-ylsulfanyl]-ethyl}-3-methylurea |
| 177 | 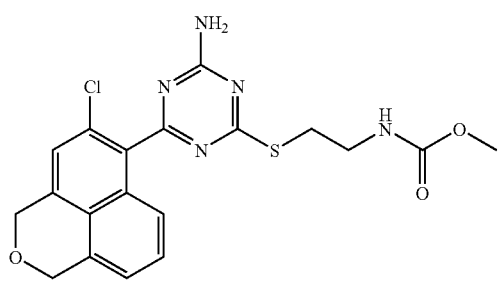 | {2-[4-amino-6-(5-chloro-1H,3H-benzo[de]isochromen-6-yl)-[1,3,5]triazin-2-ylsulfanyl]-ethyl}-carbamic acid methyl ester |
| 179 | 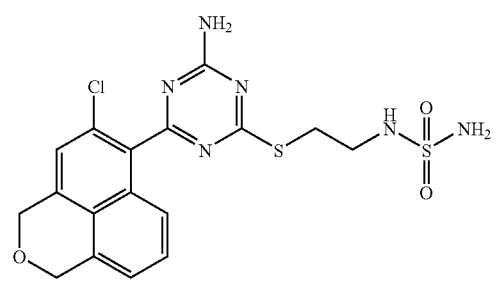 | N-{3-[4-amino-6-(5-chloro-1H,3H-benzo[de]isochromen-6-yl)-[1,3,5]triazin-2-ylsulfanyl]-ethyl}-aminosulfonamide |
| 180 | 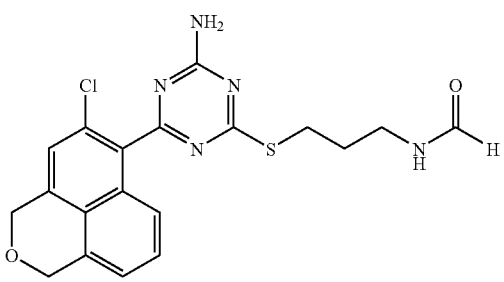 | N-{3-[4-amino-6-(5-chloro-1H,3H-benzo[de]isochromen-6-yl)-[1,3,5]triazin-2-ylsulfanyl]-propyl}-formamide |
| 181 | 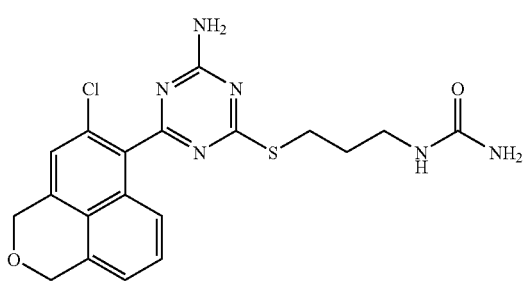 | {3-[4-amino-6-(5-chloro-1H,3H-benzo[de]isochromen-6-yl)-[1,3,5]triazin-2-ylsulfanyl]-propyl}-urea |

TABLE 1-continued

| 182 | 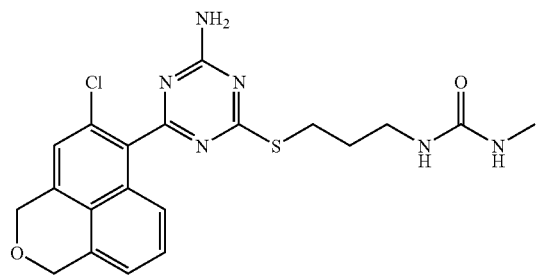 | 1-{3-[4-amino-6-(5-chloro-1H,3H-benzo[de]isochromen-6-yl)-[1,3,5]triazin-2-ylsulfanyl]-propyl}-3-methylurea |
| --- | --- | --- |
| 183 | 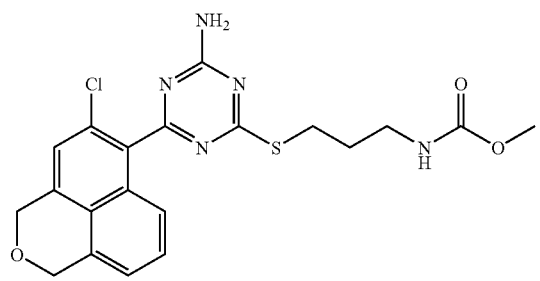 | {3-[4-amino-6-(5-chloro-1H,3H-benzo[de]isochromen-6-yl)-[1,3,5]triazin-2-ylsulfanyl]-propyl}-carbamic acid methyl ester |
| 184 | 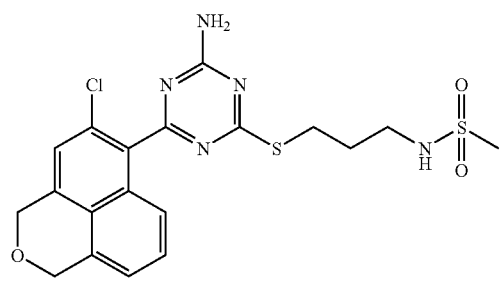 | N-{3-[4-amino-6-(5-chloro-1H,3H-benzo[de]isochromen-6-yl)-[1,3,5]triazin-2-ylsulfanyl]-propyl}-methanesulfonamide |
| 185 | 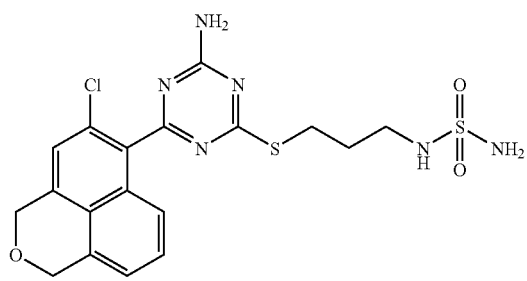 | N-{3-[4-amino-6-(5-chloro-1H,3H-benzo[de]isochromen-6-yl)-[1,3,5]triazin-2-ylsulfanyl]-propyl}-aminosulfonamide |
| 186 | 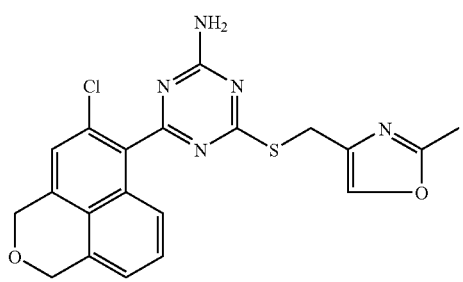 | 4-(5-chloro-1H,3H-benzo[de]isochromen-6-yl)-6-(2-methyl-oxazol-4-ylmethylsulfanyl)-[1,3,5]triazin-2-ylamine |

| | | |
|---|---|---|
| 187 | 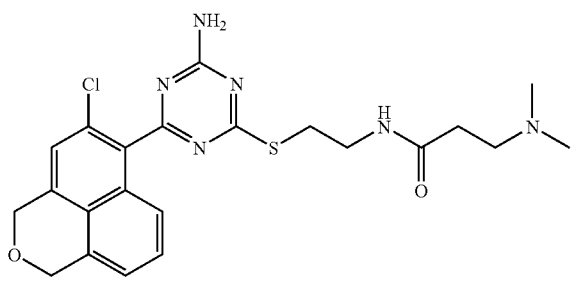 | N-{2-[4-amino-6-(5-chloro-1H,3H-benzo[de]isochromen-6-yl)-[1,3,5]triazin-2-ylsulfanyl]-ethyl}-3-dimethylaminopriopionamide |
| 188 | 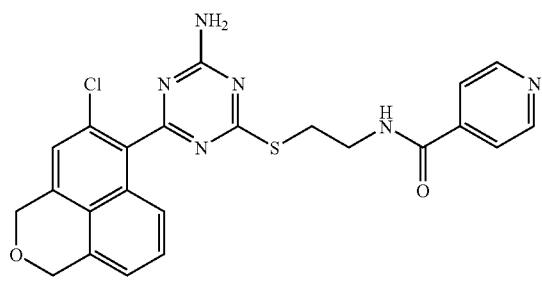 | N-{2-[4-amino-6-(5-chloro-1H,3H-benzo[de]isochromen-6-yl)-[1,3,5]triazin-2-ylsulfanyl]-ethyl}-isonicotinamide |
| 189 | 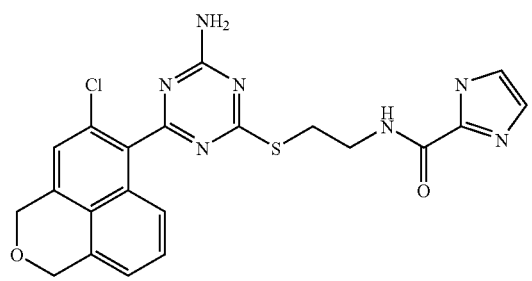 | 1H-imidazole-2-carboxylic acid {2-[4-amino-6-(5-chloro-1H,3H-benzo[de]isochromen-6-yl)-[1,3,5]triazin-2-ylsulfanyl]-ethyl}-amide |
| 190 | 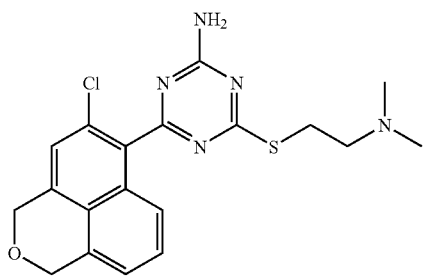 | 4-(5-chloro-1H,3H-benzo[de]isochromen-6-yl)-6-(2-dimethylamino-ethylsulfanyl)-[1,3,5]triazin-2-ylamine |
| 191 | 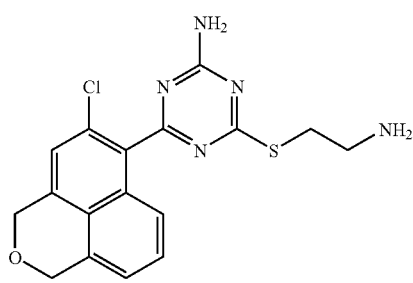 | 4-(2-aminoethylsulfanyl)-6-(5-chloro-1H,3H-benzo[de]isochromen-6-yl)-[1,3,5]triazin-2-ylamine |

TABLE 1-continued

| | | |
|---|---|---|
| 192 | 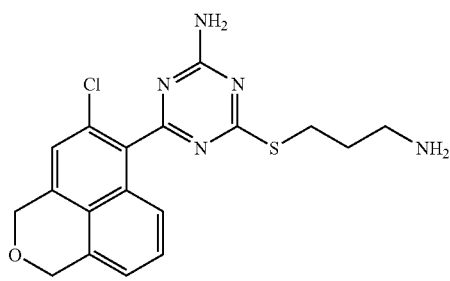 | 4-(3-aminopropylsulfanyl)-6-(5-chloro-1H,3H-benzo[de]isochromen-6-yl)-[1,3,5]triazin-2-ylamine |
| 193 | 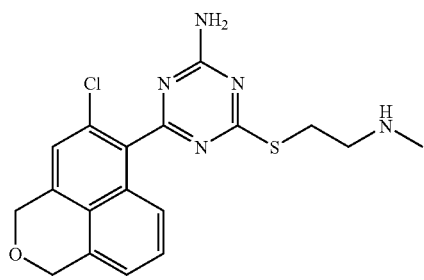 | 4-(5-chloro-1H,3H-benzo[de]isochromen-6-yl)-6-(2-methylaminoethylsulfanyl)-[1,3,5]triazin-2-ylamine |
| 194 | 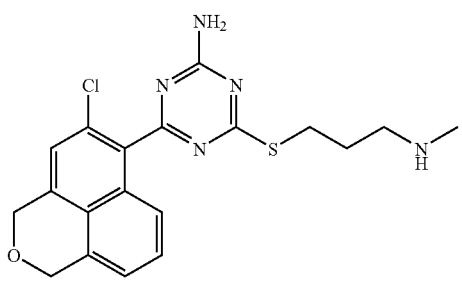 | 4-(5-chloro-1H,3H-benzo[de]isochromen-6-yl)-6-(3-methylaminopropylsulfanyl)-[1,3,5]triazin-2-ylamine |
| 195 | 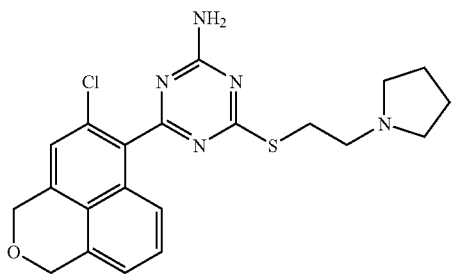 | 4-(5-chloro-1H,3H-benzo[de]isochromen-6-yl)-6-(2-pyrolidin-1-yl-ethylsulfanyl)-[1,3,5]triazin-2-ylamine |
| 196 | 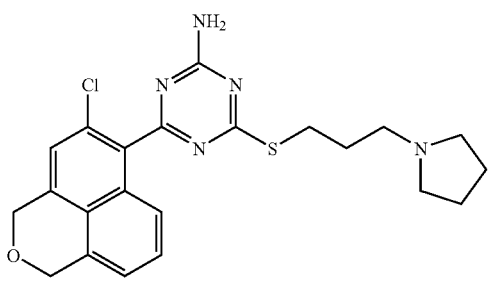 | 4-(5-chloro-1H,3H-benzo[de]isochromen-6-yl)-6-(3-pyrolidin-1-yl-propylsulfanyl)-[1,3,5]triazin-2-ylamine |

| | | |
|---|---|---|
| 197 | 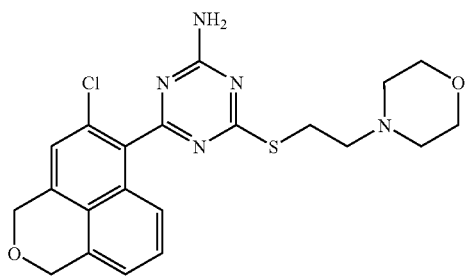 | 4-(5-chloro-1H,3H-benzo[de]isochromen-6-yl)-6-(2-morpholin-4-yl-ethylsulfanyl)-[1,3,5]triazin-2-ylamine |
| 198 | 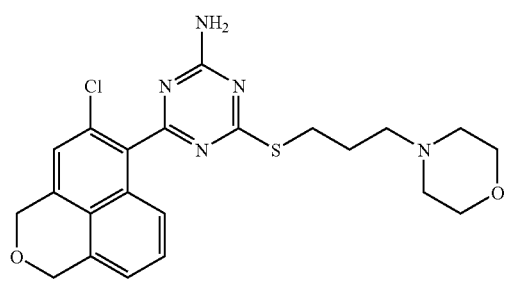 | 4-(5-chloro-1H,3H-benzo[de]isochromen-6-yl)-6-(3-morpholin-4-yl-propylsulfanyl)-[1,3,5]triazin-2-ylamine |
| 199 | 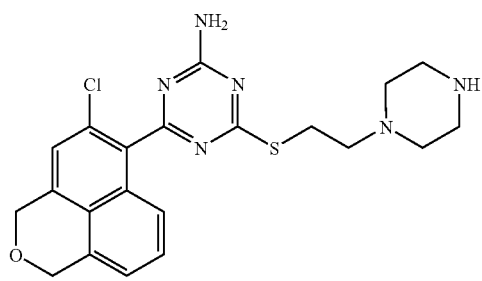 | 4-(5-chloro-1H,3H-benzo[de]isochromen-6-yl)-6-(2-piperazin-1-yl-ethylsulfanyl)-[1,3,5]triazin-2-ylamine |
| 200 | 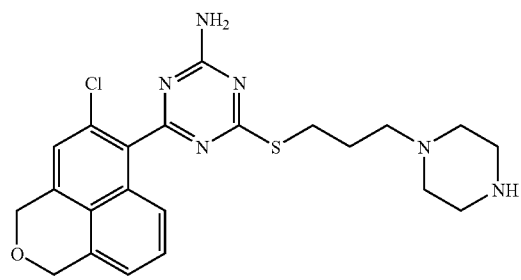 | 4-(5-chloro-1H,3H-benzo[de]isochromen-6-yl)-6-(3-piperazin-1-yl-propylsulfanyl)-[1,3,5]triazin-2-ylamine |
| 201 | 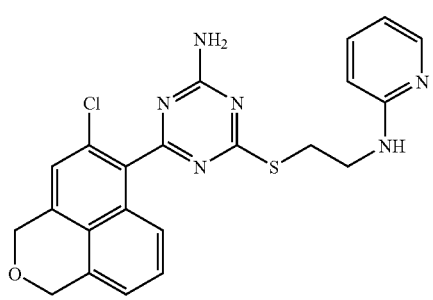 | 4-(5-chloro-1H,3H-benzo[de]isochromen-6-yl)-6-[2-(pyridin-2-ylamino)-ethylsulfanyl]-[1,3,5]triazin-2-ylamine |

TABLE 1-continued

| 202 | 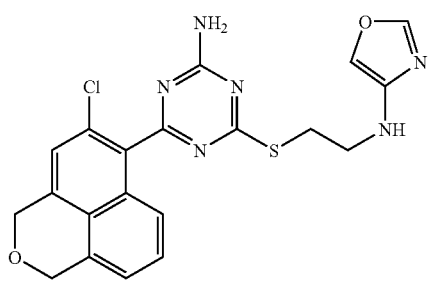 | 4-(5-chloro-1H,3H-benzo[de]isochromen-6-yl)-6-[2-(oxazol-4-ylamino)-ethylsulfanyl]-[1,3,5]triazin-2-ylamine |
| 203 | 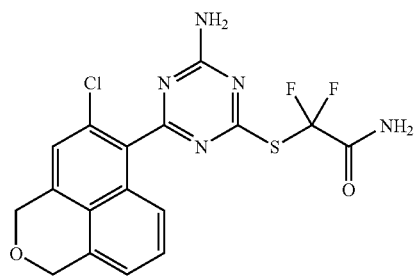 | 2-[4-amino-6-(5-chloro-1H,3H-benzo[de]isochromen-6-yl)-[1,3,5]triazin-2-ylsulfanyl]-2,2-difluoroacetamide |
| 204 | 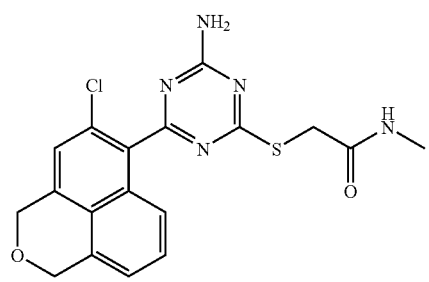 | 2-[4-amino-6-(5-chloro-1H,3H-benzo[de]isochromen-6-yl)-[1,3,5]triazin-2-ylsulfanyl]-N-methyl-acetamide |
| 206 | 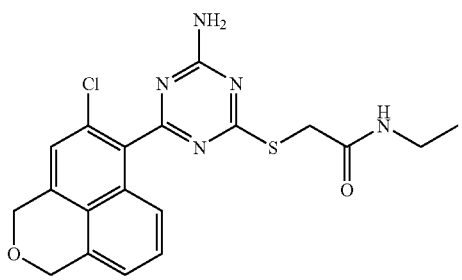 | 2-[4-amino-6-(5-chloro-1H,3H-benzo[de]isochromen-6-yl)-[1,3,5]triazin-2-ylsulfanyl]-N-ethyl-acetamide |
| 207 | 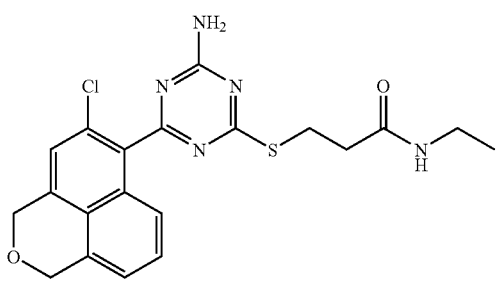 | 3-[4-amino-6-(5-chloro-1H,3H-benzo[de]isochromen-6-yl)-[1,3,5]triazin-2-ylsulfanyl]-N-ethyl-propionamide |

| | | |
|---|---|---|
| 208 | 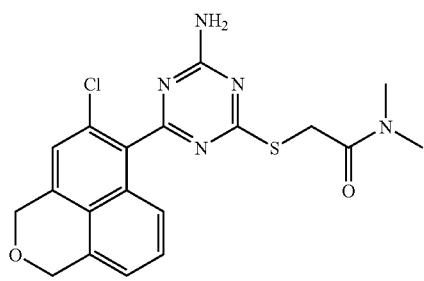 | 2-[4-amino-6-(5-chloro-1H,3H-benzo[de]isochromen-6-yl)-[1,3,5]triazin-2-ylsulfanyl]-N,N-dimethyl-acetamide |
| 209 | 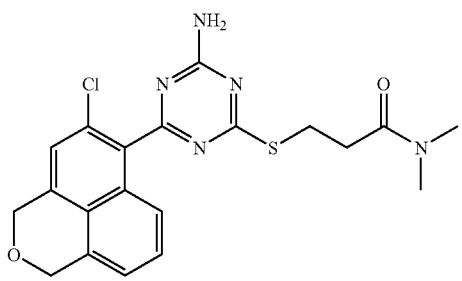 | 3-[4-amino-6-(5-chloro-1H,3H-benzo[de]isochromen-6-yl)-[1,3,5]triazin-2-ylsulfanyl]-N,N-dimethyl-propionamide |
| 210 | 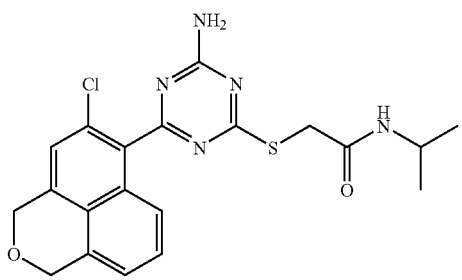 | 2-[4-amino-6-(5-chloro-1H,3H-benzo[de]isochromen-6-yl)-[1,3,5]triazin-2-ylsulfanyl]-N-isopropyl-acetamide |
| 211 | 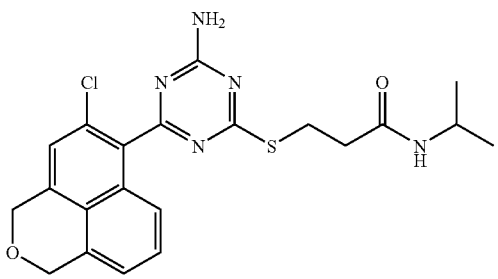 | 3-[4-amino-6-(5-chloro-1H,3H-benzo[de]isochromen-6-yl)-[1,3,5]triazin-2-ylsulfanyl]-N-isopropyl-propionamide |
| 212 | 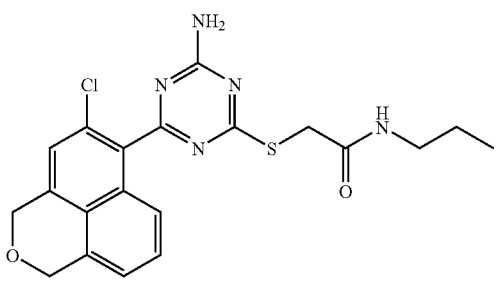 | 2-[4-amino-6-(5-chloro-1H,3H-benzo[de]isochromen-6-yl)-[1,3,5]triazin-2-ylsulfanyl]-N-propyl-acetamide |

TABLE 1-continued

| | | |
|---|---|---|
| 213 | 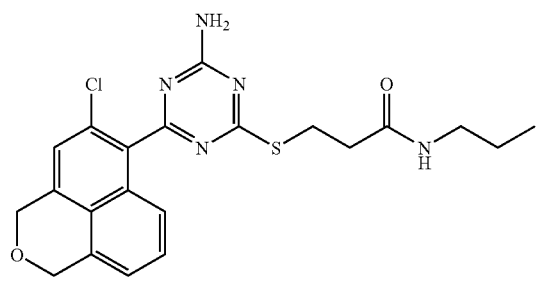 | 3-[4-amino-6-(5-chloro-1H,3H-benzo[de]isochromen-6-yl)-[1,3,5]triazin-2-ylsulfanyl]-N-propyl-propionamide |
| 214 | 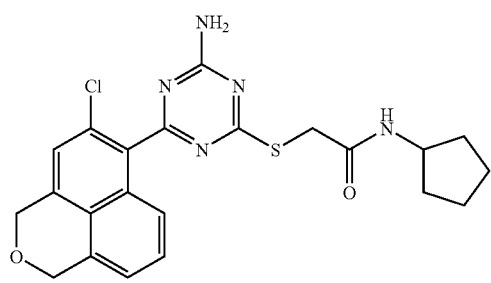 | 2-[4-amino-6-(5-chloro-1H,3H-benzo[de]isochromen-6-yl)-[1,3,5]triazin-2-ylsulfanyl]-N-cyclopentyl-acetamide |
| 215 | 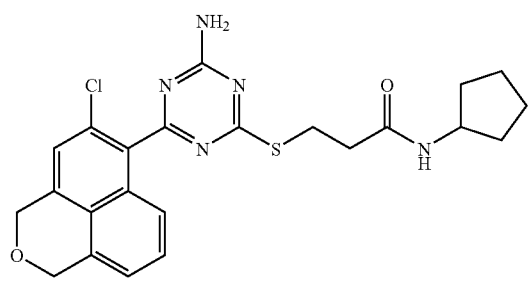 | 3-[4-amino-6-(5-chloro-1H,3H-benzo[de]isochromen-6-yl)-[1,3,5]triazin-2-ylsulfanyl]-N-cyclopentyl-propionamide |
| 216 | 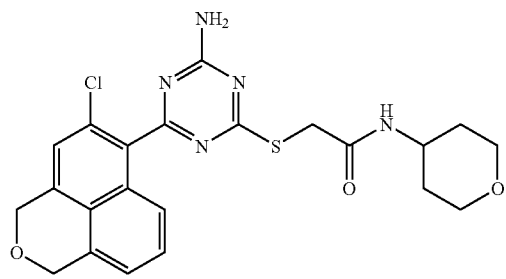 | 2-[4-amino-6-(5-chloro-1H,3H-benzo[de]isochromen-6-yl)-[1,3,5]triazin-2-ylsulfanyl]-N-(tetrahydro-pyran-4-yl)-acetamide |
| 217 | 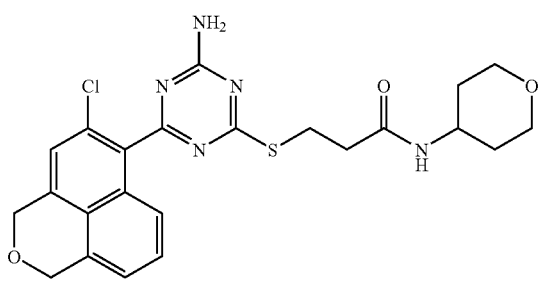 | 3-[4-amino-6-(5-chloro-1H,3H-benzo[de]isochromen-6-yl)-[1,3,5]triazin-2-ylsulfanyl]-N-(tetrahydro-pyran-4-yl)-propionamide |

| | | |
|---|---|---|
| 218 | 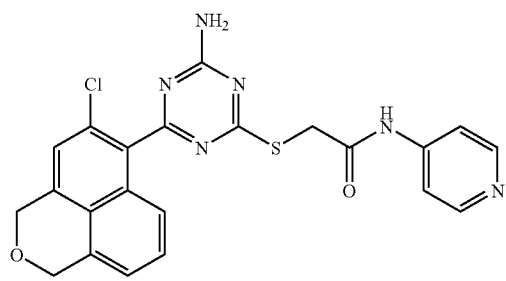 | 2-[4-amino-6-(5-chloro-1H,3H-benzo[de]isochromen-6-yl)-[1,3,5]triazin-2-ylsulfanyl]-N-pyridin-4-yl-acetamide |
| 219 | 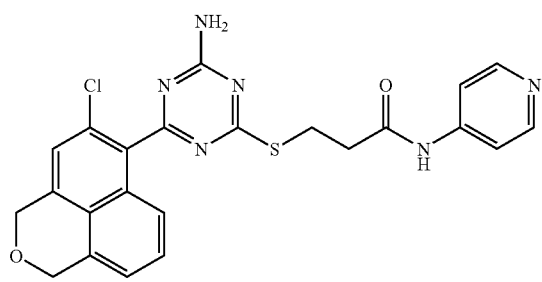 | 3-[4-amino-6-(5-chloro-1H,3H-benzo[de]isochromen-6-yl)-[1,3,5]triazin-2-ylsulfanyl]-N-pyridin-4-yl-propionamide |
| 220 | 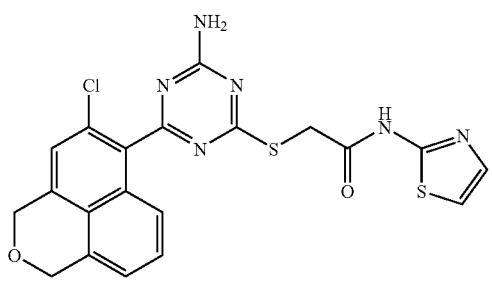 | 2-[4-amino-6-(5-chloro-1H,3H-benzo[de]isochromen-6-yl)-[1,3,5]triazin-2-ylsulfanyl]-N-thiazol-2-yl-acetamide |
| 221 | 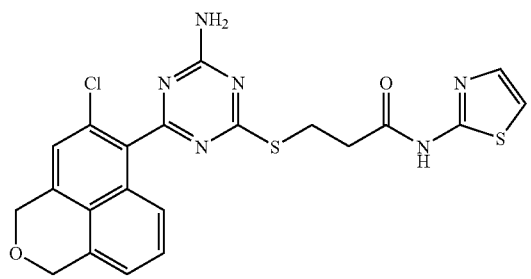 | 3-[4-amino-6-(5-chloro-1H,3H-benzo[de]isochromen-6-yl)-[1,3,5]triazin-2-ylsulfanyl]-N-thiazol-2-yl-propionamide |
| 222 | 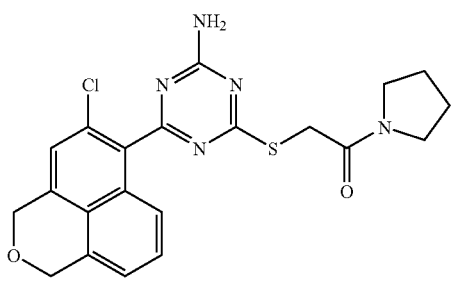 | 2-[4-amino-6-(5-chloro-1H,3H-benzo[de]isochromen-6-yl)-[1,3,5]triazin-2-ylsulfanyl]-1-pyrrolidin-1-yl-ethanone |

| | | |
|---|---|---|
| 223 | 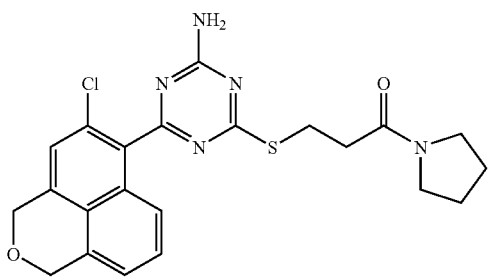 | 3-[4-amino-6-(5-chloro-1H,3H-benzo[de]isochromen-6-yl)-[1,3,5]triazin-2-ylsulfanyl]-1-pyrrolidin-1-yl-propan-1-one |
| 224 | 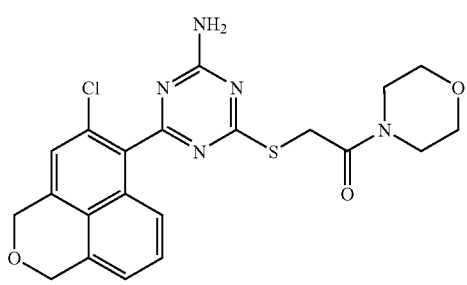 | 2-[4-amino-6-(5-chloro-1H,3H-benzo[de]isochromen-6-yl)-[1,3,5]triazin-2-ylsulfanyl]-1-morpholin-4-yl-ethanone |
| 225 | 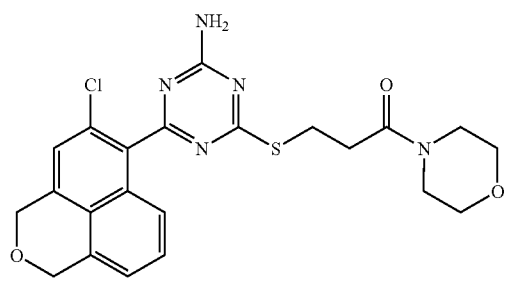 | 3-[4-amino-6-(5-chloro-1H,3H-benzo[de]isochromen-6-yl)-[1,3,5]triazin-2-ylsulfanyl]-1-morpholin-4-yl-propan-1-one |
| 226 | 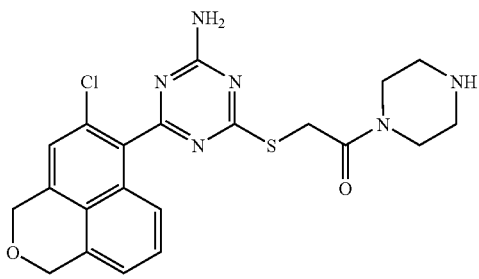 | 2-[4-amino-6-(5-chloro-1H,3H-benzo[de]isochromen-6-yl)-[1,3,5]triazin-2-ylsulfanyl]-1-piperazin-1-yl-ethanone |
| 227 | 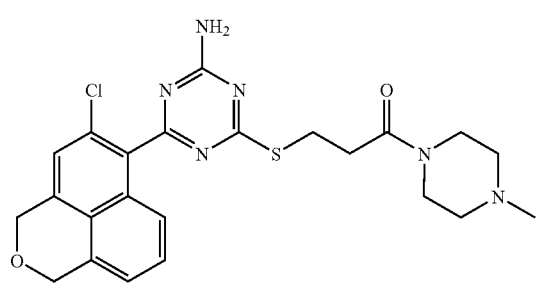 | 3-[4-amino-6-(5-chloro-1H,3H-benzo[de]isochromen-6-yl)-[1,3,5]triazin-2-ylsulfanyl]-1-(4-methyl-piperazin-1-yl)-propan-1-one |

TABLE 1-continued

| | | |
|---|---|---|
| 228 | 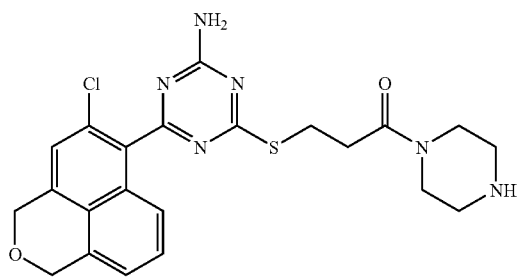 | 3-[4-amino-6-(5-chloro-1H,3H-benzo[de]isochromen-6-yl)-[1,3,5]triazin-2-ylsulfanyl]-1-piperazin-1-yl-propan-1-one |
| 229 | 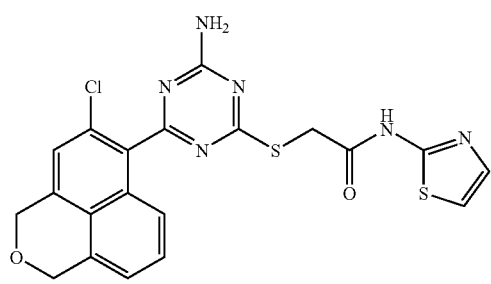 | 2-[4-amino-6-(5-chloro-1H,3H-benzo[de]isochromen-6-yl)-[1,3,5]triazin-2-ylsulfanyl]-N-thiazol-2-yl-acetamide |
| 230 | 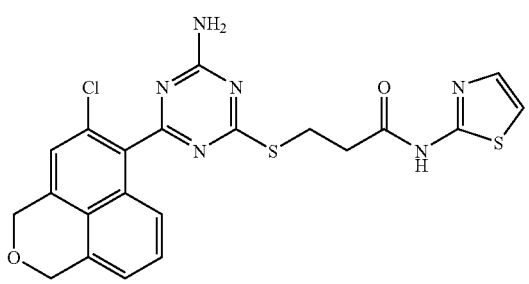 | 3-[4-amino-6-(5-chloro-1H,3H-benzo[de]isochromen-6-yl)-[1,3,5]triazin-2-ylsulfanyl]-N-thiazol-2-yl-propionamide |
| 231 | 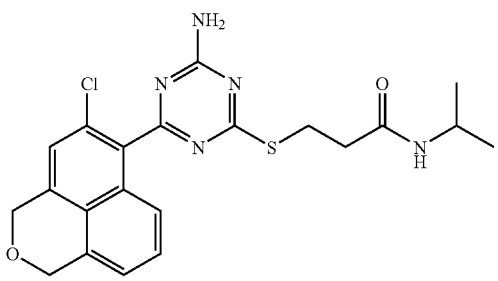 | 3-[4-amino-6-(5-chloro-1H,3H-benzo[de]isochromen-6-yl)-[1,3,5]triazin-2-ylsulfanyl]-N-isopropyl-propionamide |
| 232 | 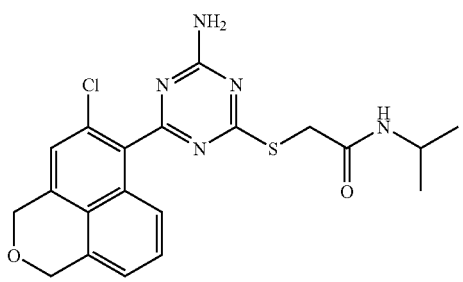 | 2-[4-amino-6-(5-chloro-1H,3H-benzo[de]isochromen-6-yl)-[1,3,5]triazin-2-ylsulfanyl]-N-isopropyl-acetamide |

| | | |
|---|---|---|
| 233 | 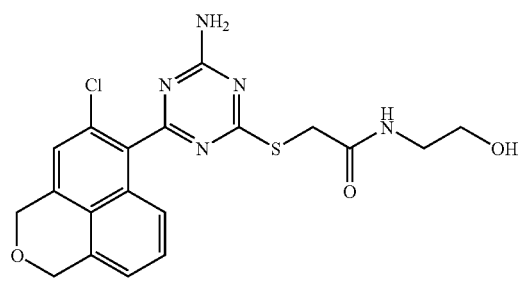 | 2-[4-amino-6-(5-chloro-1H,3H-benzo[de]isochromen-6-yl)-[1,3,5]triazin-2-ylsulfanyl]-N-(2-hydroxy-ethyl)-acetamide |
| 235 | 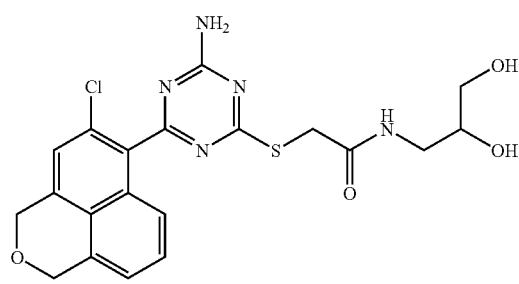 | 2-[4-amino-6-(5-chloro-1H,3H-benzo[de]isochromen-6-yl)-[1,3,5]triazin-2-ylsulfanyl]-N-(2,3-dihydroxypropyl)-acetamide |
| 236 | 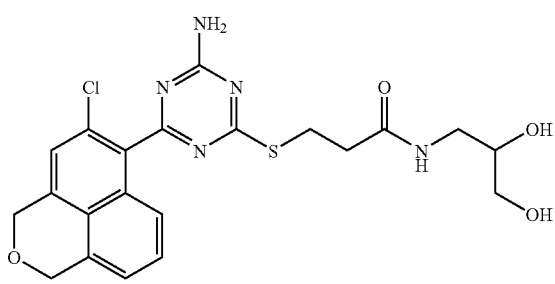 | 3-[4-amino-6-(5-chloro-1H,3H-benzo[de]isochromen-6-yl)-[1,3,5]triazin-2-ylsulfanyl]-N-(2,3-dihydroxypropyl)-propionamide |
| 237 | 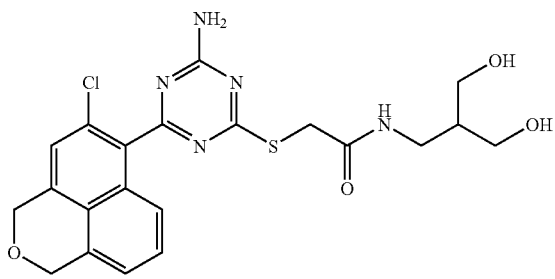 | 2-[4-amino-6-(5-chloro-1H,3H-benzo[de]isochromen-6-yl)-[1,3,5]triazin-2-ylsulfanyl]-N-(3-hydroxy-2-hydroxymethyl-propyl)-acetamide |
| 238 | 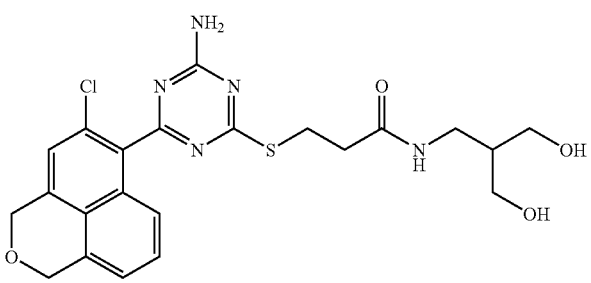 | 3-[4-amino-6-(5-chloro-1H,3H-benzo[de]isochromen-6-yl)-[1,3,5]triazin-2-ylsulfanyl]-N-(3-hydroxy-2-hydroxymethyl-propyl)-propionamide |

TABLE 1-continued

| 239 | 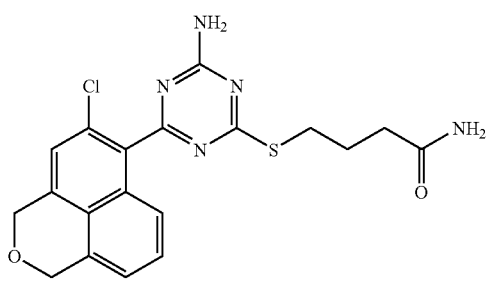 | 4-[4-amino-6-(5-chloro-1H,3H-benzo[de]isochromen-6-yl)-[1,3,5]triazin-2-ylsulfanyl]-butylamide |
| --- | --- | --- |
| 240 | 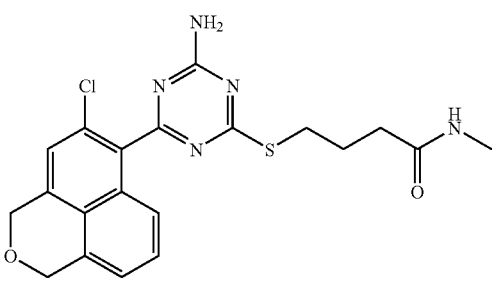 | 4-[4-amino-6-(5-chloro-1H,3H-benzo[de]isochromen-6-yl)-[1,3,5]triazin-2-ylsulfanyl]-N-methyl-butylamide |
| 241 | 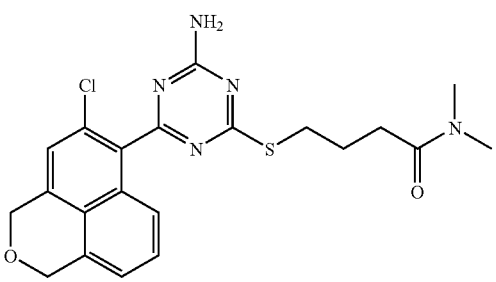 | 4-[4-amino-6-(5-chloro-1H,3H-benzo[de]isochromen-6-yl)-[1,3,5]triazin-2-ylsulfanyl]-N,N-dimethyl-butylamide |
| 242 | 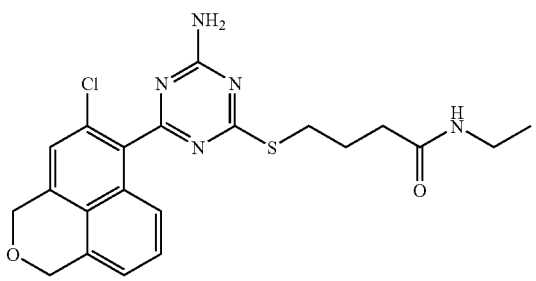 | 4-[4-amino-6-(5-chloro-1H,3H-benzo[de]isochromen-6-yl)-[1,3,5]triazin-2-ylsulfanyl]-N-ethyl-butylamide |
| 243 | 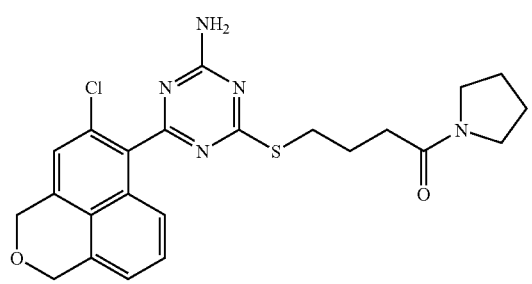 | 4-[4-amino-6-(5-chloro-1H,3H-benzo[de]isochromen-6-yl)-[1,3,5]triazin-2-ylsulfanyl]-1-pyrrolidin-1-yl-butan-1-one |

TABLE 1-continued

| 244 | 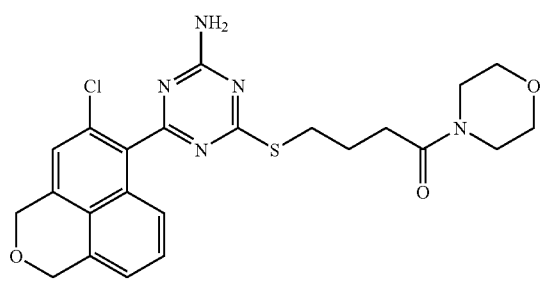 | 4-[4-amino-6-(5-chloro-1H,3H-benzo[de]isochromen-6-yl)-[1,3,5]triazin-2-ylsulfanyl]-1-morpholin-4-yl-butan-1-one |
| --- | --- | --- |
| 245 | 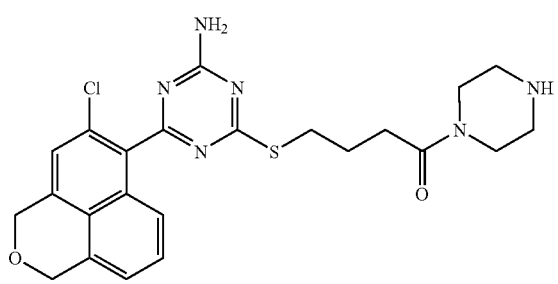 | 4-[4-amino-6-(5-chloro-1H,3H-benzo[de]isochromen-6-yl)-[1,3,5]triazin-2-ylsulfanyl]-1-piperazin-1-yl-butan-1-one |
| 246 | 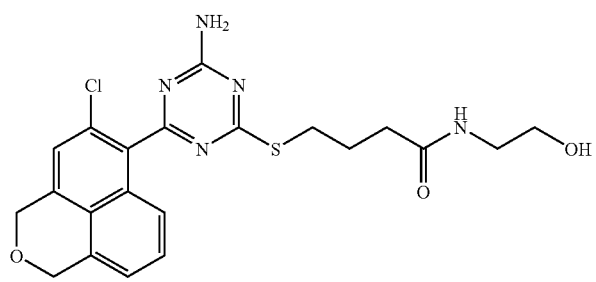 | 4-[4-amino-6-(5-chloro-1H,3H-benzo[de]isochromen-6-yl)-[1,3,5]triazin-2-ylsulfanyl]-N-(2-hydroxy-ethyl)-butylamide |
| 247 | 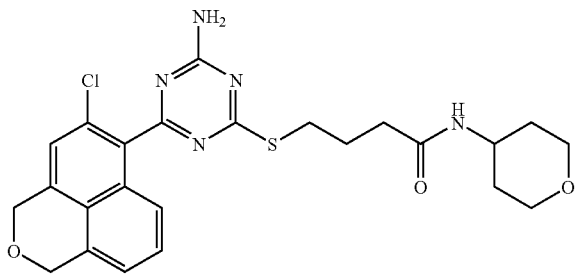 | 4-[4-amino-6-(5-chloro-1H,3H-benzo[de]isochromen-6-yl)-[1,3,5]triazin-2-ylsulfanyl]-N-(tetrahydro-pyran-4-yl)-butylamide |
| 248 | 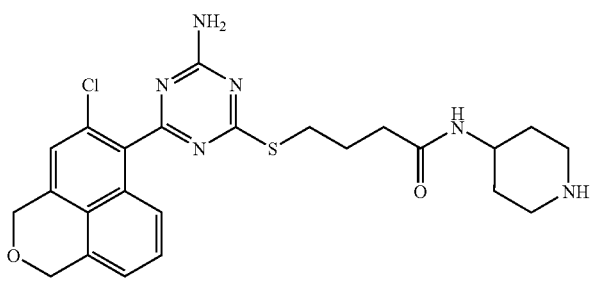 | 4-[4-amino-6-(5-chloro-1H,3H-benzo[de]isochromen-6-yl)-[1,3,5]triazin-2-ylsulfanyl]-N-piperidin-4-yl-butylamide |

| | | |
|---|---|---|
| 249 | 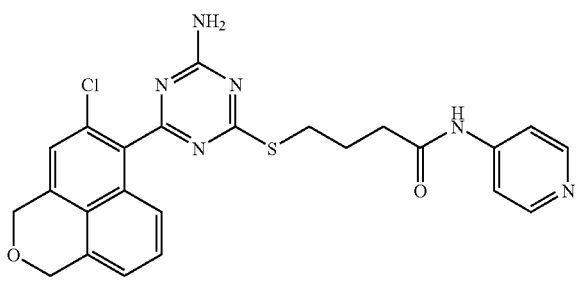 | 4-[4-amino-6-(5-chloro-1H,3H-benzo[de]isochromen-6-yl)-[1,3,5]triazin-2-ylsulfanyl]-N-pyridin-4-yl-butylamide |
| 250 | 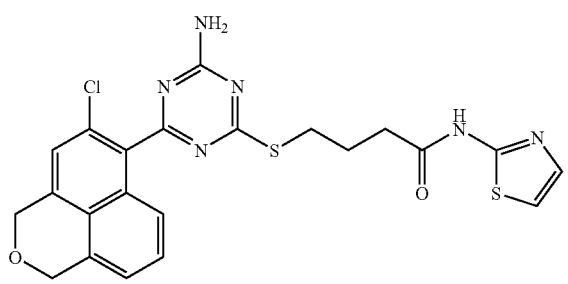 | 4-[4-amino-6-(5-chloro-1H,3H-benzo[de]isochromen-6-yl)-[1,3,5]triazin-2-ylsulfanyl]-N-thiazol-2-yl-butylamide |
| 251 | 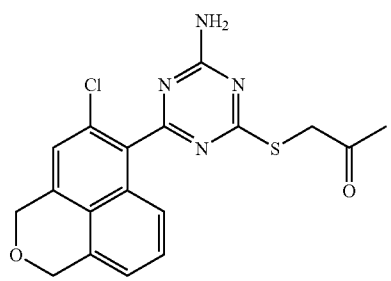 | 1-[4-amino-6-(5-chloro-1H,3H-benzo[de]isochromen-6-yl)-[1,3,5]triazin-2-ylsulfanyl]-propan-2-one |
| 252 | 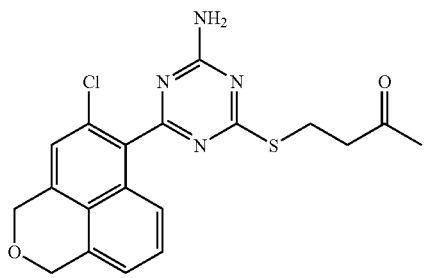 | 4-[4-amino-6-(5-chloro-1H,3H-benzo[de]isochromen-6-yl)-[1,3,5]triazin-2-ylsulfanyl]-butan-2-one |
| 253 | 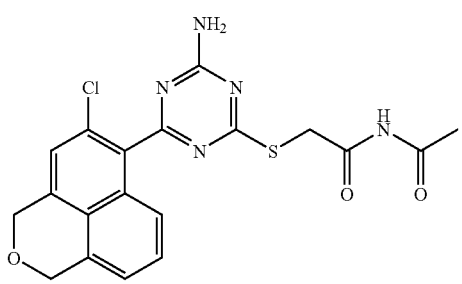 | N-{2-[4-amino-6-(5-chloro-1H,3H-benzo[de]isochromen-6-yl)-[1,3,5]triazin-2-ylsulfanyl]-acetyl}-acetamide |

TABLE 1-continued

| 254 | 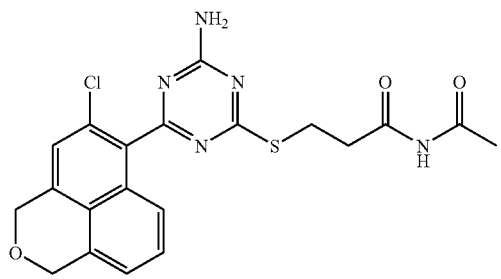 | N-{3-[4-amino-6-(5-chloro-1H,3H-benzo[de]isochromen-6-yl)-[1,3,5]triazin-2-ylsulfanyl]-propionyl}-acetamide |
| --- | --- | --- |
| 255 | 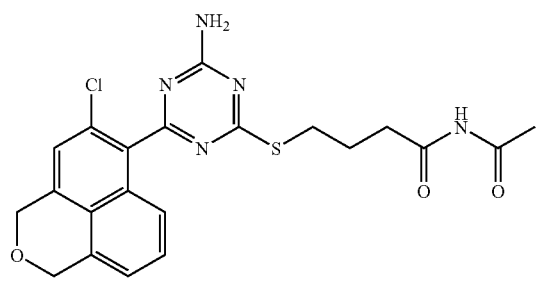 | N-{4-[4-amino-6-(5-chloro-1H,3H-benzo[de]isochromen-6-yl)-[1,3,5]triazin-2-ylsulfanyl]-butyryl}-acetamide |
| 256 | 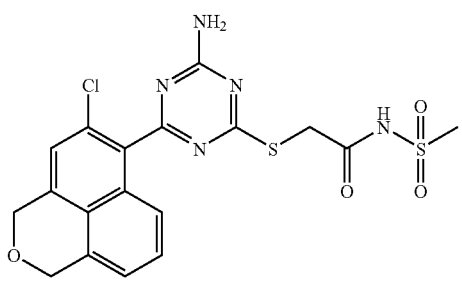 | N-{2-[4-amino-6-(5-chloro-1H,3H-benzo[de]isochromen-6-yl)-[1,3,5]triazin-2-ylsulfanyl]-acetyl}-methanesulfonamide |
| 257 | 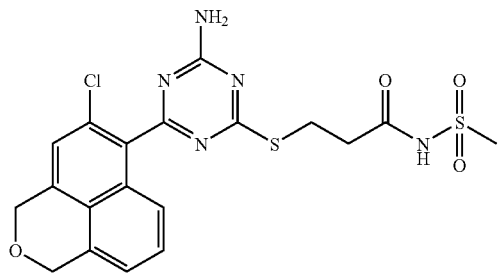 | N-{3-[4-amino-6-(5-chloro-1H,3H-benzo[de]isochromen-6-yl)-[1,3,5]triazin-2-ylsulfanyl]-propionyl}-methanesulfonamide |
| 258 | 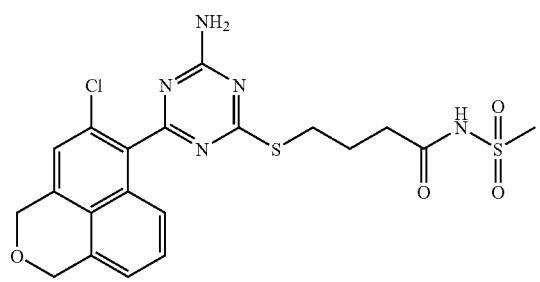 | N-{4-[4-amino-6-(5-chloro-1H,3H-benzo[de]isochromen-6-yl)-[1,3,5]triazin-2-ylsulfanyl]-butyryl}-methanesulfonamide |

| | | |
|---|---|---|
| 259 | 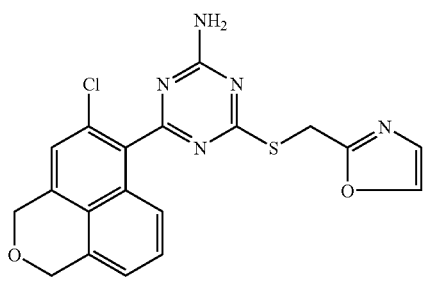 | 4-(5-chloro-1H,3H-benzo[de]isochromen-6-yl)-6-(oxazol-2-ylmethylsulfanyl)-[1,3,5]triazin-2-ylamine |
| 260 | 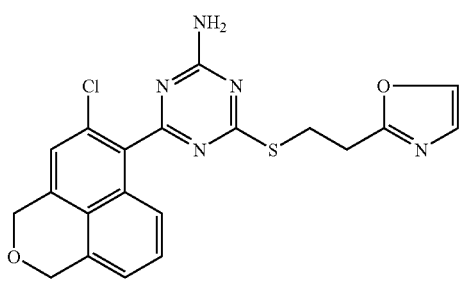 | 4-(5-chloro-1H,3H-benzo[de]isochromen-6-yl)-6-(2-oxazol-2-yl-ethylsulfanyl)-[1,3,5]triazin-2-ylamine |
| 261 | 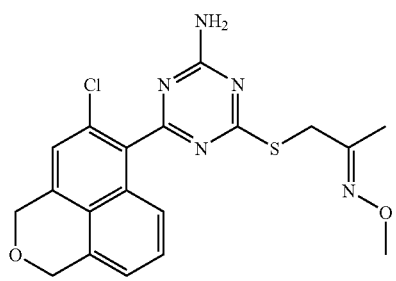 | 1-[4-amino-6-(5-chloro-1H,3H-benzo[de]isochromen-6-yl)-[1,3,5]triazin-2-ylsulfanyl]-propan-2-one O-methyl-oxime |
| 262 | 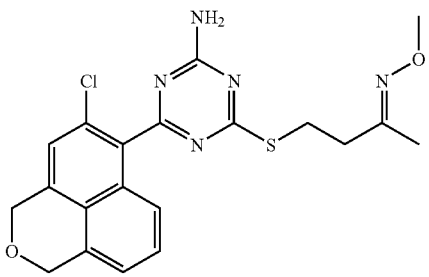 | 4-[4-amino-6-(5-chloro-1H,3H-benzo[de]isochromen-6-yl)-[1,3,5]triazin-1-ylsulfanyl]-butan-2-one O-methyl-oxime |
| 263 | 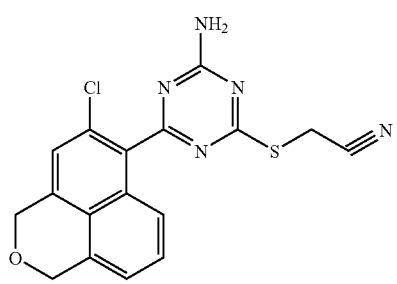 | [4-amino-6-(5-chloro-1H,3H-benzo[de]isochromen-6-yl)-[1,3,5]triazin-2-ylsulfanyl]-acetonitrile |

| | | |
|---|---|---|
| 264 | 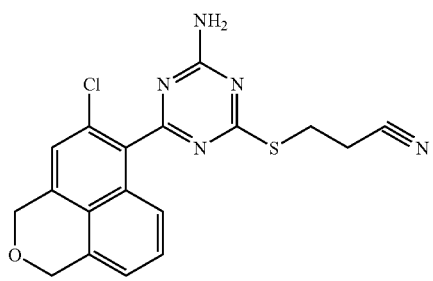 | 3-[4-amino-6-(5-chloro-1H,3H-benzo[de]isochromen-6-yl)-[1,3,5]triazin-2-ylsulfanyl]-propionitrile |
| 265 | 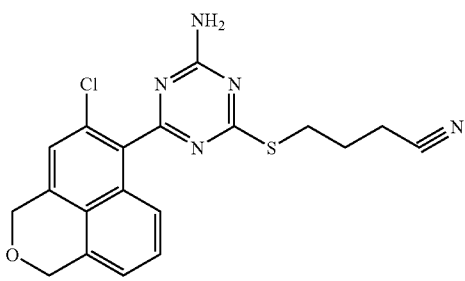 | 4-[4-amino-6-(5-chloro-1H,3H-benzo[de]isochromen-6-yl)-[1,3,5]triazin-2-ylsulfanyl]-butyronitrile |
| 266 | 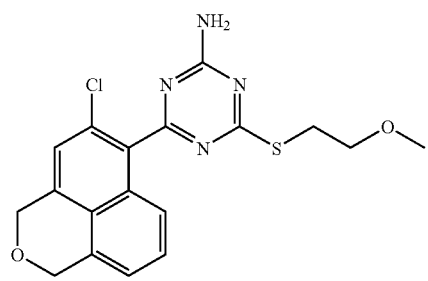 | 4-(5-chloro-1H,3H-benzo[de]isochromen-6-yl)-6-(2-methoxy-ethylsulfanyl)-[1,3,5]triazin-2-ylamine |
| 267 | 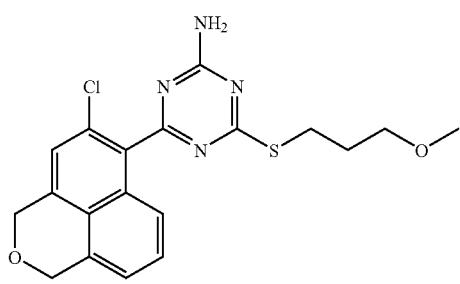 | 4-(5-chloro-1H,3H-benzo[de]isochromen-6-yl)-6-(3-methoxypropylsulfanyl)-[1,3,5]triazin-2-ylamine |
| 268 | 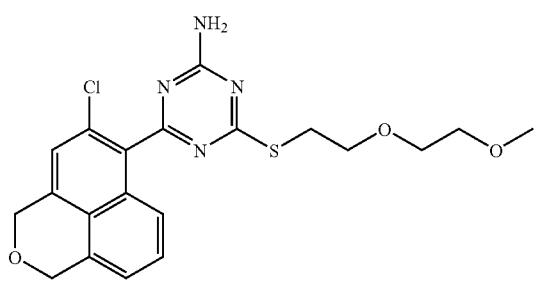 | 4-(5-chloro-1H,3H-benzo[de]isochromen-6-yl)-6-([2-(2-methoxyethoxy)-ethylsulfanyl]-[1,3,5]triazin-2-ylamine |

TABLE 1-continued

| | | |
|---|---|---|
| 269 | 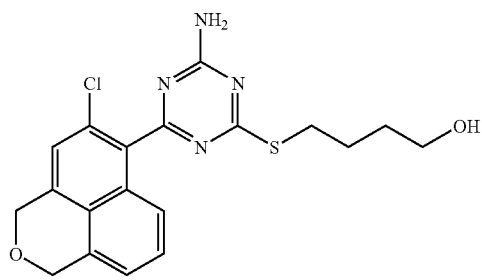 | 4-[4-amino-6-(5-chloro-1H,3H-benzo[de]isochromen-6-yl)-[1,3,5]triazin-2-ylsulfanyl]-butan-1-ol |
| 271 | 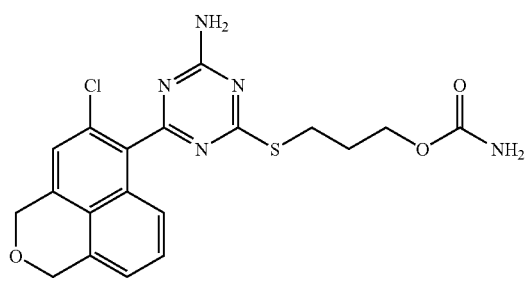 | carbamic acid 3-[4-amino-6-(5-chloro-1H,3H-benzo[de]isochromen-6-yl)-[1,3,5]triazin-2-ylsulfanyl]-propyl ester |
| 272 | 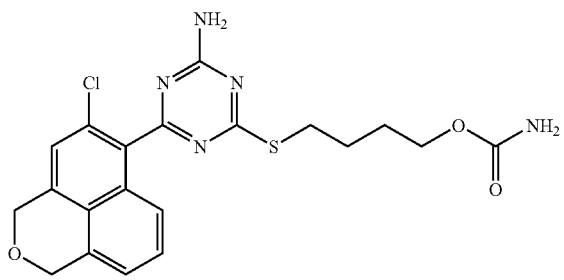 | carbamic acid 4-[4-amino-6-(5-chloro-1H,3H-benzo[de]isochromen-6-yl)-[1,3,5]triazin-2-ylsulfanyl]-butyl ester |
| 273 | 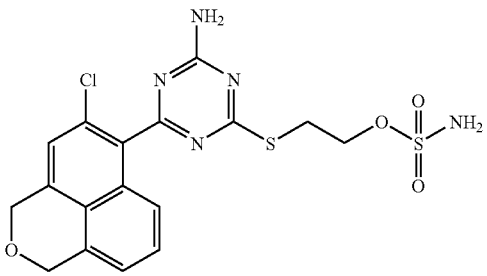 | sulfamic acid 2-[4-amino-6-(5-chloro-1H,3H-benzo[de]isochromen-6-yl)-[1,3,5]triazin-2-ylsulfanyl]-ethyl ester |
| 274 | 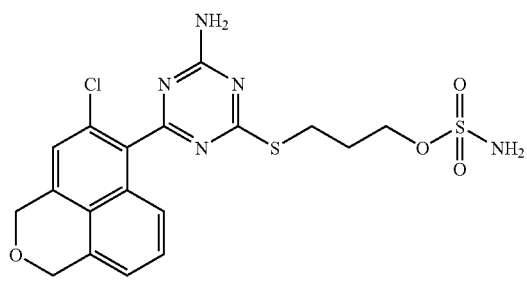 | sulfamic acid 3-[4-amino-6-(5-chloro-1H,3H-benzo[de]isochromen-6-yl)-[1,3,5]triazin-2-ylsulfanyl]-propyl ester |

| | | |
|---|---|---|
| 275 | 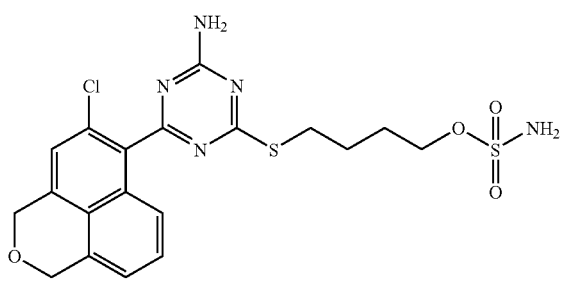 | sulfamic acid 4-[4-amino-6-(5-chloro-1H,3H-benzo[de]isochromen-6-yl)-[1,3,5]triazin-2-ylsulfanyl]-butyl ester |
| 276 | 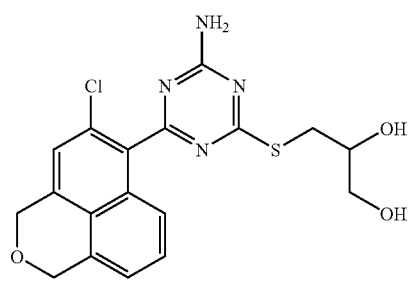 | 3-[4-amino-6-(5-chloro-1H,3H-benzo[de]isochromen-6-yl)-[1,3,5]triazin-2-ylsulfanyl]-propane-1,2-diol |
| 277 | 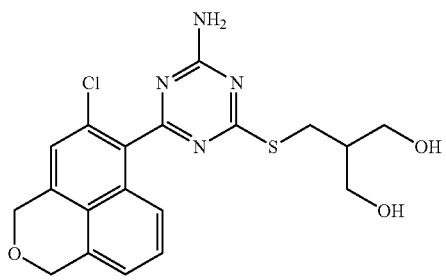 | 2-[4-amino-6-(5-chloro-1H,3H-benzo[de]isochromen-6-yl)-[1,3,5]triazin-2-ylsulfanylmethyl]-propane-1,3-diol |
| 278 | 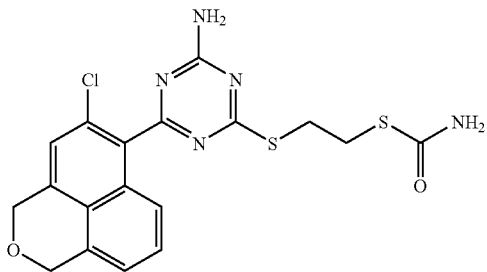 | thiocarbamic acid 2-[4-amino-6-(5-chloro-1H,3H-benzo[de]isochromen-6-yl)-[1,3,5]triazin-2-ylsulfanyl]-ethyl ester |
| 279 | 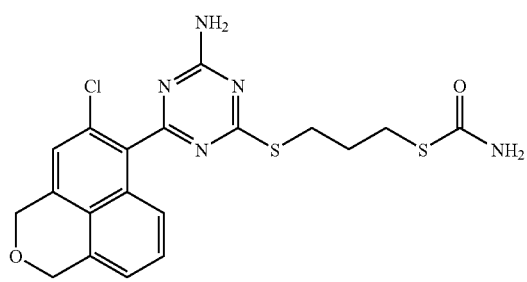 | thiocarbamic acid 3-[4-amino-6-(5-chloro-1H,3H-benzo[de]isochromen-6-yl)-[1,3,5]triazin-2-ylsulfanyl]-propyl ester |

TABLE 1-continued

| | | |
|---|---|---|
| 280 | 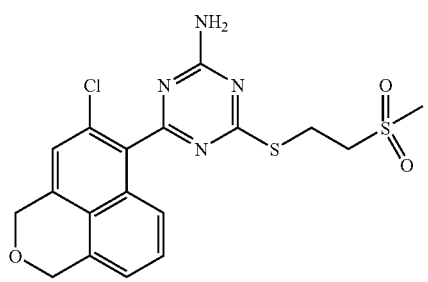 | 4-(5-chloro-1H,3H-benzo[de]isochromen-6-yl)-6-(2-methanesulfonyl-ethylsulfanyl)-[1,3,5]triazin-2-ylamine |
| 281 | 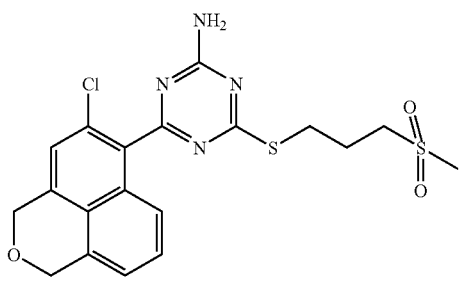 | 4-(5-chloro-1H,3H-benzo[de]isochromen-6-yl)-6-(3-methanesulfonyl-propylsulfanyl)-[1,3,5]triazin-2-ylamine |
| 282 | 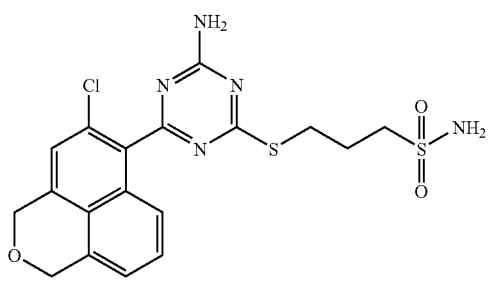 | 3-[4-amino-6-(5-chloro-1H,3H-benzo[de]isochromen-6-yl)-[1,3,5]triazin-2-ylsulfanyl]-propan-1-sulfonamide |
| 283 | 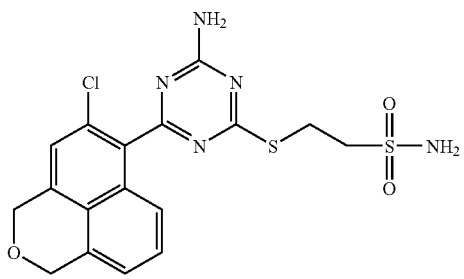 | 2-[4-amino-6-(5-chloro-1H,3H-benzo[de]isochromen-6-yl)-[1,3,5]triazin-2-ylsulfanyl]-ethanesulfonamide |
| 284 | 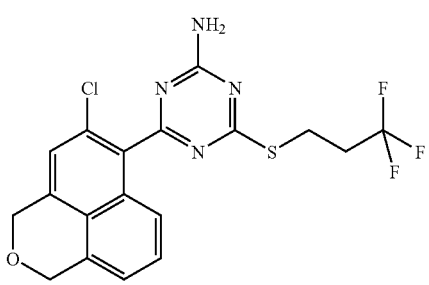 | 4-(5-chloro-1H,3H-benzo[de]isochromen-6-yl)-6-(3,3,3-trifluoro-propylsulfanyl)-[1,3,5]triazin-2-ylamine |

TABLE 1-continued

| | | |
|---|---|---|
| 285 | 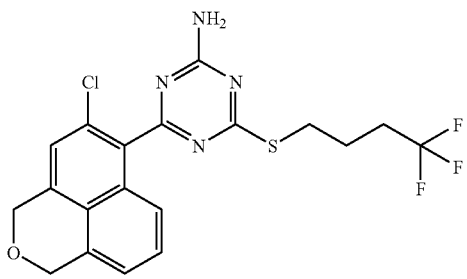 | 4-(5-chloro-1H,3H-benzo[de]isochromen-6-yl)-6-(4,4,4-trifluoro-butylsulfanyl)-[1,3,5]triazin-2-ylamine |
| 286 | 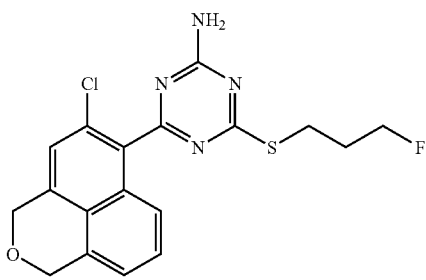 | 4-(5-chloro-1H,3H-benzo[de]isochromen-6-yl)-6-(3-fluoropropylsulfanyl)-[1,3,5]triazin-2-ylamine |
| 287 | 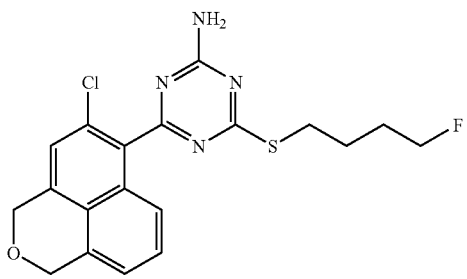 | 4-(5-chloro-1H,3H-benzo[de]isochromen-6-yl)-6-(4-fluorobutylsulfanyl)-[1,3,5]triazin-2-ylamine |
| 288 | 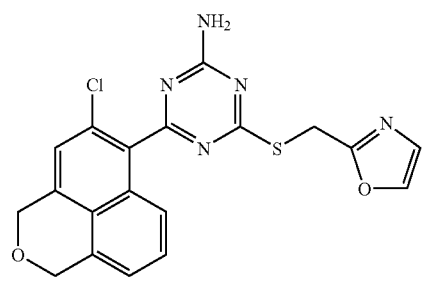 | 4-(5-chloro-1H,3H-benzo[de]isochromen-6-yl)-6-(oxazol-2-ylmethylsulfanyl)-[1,3,5]triazin-2-ylamine |
| 289 | 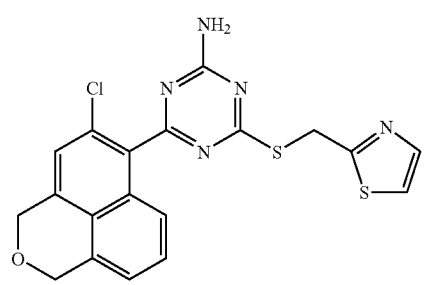 | 4-(5-chloro-1H,3H-benzo[de]isochromen-6-yl)-6-(thiazol-2-ylmethylsulfanyl)-[1,3,5]triazin-2-ylamine |

| | | |
|---|---|---|
| 290 | 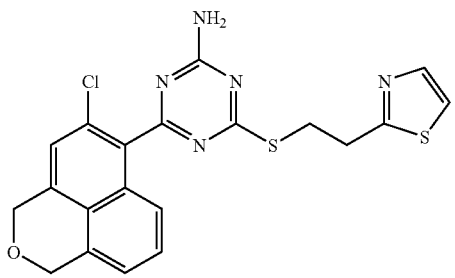 | 4-(5-chloro-1H,3H-benzo[de]isochromen-6-yl)-6-(2-thiazol-2-yl-ethylsulfanyl)-[1,3,5]triazin-2-ylamine |
| 291 | 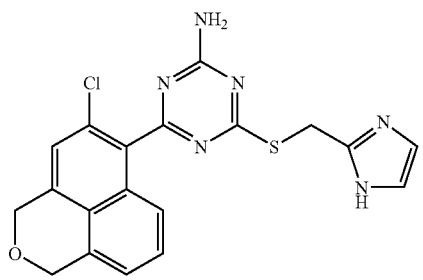 | 4-(5-chloro-1H,3H-benzo[de]isochromen-6-yl)-6-(1H-imidazol-2-ylmethylsulfanyl)-[1,3,5]triazin-2-ylamine |
| 292 | 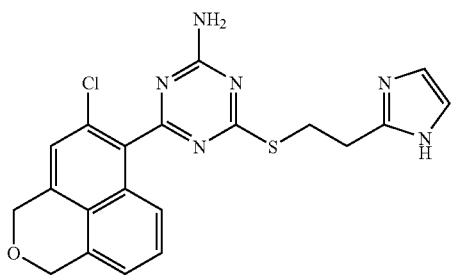 | 4-(5-chloro-1H,3H-benzo[de]isochromen-6-yl)-6-[2-(1H-imidazol-2-yl)-ethylsulfanyl]-[1,3,5]triazin-2-ylamine |
| 293 | 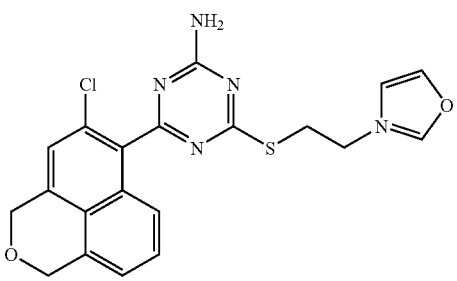 | 4-(5-chloro-1H,3H-benzo[de]isochromen-6-yl)-6-(2-oxazol-3-yl-ethylsulfanyl)-[1,3,5]triazin-2-ylamine |
| 294 | 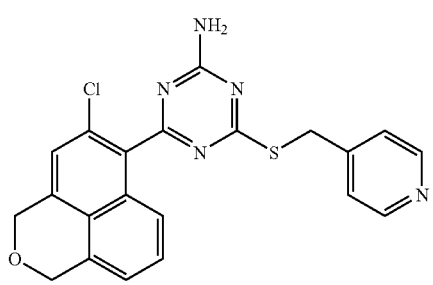 | 4-(5-chloro-1H,3H-benzo[de]isochromen-6-yl)-6-(pyridin-4-ylmethylsulfanyl)-[1,3,5]triazin-2-ylamine |

TABLE 1-continued

| | | |
|---|---|---|
| 295 | 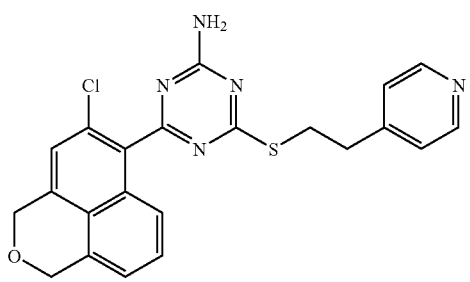 | 4-(5-chloro-1H,3H-benzo[de]isochromen-6-yl)-6-(2-pyridin-4-yl-ethylsulfanyl)-[1,3,5]triazin-2-ylamine |
| 296 | 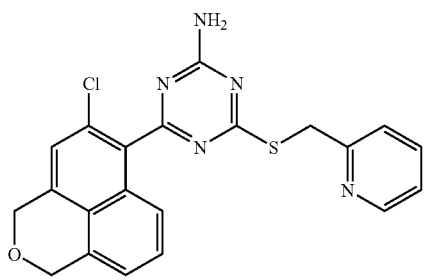 | 4-(5-chloro-1H,3H-benzo[de]isochromen-6-yl)-6-(pyridin-2-ylmethylsulfanyl)-[1,3,5]triazin-2-ylamine |
| 297 | 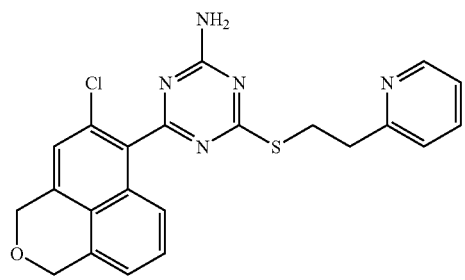 | 4-(5-chloro-1H,3H-benzo[de]isochromen-6-yl)-6-(2-pyridin-2-yl-ethylsulfanyl)-[1,3,5]triazin-2-ylamine |
| 298 | 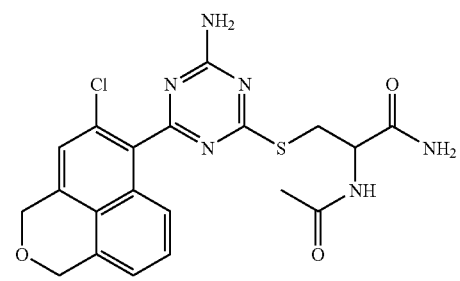 | 2-acetylamino-3-[4-amino-6-(5-chloro-1H,3H-benzo[de]isochromen-6-yl)-[1,3,5]triazin-2-ylsulfanyl]-propionamide |
| 299 | 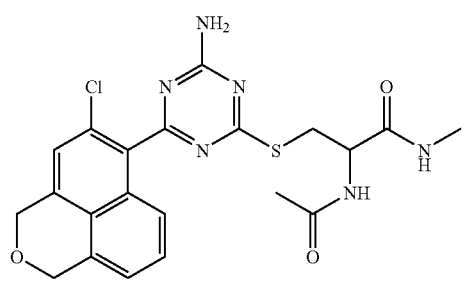 | 2-acetylamino-3-[4-amino-6-(5-chloro-1H,3H-benzo[de]isochromen-6-yl)-[1,3,5]triazin-2-ylsulfanyl]-N-methyl-propionamide |

TABLE 1-continued

| 300 | 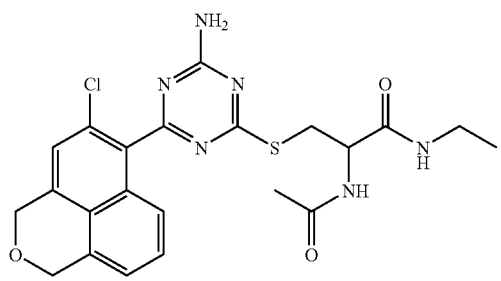 | 2-acetylamino-3-[4-amino-6-(5-chloro-1H,3H-benzo[de]isochromen-6-yl)-[1,3,5]triazin-2-ylsulfanyl]-N-ethyl-propionamide |
| 301 | 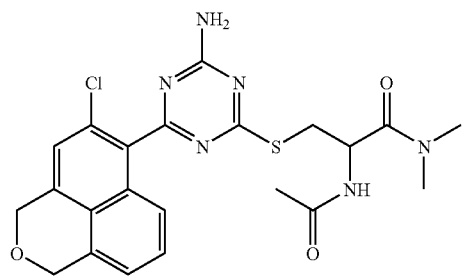 | 2-acetylamino-3-[4-amino-6-(5-chloro-1H,3H-benzo[de]isochromen-6-yl)-[1,3,5]triazin-2-ylsulfanyl]-N,N-dimethyl-propionamide |
| 302 | 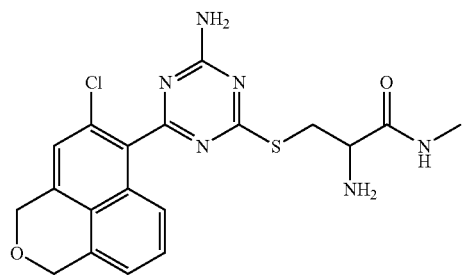 | 2-amino-3-[4-amino-6-(5-chloro-1H,3H-benzo[de]isochromen-6-yl)-[1,3,5]triazin-2-ylsulfanyl]-N-methyl-propionamide |
| 303 | 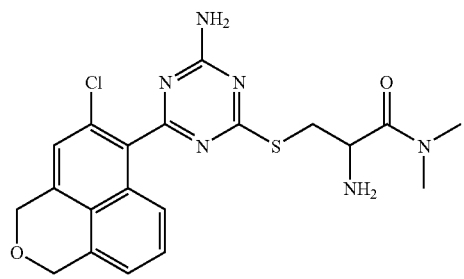 | 2-amino-3-[4-amino-6-(5-chloro-1H,3H-benzo[de]isochromen-6-yl)-[1,3,5]triazin-2-ylsulfanyl]-N,N-dimethyl-propionamide |
| 304 | 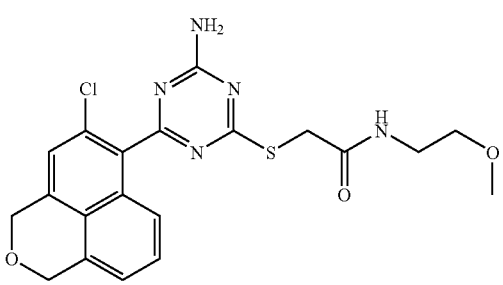 | 2-[4-amino-6-(5-chloro-1H,3H-benzo[de]isochromen-6-yl)-[1,3,5]triazin-2-ylsulfanyl]-N-(2-methoxy-ethyl)-acetamide |

TABLE 1-continued

| 305 | 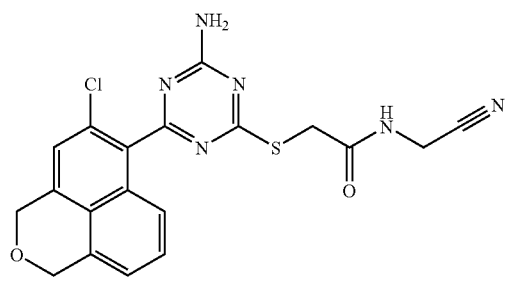 | 2-[4-amino-6-(5-chloro-1H,3H-benzo[de]isochromen-6-yl)-[1,3,5]triazin-2-ylsulfanyl]-N-cyanomethyl-acetamide |
| 306 | 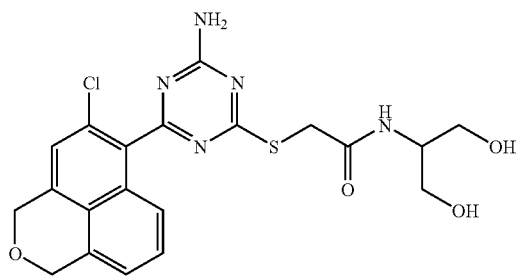 | 2-[4-amino-6-(5-chloro-1H,3H-benzo[de]isochromen-6-yl)-[1,3,5]triazin-2-ylsulfanyl]-N-(2-hydroxy-1-hydroxymethyl-ethyl)-acetamide |
| 307 | 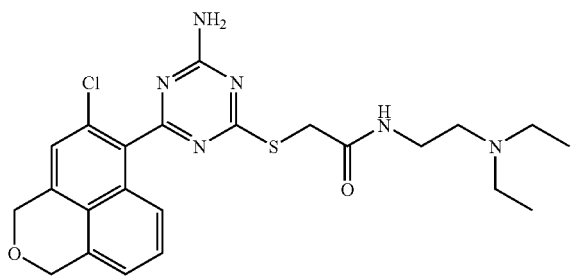 | 2-[4-amino-6-(5-chloro-1H,3H-benzo[de]isochromen-6-yl)-[1,3,5]triazin-2-ylsulfanyl]-N-(2-diethylamino-ethyl)-acetamide |
| 308 | 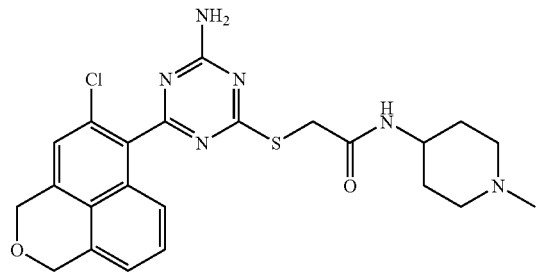 | 2-[4-amino-6-(5-chloro-1H,3H-benzo[de]isochromen-6-yl)-[1,3,5]triazin-2-ylsulfanyl]-N-(1-methyl-piperidin-4-yl)-acetamide |
| 309 | 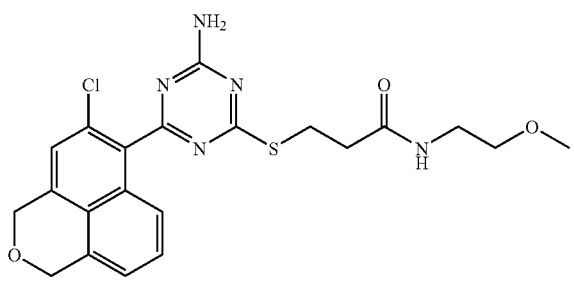 | 3-[4-amino-6-(5-chloro-1H,3H-benzo[de]isochromen-6-yl)-[1,3,5]triazin-2-ylsulfanyl]-N-(2-methoxy-ethyl)-propionamide |

TABLE 1-continued

| 310 | 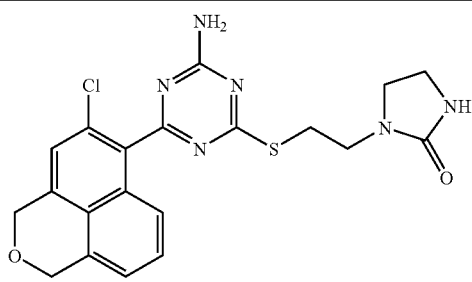 | 1-{2-[4-amino-6-(5-chloro-1H,3H-benzo[de]isochromen-6-yl)-[1,3,5]triazin-2-ylsulfanyl]-ethyl}-imidazolin-2-one |

| 311 | 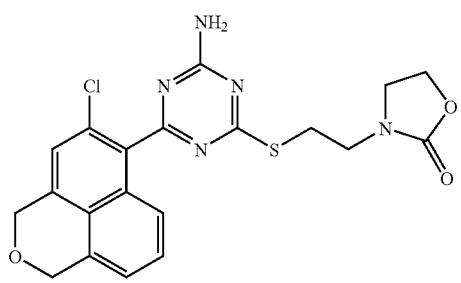 | 3-{2-[4-amino-6-(5-chloro-1H,3H-benzo[de]isochromen-6-yl)-[1,3,5]triazin-2-ylsulfanyl]-ethyl}-oxazolidin-2-one |

| 312 | 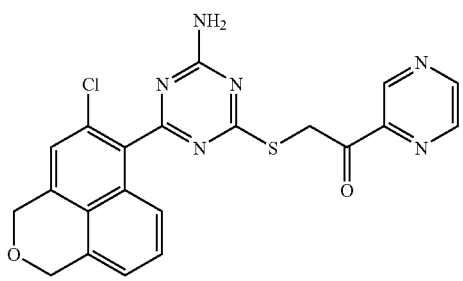 | 2-[4-amino-6-(5-chloro-1H,3H-benzo[de]isochromen-6-yl)-[1,3,5]triazin-2-ylsulfanyl]-1-pyrazin-2-yl-ethanone |

| 313 | 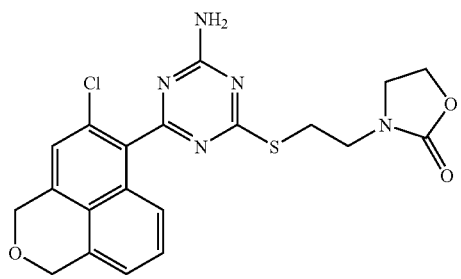 | 3-{2-[4-amino-6-(5-chloro-1H,3H-benzo[de]isochromen-6-yl)-[1,3,5]triazin-2-ylsulfanyl]-acetyl}-oxazolidin-2-one |

Test Example 1

Measurement of HSP90 Enzyme Inhibitory Activity

HSP90 enzyme inhibitory activity of the compounds of the present invention represented by formula (1) was measured by the following method. Among the 6-phenyl-N-phenyl-(1,3,5)triazin/(1,3)pyrimidin-2,4-diamine derivatives which are known LPAAT-β inhibitors, the following two compounds were used as comparative compounds, and their HSP90 enzyme inhibitory activities were measured similarly by the following method.

Example 29 of Patent Document 17 (=compound 2j shown in Table 2 on Page 2306 of Non-Patent Document 6):

The compound of Example 55 of Patent Document 17 (=compound 2p shown in Table 2 on Page 2306 of Non-Patent Document 6):

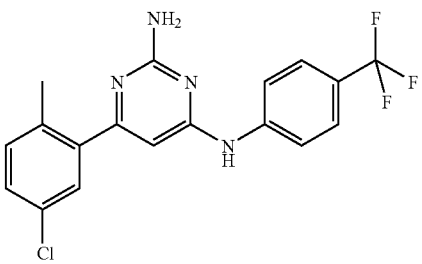

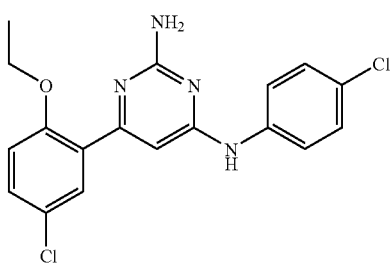

As a result, all of the compounds of the present invention showed good HSP90 enzyme inhibitory activity whereas, both of the comparative compounds did not show HSP90 enzyme inhibitory activity.

1) Methods for Preparing a Purified Enzyme Solution

Human HSP90 alpha gene (GenBank Accession No. X15183; Nucleic Acids Res. 1989 September 12; 17 (17): 7108) was inserted into the pET vector (novagen) to construct an expression plasmid, pETHuHSP90a. Introduction of pETHuHSP90a into *E. coli* (BL21 codon plus; Stratagene) was followed by O/N incubation in the presence of 0.1 mM IPTG, and the collected *E. coli* cells were disrupted by ultra-sonication in a Lysis buffer (50 mM Tris-HCl (pH8.0), 10 mM $MgCl_2$, 0.1% Triton X-100, Protease inhibitor cocktail tablets (Roche Diagnostics)). The cell lysate solution was centrifuged (10,000 rpm×30 minutes), and the supernatant obtained after centrifugation was used as a crude extract. The crude extract was fractionated using HisPrep FF column and HiTrap Q column (Amersham) to prepare a purified enzyme solution.

2) Enzyme Assay Method

An enzyme solution for assays was prepared by dilution of the purified enzyme solution using an assay buffer (50 mM Tris HCl pH7.6, 20 mM KCl, 5 mM $MgCl_2$).

80 μL aliquots of the enzyme solution for assays were placed into a 96-well plate (Falcon), and negative control wells were prepared by adding into each well, 80 μL of the assay buffer alone that does not contain the purified enzyme solution.

10 μL each of various concentrations of the test substances (10% DMSO solution) was added to each well, and for the positive control wells, 10 μL of 10% DMSO was added. 10 μL of 10% DMSO was also added to the negative control well.

10 μL of 1 mM ATP was added to all of the wells, and the reaction was carried out at 37° C. for two hours.

100 μL of malachite green solution (0.03% Malachite green, 0.2% Ammonium molybdate, 5% Triton X-100, 0.7 N HCl) was added, and OD655 was measured (BioRAD Microplate reader, model 3550-UV) after carrying out the reaction at room temperature for ten minutes.

The values of the negative control wells was subtracted as background from the values measured for all wells, and 50% inhibition concentration ($IC_{50}$) of the agent was calculated using the value of the positive control well as 0% inhibition.

3) Results

The results of measuring inhibitory activity against human HSP90 alpha are shown in Table 2. As indicated in Table 2, all of the compounds of the present invention showed good HSP90 enzyme inhibitory activity.

Test Example 2

Measurement of Cell Growth Inhibition

Cell growth inhibitory activities of the compounds of the present invention represented by formula (1) were measured by the following method. As representative examples of 6-aryl-4-mercapto/oxy-(1,3,5)triazin/(1,3)pyrimidin-2-amine derivatives having a known simple structure, compounds 12a and 12b shown on pages 59 and 67 of Non-Patent Document 5 were used as comparative compounds, and cell growth inhibitory activities were measured by the following method.

1) Methods

HCT116 cell line (CCL-247, colon cancer cell line), NCI-H460 cell line (HTB-177, lung cancer cell line), DU145 cell line (HTB-81, prostate cancer cell line), and NCI-N87 cell line (CRL-5822, gastric cancer cell line) purchased from ATCC were used for the evaluation. Cells were maintained under conditions recommended by the provider of each cell line. Cells suspended in a medium were added to solutions containing various concentrations of the test substance, and the cells were cultured at 37° C. in a 5% $CO_2$ incubator. Four days later, Cell Counting Kit-8 was added, and absorbance measurements were taken following the protocol included in the kit. The value measured for samples which does not contain the test substances was defined as 0% inhibition and the value measured for samples which does not contain test substances and the cells were defined as 100% inhibition, and the 50% inhibition concentration (IC50) was calculated.

2) Results

As an example of the results, the results of cell growth inhibitory activity on HCT116 cells are shown in Table 2. As indicated in Table 2, while both comparative compounds did not show cell growth inhibitory activity, all of the compounds of the present invention showed good cell growth inhibitory activity.

TABLE 2

| Example No. | Formula | Compound name | Enzyme inhibitory activity (IC50, μM) Human HSP 90α | Cell growth inhibitory activity (IC50, μM) HCT116 |
|---|---|---|---|---|
| Comparative compound (Compound 12b of Non-patent Document 5) | | 4-(2-chloro-phenyl)-6-methylsulfanyl-[1,3,5]triazin-2-ylamine | 5.0 | 97.3 |

TABLE 2-continued

| Example No. | Compound name | Enzyme inhibitory activity (IC50, μM) Human HSP 90α | Cell growth inhibitory activity (IC50, μM) HCT116 |
|---|---|---|---|
| Comparative compound (Compound 12a of Non-patent Document 5) | 4-methylsulfanyl-6-phenyl-[1,3,5]triazin-2-ylamine | 33.8 | >100 |
| 4 | 4-(5-benzyloxy-2,4-dichlorophenyl)-6-benzylsulfanyl[1,3,5]triazin-2-ylamine | 1.2 | 8.5 |
| 15 | (5-{4-amino-6-[2-methoxy-4-(4-methyl-piperazin-1-carbonyl)-phenylsulfanyl]-[1,3,5]triazin-2-yl}-2,4-dichlorophenoxy)-acetonitrile | 2.0 | 0.35 |
| 24 | 4-(2,4-dichloro-5-pyrimidin-2-yl-phenyl)-6-methylsulfanyl-[1,3,5]triazin-2-ylamine | 2.1 | 1.0 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 25 | | N-{2-[4-amino-6-(2,4-dichloro-5-pyrimidin-2-yl-phenyl)-[1,3,5]triazin-2-ylsulfanyl]-ethyl}-acetamide | 2.6 | 0.66 |
| 26 | | 5-(4-amino-6-benzylsulfanyl-[1,3,5]triazin-2-yl)-2,4-dichlorobenzamide | 2.8 | 1.3 |
| 28 | | 5-(4-amino-6-benzylsulfanyl-[1,3,5]triazin-2-yl)-2,4-dichloro-N-(2-hydroxy-1-hydroxymethylethyl)-benzamide | 1.2 | 1.2 |
| 37 | | 5-[4-amino-6-(2,3-dihydroxypropylsulfanyl)-[1,3,5]triazin-2-yl]-2,4-dimethylbenzoic acid methyl ester | 1.4 | 6.6 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 39 | | 4-(2,4-dichlorophenyl)-6-(2,5-dimethoxyphenylsulfanyl)-pyrimidin-2-ylamine | 1.8 | 8.5 |
| 44 | | 3-{4-[2-amino-6-(2,5-dimethoxyphenylsulfanyl)-pyrimidin-4-yl]-3-methylphenoxy}-propan-1-ol | 2.2 | 14.5 |
| 45 | | {4-[2-amino-6-(2,5-dimethoxyphenylsulfanyl)-pyrimidin-4-yl]-3-methylphenoxy}-acetonitrile | 1.4 | 4.1 |
| 46 | | 2-{4-[2-amino-6-(2,5-dimethoxyphenylsulfanyl)-pyrimidin-4-yl]-3-methylphenoxy}-acetamide | 1.5 | 8.1 |
| 48 | | 4-(5-benzyloxy-2,4-dichlorophenyl)-6-(2,5-dimethoxyphenylsulfanyl)-pyrimidin-2-ylamine | 2.5 | 42.9 |

| Example No. | Formula | Compound name | Enzyme inhibitory activity (IC50, μM) Human HSP 90α | Cell growth inhibitory activity (IC50, μM) HCT116 |
| --- | --- | --- | --- | --- |
| 52 | | {5-[2-amino-6-(2,5-dimethoxyphenylsulfanyl)-pyrimidin-4-yl]-2,4-dichlorophenyoxy}-acetonitrile | 1.7 | 1.4 |
| 54 | | {5-[2-amino-6-(1H-benzimidazol-2-ylsulfanyl)-pyrimidin-4-yl]-2,4-dichlorophenoxy}-acetonitrile | 1.5 | 1.1 |
| 55 | | 2-[2-amino-6-(2,4-dichloro-5-cyanomethoxyphenyl)-pyrimidin-4-ylsulfanyl]-3H-imidazol-4-carboxylic acid ethyl ester | 1.7 | 5.3 |
| 59 | | N-{2-[4-amino-6-(2,4-dichloro-5-cyanomethoxy-phenyl)-[1,3,5]triazin-2-ylsulfanyl]-ethyl}-acetamide | 1.0 | 0.12 |

TABLE 2-continued

| Example No. | Compound name | Enzyme inhibitory activity (IC50, μM) Human HSP 90α | Cell growth inhibitory activity (IC50, μM) HCT116 |
| --- | --- | --- | --- |
| 63 | {5-[4-amino-6-(3-morpholin-4-yl-3-oxo-propylsulfanyl)-[1,3,5]triazin-2-yl]-2,4-dichlorophenoxy}-acetonitrile | 2.0 | 0.74 |
| 82 | 4-(5-chloro-1H,3H-benzo[de]isochromen-6-yl)-6-(3,4-dimethoxyphenoxy)-[1,3,5]triazin-2-ylamine | 1.4 | 6.1 |
| 92 | 4-(5-chloro-1H,3H-benzo[de]isochromen-6-yl)-6-cyclohexylsulfanyl-[1,3,5]triazin-2-ylamine | 1.1 | 9.2 |
| 111 | [4-amino-6-(5-chloro-1H,3H-benzo[de]isochromen-6-yl)-[1,3,5]triazin-2-ylsulfanyl]-acetic acid methyl ester | 1.1 | 0.2 |
| 113 | N-{2-[4-amino-6-(5-chloro-1H,3H-benzo[de]isochromen-6-yl)-[1,3,5]triazin-2-ylsulfanyl]-ethyl}-acetamide | 1.0 | 0.13 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 119 | | 2-[4-amino-6-(5-chloro-1H,3H-benzo[de]isochromen-6-yl)-[1,3,5]triazin-2-ylsulfanyl]-acetamide | 0.8 | 0.27 |
| 125 | | 3-[4-amino-6-(5-chloro-1H,3H-benzo[de]isochromen-6-yl)-[1,3,5]triazin-2-ylsulfanyl]-propionamide | 1.4 | 0.12 |
| 143 | | N-{2-[4-amino-6-(5-chloro-1H,3H-benzo[de]isochromen-6-yl)-[1,3,5]triazin-2-ylsulfanylmethyl]-phenyl}-acetamide | 1.0 | 0.28 |
| 145 | | 4-(5-chloro-1H,3H-benzo[de]isochromen-6-yl)-6-(2,5-dimethoxyphenylsulfanyl)-[1,3,5]triazin-2-ylamine | 1.9 | 0.24 |
| 149 | | N-{3-[4-Amino-6-(5-chloro-1H,3H-benzo[de]isochromen-6-yl)-[1,3,5]triazin-2-ylsulfanyl]-propyl}-acetamide | 2,8 | 0.11 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 175 | | {2-[4-amino-6-(5-chloro-1H,3H-benzo[de]isochromen-6-yl)-[1,3,5]triazin-2-ylsulfanyl]-ethyl}-urea | 1.3 | 0.23 |
| 178 | | N-{2-[4-Amino-6-(5-chloro-1H,3H-benzo[de]isochromen-6-yl)-[1,3,5]triazin-2-ylsulfanyl]-ethyl}-methanesulfonamide | 1.5 | 0.12 |
| 205 | | 3-[4-Amino-6-(5-chloro-1H,3H-benzo[de]isochromen-6-yl)-[1,3,5]triazin-2-ylsulfanyl]-N-methyl-propionamide | 1.9 | 0.086 |
| 234 | | 3-[4-Amino-6-(5-chloro-1H,3H-benzo[de]isochromen-6-yl)-[1,3,5]triazin-2-ylsulfanyl]-N-(2-hydroxy-ethyl)-propionamide | 2.0 | 0.29 |
| 270 | | carbamic acid 2-[4-amino-6-(5-chloro-1H,3H-benzo[de]isochromen-6-yl)-[1,3,5]triazin-2-yl sulfanyl]-ethyl ester | 1.7 | 0.076 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 314 | | 2-[2-amino-6-(5-chloro-1H,3H-benzo[de]isochromen-6-yl)-pyrimidin-4-ylsulfanyl]-acetamide | 1.3 | 1.1 |
| 315 | | 2-[2-amino-6-(5-chloro-1H,3H-benzo[de]isochromen-6-yl)-pyrimidin-4-ylsulfanyl]-N-cyanomethyl-acetamide | 1.9 | 2.1 |
| 316 | | 3-[2-amino-6-(5-chloro-1H,3H-benzo[de]isochromen-6-yl)-pyrimidin-4-ylsulfanyl]-propionamide | 2.1 | 0.45 |
| 317 | | 3-[2-amino-6-(5-chloro-1H,3H-benzo[de]isochromen-6-yl)-pyrimidin-4-ylsulfanyl]-N-(2-hydroxy-ethyl)-propionamide | 1.3 | 0.41 |
| 318 | | 3-[2-amino-6-(5-chloro-1H,3H-benzo[de]isochromen-6-yl)-pyrimidin-4-ylsulfanyl]-N-methyl-propionamide | 1.4 | 0.22 |

TABLE 2-continued

| Example No. | Compound name | Enzyme inhibitory activity (IC50, μM) Human HSP 90α | Cell growth inhibitory activity (IC50, μM) HCT116 |
|---|---|---|---|
| 319 | 3-[2-amino-6-(5-chloro-1H,3H-benzo[de]isochromen-6-yl)-pyrimidin-4-ylsulfanyl]-N-(2-methoxy-ethyl)-propionamide | 2.1 | 0.62 |
| 320 | 3-[2-amino-6-(5-chloro-1H,3H-benzo[de]isochromen-6-yl)-pyrimidin-4-ylsulfanyl]-N-((R)-2,3-dihydroxy-propyl)-propionamide | 1.4 | 0.63 |
| 321 | 3-[2-amino-6-(5-chloro-1H,3H-benzo[de]isochromen-6-yl)-pyrimidin-4-ylsulfanyl]-2-methyl-propionamide | 1.3 | 0.13 |
| 322 | 3-[2-amino-6-(5-chloro-1H,3H-benzo[de]isochromen-6-yl)-pyrimidin-4-ylsulfanyl]-2,N-dimethyl-propionamide | 1.7 | 0.08 |
| 323 | 3-[2-amino-6-(5-chloro-1H,3H-benzo[de]isochromen-6-yl)-pyrimidin-4-ylsulfanyl]-N-(2-hydroxy-ethyl)-2-methyl-propionamide | 2.8 | 0.21 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 324 | | 4-[2-amino-6-(5-chloro-1H,3H-benzo[de]isochromen-6-yl)-pyrimidin-4-ylsulfanyl]-butylamide | 1.8 | 0.16 |
| 325 | | carbamic acid 2-[2-amino-6-(5-chloro-1H,3H-benzo[de]isochromen-6-yl)-pyrimidin-4-ylsulfanyl]-ethyl ester | 2.1 | 0.26 |
| 326 | | 3-[2-amino-6-(5-chloro-1H,3H-benzo[de]isochromen-6-yl)-pyrimidin-4-ylsulfanyl]-propan-1-ol | 2.1 | 0.52 |
| 327 | | N-{2-[2-amino-6-(5-chloro-1H,3H-benzo[de]isochromen-6-yl)-pyrimidin-4-ylsulfanyl]-ethyl}-acetamide | 2.1 | 0.93 |
| 328 | | N-{3-[2-amino-6-(5-chloro-1H,3H-benzo[de]isochromen-6-yl)-pyrimidin-4-ylsulfanyl]-propyl}-acetamide | 2.1 | 0.20 |

TABLE 2-continued

| Example No. | Formula | Compound name | Enzyme inhibitory activity (IC50, μM) Human HSP 90α | Cell growth inhibitory activity (IC50, μM) HCT116 |
|---|---|---|---|---|
| 329 | | N-{2-[2-amino-6-(5-chloro-1H,3H-benzo[de]isochromen-6-yl)-pyrimidin-4-ylsulfanyl]-ethyl}-methanesulfonamide | 1.0 | 0.31 |
| 330 | | 5-[2-amino-6-(5-chloro-1H,3H-benzo[de]isochromen-6-yl)-pyrimidin-4-ylsulfanylmethyl]-oxazolidin-2-one | 1.2 | 2.1 |
| 331 | | N-{2-[2-amino-6-(5-chloro-1H,3H-benzo[de]isochromen-6-yl)-pyrimidin-4-ylsulfanyl]-ethyl}-2-hydroxy-acetamide | 1.5 | 1.9 |
| 332 | | {2-[2-amino-6-(5-chloro-1H,3H-benzo[de]isochromen-6-yl)-pyrimidin-4-ylsulfanyl]-ethyl}-urea | 2.2 | 0.47 |
| 333 | | 2-[4-Amino-6-(5-chloro-1H,3H-benzo[de]isochromen-6-yl)-[1,3,5]triazin-2-ylsulfanyl]-N-cyanomethyl-acetamide | 1.9 | 0.38 |

TABLE 2-continued

| Example No. | Compound name | Enzyme inhibitory activity (IC50, μM) Human HSP 90α | Cell growth inhibitory activity (IC50, μM) HCT116 |
|---|---|---|---|
| 334 | 3-[4-Amino-6-(5-chloro-1H,3H-benzo[de]isochromen-6-yl)-[1,3,5]triazin-2-ylsulfanyl]-N-(2-methoxy-ethyl)-propionamide | 1.3 | 0.16 |
| 335 | 3-[4-Amino-6-(5-chloro-1H,3H-benzo[de]isochromen-6-yl)-[1,3,5]triazin-2-ylsulfanyl]-N-((R)-2,3-dihydroxy-propyl)-propionamide | 1.2 | 0.49 |
| 336 | 3-[4-Amino-6-(5-chloro-1H,3H-benzo[de]isochromen-6-yl)-[1,3,5]triazin-2-ylsulfanyl]-2-methyl-propionamide | 2.3 | 0.048 |
| 337 | 3-[4-Amino-6-(5-chloro-1H,3H-benzo[de]isochromen-6-yl)-[1,3,5]triazin-2-ylsulfanyl]-2,N-dimethyl-propionamide | 1.5 | 0.018 |
| 338 | 3-[4-Amino-6-(5-chloro-1H,3H-benzo[de]isochromen-6-yl)-[1,3,5]triazin-2-ylsulfanyl]-N-(2-hydroxy-ethyl)-2-methyl-propionamide | 1.5 | 0.12 |

TABLE 2-continued

| Example No. | Compound name | Enzyme inhibitory activity (IC50, μM) Human HSP 90α | Cell growth inhibitory activity (IC50, μM) HCT116 |
|---|---|---|---|
| 339 | 4-[4-Amino-6-(5-chloro-1H,3H-benzo[de]isochromen-6-yl)-[1,3,5]triazin-2-ylsulfanyl]-butyramide | 2.0 | 0.098 |
| 340 (=115) | 3-[4-amino-6-(5-chloro-1H,3H-benzo[de]isochromen-6-yl)-[1,3,5]triazin-2-ylsulfanyl]-propan-1-ol | 3.3 | 0.12 |
| 341 | 5-[4-Amino-6-(5-chloro-1H,3H-benzo[de]isochromen-6-yl)-[1,3,5]triazin-2-ylsulfanylmethyl]-oxazolidin-2-one | 1.8 | 0.25 |
| 342 | N-{2-[4-Amino-6-(5-chloro-1H,3H-benzo[de]isochromen-6-yl)-[1,3,5]triazin-2-ylsulfanyl]-ethyl}-2-hydroxy-acetamide | 1.3 | 0.49 |
| 343 | 4-[4-Amino-6-(5-chloro-1H,3H-2-thia-phenalen-6-yl)-[1,3,5]triazin-2-ylsulfanyl]-butyramide | 1.8 | 0.015 |

Test Example 3

Comparative Analysis

Comparative analysis (Journal of the National Cancer Institute, Vol. 81, No. 14, 1088-1092, Jul. 19, 1989) was carried out to confirm that the compounds of the present invention and 6-phenyl-N-phenyl-(1,3,5)triazin/(1,3)pyrimidin-2,4-diamine derivatives known as LPAAT-β inhibitors are different types of compounds. Generally, in Comparative analysis, a correlation coefficient of 0.6 or higher is considered "correlated", and such antitumor activities are very likely to be based on similar mechanisms. This is suggested more strongly as the correlation coefficient approaches to 1. On the other hand, if a correlation coefficient is less than 0.4 is considered to be "not correlated", and such antitumor activities are very likely to be based on dissimilar mechanisms. This is suggested more strongly as the correlation coefficient approaches to 0.

The two compounds from the compounds of the present invention and the two compounds of Examples 29 and 55 of Patent Document 17 which were used as comparative compounds in Test Example 1 were used to perform Comparative analysis. The results showed that the correlation coefficients were greater than 0.6 between the two compounds of the present invention and also between the two comparative compounds. On the other hand, the correlation coefficients indicated between the compound of the present invention and the comparative compound were less than 0.2 in all cases. Therefore, this suggested that the compounds of the present invention and the comparative compounds are different types of compounds.

INDUSTRIAL APPLICABILITY

As described in the Examples above, compounds of the present invention represented by formula (1) have both HSP90 enzyme inhibitory activity and cell growth inhibitory activity that are not observed in known compounds, and are useful as a unique anticancer agent exerting activity towards a multiple of important targets at the same time. Furthermore, as indicated in the above-mentioned Examples, some of the compounds of the present invention represented by formula (1) are also useful as synthetic intermediates of other such compounds. Similarly, compounds represented by formula (7) and compounds represented by formula (8) are useful as synthetic intermediates of compounds of the present invention represented by formula (1).

The invention claimed is:

1. A compound represented by formula (4) or a pharmaceutically acceptable salt thereof:

$$\text{(4)}$$

wherein,
A represents O or S;
X represents CH or N;
Y represents O or S;
Z represents an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{6-12}$ aryl group, an optionally substituted 5- to 12-membered heteroaryl group, or an optionally substituted 3- to 12-membered heterocycle;
n is an integer from 0 to 2; and
$R_1$ represents a hydrogen atom, halogen atom, cyano group, $C_{1-6}$ alkyl group, $C_{1-4}$ haloalkyl group, $C_{2-6}$ alkenyl group, $C_{2-6}$ alkynyl group, $C_{1-6}$ alkoxy group, or $C_{1-6}$ alkylthio group.

2. The compound or a pharmaceutically acceptable salt thereof according to claim 1, wherein $R_1$ is a halogen atom, $C_{1-4}$ alkyl group or $C_{1-4}$ haloalkyl group.

3. The compound or a pharmaceutically acceptable salt thereof according to claim 2, wherein $R_1$ is a chlorine atom.

4. The compound or a pharmaceutically acceptable salt thereof according to claim 2, wherein $R_1$ is a methyl group.

5. The compound or a pharmaceutically acceptable salt thereof according to claim 1, wherein $R_1$ is a halogen atom.

6. The compound or a pharmaceutically acceptable salt thereof according to claim 1, wherein Z is a substituted $C_{1-10}$ alkyl group, a substituted $C_{3-10}$ cycloalkyl group, a substituted $C_{2-10}$ alkenyl group, a substituted $C_{2-10}$ alkynyl group, a substituted $C_{6-12}$ aryl group, a substituted 5- to 12-membered heteroaryl group, or a substituted 3- to 12-membered heterocycle.

7. The compound or a pharmaceutically acceptable salt thereof according to claim 6, wherein Z is a substituted $C_{1-10}$ alkyl group, a substituted $C_{6-12}$ aryl group, or a substituted 3- to 12-membered heterocycle.

8. The compound or a pharmaceutically acceptable salt thereof according to claim 7, wherein the substituent in Z is a hydroxyl group, oxo group, a group represented by formula (5):

$$\text{(5)}$$

wherein $R_{10}$ and $R_{11}$ are the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or $R_{10}$ and $R_{11}$ together form an optionally substituted 3- to 12-membered heterocycle;

a group represented by formula (6):

$$\text{(6)}$$

wherein $R_{12}$ and $R_{13}$ are the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or an optionally substituted 5- to 12-membered heteroaryl group, or $R_{12}$ and $R_{13}$ are taken together to form an optionally substituted 3- to 12-membered heterocycle;

a group represented by the formula (34):

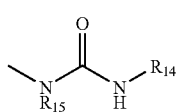
(34)

wherein $R_{14}$ and $R_{15}$ are the same or different, and represent a hydrogen atom, an optionally substituted $C_{1-6}$ alkyl group, an optionally substituted $C_{1-6}$ alkenyl group, or an optionally substituted $C_{1-6}$ alkynyl group, or $R_{14}$ and $R_{15}$ are taken together to form an optionally substituted 3- to 12-membered heterocycle;
a group represented by formula (35):

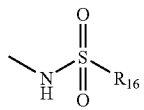
(35)

wherein $R_{16}$ represents an optionally substituted $C_{1-6}$ alkyl group, an optionally substituted $C_{1-6}$ alkenyl group, or an optionally substituted $C_{1-6}$ alkynyl group; or
a group represented by formula (36):

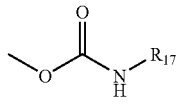
(36)

wherein $R_{17}$ represents a hydrogen atom, an optionally substituted $C_{1-6}$ alkyl group, an optionally substituted $C_{1-6}$ alkenyl group, or an optionally substituted $C_{1-6}$ alkynyl group.

9. The compound or a pharmaceutically acceptable salt thereof according to claim 8, wherein the substituent in Z is a hydroxyl group, oxo group, a group represented by formula (5):

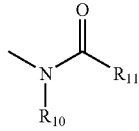
(5)

wherein $R_{10}$ is a hydrogen atom; and $R_{11}$ is an optionally substituted $C_{1-6}$ alkyl group;
a group represented by formula (6):

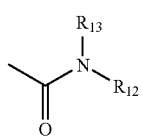
(6)

wherein $R_{12}$ and $R_{13}$ are the same or different, and represent a hydrogen atom, or an optionally substituted $C_{1-6}$ alkyl group;

a group represented by formula (34):

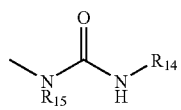
(34)

wherein $R_{14}$ and $R_{15}$ are hydrogen atoms;
a group represented by formula (35):

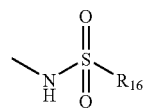
(35)

wherein $R_{16}$ represents a $C_{1-6}$ alkyl group; or
a group represented by formula (36):

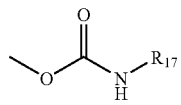
(36)

wherein $R_{17}$ represents a hydrogen atom.

10. The compound or a pharmaceutically acceptable salt thereof according to claim 1, wherein X is CH.

11. The compound or a pharmaceutically acceptable salt thereof according to claim 1, wherein Y is S.

12. A compound or a pharmaceutically acceptable salt thereof, wherein the compound is selected from the group consisting of:
(71): 4-(5-chloro-1H,3H-benzo[de]isochromen-6-yl)-6-(2-methoxyphenylsulfanyl)-[1,3,5]triazin-2-ylamine;
(72): 4-(5-chloro-1H,3H-benzo[de]isochromen-6-yl)-6-(2-chlorophenylsulfanyl)-[1,3,5]triazin-2-ylamine;
(73): 4-(5-chloro-1H,3H-benzo[de]isochromen-6-yl)-6-(3-chlorophenylsulfanyl)-[1,3,5]triazin-2-ylamine;
(74): 4-(5-chloro-1H,3H-benzo[de]isochromen-6-yl)-6-(4-chlorophenylsulfanyl)-[1,3,5]triazin-2-ylamine;
(75): 4-(5-chloro-1H,3H-benzo[de]isochromen-6-yl)-6-(4-methylsulfanyl-phenylsulfanyl)-[1,3,5]triazin-2-ylamine;
(76): 4-(5-chloro-1H,3H-benzo[de]isochromen-6-yl)-6-(3-methoxyphenylsulfanyl)-[1,3,5]triazin-2-ylamine;
(77): 4-(5-chloro-1H,3H-benzo[de]isochromen-6-yl)-6-(4-methoxyphenylsulfanyl)-[1,3,5]triazin-2-ylamine;
(78): 4-(5-chloro-1H,3H-benzo[de]isochromen-6-yl)-6-(2,5-difluorophenylsulfanyl)-[1,3,5]triazin-2-ylamine;
(79): 4-(5-chloro-1H,3H-benzo[de]isochromen-6-yl)-6-(2-fluorophenylsulfanyl)-[1,3,5]triazin-2-ylamine;
(80): 4-(5-chloro-1H,3H-benzo[de]isochromen-6-yl)-6-(4-fluorophenylsulfanyl)-[1,3,5]triazin-2-ylamine;
(81): 4-(2-bromophenoxy)-6-(5-chloro-1H,3H-benzo[de]isochromen-6-yl)-[1,3,5]triazin-2-ylamine;
(82): 4-(5-chloro-1H,3H-benzo[de]isochromen-6-yl)-6-(3,4-dimethoxyphenoxy)-[1,3,5]triazin-2-ylamine;
(83): 4-(5-chloro-1H,3H-benzo[de]isochromen-6-yl)-6-(3,5-dimethoxyphenoxy)-[1,3,5]triazin-2-ylamine;
(84): 4-(5-chloro-1H,3H-benzo[de]isochromen-6-yl)-6-(1H-imidazol-2-ylsulfanyl)-[1,3,5]triazin-2-ylamine;

(85): 4-(5-chloro-1H,3H-benzo[de]isochromen-6-yl)-6-(naphthalen-1-ylsulfanyl)-[1,3,5]triazin-2-ylamine;
(86): 4-(5-chloro-1H,3H-benzo[de]isochromen-6-yl)-6-(naphthalen-2-ylsulfanyl)-[1,3,5]triazin-2-ylamine;
(87): 4-(5-chloro-1H,3H-benzo[de]isochromen-6-yl)-6-(3,4-dimethoxy-phenylsulfanyl)-[1,3,5]triazin-2-ylamine;
(88): 4-(5-chloro-1H,3H-benzo[de]isochromen-6-yl)-6-(3-trifluoromethoxyphenylsulfanyl)-[1,3,5]triazin-2-ylamine;
(89): 4-(5-chloro-1H,3H-benzo[de]isochromen-6-yl)-6-(4-trifluoromethoxyphenylsulfanyl)-[1,3,5]triazin-2-ylamine;
(90): 4-(5-chloro-1H,3H-benzo[de]isochromen-6-yl)-6-(2,5-dichlorophenylsulfanyl)-[1,3,5]triazin-2-ylamine;
(91): 4-(2-bromophenylsulfanyl)-6-(5-chloro-1H,3H-benzo[de]isochromen-6-yl)-[1,3,5]triazin-2-ylamine;
(92): 4-(5-chloro-1H,3H-benzo[de]isochromen-6-yl)-6-cyclohexylsulfanyl-[1,3,5]triazin-2-ylamine;
(93): 4-(5-chloro-1H,3H-benzo[de]isochromen-6-yl)-6-isobutylsulfanyl-[1,3,5]triazin-2-ylamine;
(94): 4-(5-chloro-1H,3H-benzo[de]isochromen-6-yl)-6-isopropylsulfanyl-[1,3,5]triazin-2-ylamine;
(95): N-{4-[4-amino-6-(5-chloro-1H,3H-benzo[de]isochromen-6-yl)-[1,3,5]triazin-2-ylsulfanyl]-phenyl}-acetamide;
(96): 4-(5-chloro-1H,3H-benzo[de]isochromen-6-yl)-6-(4-methoxybenzylsulfanyl)-[1,3,5]triazin-2-ylamine;
(97): 4-(5-chloro-1H,3H-benzo[de]isochromen-6-yl)-6-(3-chlorobenzyloxy)-[1,3,5]triazin-2-ylamine;
(98): 4-(5-chloro-1H,3H-benzo[de]isochromen-6-yl)-6-(3-methoxyphenoxy)-[1,3,5]triazin-2-ylamine;
(99): {4-[4-amino-6-(5-chloro-1H,3H-benzo[de]isochromen-6-yl)-[1,3,5]triazin-2-yloxy]-phenyl}-methanol;
(100): 4-(5-chloro-1H,3H-benzo[de]isochromen-6-yl)-6-(4-methoxyphenoxy)-[1,3,5]triazin-2-ylamine;
(101): 4-(5-chloro-1H,3H-benzo[de]isochromen-6-yl)-6-(2-methoxyphenoxy)-[1,3,5]triazin-2-ylamine;
(102): N-{3-[4-amino-6-(5-chloro-1H,3H-benzo[de]isochromen-6-yl)-[1,3,5]triazin-2-yloxy]-phenyl}-acetamide;
(103): 2-{3-[4-amino-6-(5-chloro-1H,3H-benzo[de]isochromen-6-yl)-[1,3,5]triazin-2-yloxy]-phenyl}-ethanol;
(104): {3-[4-amino-6-(5-chloro-1H,3H-benzo[de]isochromen-6-yl)-[1,3,5]triazin-2-yloxy]-phenyl}-urea;
(105): 4-[4-amino-6-(5-chloro-1H,3H-benzo[de]isochromen-6-yl)-[1,3,5]triazin-2-ylsulfanyl]-phenol;
(106): 4-(5-chloro-1H,3H-benzo[de]isochromen-6-yl)-6-(4-nitrophenylsulfanyl)-[1,3,5]triazin-2-ylamine;
(107): 4-(5-chloro-1H,3H-benzo[de]isochromen-6-yl)-6-(2-methyl-furan-3-ylsulfanyl)-[1,3,5]triazin-2-ylamine;
(108): 4-(5-chloro-1H,3H-benzo[de]isochromen-6-yl)-6-(2,5-dimethoxyphenoxy)-[1,3,5]triazin-2-ylamine;
(109): 4-(3-aminophenylsulfanyl)-6-(5-chloro-1H,3H-benzo[de]isochromen-6-yl)-[1,3,5]triazin-2-ylamine;
(110): 4-(5-chloro-1H,3H-benzo[de]isochromen-6-yl)-6-propylsulfanyl-[1,3,5]triazin-2-ylamine;
(111): [4-amino-6-(5-chloro-1H,3H-benzo[de]isochromen-6-yl)-[1,3,5]triazin-2-ylsulfanyl]-acetic acid methyl ester;
(112): [4-amino-6-(5-chloro-1H,3H-benzo[de]isochromen-6-yl)-[1,3,5]triazin-2-ylsulfanyl]-acetic acid;
(113): N-{2-[4-amino-6-(5-chloro-1H,3H-benzo[de]isochromen-6-yl)-[1,3,5]triazin-2-ylsulfanyl]-ethyl}-acetamide;
(114): 4-(5-chloro-1H,3H-benzo[de]isochromen-6-yl)-6-(2-dimethylaminoethylsulfanyl)-[1,3,5]triazin-2-ylamine;
(115): 3-[4-amino-6-(5-chloro-1H,3H-benzo[de]isochromen-6-yl)-[1,3,5]triazin-2-ylsulfanyl]-propan-1-ol;
(116): 1-(4-{3-[4-amino-6-(5-chloro-1H,3H-benzo[de]isochromen-6-yl)-[1,3,5]triazin-2-yloxy]-phenyl}-piperazin-1-yl)-ethanone;
(117): 2-[4-amino-6-(5-chloro-1H,3H-benzo[de]isochromen-6-yl)-[1,3,5]triazin-2-ylsulfanyl]-phenol;
(118): 4-(5-chloro-1H,3H-benzo[de]isochromen-6-yl)-6-o tolylsulfanyl-[1,3,5]triazin-2-ylamine;
(119): 2-[4-amino-6-(5-chloro-1H,3H-benzo[de]isochromen-6-yl)-[1,3,5]triazin-2-ylsulfanyl]-acetamide;
(120): 4-(5-chloro-1H,3H-benzo[de]isochromen-6-yl)-6-(2-methoxybenzyloxy)-[1,3,5]triazin-2-ylamine;
(121): 4-(5-chloro-1H,3H-benzo[de]isochromen-6-yl)-6-(3-methoxybenzyloxy)-[1,3,5]triazin-2-ylamine;
(122): 4-(5-chloro-1H,3H-benzo[de]isochromen-6-yl)-6-(4-methoxybenzyloxy)-[1,3,5]triazin-2-ylamine;
(123): 4-(5-chloro-1H,3H-benzo[de]isochromen-6-yl)-6-(4-dimethylaminophenylsulfanyl)-[1,3,5]triazin-2-ylamine;
(124): 3-[4-amino-6-(5-chloro-1H,3H-benzo[de]isochromen-6-yl)-[1,3,5]triazin-2-ylsulfanyl]-propionic acid methyl ester;
(125): 3-[4-amino-6-(5-chloro-1H,3H-benzo[de]isochromen-6-yl)-[1,3,5]triazin-2-ylsulfanyl]-propionamide;
(126): 3-[4-amino-6-(5-chloro-1H,3H-benzo[de]isochromen-6-yl)-[1,3,5]triazin-2-ylsulfanyl]-propionic acid;
(127): N-{2-[4-amino-6-(5-chloro-1H,3H-benzo[de]isochromen-6-yl)-[1,3,5]triazin-2-yloxymethyl]-phenyl}-acetamide;
(128): N-{4-[4-amino-6-(5-chloro-1H,3H-benzo[de]isochromen-6-yl)-[1,3,5]triazin-2-yloxymethyl]-phenyl}-acetamide;
(129): N-{3-[4-amino-6-(5-chloro-1H,3H-benzo[de]isochromen-6-yl)-[1,3,5]triazin-2-yloxymethyl]-phenyl}-acetamide;
(130): (R)-2-[4-amino-6-(5-chloro-1H,3H-benzo[de]isochromen-6-yl)-[1,3,5]triazin-2-ylsulfanylmethyl]-4-oxo-pentanoic acid;
(131): 3-[4-amino-6-(5-chloro-1H,3H-benzo[de]isochromen-6-yl)-[1,3,5]triazin-2-ylsulfanyl]-2-methyl-propionic acid;
(132): 2-[4-amino-6-(5-chloro-1H,3H-benzo[de]isochromen-6-yl)-[1,3,5]triazin-2-ylsulfanyl]-ethanol;
(133): {2-[4-amino-6-(5-chloro-1H,3H-benzo[de]isochromen-6-yl)-[1,3,5]triazin-2-ylsulfanyl]-ethyl}-carbamic acid tert-butyl ester;
(134): 4-(5-chloro-1H,3H-benzo[de]isochromen-6-yl)-6-(3-dimethylaminophenylsulfanyl)-[1,3,5]triazin-2-ylamine;
(135): 3-[4-amino-6-(5-chloro-1H,3H-benzo[de]isochromen-6-yl)-[1,3,5]triazin-2-ylsulfanyl]-2-methyl-propionic acid methyl ester;
(136): (R)-2-acetylamino-3-[4-amino-6-(5-chloro-1H,3H-benzo[de]isochromen-6-yl)-[1,3,5]triazin-2-ylsulfanyl]-propionic acid methyl ester;
(137): 4-(4-aminophenylsulfanyl)-6-(5-chloro-1H,3H-benzo[de]isochromen-6-yl)-[1,3,5]triazin-2-ylamine;

(138): 4-(5-chloro-1H,3H-benzo[de]isochromen-6-yl)-6-(3-chloropropylsulfanyl)-[1,3,5]triazin-2-ylamine;
(139): 4-[4-(N,N-dimethylaminosulfonyl)amino-phenylsulfanyl]-6-(5-chloro-1H,3H-benzo[de]isochromen-6-yl)-[1,3,5]triazin-2-ylamine;
(140): N-{4-[4-amino-6-(5-chloro-1H,3H-benzo[de]isochromen-6-yl)-[1,3,5]triazin-2-ylsulfanylmethyl]-phenyl}-acetamide;
(141): 4-(5-chloro-1H,3H-benzo[de]isochromen-6-yl)-6-(3-dimethylaminopropylsulfanyl)-[1,3,5]triazin-2-ylamine;
(142): 4-(4-aminosulfonyl)amino-phenylsulfanyl-6-(5-chloro-1H,3H-benzo[de]isochromen-6-yl)-[1,3,5]triazin-2-ylamine;
(143): N-{2-[4-amino-6-(5-chloro-1H,3H-benzo[de]isochromen-6-yl)-[1,3,5]triazin-2-ylsulfanylmethyl]-phenyl}-acetamide;
(144): N-{3-[4-amino-6-(5-chloro-1H,3H-benzo[de]isochromen-6-yl)-[1,3,5]triazin-2-ylsulfanylmethyl]-phenyl}-acetamide;
(145): 4-(5-chloro-1H,3H-benzo[de]isochromen-6-yl)-6-(2,5-dimethoxyphenylsulfanyl)-[1,3,5]triazin-2-ylamine;
(149): N-{3-[4-amino-6-(5-chloro-1H,3H-benzo[de]isochromen-6-yl)-[1,3,5]triazin-2-ylsulfanyl]-propyl}-acetamide;
(150): N-{4-[4-amino-6-(5-chloro-1H,3H-benzo[de]isochromen-6-yl)-[1,3,5]triazin-2-ylsulfanyl]-butyl}-acetamide;
(151): N-{2-[4-amino-6-(5-chloro-1H,3H-benzo[de]isochromen-6-yl)-[1,3,5]triazin-2-ylsulfanyl]-ethyl}-propionamide;
(152): N-{2-[4-amino-6-(5-chloro-1H,3H-benzo[de]isochromen-6-yl)-[1,3,5]triazin-2-ylsulfanyl]-ethyl}-butylamide;
(153): N-{2-[4-amino-6-(5-chloro-1H,3H-benzo[de]isochromen-6-yl)-[1,3,5]triazin-2-ylsulfanyl]-ethyl}-isobutylamide;
(154): cyclopropane carboxylic acid {2-[4-amino-6-(5-chloro-1H,3H-benzo[de]isochromen-6-yl)-[1,3,5]triazin-2-ylsulfanyl]-ethyl}-amide;
(155): cyclopentane carboxylic acid {2-[4-amino-6-(5-chloro-1H,3H-benzo[de]isochromen-6-yl)-[1,3,5]triazin-2-ylsulfanyl]-ethyl}-amide;
(156): tetrahydro-pyran-4-carboxylic acid {2-[4-amino-6-(5-chloro-1H,3H-benzo[de]isochromen-6-yl)-[1,3,5]triazin-2-ylsulfanyl]-ethyl}-amide;
(157): piperidine-4-carboxylic acid {2-[4-amino-6-(5-chloro-1H,3H-benzo[de]isochromen-6-yl)-[1,3,5]triazin-2-ylsulfanyl]-ethyl}-amide;
(158): 1-methyl-piperidine-4-carboxylic acid {2-[4-amino-6-(5-chloro-1H,3H-benzo[de]isochromen-6-yl)-[1,3,5]triazin-2-ylsulfanyl]-ethyl}-amide;
(159): N-{2-[4-amino-6-(5-chloro-1H,3H-benzo[de]isochromen-6-yl)-[1,3,5]triazin-2-ylsulfanyl]-ethyl}-3-hydroxypropionamide;
(160): N-{2-[4-amino-6-(5-chloro-1H,3H-benzo[de]isochromen-6-yl)-[1,3,5]triazin-2-ylsulfanyl]-ethyl}-3,4-dihydroxybutylamide;
(161): N-{2-[4-amino-6-(5-chloro-1H,3H-benzo[de]isochromen-6-yl)-[1,3,5]triazin-2-ylsulfanyl]-ethyl}-4-hydroxy-3-hydroxymethylbutylamide;
(162): N-{2-[4-amino-6-(5-chloro-1H,3H-benzo[de]isochromen-6-yl)-[1,3,5]triazin-2-ylsulfanyl]-ethyl}-N-methyl-acetamide;
(163): 1-{2-[4-amino-6-(5-chloro-1H,3H-benzo[de]isochromen-6-yl)-[1,3,5]triazin-2-ylsulfanyl]-ethyl}-pyrrolidin-2-one;
(164): N-{3-[4-amino-6-(5-chloro-1H,3H-benzo[de]isochromen-6-yl)-[1,3,5]triazin-2-ylsulfanyl]-propyl}-propionamide;
(165): N-{3-[4-amino-6-(5-chloro-1H,3H-benzo[de]isochromen-6-yl)-[1,3,5]triazin-2-ylsulfanyl]-propyl}-N-methyl-acetamide;
(166): N-{3-[4-amino-6-(5-chloro-1H,3H-benzo[de]isochromen-6-yl)-[1,3,5]triazin-2-ylsulfanyl]-propyl}-3-hydroxypropionamide;
(167): N-{3-[4-amino-6-(5-chloro-1H,3H-benzo[de]isochromen-6-yl)-[1,3,5]triazin-2-ylsulfanyl]-propyl}-3,4-dihydroxy-butylamide;
(168): N-{3-[4-amino-6-(5-chloro-1H,3H-benzo[de]isochromen-6-yl)-[1,3,5]triazin-2-ylsulfanyl]-propyl}-4-hydroxy-3-hydroxymethyl-butylamide;
(169): 1-{3-[4-amino-6-(5-chloro-1H,3H-benzo[de]isochromen-6-yl)-[1,3,5]triazin-2-ylsulfanyl]-propyl}-pyrrolidin-2-one;
(170): cyclopropane carboxylic acid {3-[4-amino-6-(5-chloro-1H,3H-benzo[de]isochromen-6-yl)-[1,3,5]triazin-2-ylsulfanyl]-propyl}-amide;
(171): cyclopentane carboxylic acid {3-[4-amino-6-(5-chloro-1H,3H-benzo[de]isochromen-6-yl)-[1,3,5]triazin-2-ylsulfanyl]-propyl}-amide;
(172): tetrahydro-pyran-4-carboxylic acid {3-[4-amino-6-(5-chloro-1H,3H-benzo[de]isochromen-6-yl)-[1,3,5]triazin-2-ylsulfanyl]-propyl}-amide;
(173): piperidin-4-carboxylic acid {3-[4-amino-6-(5-chloro-1H,3H-benzo[de]isochromen-6-yl)-[1,3,5]triazin-2-ylsulfanyl]-propyl}-amide;
(174): N-{2-[4-amino-6-(5-chloro-1H,3H-benzo[de]isochromen-6-yl)-[1,3,5]triazin-2-ylsulfanyl]-ethyl}-formamide;
(175): {2-[4-amino-6-(5-chloro-1H,3H-benzo[de]isochromen-6-yl)-[1,3,5]triazin-2-ylsulfanyl]-ethyl}-urea;
(176): 1-{2-[4-amino-6-(5-chloro-1H,3H-benzo[de]isochromen-6-yl)-[1,3,5]triazin-2-ylsulfanyl]-ethyl}-3-methylurea;
(177): {2-[4-amino-6-(5-chloro-1H,3H-benzo[de]isochromen-6-yl)-[1,3,5]triazin-2-ylsulfanyl]-ethyl}-carbamic acid methyl ester;
(178): N-{2-[4-amino-6-(5-chloro-1H,3H-benzo[de]isochromen-6-yl)-[1,3,5]triazin-2-ylsulfanyl]-ethyl}-methanesulfonamide;
(179): N-{2-[4-amino-6-(5-chloro-1H,3H-benzo[de]isochromen-6-yl)-[1,3,5]triazin-2-ylsulfanyl]-ethyl}-aminosulfonamide;
(180): N-{3-[4-amino-6-(5-chloro-1H,3H-benzo[de]isochromen-6-yl)-[1,3,5]triazin-2-ylsulfanyl]-propyl}-formamide;
(181): {3-[4-amino-6-(5-chloro-1H,3H-benzo[de]isochromen-6-yl)-[1,3,5]triazin-2-ylsulfanyl]-propyl}-urea;
(182): 1-{3-[4-amino-6-(5-chloro-1H,3H-benzo[de]isochromen-6-yl)-[1,3,5]triazin-2-ylsulfanyl]-propyl}-3-methylurea;
(183): {3-[4-amino-6-(5-chloro-1H,3H-benzo[de]isochromen-6-yl)-[1,3,5]triazin-2-ylsulfanyl]-propyl}-carbamic acid methyl ester;
(184): N-{3-[4-amino-6-(5-chloro-1H,3H-benzo[de]isochromen-6-yl)-[1,3,5]triazin-2-ylsulfanyl]-propyl}-methanesulfonamide;
(185): N-{3-[4-amino-6-(5-chloro-1H,3H-benzo[de]isochromen-6-yl)-[1,3,5]triazin-2-ylsulfanyl]-propyl}-aminosulfonamide;

(186): 4-(5-chloro-1H,3H-benzo[de]isochromen-6-yl)-6-(2-methyl-oxazol-4-ylmethylsulfanyl)-[1,3,5]triazin-2-ylamine;
(187): N-{2-[4-amino-6-(5-chloro-1H,3H-benzo[de]isochromen-6-yl)-[1,3,5]triazin-2-ylsulfanyl]-ethyl}-3-dimethylaminopriopionamide;
(188): N-{2-[4-amino-6-(5-chloro-1H,3H-benzo[de]isochromen-6-yl)-[1,3,5]triazin-2-ylsulfanyl]-ethyl}-isonicotinamide;
(189): 1H-imidazole-2-carboxylic acid {2-[4-amino-6-(5-chloro-1H,3H-benzo[de]isochromen-6-yl)-[1,3,5]triazin-2-ylsulfanyl]-ethyl}-amide;
(190): 4-(5-chloro-1H,3H-benzo[de]isochromen-6-yl)-6-(2-dimethylamino-ethylsulfanyl)-[1,3,5]triazin-2-ylamine;
(191): 4-(2-aminoethylsulfanyl)-6-(5-chloro-1H,3H-benzo[de]isochromen-6-yl)-[1,3,5]triazin-2-ylamine;
(192): 4-(3-aminopropylsulfanyl)-6-(5-chloro-1H,3H-benzo[de]isochromen-6-yl)-[1,3,5]triazin-2-ylamine;
(193): 4-(5-chloro-1H,3H-benzo[de]isochromen-6-yl)-6-(2-methylaminoethylsulfanyl)-[1,3,5]triazin-2-ylamine;
(194): 4-(5-chloro-1H,3H-benzo[de]isochromen-6-yl)-6-(3-methylaminopropylsulfanyl)-[1,3,5]triazin-2-ylamine;
(195): 4-(5-chloro-1H,3H-benzo[de]isochromen-6-yl)-6-(2-pyrrolidin-1-yl-ethylsulfanyl)-[1,3,5]triazin-2-ylamine;
(196): 4-(5-chloro-1H,3H-benzo[de]isochromen-6-yl)-6-(3-pyrrolidin-1-yl-propylsulfanyl)-[1,3,5]triazin-2-ylamine;
(197): 4-(5-chloro-1H,3H-benzo[de]isochromen-6-yl)-6-(2-morpholin-4-yl-ethylsulfanyl)-[1,3,5]triazin-2-ylamine;
(198): 4-(5-chloro-1H,3H-benzo[de]isochromen-6-yl)-6-(3-morpholin-4-yl-propylsulfanyl)-[1,3,5]triazin-2-ylamine;
(199): 4-(5-chloro-1H,3H-benzo[de]isochromen-6-yl)-6-(2-piperazin-1-yl-ethylsulfanyl)-[1,3,5]triazin-2-ylamine;
(200): 4-(5-chloro-1H,3H-benzo[de]isochromen-6-yl)-6-(3-piperazin-1-yl-propylsulfanyl)-[1,3,5]triazin-2-ylamine;
(201): 4-(5-chloro-1H,3H-benzo[de]isochromen-6-yl)-6-[2-(pyridin-2-ylamino)-ethylsulfanyl]-[1,3,5]triazin-2-ylamine;
(202): 4-(5-chloro-1H,3H-benzo[de]isochromen-6-yl)-6-[2-(oxazol-4-ylamino)-ethylsulfanyl]-[1,3,5]triazin-2-ylamine;
(203): 2-[4-amino-6-(5-chloro-1H,3H-benzo[de]isochromen-6-yl)-[1,3,5]triazin-2-ylsulfanyl]-2,2-difluoro-acetamide;
(204): 2-[4-amino-6-(5-chloro-1H,3H-benzo[de]isochromen-6-yl)-[1,3,5]triazin-2-ylsulfanyl]-N-methyl-acetamide;
(205): 3-[4-amino-6-(5-chloro-1H,3H-benzo[de]isochromen-6-yl)-[1,3,5]triazin-2-ylsulfanyl]-N-methyl-propionamide;
(206): 2-[4-amino-6-(5-chloro-1H,3H-benzo[de]isochromen-6-yl)-[1,3,5]triazin-2-ylsulfanyl]-N-ethyl-acetamide;
(207): 3-[4-amino-6-(5-chloro-1H,3H-benzo[de]isochromen-6-yl)-[1,3,5]triazin-2-ylsulfanyl]-N-ethyl-propionamide;
(208): 2-[4-amino-6-(5-chloro-1H,3H-benzo[de]isochromen-6-yl)-[1,3,5]triazin-2-ylsulfanyl]-N,N-dimethyl-acetamide;
(209): 3-[4-amino-6-(5-chloro-1H,3H-benzo[de]isochromen-6-yl)-[1,3,5]triazin-2-ylsulfanyl]-N,N-dimethyl-propionamide;
(210): 2-[4-amino-6-(5-chloro-1H,3H-benzo[de]isochromen-6-yl)-[1,3,5]triazin-2-ylsulfanyl]-N-isopropyl-acetamide;
(211): 3-[4-amino-6-(5-chloro-1H,3H-benzo[de]isochromen-6-yl)-[1,3,5]triazin-2-ylsulfanyl]-N-isopropyl-propionamide;
(212): 2-[4-amino-6-(5-chloro-1H,3H-benzo[de]isochromen-6-yl)-[1,3,5]triazin-2-ylsulfanyl]-N-propyl-acetamide;
(213): 3-[4-amino-6-(5-chloro-1H,3H-benzo[de]isochromen-6-yl)-[1,3,5]triazin-2-ylsulfanyl]-N-propyl-propionamide;
(214): 2-[4-amino-6-(5-chloro-1H,3H-benzo[de]isochromen-6-yl)-[1,3,5]triazin-2-ylsulfanyl]-N-cyclopentyl-acetamide;
(215): 3-[4-amino-6-(5-chloro-1H,3H-benzo[de]isochromen-6-yl)-[1,3,5]triazin-2-ylsulfanyl]-N-cyclopentyl-propionamide;
(216): 2-[4-amino-6-(5-chloro-1H,3H-benzo[de]isochromen-6-yl)-[1,3,5]triazin-2-ylsulfanyl]-N-(tetrahydro-pyran-4-yl)-acetamide;
(217): 3-[4-amino-6-(5-chloro-1H,3H-benzo[de]isochromen-6-yl)-[1,3,5]triazin-2-ylsulfanyl]-N-(tetrahydro-pyran-4-yl)-propionamide;
(218): 2-[4-amino-6-(5-chloro-1H,3H-benzo[de]isochromen-6-yl)-[1,3,5]triazin-2-ylsulfanyl]-N-pyridin-4-yl-acetamide;
(219): 3-[4-amino-6-(5-chloro-1H,3H-benzo[de]isochromen-6-yl)-[1,3,5]triazin-2-ylsulfanyl]-N-pyridin-4-yl-propionamide;
(220): 2-[4-amino-6-(5-chloro-1H,3H-benzo[de]isochromen-6-yl)-[1,3,5]triazin-2-ylsulfanyl]-N-thiazol-2-yl-acetamide;
(221): 3-[4-amino-6-(5-chloro-1H,3H-benzo[de]isochromen-6-yl)-[1,3,5]triazin-2-ylsulfanyl]-N-thiazol-2-yl-propionamide;
(222): 2-[4-amino-6-(5-chloro-1H,3H-benzo[de]isochromen-6-yl)-[1,3,5]triazin-2-ylsulfanyl]-1-pyrrolidin-1-yl-ethanone;
(223): 3-[4-amino-6-(5-chloro-1H,3H-benzo[de]isochromen-6-yl)-[1,3,5]triazin-2-ylsulfanyl]-1-pyrrolidin-1-yl-propan-1-one;
(224): 2-[4-amino-6-(5-chloro-1H,3H-benzo[de]isochromen-6-yl)-[1,3,5]triazin-2-ylsulfanyl]-1-morpholin-4-yl-ethanone;
(225): 3-[4-amino-6-(5-chloro-1H,3H-benzo[de]isochromen-6-yl)-[1,3,5]triazin-2-ylsulfanyl]-1-morpholin-4-yl-propan-1-one;
(226): 2-[4-amino-6-(5-chloro-1H,3H-benzo[de]isochromen-6-yl)-[1,3,5]triazin-2-ylsulfanyl]-1-piperazin-1-yl-ethanone;
(227): 3-[4-amino-6-(5-chloro-1H,3H-benzo[de]isochromen-6-yl)-[1,3,5]triazin-2-ylsulfanyl]-1-(4-methyl-piperazin-1-yl)-propan-1-one;
(228): 3-[4-amino-6-(5-chloro-1H,3H-benzo[de]isochromen-6-yl)-[1,3,5]triazin-2-ylsulfanyl]-1-piperazin-1-yl-propan-1-one;
(229): 2-[4-amino-6-(5-chloro-1H,3H-benzo[de]isochromen-6-yl)-[1,3,5]triazin-2-ylsulfanyl]-N-thiazol-2-yl-acetamide;
(230): 3-[4-amino-6-(5-chloro-1H,3H-benzo[de]isochromen-6-yl)-[1,3,5]triazin-2-ylsulfanyl]-N-thiazol-2-yl-propionamide;

(231): 3-[4-amino-6-(5-chloro-1H,3H-benzo[de]isochromen-6-yl)-[1,3,5]triazin-2-ylsulfanyl]-N-isopropyl-propionamide;
(232): 2-[4-amino-6-(5-chloro-1H,3H-benzo[de]isochromen-6-yl)-[1,3,5]triazin-2-ylsulfanyl]-N-isopropyl-acetamide;
(233): 2-[4-amino-6-(5-chloro-1H,3H-benzo[de]isochromen-6-yl)-[1,3,5]triazin-2-ylsulfanyl]-N-(2-hydroxy-ethyl)-acetamide;
(234): 3-[4-amino-6-(5-chloro-1H,3H-benzo[de]isochromen-6-yl)-[1,3,5]triazin-2-ylsulfanyl]-N-(2-hydroxy-ethyl)-propionamide;
(235): 2-[4-amino-6-(5-chloro-1H,3H-benzo[de]isochromen-6-yl)-[1,3,5]triazin-2-ylsulfanyl]-N-(2,3-dihydroxypropyl)-acetamide;
(236): 3-[4-amino-6-(5-chloro-1H,3H-benzo[de]isochromen-6-yl)-[1,3,5]triazin-2-ylsulfanyl]-N-(2,3-dihydroxypropyl)-propionamide;
(237): 2-[4-amino-6-(5-chloro-1H,3H-benzo[de]isochromen-6-yl)-[1,3,5]triazin-2-ylsulfanyl]-N-(3-hydroxy-2-hydroxymethyl-propyl)-acetamide;
(238): 3-[4-amino-6-(5-chloro-1H,3H-benzo[de]isochromen-6-yl)-[1,3,5]triazin-2-ylsulfanyl]-N-(3-hydroxy-2-hydroxymethyl-propyl)-propionamide;
(239): 4-[4-amino-6-(5-chloro-1H,3H-benzo[de]isochromen-6-yl)-[1,3,5]triazin-2-ylsulfanyl]-butylamide;
(240): 4-[4-amino-6-(5-chloro-1H,3H-benzo[de]isochromen-6-yl)-[1,3,5]triazin-2-ylsulfanyl]-N-methyl-butylamide;
(241): 4-[4-amino-6-(5-chloro-1H,3H-benzo[de]isochromen-6-yl)-[1,3,5]triazin-2-ylsulfanyl]-N,N-dimethyl-butylamide;
(242): 4-[4-amino-6-(5-chloro-1H,3H-benzo[de]isochromen-6-yl)-[1,3,5]triazin-2-ylsulfanyl]-N-ethyl-butylamide;
(243): 4-[4-amino-6-(5-chloro-1H,3H-benzo[de]isochromen-6-yl)-[1,3,5]triazin-2-ylsulfanyl]-1-pyrrolidin-1-yl-butan-1-one;
(244): 4-[4-amino-6-(5-chloro-1H,3H-benzo[de]isochromen-6-yl)-[1,3,5]triazin-2-ylsulfanyl]-1-morpholin-4-yl-butan-1-one;
(245): 4-[4-amino-6-(5-chloro-1H,3H-benzo[de]isochromen-6-yl)-[1,3,5]triazin-2-ylsulfanyl]-1-piperazin-1-yl-butan-1-one;
(246): 4-[4-amino-6-(5-chloro-1H,3H-benzo[de]isochromen-6-yl)-[1,3,5]triazin-2-ylsulfanyl]-N-(2-hydroxy-ethyl)-butylamide;
(247): 4-[4-amino-6-(5-chloro-1H,3H-benzo[de]isochromen-6-yl)-[1,3,5]triazin-2-ylsulfanyl]-N-(tetrahydro-pyran-4-yl)-butylamide;
(248): 4-[4-amino-6-(5-chloro-1H,3H-benzo[de]isochromen-6-yl)-[1,3,5]triazin-2-ylsulfanyl]-N-piperidin-4-yl-butylamide;
(249): 4-[4-amino-6-(5-chloro-1H,3H-benzo[de]isochromen-6-yl)-[1,3,5]triazin-2-ylsulfanyl]-N-pyridin-4-yl-butylamide;
(250): 4-[4-amino-6-(5-chloro-1H,3H-benzo[de]isochromen-6-yl)-[1,3,5]triazin-2-ylsulfanyl]-N-thiazol-2-yl-butylamide;
(251): 1-[4-amino-6-(5-chloro-1H,3H-benzo[de]isochromen-6-yl)-[1,3,5]triazin-2-ylsulfanyl]-propan-2-one;
(252): 4-[4-amino-6-(5-chloro-1H,3H-benzo[de]isochromen-6-yl)-[1,3,5]triazin-2-ylsulfanyl]-butan-2-one;
(253): N-{2-[4-amino-6-(5-chloro-1H,3H-benzo[de]isochromen-6-yl)-[1,3,5]triazin-2-ylsulfanyl]-acetyl}-acetamide;
(254): N-{3-[4-amino-6-(5-chloro-1H,3H-benzo[de]isochromen-6-yl)-[1,3,5]triazin-2-ylsulfanyl]-propionyl}-acetamide;
(255): N-{4-[4-amino-6-(5-chloro-1H,3H-benzo[de]isochromen-6-yl)-[1,3,5]triazin-2-ylsulfanyl]-butyryl}-acetamide;
(256): N-{2-[4-amino-6-(5-chloro-1H,3H-benzo[de]isochromen-6-yl)-[1,3,5]triazin-2-ylsulfanyl]-acetyl}-methanesulfonamide;
(257): N-{3-[4-amino-6-(5-chloro-1H,3H-benzo[de]isochromen-6-yl)-[1,3,5]triazin-2-ylsulfanyl]-propionyl}-methanesulfonamide;
(258): N-{4-[4-amino-6-(5-chloro-1H,3H-benzo[de]isochromen-6-yl)-[1,3,5]triazin-2-ylsulfanyl]-butyryl}-methanesulfonamide;
(259): 4-(5-chloro-1H,3H-benzo[de]isochromen-6-yl)-6-(oxazol-2-ylmethylsulfanyl)-[1,3,5]triazin-2-ylamine;
(260): 4-(5-chloro-1H,3H-benzo[de]isochromen-6-yl)-6-(2-oxazol-2-yl-ethylsulfanyl)-[1,3,5]triazin-2-ylamine;
(261): 1-[4-amino-6-(5-chloro-1H,3H-benzo[de]isochromen-6-yl)-[1,3,5]triazin-2-ylsulfanyl]-propan-2-one O-methyl-oxime;
(262): 4-[4-amino-6-(5-chloro-1H,3H-benzo[de]isochromen-6-yl)-[1,3,5]triazin-2-ylsulfanyl]-butan-2-one O-methyl-oxime;
(263): [4-amino-6-(5-chloro-1H,3H-benzo[de]isochromen-6-yl)-[1,3,5]triazin-2-ylsulfanyl]-acetonitrile;
(264): 3-[4-amino-6-(5-chloro-1H,3H-benzo[de]isochromen-6-yl)-[1,3,5]triazin-2-ylsulfanyl]-propionitrile;
(265): 4-[4-amino-6-(5-chloro-1H,3H-benzo[de]isochromen-6-yl)-[1,3,5]triazin-2-ylsulfanyl]-butyronitrile;
(266): 4-(5-chloro-1H,3H-benzo[de]isochromen-6-yl)-6-(2-methoxy-ethylsulfanyl)-[1,3,5]triazin-2-ylamine;
(267): 4-(5-chloro-1H,3H-benzo[de]isochromen-6-yl)-6-(3-methoxypropylsulfanyl)-[1,3,5]triazin-2-ylamine;
(268): 4-(5-chloro-1H,3H-benzo[de]isochromen-6-yl)-6-[2-(2-methoxyethoxy)-ethylsulfanyl]-[1,3,5]triazin-2-ylamine;
(269): 4-[4-amino-6-(5-chloro-1H,3H-benzo[de]isochromen-6-yl)-[1,3,5]triazin-2-ylsulfanyl]-butan-1-ol;
(270): carbamic acid 2-[4-amino-6-(5-chloro-1H,3H-benzo[de]isochromen-6-yl)-[1,3,5]triazin-2-ylsulfanyl]-ethyl ester;
(271): carbamic acid 3-[4-amino-6-(5-chloro-1H,3H-benzo[de]isochromen-6-yl)-[1,3,5]triazin-2-ylsulfanyl]-propyl ester;
(272): carbamic acid 4-[4-amino-6-(5-chloro-1H,3H-benzo[de]isochromen-6-yl)-[1,3,5]triazin-2-ylsulfanyl]-butyl ester;
(273): sulfamic acid 2-[4-amino-6-(5-chloro-1H,3H-benzo[de]isochromen-6-yl)-[1,3,5]triazin-2-ylsulfanyl]-ethyl ester;
(274): sulfamic acid 3-[4-amino-6-(5-chloro-1H,3H-benzo[de]isochromen-6-yl)-[1,3,5]triazin-2-ylsulfanyl]-propyl ester;
(275): sulfamic acid 4-[4-amino-6-(5-chloro-1H,3H-benzo[de]isochromen-6-yl)-[1,3,5]triazin-2-ylsulfanyl]-butyl ester;
(276): 3-[4-amino-6-(5-chloro-1H,3H-benzo[de]isochromen-6-yl)-[1,3,5]triazin-2-ylsulfanyl]-propane-1,2-diol;
(277): 2-[4-amino-6-(5-chloro-1H,3H-benzo[de]isochromen-6-yl)-[1,3,5]triazin-2-ylsulfanylmethyl]-propane-1,3-diol;
(278): thiocarbamic acid 2-[4-amino-6-(5-chloro-1H,3H-benzo[de]isochromen-6-yl)-[1,3,5]triazin-2-ylsulfanyl]-ethyl ester;

(279): thiocarbamic acid 3-[4-amino-6-(5-chloro-1H,3H-benzo[de]isochromen-6-yl)-[1,3,5]triazin-2-ylsulfanyl]-propyl ester;
(280): 4-(5-chloro-1H,3H-benzo[de]isochromen-6-yl)-6-(2-methanesulfonyl-ethylsulfanyl)-[1,3,5]triazin-2-ylamine;
(281): 4-(5-chloro-1H,3H-benzo[de]isochromen-6-yl)-6-(3-methanesulfonyl-propylsulfanyl)-[1,3,5]triazin-2-ylamine;
(282): 3-[4-amino-6-(5-chloro-1H,3H-benzo[de]isochromen-6-yl)-[1,3,5]triazin-2-ylsulfanyl-propan-1-sulfonamide;
(283): 2-[4-amino-6-(5-chloro-1H,3H-benzo[de]isochromen-6-yl)-[1,3,5]triazin-2-ylsulfanyl]-ethanesulfonamide;
(284): 4-(5-chloro-1H,3H-benzo[de]isochromen-6-yl)-6-(3,3,3-trifluoro-propylsulfanyl)-[1,3,5]triazin-2-ylamine;
(285): 4-(5-chloro-1H,3H-benzo[de]isochromen-6-yl)-6-(4,4,4-trifluoro-butylsulfanyl)-[1,3,5]triazin-2-ylamine;
(286): 4-(5-chloro-1H,3H-benzo[de]isochromen-6-yl)-6-(3-fluoropropylsulfanyl)-[1,3,5]triazin-2-ylamine;
(287): 4-(5-chloro-1H,3H-benzo[de]isochromen-6-yl)-6-(4-fluorobutylsulfanyl)-[1,3,5]triazin-2-ylamine;
(288): 4-(5-chloro-1H,3H-benzo[de]isochromen-6-yl)-6-(oxazol-2-ylmethylsulfanyl)-[1,3,5]triazin-2-ylamine;
(289): 4-(5-chloro-1H,3H-benzo[de]isochromen-6-yl)-6-(thiazol-2-ylmethylsulfanyl)-[1,3,5]triazin-2-ylamine;
(290): 4-(5-chloro-1H,3H-benzo[de]isochromen-6-yl)-6-(2-thiazol-2-yl-ethylsulfanyl)-[1,3,5]triazin-2-ylamine;
(291): 4-(5-chloro-1H,3H-benzo[de]isochromen-6-yl)-6-(1H-imidazol-2-ylmethylsulfanyl)-[1,3,5]triazin-2-ylamine;
(292): 4-(5-chloro-1H,3H-benzo[de]isochromen-6-yl)-6-[2-(1H-imidazol-2-yl)-ethylsulfanyl]-[1,3,5]triazin-2-ylamine;
(293): 4-(5-chloro-1H,3H-benzo[de]isochromen-6-yl)-6-(2-oxazol-3-yl-ethylsulfanyl)-[1,3,5]triazin-2-ylamine;
(294): 4-(5-chloro-1H,3H-benzo[de]isochromen-6-yl)-6-(pyridin-4-ylmethylsulfanyl)-[1,3,5]triazin-2-ylamine;
(295): 4-(5-chloro-1H,3H-benzo[de]isochromen-6-yl)-6-(2-pyridin-4-yl-ethylsulfanyl)-[1,3,5]triazin-2-ylamine;
(296): 4-(5-chloro-1H,3H-benzo[de]isochromen-6-yl)-6-(pyridin-2-ylmethylsulfanyl)-[1,3,5]triazin-2-ylamine;
(297): 4-(5-chloro-1H,3H-benzo[de]isochromen-6-yl)-6-(2-pyridin-2-yl-ethylsulfanyl)-[1,3,5]triazin-2-ylamine;
(298): 2-acetylamino-3-[4-amino-6-(5-chloro-1H,3H-benzo[de]isochromen-6-yl)-[1,3,5]triazin-2-ylsulfanyl]-propionamide;
(299): 2-acetylamino-3-[4-amino-6-(5-chloro-1H,3H-benzo[de]isochromen-6-yl)-[1,3,5]triazin-2-ylsulfanyl]-N-methyl-propionamide;
(300): 2-acetylamino-3-[4-amino-6-(5-chloro-1H,3H-benzo[de]isochromen-6-yl)-[1,3,5]triazin-2-ylsulfanyl]-N-ethyl-propionamide;
(301): 2-acetylamino-3-[4-amino-6-(5-chloro-1H,3H-benzo[de]isochromen-6-yl)-[1,3,5]triazin-2-ylsulfanyl]-N,N-dimethyl-propionamide;
(302): 2-amino-3-[4-amino-6-(5-chloro-1H,3H-benzo[de]isochromen-6-yl)-[1,3,5]triazin-2-ylsulfanyl]-N-methyl-propionamide;
(303): 2-amino-3-[4-amino-6-(5-chloro-1H,3H-benzo[de]isochromen-6-yl)-[1,3,5]triazin-2-ylsulfanyl]-N,N-dimethyl-propionamide;
(304): 2-[4-amino-6-(5-chloro-1H,3H-benzo[de]isochromen-6-yl)-[1,3,5]triazin-2-ylsulfanyl]-N-(2-methoxy-ethyl)-acetamide;
(305): 2-[4-amino-6-(5-chloro-1H,3H-benzo[de]isochromen-6-yl)-[1,3,5]triazin-2-ylsulfanyl]-N-cyanomethyl-acetamide;
(306): 2-[4-amino-6-(5-chloro-1H,3H-benzo[de]isochromen-6-yl)-[1,3,5]triazin-2-ylsulfanyl]-N-(2-hydroxy-1-hydroxymethyl-ethyl)-acetamide;
(307): 2-[4-amino-6-(5-chloro-1H,3H-benzo[de]isochromen-6-yl)-[1,3,5]triazin-2-ylsulfanyl]-N-(2-diethylamino-ethyl)-acetamide;
(308): 2-[4-amino-6-(5-chloro-1H,3H-benzo[de]isochromen-6-yl)-[1,3,5]triazin-2-ylsulfanyl]-N-(1-methyl-piperidin-4-yl)-acetamide;
(309): 3-[4-amino-6-(5-chloro-1H,3H-benzo[de]isochromen-6-yl)-[1,3,5]triazin-2-ylsulfanyl]-N-(2-methoxy-ethyl)-propionamide;
(310): 1-{2-[4-amino-6-(5-chloro-1H,3H-benzo[de]isochromen-6-yl)-[1,3,5]triazin-2-ylsulfanyl]-ethyl}-imidazolin-2-one;
(311): 3-{2-[4-amino-6-(5-chloro-1H,3H-benzo[de]isochromen-6-yl)-[1,3,5]triazin-2-ylsulfanyl]-ethyl}-oxazolidin-2-one;
(312): 2-[4-amino-6-(5-chloro-1H,3H-benzo[de]isochromen-6-yl)-[1,3,5]triazin-2-ylsulfanyl]-1-pyrazin-2-yl-ethanone;
(313): 3-{2-[4-amino-6-(5-chloro-1H,3H-benzo[de]isochromen-6-yl)-[1,3,5]triazin-2-ylsulfanyl]-acetyl}-oxazolidin-2-one;
(314): 2-[2-amino-6-(5-chloro-1H,3H-benzo[de]isochromen-6-yl)-pyrimidin-4-ylsulfanyl]-acetamide;
(315): 2-[2-amino-6-(5-chloro-1H,3H-benzo[de]isochromen-6-yl)-pyrimidin-4-ylsulfanyl]-N-cyanomethyl-acetamide;
(316): 3-[2-amino-6-(5-chloro-1H,3H-benzo[de]isochromen-6-yl)-pyrimidin-4-ylsulfanyl]-propionamide;
(317): 3-[2-amino-6-(5-chloro-1H,3H-benzo[de]isochromen-6-yl)-pyrimidin-4-ylsulfanyl]-N-(2-hydroxy-ethyl)-propionamide;
(318): 3-[2-amino-6-(5-chloro-1H,3H-benzo[de]isochromen-6-yl)-pyrimidin-4-ylsulfanyl]-N-methyl-propionamide;
(319): 3-[2-amino-6-(5-chloro-1H,3H-benzo[de]isochromen-6-yl)-pyrimidin-4-ylsulfanyl]-N-(2-methoxy-ethyl)-propionamide;
(320): 3-[2-amino-6-(5-chloro-1H,3H-benzo[de]isochromen-6-yl)-pyrimidin-4-ylsulfanyl]-N-((R)-2,3-dihydroxy-propyl)-propionamide;
(321): 3-[2-amino-6-(5-chloro-1H,3H-benzo[de]isochromen-6-yl)-pyrimidin-4-ylsulfanyl]-2-methyl-propionamide;
(322): 3-[2-amino-6-(5-chloro-1H,3H-benzo[de]isochromen-6-yl)-pyrimidin-4-ylsulfanyl]-2,N-dimethyl-propionamide;
(323): 3-[2-amino-6-(5-chloro-1H,3H-benzo[de]isochromen-6-yl)-pyrimidin-4-ylsulfanyl]-N-(2-hydroxy-ethyl)-2-methyl-propionamide;
(324): 4-[2-amino-6-(5-chloro-1H,3H-benzo[de]isochromen-6-yl)-pyrimidin-4-ylsulfanyl]-butylamide;
(325): carbamic acid 2-[2-amino-6-(5-chloro-1H,3H-benzo[de]isochromen-6-yl)-pyrimidin-4-ylsulfanyl]-ethyl ester;
(326): 3-[2-amino-6-(5-chloro-1H,3H-benzo[de]isochromen-6-yl)-pyrimidin-4-ylsulfanyl]-propan-1-ol;

(327): N-{2-[2-amino-6-(5-chloro-1H,3H-benzo[de]isochromen-6-yl)-pyrimidin-4-ylsulfanyl]-ethyl}-acetamide;

(328): N-{3-[2-amino-6-(5-chloro-1H,3H-benzo[de]isochromen-6-yl)-pyrimidin-4-ylsulfanyl]-propyl}-acetamide;

(329): N-{2-[2-amino-6-(5-chloro-1H,3H-benzo[de]isochromen-6-yl)-pyrimidin-4-ylsulfanyl]-ethyl}-methanesulfonamide;

(330): 5-[2-amino-6-(5-chloro-1H,3H-benzo[de]isochromen-6-yl)-pyrimidin-4-ylsulfanylmethyl]-oxazolidin-2-one;

(331): N-{2-[2-amino-6-(5-chloro-1H,3H-benzo[de]isochromen-6-yl)-pyrimidin-4-ylsulfanyl]-ethyl}-2-hydroxy-acetamide;

(332): {2-[2-amino-6-(5-chloro-1H,3H-benzo[de]isochromen-6-yl)-pyrimidin-4-ylsulfanyl]-ethyl}-urea;

(333): 2-[4-amino-6-(5-chloro-1H,3H-benzo[de]isochromen-6-yl)-[1,3,5]triazin-2-ylsulfanyl]-N-cyanomethyl-acetamide;

(334): 3-[4-amino-6-(5-chloro-1H,3H-benzo[de]isochromen-6-yl)-[1,3,5]triazin-2-ylsulfanyl]-N-(2-methoxy-ethyl)-propionamide;

(335): 3-[4-amino-6-(5-chloro-1H,3H-benzo[de]isochromen-6-yl)-[1,3,5]triazin-2-ylsulfanyl]-N-((R)-2,3-dihydroxy-propyl)-propionamide;

(336): 3-[4-amino-6-(5-chloro-1H,3H-benzo[de]isochromen-6-yl)-[1,3,5]triazin-2-ylsulfanyl]-2-methyl-propionamide;

(337): 3-[4-amino-6-(5-chloro-1H,3H-benzo[de]isochromen-6-yl)-[1,3,5]triazin-2-ylsulfanyl]-2,N-dimethyl-propionamide;

(338): 3-[4-amino-6-(5-chloro-1H,3H-benzo[de]isochromen-6-yl)-[1,3,5]triazin-2-ylsulfanyl]-N-(2-hydroxy-ethyl)-2-methyl-propionamide;

(339): 4-[4-amino-6-(5-chloro-1H,3H-benzo[de]isochromen-6-yl)-[1,3,5]triazin-2-ylsulfanyl]-butyramide;

(340): 3-[4-amino-6-(5-chloro-1H,3H-benzo[de]isochromen-6-yl)-[1,3,5]triazin-2-ylsulfanyl]-propan-1-ol;

(341): 5-[4-amino-6-(5-chloro-1H,3H-benzo[de]isochromen-6-yl)-[1,3,5]triazin-2-ylsulfanylmethyl]-oxazolidin-2-one;

(342): N-{2-[4-amino-6-(5-chloro-1H,3H-benzo[de]isochromen-6-yl)-[1,3,5]triazin-2-ylsulfanyl]-ethyl}-2-hydroxy-acetamide; and (343): 4-[4-amino-6-(5-chloro-1H,3H-2-thia-phenalen-6-yl)-[1,3,5]triazin-2-ylsulfanyl]-butyramide.

13. A compound or a pharmaceutically acceptable salt thereof, wherein the compound is selected from the group consisting of:

(82): 4-(5-chloro-1H,3H-benzo[de]isochromen-6-yl)-6-(3,4-dimethoxyphenoxy)-[1,3,5]triazin-2-ylamine;

(92): 4-(5-chloro-1H,3H-benzo[de]isochromen-6-yl)-6-cyclohexylsulfanyl-[1,3,5]triazin-2-ylamine;

(111): [4-amino-6-(5-chloro-1H,3H-benzo[de]isochromen-6-yl)-[1,3,5]triazin-2-ylsulfanyl]-acetic acid methyl ester;

(113): N-{2-[4-amino-6-(5-chloro-1H,3H-benzo[de]isochromen-6-yl)-[1,3,5]triazin-2-ylsulfanyl]-ethyl}-acetamide;

(119): 2-[4-amino-6-(5-chloro-1H,3H-benzo[de]isochromen-6-yl)-[1,3,5]triazin-2-ylsulfanyl]-acetamide;

(125): 3-[4-amino-6-(5-chloro-1H,3H-benzo[de]isochromen-6-yl)-[1,3,5]triazin-2-ylsulfanyl]-propionamide;

(143): N-{2-[4-amino-6-(5-chloro-1H,3H-benzo[de]isochromen-6-yl)-[1,3,5]triazin-2-ylsulfanylmethyl]-phenyl}-acetamide;

(145): 4-(5-chloro-1H,3H-benzo[de]isochromen-6-yl)-6-(2,5-dimethoxyphenylsulfanyl)-[1,3,5]triazin-2-ylamine;

(149): N-{3-[4-amino-6-(5-chloro-1H,3H-benzo[de]isochromen-6-yl)-[1,3,5]triazin-2-ylsulfanyl]-propyl}-acetamide;

(175): {2-[4-amino-6-(5-chloro-1H,3H-benzo[de]isochromen-6-yl)-[1,3,5]triazin-2-ylsulfanyl]-ethyl}-urea;

(178): N-{2-[4-amino-6-(5-chloro-1H,3H-benzo[de]isochromen-6-yl)-[1,3,5]triazin-2-ylsulfanyl]-ethyl}-methanesulfonamide;

(205): 3-[4-amino-6-(5-chloro-1H,3H-benzo[de]isochromen-6-yl)-[1,3,5]triazin-2-ylsulfanyl]-N-methyl-propionamide;

(234): 3-[4-amino-6-(5-chloro-1H,3H-benzo[de]isochromen-6-yl)-[1,3,5]triazin-2-ylsulfanyl]-N-(2-hydroxy-ethyl)-propionamide;

(270): carbamic acid 2-[4-amino-6-(5-chloro-1H,3H-benzo[de]isochromen-6-yl)-[1,3,5]triazin-2-ylsulfanyl]-ethyl ester;

(314): 2-[2-amino-6-(5-chloro-1H,3H-benzo[de]isochromen-6-yl)-pyrimidin-4-ylsulfanyl]-acetamide;

(315): 2-[2-amino-6-(5-chloro-1H,3H-benzo[de]isochromen-6-yl)-pyrimidin-4-ylsulfanyl]-N-cyanomethyl-acetamide;

(316): 3-[2-amino-6-(5-chloro-1H,3H-benzo[de]isochromen-6-yl)-pyrimidin-4-ylsulfanyl]-propionamide;

(317): 3-[2-amino-6-(5-chloro-1H,3H-benzo[de]isochromen-6-yl)-pyrimidin-4-ylsulfanyl]-N-(2-hydroxy-ethyl)-propionamide;

(318): 3-[2-amino-6-(5-chloro-1H,3H-benzo[de]isochromen-6-yl)-pyrimidin-4-ylsulfanyl]-N-methyl-propionamide;

(319): 3-[2-amino-6-(5-chloro-1H,3H-benzo[de]isochromen-6-yl)-pyrimidin-4-ylsulfanyl]-N-(2-methoxy-ethyl)-propionamide;

(320): 3-[2-amino-6-(5-chloro-1H,3H-benzo[de]isochromen-6-yl)-pyrimidin-4-ylsulfanyl]-N-((R)-2,3-dihydroxy-propyl)-propionamide;

(321): 3-[2-amino-6-(5-chloro-1H,3H-benzo[de]isochromen-6-yl)-pyrimidin-4-ylsulfanyl]-2-methyl-propionamide;

(322): 3-[2-amino-6-(5-chloro-1H,3H-benzo[de]isochromen-6-yl)-pyrimidin-4-ylsulfanyl]-2,N-dimethyl-propionamide;

(323): 3-[2-amino-6-(5-chloro-1H,3H-benzo[de]isochromen-6-yl)-pyrimidin-4-ylsulfanyl]-N-(2-hydroxy-ethyl)-2-methyl-propionamide;

(324): 4-[2-amino-6-(5-chloro-1H,3H-benzo[de]isochromen-6-yl)-pyrimidin-4-ylsulfanyl]-butylamide;

(325): carbamic acid 2-[2-amino-6-(5-chloro-1H,3H-benzo[de]isochromen-6-yl)-pyrimidin-4-ylsulfanyl]-ethyl ester;

(326): 3-[2-amino-6-(5-chloro-1H,3H-benzo[de]isochromen-6-yl)-pyrimidin-4-ylsulfanyl]-propan-1-ol;

(327): N-{2-[2-amino-6-(5-chloro-1H,3H-benzo[de]isochromen-6-yl)-pyrimidin-4-ylsulfanyl]-ethyl}-acetamide;

(328): N-{3-[2-amino-6-(5-chloro-1H,3H-benzo[de]isochromen-6-yl)-pyrimidin-4-ylsulfanyl]-propyl}-acetamide;

(329): N-{2-[2-amino-6-(5-chloro-1H,3H-benzo[de]isochromen-6-yl)-pyrimidin-4-ylsulfanyl]-ethyl}-methanesulfonamide;
(330): 5-[2-amino-6-(5-chloro-1H,3H-benzo[de]isochromen-6-yl)-pyrimidin-4-ylsulfanylmethyl]-oxazolidin-2-one;
(331): N-{2-[2-amino-6-(5-chloro-1H,3H-benzo[de]isochromen-6-yl)-pyrimidin-4-ylsulfanyl]-ethyl}-2-hydroxy-acetamide;
(332): {2-[2-amino-6-(5-chloro-1H,3H-benzo[de]isochromen-6-yl)-pyrimidin-4-ylsulfanyl]-ethyl}-urea;
(333): 2-[4-amino-6-(5-chloro-1H,3H-benzo[de]isochromen-6-yl)-[1,3,5]triazin-2-ylsulfanyl]-N-cyanomethyl-acetamide;
(334): 3-[4-amino-6-(5-chloro-1H,3H-benzo[de]isochromen-6-yl)-[1,3,5]triazin-2-ylsulfanyl]-N-(2-methoxy-ethyl)-propionamide;
(335): 3-[4-amino-6-(5-chloro-1H,3H-benzo[de]isochromen-6-yl)-[1,3,5]triazin-2-ylsulfanyl]-N-((R)-2,3-dihydroxy-propyl)-propionamide;
(336): 3-[4-amino-6-(5-chloro-1H,3H-benzo[de]isochromen-6-yl)-[1,3,5]triazin-2-ylsulfanyl]-2-methyl-propionamide;
(337): 3-[4-amino-6-(5-chloro-1H,3H-benzo[de]isochromen-6-yl)-[1,3,5]triazin-2-ylsulfanyl]-2,N-dimethyl-propionamide;
(338): 3-[4-amino-6-(5-chloro-1H,3H-benzo[de]isochromen-6-yl)-[1,3,5]triazin-2-ylsulfanyl]-N-(2-hydroxy-ethyl)-2-methyl-propionamide;
(339): 4-[4-amino-6-(5-chloro-1H,3H-benzo[de]isochromen-6-yl)-[1,3,5]triazin-2-ylsulfanyl]-butyramide;
(340): 3-[4-amino-6-(5-chloro-1H,3H-benzo[de]isochromen-6-yl)-[1,3,5]triazin-2-ylsulfanyl]-propan-1-ol;
(341): 5-[4-amino-6-(5-chloro-1H,3H-benzo[de]isochromen-6-yl)-[1,3,5]triazin-2-ylsulfanylmethyl]-oxazolidin-2-one;
(342): N-{2-[4-amino-6-(5-chloro-1H,3H-benzo[de]isochromen-6-yl)-[1,3,5]triazin-2-ylsulfanyl]-ethyl}-2-hydroxy-acetamide; and
(343): 4-[4-amino-6-(5-chloro-1H,3H-2-thia-phenalen-6-yl)-[1,3,5]triazin-2-ylsulfanyl]-butyramide.

14. A pharmaceutical composition comprising the compound or a pharmaceutically acceptable salt thereof according to claim 1, and a pharmaceutically acceptable carrier.

15. A compound represented by formula (8a) or a salt thereof:

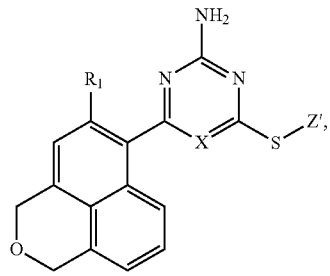

(8a)

wherein,
X represents CH or N;
$R_1$ represents a hydrogen atom, halogen atom, cyano group, $C_{1-6}$ alkyl group, $C_{1-4}$ haloalkyl group, $C_{2-6}$ alkenyl group, $C_{2-6}$ alkynyl group, $C_{1-6}$ alkoxy group, or $C_{1-6}$ alkylthio group; and
Z' represents a hydrogen atom, an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{6-12}$ aryl group, an optionally substituted 5- to 12-membered heteroaryl group, or an optionally substituted 3- to 12-membered heterocycle.

16. The compound or salt thereof of claim 15, wherein Z' is a hydrogen atom, or an optionally substituted $C_{1-10}$ alkyl group.

17. The compound or salt thereof of claim 16, wherein Z' is a hydrogen atom, $C_{1-6}$ alkyl group, or benzyl group.

18. A method for treating breast cancer, comprising administering to a subject in need thereof an effective amount of the compound or a pharmaceutically acceptable salt thereof according to claim 1.

19. A method for treating colon cancer, comprising administering to a subject in need thereof an effective amount of the compound or a pharmaceutically acceptable salt thereof according to claim 1.

* * * * *